(12) United States Patent
Adams et al.

(10) Patent No.: US 10,093,663 B2
(45) Date of Patent: Oct. 9, 2018

(54) PIPERIDINYL-INDOLE DERIVATIVES COMPLEMENT FACTOR B INHIBITORS AND USES THEREOF

(71) Applicant: Novartis AG, Basel (CH)

(72) Inventors: Christopher Michael Adams, Somerville, MA (US); Michael Paul Capparelli, Cambridge, MA (US); Takeru Ehara, Arlington, MA (US); Rajeshri Ganesh Karki, Somerville, MA (US); Nello Mainolfi, Boston, MA (US); Chun Zhang, Waltham, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/626,981

(22) Filed: Jun. 19, 2017

(65) Prior Publication Data
US 2018/0009795 A1    Jan. 11, 2018

Related U.S. Application Data

(62) Division of application No. 14/904,694, filed as application No. PCT/US2014/046515 on Jul. 14, 2014, now Pat. No. 9,682,968.

(60) Provisional application No. 61/977,028, filed on Apr. 8, 2014, provisional application No. 61/846,355, filed on Jul. 15, 2013.

(51) Int. Cl.
| C07D 401/06 | (2006.01) |
| C07D 403/06 | (2006.01) |
| C07D 413/06 | (2006.01) |
| C07D 401/14 | (2006.01) |
| C07D 413/14 | (2006.01) |
| C07D 417/14 | (2006.01) |
| A61K 31/404 | (2006.01) |
| A61K 31/438 | (2006.01) |
| A61K 31/4439 | (2006.01) |
| A61K 31/454 | (2006.01) |
| A61K 31/5377 | (2006.01) |
| A61K 31/55 | (2006.01) |

(52) U.S. Cl.
CPC .......... *C07D 413/06* (2013.01); *A61K 31/404* (2013.01); *A61K 31/438* (2013.01); *A61K 31/4439* (2013.01); *A61K 31/454* (2013.01); *A61K 31/5377* (2013.01); *A61K 31/55* (2013.01); *C07D 401/06* (2013.01); *C07D 401/14* (2013.01); *C07D 403/06* (2013.01); *C07D 413/14* (2013.01); *C07D 417/14* (2013.01)

(58) Field of Classification Search
None
See application file for complete search history.

(56) References Cited

U.S. PATENT DOCUMENTS

| 9,682,968 B2 | 6/2017 | Adams et al. |
| 2005/0153980 A1 | 7/2005 | Schadt et al. |
| 2008/0004259 A1 | 1/2008 | Arrington et al. |
| 2009/0215828 A1 | 8/2009 | Schunk et al. |

FOREIGN PATENT DOCUMENTS

| WO | 2002/016349 A1 | 2/2002 |
| WO | 2004/022057 A1 | 3/2004 |
| WO | 2004/056806 A1 | 7/2004 |
| WO | 2004/099170 A2 | 11/2004 |
| WO | 2006/055625 A2 | 5/2006 |
| WO | WO2006/086255 A3 | 8/2006 |
| WO | 2009042092 A1 | 4/2009 |
| WO | 2009076404 A1 | 6/2009 |
| WO | 2011/006794 A1 | 1/2011 |
| WO | 2011/109059 A1 | 9/2011 |
| WO | 2012/068589 A2 | 5/2012 |
| WO | 2012/093101 A1 | 7/2012 |
| WO | 2013/164802 A1 | 11/2013 |
| WO | 2013/192345 A1 | 12/2013 |

OTHER PUBLICATIONS

Hiriyakkanavar, et al., "Synthetic studies in the indole field. III. 2-Phenyl-7-methylindole derivatives of biological Interest", Journal of the Karnatak University, vol. 7, pp. 157-163, 1962.
Hiriyakkanavar, et al., "Synthetic studies in the indole field. III. 2-Phenyl-7-methylindole derivatives of biological interest", Journal of the Karnatak University, vol. 7, pp. 149-150, 1962.
CAS Registry No. 1622564-43-5, Chemical or Trade Name: 1H-Indole, 1-ethyl-4-[[2-(3-methyl-1H-1,2,4-triazol-5-yl)-1-pyrrolidinyl]methyl]-, Entry Date: Sep. 12, 2014.
CAS Registry No. 1622551-49-8, Chemical or Trade Name: 1H-Indole, 1-ethyl-4-[[2-[3-(2-methoxyethyl)-1,2,4-oxadiazol-5-yl]-1-piperidinyl]methyl], Entry Date: Sep. 12, 2014.

(Continued)

Primary Examiner — Jeffrey S Lundgren
Assistant Examiner — Meghan Finn
(74) Attorney, Agent, or Firm — David Kurlandsky

(57) ABSTRACT

The present invention provides a compound of formula I:

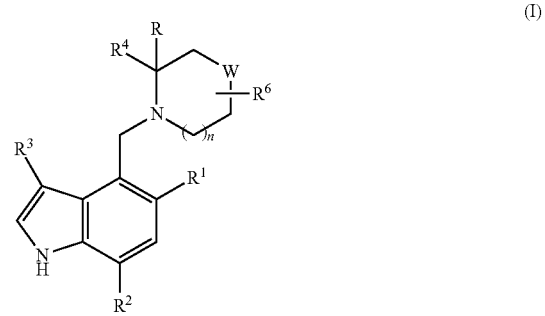

a method for manufacturing the compounds of the invention, and its therapeutic uses. The present invention further provides a combination of pharmacologically active agents and a pharmaceutical composition.

18 Claims, No Drawings

(56) References Cited

OTHER PUBLICATIONS

CAS Registry No. 1574295-31-0, Chemical or Trade Name: Methanone, [(2S)-2-(1H-benzimidazol-2-yl)-1-pyrrolidinyl] (1-methyl-1H-indol-4-yl)-, Entry Date: Mar. 26, 2014.
CAS Registry No. 1452992-50-5, Chemical or Trade Name: Methanone, (1-methyl-1H-indol-4-yl)[2-(3-phenyl-1,2,4-oxadiazol-5-yl)-1-pyrrolidinyl]-, Entry Date: Sep. 22, 2013.
CAS Registry No. 1423746-15-9, Chemical or Trade Name: Methanone, 1H-indol-4-yl[2-(6,7,8,9-tetrahydro-5H-1,2,4-triazolo[4,3-a]azepin-3-yl)-1-pyrrolidinyl]-, Entry Date: Mar. 14, 2013.
CAS Registry No. 1413511-81-5, Chemical or Trade Name: Methanone, [2-(3-methoxyphenyl)-1-piperidinyl](1-methyl-1H-indol-4-yl)-, Entry Date: Dec. 11, 2012.
CAS Registry No. 1394609-85-8, Chemical or Trade Name: Methanone, [2-(6-methyl-1H-benzimidazol-2-yl)-1-pyrrolidinyl](1-methyl-1H-indol-4-yl)-, Entry Date: Sep. 18, 2012.
CAS Registry No. 1384593-93-4, Chemical or Trade Name: Methanone, [2-[5-(1-methylethyl)-1,2,4-oxadiazol-3-yl]-1-pyrrolidinyl](1-methyl-1H-indol-4-yl)-, Entry Date: Jul. 27, 2012.
CAS Registry No. 1381075-33-7, Chemical or Trade Name: Index Name Not Yet Assigned, Entry Date: Jul. 4, 2012.
CAS Registry No. 1381073-50-2, Chemical or Trade Name: 1H-Indole, 4-[[2-[6-(1H-imidazol-1-yl)-2-pyridinyl]-1-pyrrolidinyl]methyl]-, Entry Date: Jul. 4, 2012.
CAS Registry No. 1376298-12-2, Chemical or Trade Name: Methanone, [2-(5-cyclopropyl-1,2,4-oxadiazol-3-yl)-1-pyrrolidinyl](1-methyl-1H-indol-4-yl)-, Entry Date: Jun. 7, 2012.
CAS Registry No. 1341030-47-4, Chemical or Trade Name: Methanone, [2-[4-(cyclopropylmethyl)-4H-1,2,4-triazol-3-yl]-1-piperidinyl]-1H-indol-4-yl-, Entry Date: Nov. 4, 2011.
CAS Registry No. 1340777-96-9, Chemical or Trade Name: Methanone, 1H-indol-4-yl[2-(3-methyl-1,2,4-oxadiazol-5-yl)-1-piperidinyl]-, Entry Date: Nov. 4, 2011.
CAS Registry No. 1340699-81-1, Chemical or Trade Name: 1H-Indole, 4-[[2-[4-(cyclopropylmethyl)-4H-1,2,4-triazol-3-yl]-1-piperidinyl]methyl]-, Entry Date: Nov. 4, 2011.
CAS Registry No. 1311913-08-2, Chemical or Trade Name: Methanone, (1-methyl-1H-indol-4-yl)[2-(2-pyridinyl)-1-pyrrolidinyl]-, Entry Date: Jul. 7, 2011.
CAS Registry No. 1286419-78-0, Chemical or Trade Name: Methanone, [2-[3-(3-chlorophenyl)-1,2,4-oxadiazol-5-yl]-1-pyrrolidinyl]-1H-indol-4-yl-, Entry Date: Apr. 27, 2011.
CAS Registry No. 1183767-98-7, Chemical or Trade Name: Methanone, 1N-indol-4-yl[2-(3-thienyl)-1-pyrrolidinyl]-, Entry Date: Sep. 13, 2009.
CAS Registry No. 1183406-26-9, Chemical or Trade Name: Methanone, 1H-indol-4-yl[2-(1H-pyrrol-2-yl)-1-pyrrolidinyl]-, Entry Date: Sep. 13, 2009.
CAS Registry No. 1178662-01-5, Chemical or Trade Name: Methanone, 1H-indol-4-yl[2-(1H-pyrrol-2-yl)-1-pyrrolidinyl]-, Entry Date: Sep. 1, 2009.
CAS registry No. 1445695-82-8, Chemical or Trade Name: 3-Pyrrolidinecarbonitrile, 4-hydroxy-1-[6-methyl-2-[(2S)-1[(1-methyl-1H-indol-4-yl)carbonyl]-2-piperidinyl]pyrazolo[1,5-a]pyrimidin-5-yl]-, (3S,4R)-, Entry Date: Jul. 19, 2013.
CAS Registry No. 1353630-94-0, Chemical or Trade Name: Index Name Not Yet Assigned, Entry Date: Jan. 18, 2012.
CAS Registry No. 1353627-43-6, Chemical or Trade Name: Methanone, [(2S)-2-[5-[(3S)-3-amino-1-pyrrolidinyl]-6-,methylpyrazolo[1,5-a]pyrimidin-2-yl]-1-piperidinyl](1-methyl-1H-indol-4-yl)-, Entry Date: Jan. 18, 2012.
CAS Registry No. 1231730-72-5, Chemical or Trade Name: 3-Piperidinecarboxamide, N-[3-(1,1-dimethylethyl) phenyl]-1-(1H-indol-4-ylcarbonyl)-2-phenyl-, (2R,3S)-rel-, Entry Date: Jul. 13, 2010.
CAS Registry No. 905999-50-0, Chemical or Trade Name: 1H-Indazole-6-carbonitrile, 3-[4-[[2-(2-benzothiazolyl)-1-pyrrolidinyl]methyl]-1H-indol-2-yl]-, 2,2,2-trifluoroacetate (1:1), Entry Date: Sep. 7, 2006.
CAS Registry No. 905999-30-6, Chemical or Trade Name: 1H-Indazole-6-carbonitrile, 3-[4-[[2-(1H-indol-2-yl)-1-pyrrolidinyl]methyl]-1H-indol-2-yl]-, 2,2,2-trifluoroacetate (1:1), Entry Date: Sep. 7, 2006.
CAS Registry No. 905999-22-6, Chemical or Trade Name: 1H-Indazole-6-carbonitrile, 3-[4-[[2-(1-methyl-1H-imidazol-2-yl)-1-piperidinyl]methyl]-1H-indol-2-yl]-, 2,2,2-trifluoroacetate (1:1), Entry Date: Sep. 7, 2006.
CAS Registry No. 905999-16-8, Chemical or Trade Name: 1H-Indazole-6-carbonitrile, 3-[4-[[2-(2,5-dihydro-5-oxo-1H-1,2,4-triazol-3-yl)-1-pyrrolidinyl]methyl]-1H-indol-2-yl]-, 2,2,2-trifluoroacetate (1:1), Entry Date: Sep. 7, 2006.
CAS Registry No. 905999-14-6, Chemical or Trade Name: 1H-Indazole-6-carbonitrile, 3-[4-[[2-(4-methyl-1,2,5-oxadiazol-3-yl)-1-pyrrolidinyl]methyl]-1H-indol-2-yl]- 2,2,2-trifluoroacetate (1:1), Entry Date: Sep. 7, 2006.
CAS Registry No. 905997-74-2, Chemical or Trade Name: 1H-Indazole-6-carbonitrile, 3-[4-[[2-(2-benzothiazolyl)-1-pyrrolidinyl]methyl]-1H-indol-2-yl]-, Entry Date: Sep. 7, 2006.
CAS Registry No. 905997-55-9, Chemical or Trade Name: 1H-Indazole-6-carbonitrile, 3-[4-[[2-(1H-indol-2-yl)-1-pyrrolidinyl]methyl]-1H-indol-2-yl]-, Entry Date: Sep. 7, 2006.
CAS Registry No. 905997-47-9, Chemical or Trade Name: 1H-Indazole-6-carbonitrile, 3-[4-[[2-(1-methyl-1H-imidazol-2-yl)-1-piperidinyl]methyl]-1H-indol-2-yl]-, Entry Date: Sep. 7, 2006.
CAS Registry No. 905997-41-3, Chemical or Trade Name: 1H-Indazole-6-carbonitrile, 3-[4-[[2-(2,5-dihydro-5-oxo-1H-1,2,4-triazol-3-yl)-1-pyrrolidinyl]methyl]-1H-indol-2-yl]-, Entry Date: Sep. 7, 2006.
CAS Registry No. 905997-39-9, Chemical or Trade Name: 1H-Indazole-6-carbonitrile, 3-[4-[[2-(4-methyl-1,2,5-oxadiazol-3-yl)-1-pyrrolidinyl]methyl]-1H-indol-2-yl]-, Entry Date: Sep. 7, 2006.
Le, et al., "Profiling the Enzymatic Properties and Inhibition of Human Complement Factor B", Journal of Biological Chemistry, 28(48):34809-34819, 2007.
Ruiz_Gomez, et al., "Structure—Activity Relationships for Suibstrate-Based Inhibitors of Human Complement Factor B", Journal of Medicinal Chemistry, vol. 52, pp. 6042-6052, 2009.

PIPERIDINYL-INDOLE DERIVATIVES COMPLEMENT FACTOR B INHIBITORS AND USES THEREOF

This application is a Divisional of U.S. patent application Ser. No. 14/904,694 filed on Jan. 12, 2016; which is a U.S. National Phase filing of International Application No. PCT/US2014/046515 filed Jul. 14, 2014, which claims priority to U.S. Application Nos. 61/846,355 filed Jul. 15, 2013 and 61/977,028 filed Apr. 8, 2014, the contents of which are incorporated herein by reference in their entirety.

FIELD OF THE INVENTION

The invention relates to the inhibition of the complement alternative pathway and particularly to inhibition of Factor B, in patients suffering from conditions and diseases associated with complement alternative pathway activation such as age-related macular degeneration, diabetic retinopathy and related ophthalmic diseases.

BACKGROUND OF THE INVENTION

The complement system is a crucial component of the innate immunity system and comprises a group of proteins that are normally present in an inactive state. These proteins are organized in three activation pathways: the classical, the lectin, and the alternative pathways (V. M. Holers, In Clinical Immunology: Principles and Practice, ed. R. R. Rich, Mosby Press; 1996, 363-391). Molecules from microorganisms, antibodies or cellular components can activate these pathways resulting in the formation of protease complexes known as the C3-convertase and the C5-convertase. The classical pathway is a calcium/magnesium-dependent cascade, which is normally activated by the formation of antigen-antibody complexes. It can also be activated in an antibody-independent manner by the binding of C-reactive protein complexed to ligand and by many pathogens including gram-negative bacteria. The alternative pathway is a magnesium-dependent cascade which is activated by deposition and activation of C3 on certain susceptible surfaces (e.g., cell wall polysaccharides of yeast and bacteria, and certain biopolymer materials).

Factor B may be a suitable target for the inhibition of this amplification of the complement pathways because its plasma concentration in humans is typically about 200 μg/mL (or about 2 μM), and it has been shown to be a critical enzyme for activation of the alternative complement pathway (P. H. Lesavre and H. J. Müller-Eberhard. J. Exp. Med., 1978; 148: 1498-1510; J. E. Volanakis et al., New Eng. J. Med., 1985; 312:395-401).

Macular degeneration is a clinical term that is used to describe a family of diseases that are characterized by a progressive loss of central vision associated with abnormalities of Bruch's membrane, the choroid, the neural retina and/or the retinal pigment epithelium. In the center of the retina is the macula lutea, which is about ⅓ to ½ cm in diameter. The macula provides detailed vision, particularly in the center (the fovea), because the cones are higher in density and because of the high ratio of ganglion cells to photoreceptor cells. Blood vessels, ganglion cells, inner nuclear layer and cells, and the plexiform layers are all displaced to the side (rather than resting above the photoreceptor cells), thereby allowing light a more direct path to the cones. Under the retina is the choroid, a part of the uveal tract, and the retinal pigmented epithelium (RPE), which is between the neural retina and the choroid. The choroidal blood vessels provide nutrition to the retina and its visual cells.

Age-related macular degeneration (AMD), the most prevalent form of macular degeneration, is associated with progressive loss of visual acuity in the central portion of the visual field, changes in color vision, and abnormal dark adaptation and sensitivity. Two principal clinical manifestations of AMD have been described as the dry, or atrophic, form and the neovascular, or exudative, form. The dry form is associated with atrophic cell death of the central retina or macula, which is required for fine vision used for activities such as reading, driving or recognizing faces. About 10-20% of these AMD patients progress to the second form of AMD, known as neovascular AMD (also referred to as wet AMD).

Neovascular AMD is characterized by the abnormal growth of blood vessels under the macula and vascular leakage, resulting in displacement of the retina, hemorrhage and scarring. This results in a deterioration of sight over a period of weeks to years. Neovascular AMD cases originate from Intermediate or advanced dry AMD. The neovascular form accounts for 85% of legal blindness due to AMD. In neovascular AMD, as the abnormal blood vessels leak fluid and blood, scar tissue is formed that destroys the central retina.

The new blood vessels in neovascular AMD are usually derived from the choroid and are referred to as choroidal neovascularizaton (CNV). The pathogenesis of new choroidal vessels is poorly understood, but such factors as inflammation, ischemia, and local production of angiogenic factors are thought to be important. A published study suggests that CNV is caused by complement activation in a mouse laser model (Bora P. S., J. Immunol. 2005; 174; 491-497).

Human genetic evidence implicates the involvement of the complement system, particularly the alternative pathway, in the pathogenesis of Age-related Macular Degeneration (AMD). Significant associations have been found between AMD and polymorphisms in complement factor H (CFH) (Edwards A O, et al. Complement factor H polymorphism and age-related macular degeneration. Science. 2005 Apr. 15; 308(5720):421-4; Hageman G S, et al A common haplotype in the complement regulatory gene factor H (HF1/CFH) predisposes individuals to age-related macular degeneration. Proc Natl Acad Sci USA. 2005 May 17; 102(20):7227-32; Haines J L, et al. Complement factor H variant increases the risk of age-related macular degeneration. Science. 2005 Apr. 15; 308(5720):419-21; Klein R J, et al Complement factor H polymorphism in age-related macular degeneration. Science. 2005 Apr. 15; 308(5720):385-9; Lau L I, et al. Association of the Y402H polymorphism in complement factor H gene and neovascular age-related macular degeneration in Chinese patients. Invest Ophthalmol Vis Sci. 2006 August; 47(8):3242-6; Simonelli F, et al. Polymorphism p.402Y>H in the complement factor H protein is a risk factor for age related macular degeneration in an Italian population. Br J Ophthalmol. 2006 September; 90(9):1142-5; and Zareparsi S, et al Strong association of the Y402H variant in complement factor H at 1q32 with susceptibility to age-related macular degeneration. Am J Hum Genet. 2005 July; 77(1):149-53.), complement factor B (CFB) and complement C2 (Gold B, et al. Variation in factor B (BF) and complement component 2 (C2) genes is associated with age-related macular degeneration. Nat Genet. 2006 April; 38(4):458-62 and Jakobsdottir J, et al. C2 and CFB genes in age-related maculopathy and joint action with CFH and LOC387715 genes. PLoS One. 2008 May 21; 3(5):e2199), and most recently in complement C3 (Despriet D D, et al Complement component C3 and risk of age-related macular degeneration. Ophthalmology. 2009 March; 116(3):474-480.e2; Maller J B, et al Variation in complement factor 3 is associated with risk of age-related macular degeneration. Nat Genet. 2007 October; 39(10):1200-1 and Park K H, et al Complement component 3 (C3) haplotypes and risk of advanced age-related macular degeneration. Invest Ophthalmol Vis Sci. 2009 July; 50(7):3386-93. Epub 2009 Feb. 21.). Taken together, the genetic variations in the alternative pathway components CFH, CFB, and C3 can predict clinical outcome in nearly 80% of cases.

Currently there is no proven medical therapy for dry AMD and many patients with neovascular AMD become legally blind despite current therapy with anti-VEGF agents such as Lucentis. Thus, it would be desirable to provide therapeutic agents for the treatment or prevention of complement mediated diseases and particularly for the treatment of AMD.

SUMMARY OF THE INVENTION

The present invention provides compounds that modulate, and preferably inhibit, activation of the alternative complement pathway. In certain embodiments, the present invention provides compounds that modulate, and preferably inhibit, Factor B activity and/or Factor B mediated complement pathway activation. Such Factor B modulators are preferably high affinity Factor B inhibitors that inhibit the catalytic activity of complement Factor B, such as primate Factor B and particularly human Factor B.

The compounds of the present invention inhibit or suppress the amplification of the complement system caused by C3 activation irrespective of the initial mechanism of activation (including for example activation of the classical, lectin or alternative pathways).

Various embodiments of the invention are described herein. It will be recognized that features specified in each embodiment may be combined with other specified features to provide further embodiments.

Within certain aspects, Factor B modulators provided herein are compounds of Formula I and salts and tautomers thereof:

In another embodiment, the invention provides a pharmaceutical composition comprising a therapeutically effective amount of a compound according to the definition of formula (I) or subformulae thereof and one or more pharmaceutically acceptable carriers.

In another embodiment, the invention provides a combination, in particular a pharmaceutical combination, comprising a therapeutically effective amount of the compound according to the definition of formula (I) or subformulae thereof and one or more additional therapeutically active agents.

The invention further provides methods of treating or preventing complement mediated diseases, the method comprising the steps of identifying a patient in need of complement modulation therapy and administering a compound of Formula (I) or a subformulae thereof. Complement mediated diseases include ophthalmic diseases (including early or neovascular age-related macular degeneration and geographic atrophy), autoimmune diseases (including arthritis, rheumatoid arthritis), Respiratory diseases, cardiovascular diseases.

Other aspects of the invention are discussed infra.

DETAILED DESCRIPTION OF THE INVENTION

As noted above, the present invention provides compounds that modulate Factor B activation and/or Factor B-mediated signal transduction of the complement system. Such compounds may be used in vitro or in vivo to modulate (preferably inhibit) Factor B activity in a variety of contexts.

In a first embodiment, the invention provides compounds of Formula I and salts and tautomers thereof, which modulate the alternative pathway of the complement system. Compounds of Formula I are represented by the structure:

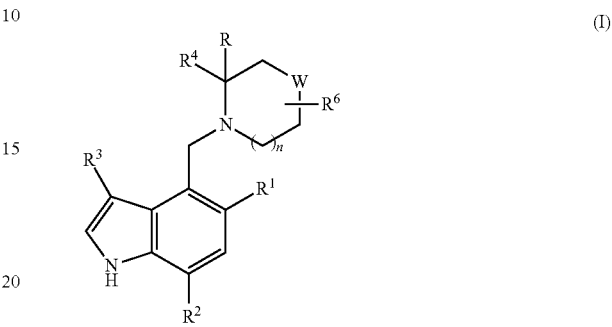

(I)

Wherein
n is 0, 1 or 2;
R is hydrogen, $C_1$-$C_4$alkyl, or hydroxy$C_1$-$C_4$alkyl;
$R^1$ is halogen, hydroxy, $C_1$-$C_6$alkyl, $C_2$-$C_6$alkenyl, $C_3$-$C_6$cycloalkyl, $C_1$-$C_6$alkoxy, halo$C_1$-$C_6$alkyl, hydroxy$C_1$-$C_6$alkyl, amino$C_1$-$C_6$alkyl, $C_1$-$C_6$alkoxy$C_1$-$C_6$alkyl, $C_1$-$C_6$alkoxy$C_1$-$C_6$alkoxy, $C_3$-$C_6$cycloalkyl$C_1$-$C_6$alkoxy, halo$C_1$-$C_6$alkoxy, —S(O)$_p$$C_1$-$C_6$alkyl, —CH$_2$NHC(O)$C_1$-$C_4$alkyl or —OCH$_2$C(O)$R^7$,
p is 0, 1, or 2;
$R^2$ is $C_1$-$C_6$alkyl, $C_1$-$C_6$alkoxy, hydroxy$C_1$-$C_6$alkyl or halogen;
$R^3$ is hydrogen, halogen, cyano, $C_1$-$C_4$alkyl, halo$C_1$-$C_4$alkyl, —CH$_2$C(O)$R^7$, phenyl or 5 or 6 member heteroaryl having 1, 2 or 3 ring heteroatoms independently selected from N, O or S, wherein the phenyl or heteroaryl is optionally substituted with 0, 1, or 2 $C_1$-$C_4$alkyl groups, and wherein alkyl and haloalkyl optionally substituted with 0 or 1 hydroxy;
$R^4$ is phenyl, naphthyl or heteroaryl, where the heteroaryl is a five or six member heteroaryl having 1, 2 or 3 ring heteroatoms independently selected from N, O or S, and where the phenyl or heteroaryl is optionally substituted by $R^5$ and further substituted by 0 or 1 substituents selected from halogen, $C_1$-$C_4$alkyl, $C_1$-$C_4$alkoxy, hydroxy$C_1$-$C_4$alkyl, hydroxy, and cyanomethyl;
$R^5$ is —C(O)$R^8$, —CH$_2$C(O)$R^8$, $R^9$, —C(O)NHSO$_2$$C_1$-$C_4$alkyl, —SO$_2$NHC(O)$C_1$-$C_4$alkyl, —SO$_2$N(H)$_m$($C_1$-$C_4$alkyl)$_{2-m}$, —SO$_2$$C_1$-$C_4$alkyl, cyano, halogen, hydroxy$C_1$-$C_4$alkyl and 5 member heteroaryl having 1-4 ring nitrogen atoms and 0 or 1 ring sulfur or oxygen atoms;
m is 0, 1, or 2;
W is O or C($R^6$)$_2$;
$R^6$ is independently selected at each occurrence from the group consisting of hydrogen, hydroxy, amino, mono- and di-$C_1$-$C_4$alkylamino, $C_1$-$C_4$alkyl, hydroxy$C_1$-$C_4$alkyl, cyano$C_1$-$C_4$alkyl or $C_1$-$C_4$alkoxy; or
C($R^6$)$_2$, taken in combination, form a spirocyclic carbocycle having 3 to 6 ring atoms;
$R^7$ is hydroxy, $C_1$-$C_4$alkoxy, amino or mono- and di-$C_1$-$C_4$alkylamino;
$R^8$ is hydroxy, $C_1$-$C_4$alkoxy, amino or a 5 to 7 member saturated heterocycle having 1, 2, or 3 ring heteroatoms independently selected from N, O or S; or $R^8$ is mono- and di-$C_1$-$C_4$alkylamino which is unsubstituted or substituted with halogen, hydroxy or $C_1$-$C_4$alkyl; and $R^9$ is a 5 membered heteroaryl having 1 to 4 ring nitrogen atoms and 0 or 1 ring oxygen or sulfur atoms, which heterocycle is optionally substituted by 0 to 2 $C_1$-$C_4$alkyl groups.

In a second embodiment, the invention provides compounds, salts thereof and tautomers thereof of the first embodiment, in which n is 0 or 1. In certain compounds of the second embodiment, n is 1.

In a third embodiment, the invention provides compounds, salts thereof and tautomers thereof of the first or second embodiment in which W is $CHR^6$ or $C(CH_3)R^6$.

In a fourth embodiment, the invention provides compounds, salts thereof and tautomers thereof of any one of embodiments 1 to 3 in which $R^1$ is hydrogen, $C_1$-$C_4$alkyl, $C_1$-$C_4$alkoxy, or cyclopropyl.

In a fifth embodiment, the invention provides compounds, salts thereof and tautomers thereof of any one of embodiments 1 to 4 in which $R^2$ is $C_1$-$C_4$alkyl. In certain compounds of the fifth embodiment, $R^2$ is methyl.

In a sixth embodiment, the invention provides compounds, salts thereof and tautomers thereof of any one of embodiments 1 to 5 in which $R^3$ is hydrogen, halogen or $C_1$-$C_4$alkyl. In certain compounds of the sixth embodiment, $R^3$ is hydrogen or $R^3$ is chloro or bromo or $R^3$ is methyl. In certain other compounds of the sixth embodiment, $R^3$ is hydrogen.

In a seventh embodiment, the invention provides compounds, salts thereof and tautomers thereof of any one of embodiments 1 to 6 in which $R^3$ is hydrogen.

In an eighth embodiment, the invention provides compounds, salts thereof and tautomers thereof of any one of embodiments 1 to 7 in which the compound is represented by Formula (IIa) or (IIb):

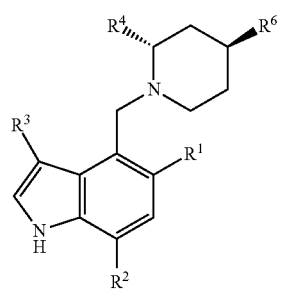
(IIa)

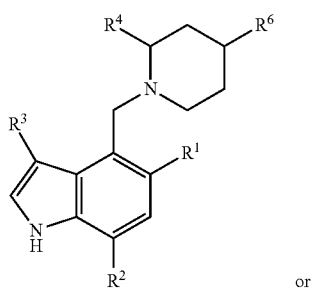
or
(IIb)

Certain preferred compounds of the eighth embodiment include compounds represented by Formula (IIc) (IId) or (IIe):

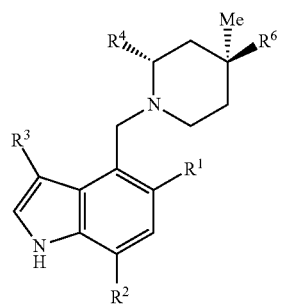
(IIc)

or

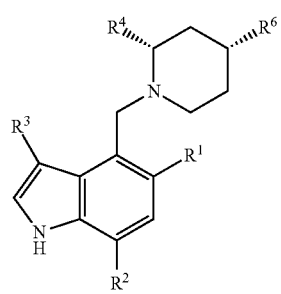
(IId)

or

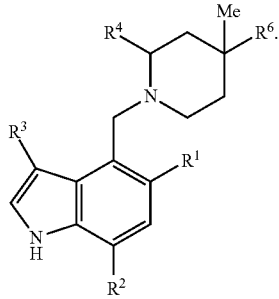
(IIe)

In a ninth embodiment, the invention provides compounds, salts thereof and tautomers thereof of any one of embodiments 1 to 8 in which the compound is represented by Formula (IIIa) or (IIIb):

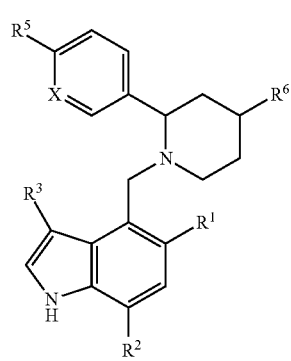
(IIIa)

or (IIIb)

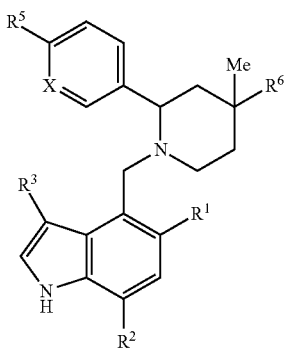

Wherein X is N or CH.

Certain preferred compounds of the ninth embodiment include compounds represented by Formula (IIIc), (IIId) or (IIIe):

(IIIc)

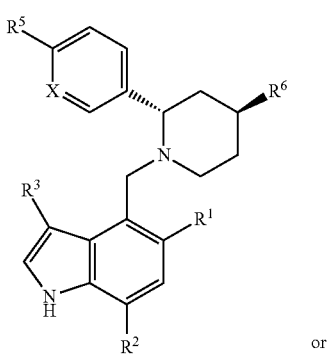

or (IIId)

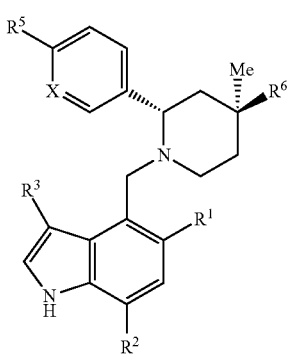

or (IIIe)

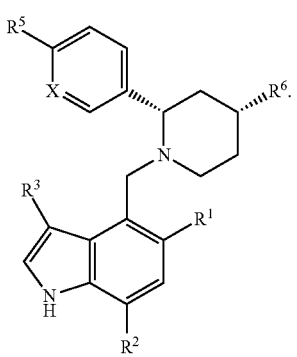

In a tenth embodiment, the invention provides compounds, salts thereof and tautomers thereof of any one of embodiments 1 to 8 in which $R^4$ is pyridin-3-yl which is substituted para to the piperidine ring with $R^5$.

In an eleventh embodiment, the invention provides compounds, salts thereof and tautomers thereof of any one of embodiments 1 to 8 in which $R^4$ is phenyl substituted para to the piperidine ring with $R^5$ and optionally substituted with fluoro, methoxy, hydroxymethyl or hydroxy.

In a twelfth embodiment, the invention provides compounds, salts thereof and tautomers thereof of any one of embodiments 1 to 8 in which $R^4$ is phenyl substituted para to the piperidine ring with $R^5$.

In a thirteenth embodiment, the invention provides compounds, salts thereof and tautomers thereof of any one of embodiments 1 to 8 in which Formula (IVa) or (IVb):

(IVa)

(IVb)

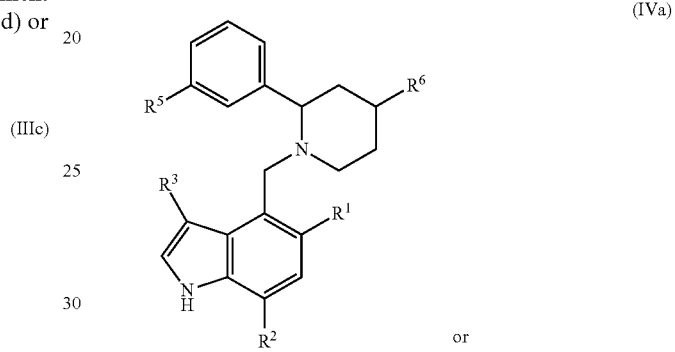

Certain preferred compounds of the thirteenth embodiment include compounds represented by Formula (IVc), (IVd) or (IVe):

(IVc)

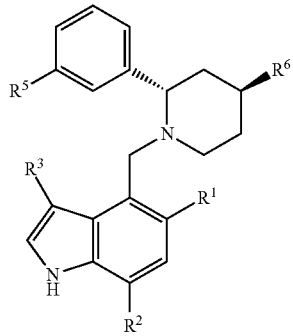

or

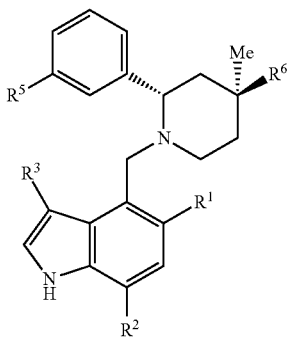

(IVd)

or

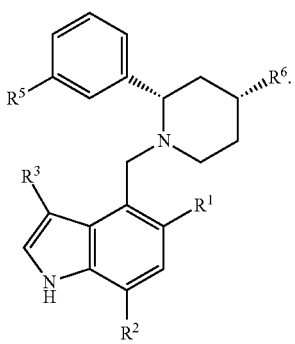

(IVe)

In a fourteenth embodiment, the invention provides compounds, salts thereof and tautomers thereof of any one of embodiments 1 to 13 in which $R^5$ is $CO_2H$, $CO_2NH_2$, $SO_2NH_2$ or tetrazolyl.

In a fifteenth embodiment, the invention provides compounds, salts thereof and tautomers thereof of embodiment 1 in which compound is selected from the group consisting of:

1-((5,7-dimethyl-1H-indol-4-yl)methyl)-2-phenylpiperidin-4-ol;
4-((4-methoxy-2-phenylpiperidin-1-yl)methyl)-5,7-dimethyl-1H-indole;
5,7-dimethyl-4-((2-phenylpiperidin-1-yl)methyl)-1H-indole;
1-((5,7-dimethyl-1H-indol-4-yl)methyl)-2-phenyl-piperidin-4-yl)methanol;
4-(1-((5,7-dimethyl-1H-indol-4-yl)methyl)piperidin-2-yl)benzenesulfonamide;
3-(1-((5,7-dimethyl-1H-indol-4-yl)methyl)piperidin-2-yl)benzenesulfonamide;
4-(1-((5,7-dimethyl-1H-indol-4-yl)methyl)piperidin-2-yl)-N-methylbenzenesulfonamide;
3-(1-((5,7-dimethyl-1H-indol-4-yl)methyl)piperidin-2-yl)-N-methylbenzenesulfonamide;
4-((2-(4-fluorophenyl)-4-methoxypiperidin-1-yl)methyl)-5,7-dimethyl-1H-indole;
(1-((5,7-dimethyl-1H-indol-4-yl)methyl)-2-phenylpiperidin-2-yl)methanol;
(4-(1-((5,7-dimethyl-1H-indol-4-yl)methyl)piperidin-2-yl)phenyl)methanol;
5,7-dimethyl-4-((2-(4-(methylsulfonyl)phenyl)piperidin-1-yl)methyl)-1H-indole;
4-((2-(4-(2H-tetrazol-5-yl)phenyl)piperidin-1-yl)methyl)-5,7-dimethyl-1H-indole;
1-((5,7-dimethyl-1H-indol-4-yl)methyl)-2-phenylpiperidin-4-amine;
4-(1-((5,7-dimethyl-1H-indol-4-yl)methyl)piperidin-2-yl)benzamide;
4-(1-((5-chloro-7-methyl-1H-indol-4-yl)methyl)piperidin-2-yl)benzamide;
4-(1-((5,7-dimethyl-1H-indol-4-yl)methyl)-4-methoxypiperidin-2-yl)benzamide;
4-(4-methoxy-1-((5-methoxy-7-methyl-1H-indol-4-yl)methyl)-4-methylpiperidin-2-yl)benzamide;
4-(1-((5,7-dimethyl-1H-indol-4-yl)methyl)-4-hydroxypiperidin-2-yl)benzoic acid;
4-(1-((5-chloro-7-methyl-1H-indol-4-yl)methyl)piperidin-2-yl)benzoic acid;
methyl 4-(1-((5,7-dimethyl-1H-indol-4-yl)methyl)-4-methoxypiperidin-2-yl)benzoate;
4-(1-((5-cyclopropyl-7-methyl-1H-indol-4-yl)methyl)piperidin-2-yl)-2-fluorobenzoic acid;
4-(1-((5-cyclopropyl-7-methyl-1H-indol-4-yl)methyl)pyrrolidin-2-yl)benzoic acid;
5-(1-((5-cyclopropyl-7-methyl-1H-indol-4-yl)methyl)piperidin-2-yl)picolinic acid;
4-(1-((5-cyclopropyl-7-methyl-1H-indol-4-yl)methyl)piperidin-2-yl)-3-methoxybenzoic acid;
4-(1-((5-methoxy-7-methyl-1H-indol-4-yl)methyl)piperidin-2-yl)benzoic acid;
5-methoxy-7-methyl-4-((2-(pyridin-4-yl)piperidin-1-yl)methyl)-1H-indole;
5-methoxy-7-methyl-4-((2-(pyridin-3-yl)piperidin-1-yl)methyl)-1H-indole;
3-fluoro-4-(1-((5-methoxy-7-methyl-1H-indol-4-yl)methyl)piperidin-2-yl)benzoic acid;
4-(4-((5-methoxy-7-methyl-1H-indol-4-yl)methyl)morpholin-3-yl)benzoic acid;
6-(1-((5-methoxy-7-methyl-1H-indol-4-yl)methyl)piperidin-2-yl)nicotinic acid;
4-(1-((5-methoxy-7-methyl-1H-indol-4-yl)methyl)-4-propoxypiperidin-2-yl)benzoic acid;
4-(4-hydroxy-1-((5-methoxy-7-methyl-1H-indol-4-yl)methyl)piperidin-2-yl)benzoic acid;
4-(1-((5-methoxy-7-methyl-1H-indol-4-yl)methyl)piperidin-2-yl)-3-methylbenzoic acid;
4-(1-((5-methoxy-7-methyl-1H-indol-4-yl)methyl)-5-methylpiperidin-2-yl)benzoic acid;
4-(1-((5-methoxy-7-methyl-1H-indol-4-yl)methyl)-4-ethylpiperidin-2-yl)benzoic acid;
2-(4-(1-((5-methoxy-7-methyl-1H-indol-4-yl)methyl)piperidin-2-yl)phenyl)acetic acid;
2-(3-(1-((5-methoxy-7-methyl-1H-indol-4-yl)methyl)piperidin-2-yl)phenyl)acetic acid;
5-(1-((5-cyclopropyl-7-methyl-1H-indol-4-yl)methyl)-4-methoxypiperidin-2-yl)picolinic acid;
2-(1-((5-methoxy-7-methyl-1H-indol-4-yl)methyl)piperidin-2-yl)thiazole-4-carboxylic acid;
2-(1-((5-methoxy-7-methyl-1H-indol-4-yl)methyl)piperidin-2-yl)-4-methylthiazole-5-carboxylic acid;
3-(1-((5,7-dimethyl-1H-indol-4-yl)methyl)piperidin-2-yl)benzoic acid;
4-(1-((5-methoxy-7-methyl-1H-indol-4-yl)methyl)azepan-2-yl)benzoic acid;
4-((2-(4-(1H-pyrazol-4-yl)phenyl)piperidin-1-yl)methyl)-5-methoxy-7-methyl-1H-indole;
4-((2-(4-(1H-pyrazol-3-yl)phenyl)piperidin-1-yl)methyl)-5-methoxy-7-methyl-1H-indole;
4-(1-((5-methoxy-7-methyl-1H-indol-4-yl)methyl)piperidin-2-yl)-1-naphthoic acid;
1-(2,2,2-trifluoro-1-(5-methoxy-7-methyl-1H-indol-4-yl)ethyl)piperidin-2-yl)benzoic acid;

2-methoxy-4-(1-((5-methoxy-7-methyl-1H-indol-4-yl) methyl)piperidin-2-yl)benzoic acid;
2-(1-((5,7-dimethyl-1H-indol-4-yl)methyl)-2-phenylpiperidin-4-yl)acetonitrile;
4-(1-((5-methoxy-7-methyl-1H-indol-4-yl)methyl)-4-methylpiperidin-2-yl)benzoic acid;
4-(4-methoxy-1-((5-methoxy-7-methyl-1H-indol-4-yl) methyl)piperidin-2-yl)benzoic acid;
5-(4-ethoxy-1-((5-methoxy-7-methyl-1H-indol-4-yl) methyl)piperidin-2-yl)picolinic acid;
4-(1-((5-methoxy-7-methyl-1H-indol-4-yl)methyl)-4,4-dimethylpiperidin-2-yl)benzoic acid;
4-(4-ethoxy-1-((5-methoxy-7-methyl-1H-indol-4-yl) methyl)piperidin-2-yl)benzonitrile;
4-(1-((5,7-dimethyl-1H-indol-4-yl)methyl)piperidin-2-yl) benzoic acid;
4-((4-ethoxy-1-((5-methoxy-7-methyl-1H-indol-4-yl) methyl)piperidin-2-yl)benzoic acid;
4-(1-((5,7-dimethyl-1H-indol-4-yl)methyl)-4-methoxypiperidin-2-yl)benzoic acid;
4-(1-((5,7-dimethyl-1H-indol-4-yl)methyl)-4-ethoxypiperidin-2-yl)benzoic acid;
4-(1-((5,7-dimethyl-1H-indol-4-yl)methyl)-4-ethoxypiperidin-2-yl)benzoic acid;
4-(1-((5-cyclopropyl-7-methyl-1H-indol-4-yl)methyl)-4-methoxypiperidin-2-yl)benzoic acid;
4-(1-((5-cyclopropyl-7-methyl-1H-indol-4-yl)methyl)-4-ethoxypiperidin-2-yl)benzoic acid;
4-(1-((5-cyclopropyl-7-methyl-1H-indol-4-yl)methyl)-4-ethoxypiperidin-2-yl)benzoic acid;
4-(5-methoxy-1-((5-methoxy-7-methyl-1H-indol-4-yl) methyl)piperidin-2-yl)benzoic acid;
4-(5-methoxy-1-((5-methoxy-7-methyl-1H-indol-4-yl) methyl)piperidin-2-yl)benzamide;
4-(5-methoxy-1-((5-methoxy-7-methyl-1H-indol-4-yl) methyl)piperidin-2-yl)benzoic acid;
4-(5-hydroxy-1-((5-methoxy-7-methyl-1H-indol-4-yl) methyl)piperidin-2-yl)benzoic acid;
1-((5,7-dimethyl-1H-indol-4-yl)methyl)-N-methyl-2-phenylpiperidin-4-amine;
(4-(1-((5,7-dimethyl-1H-indol-4-yl)methyl)piperidin-2-yl) phenyl)methanamine;
(4-(4-methoxy-1-((5-methoxy-7-methyl-1H-indol-4-yl) methyl)piperidin-2-yl)phenyl)methanol;
4-((2-(3-(2H-tetrazol-5-yl)phenyl)piperidin-1-yl)methyl)-5, 7-dimethyl-1H-indole;
3-(1-((5,7-dimethyl-1H-indol-4-yl)methyl)piperidin-2-yl) benzamide;
(3-(1-((5,7-dimethyl-1H-indol-4-yl)methyl)piperidin-2-yl) phenyl)methanol;
(4-((2-(4-(1H-tetrazol-5-yl)phenyl)-4-ethoxypiperidin-1-yl) methyl)-5-methoxy-7-methyl-1H-indole;
4-(4-ethoxy-1-((5-methoxy-7-methyl-1H-indol-4-yl) methyl)piperidin-2-yl)-N-(methylsulfonyl)benzamide;
4-(4-methoxy-1-((5-methoxy-7-methyl-1H-indol-4-yl) methyl)piperidin-2-yl)-N-methylbenzamide;
4-(4-methoxy-1-((5-methoxy-7-methyl-1H-indol-4-yl) methyl)piperidin-2-yl)-N,N-dimethylbenzamide;
(4-(4-methoxy-1-((5-methoxy-7-methyl-1H-indol-4-yl) methyl)piperidin-2-yl)phenyl)(morpholino)methanone;
N-(2-hydroxyethyl)-4-(4-methoxy-1-((5-methoxy-7-methyl-1H-indol-4-yl)methyl)piperidin-2-yl)benzamide;
4-(4-methoxy-1-((5-methoxy-7-methyl-1H-indol-4-yl) methyl)piperidin-2-yl)-N-(2-methoxyethyl)benzamide;
N-((4-(1-((5-cyclopropyl-7-methyl-1H-indol-4-yl)methyl) piperidin-2-yl)phenyl)sulfonyl)acetamide;
4-(6-((5-methoxy-7-methyl-1H-indol-4-yl)methyl)-6-azaspiro[2.5]octan-5-yl)benzoic acid;
4-ethyl-1-((5-methoxy-7-methyl-1H-indol-4-yl)methyl)piperidin-2-yl)benzoic acid;
ethyl 4-((2S,4R)-1-((5-methoxy-7-methyl-1H-indol-4-yl) methyl)-4-methylpiperidin-2-yl)benzoate;
ethyl 4-((2S,4S)-4-ethoxy-1-((5-methoxy-7-methyl-1H-indol-4-yl)methyl)piperidin-2-yl)benzoate and
salts, stereoisomers and tautomers thereof.

In a sixteenth embodiment, the invention provides compounds, salts thereof and tautomers thereof of embodiment 1 in which compound is selected from the group consisting of:

(−)-1-((5,7-dimethyl-1H-indol-4-yl)methyl)-2-phenylpiperidin-4-ol (diastereomer-2);
(±)-4-((4-methoxy-2-phenylpiperidin-1-yl)methyl)-5,7-dimethyl-1H-indole (diastereomer-1);
(−)-4-((4-methoxy-2-phenylpiperidin-1-yl)methyl)-5,7-dimethyl-1H-indole (diastereomer-2);
(±)-5,7-dimethyl-4-((2-phenylpiperidin-1-yl)methyl)-1H-indole;
(±)-1-((5,7-dimethyl-1H-indol-4-yl)methyl)-2-phenyl-piperidin-4-yl)methanol (diastereomer-1);
(±)-1-((5,7-dimethyl-1H-indol-4-yl)methyl)-2-phenyl-piperidin-4-yl)methanol (diastereomer-2);
(±)-4-(1-((5,7-dimethyl-1H-indol-4-yl)methyl)piperidin-2-yl)benzenesulfonamide;
(±)-3-(1-((5,7-dimethyl-1H-indol-4-yl)methyl)piperidin-2-yl)benzenesulfonamide;
(±)-4-(1-((5,7-dimethyl-1H-indol-4-yl)methyl)piperidin-2-yl)-N-methylbenzenesulfonamide;
(±)-3-(1-((5,7-dimethyl-1H-indol-4-yl)methyl)piperidin-2-yl)-N-methylbenzenesulfonamide;
(±)-4-((2-(4-fluorophenyl)-4-methoxypiperidin-1-yl) methyl)-5,7-dimethyl-1H-indole;
(±)-(1-((5,7-dimethyl-1H-indol-4-yl)methyl)-2-phenylpiperidin-2-yl)methanol;
(4-(1-((5,7-dimethyl-1H-indol-4-yl)methyl)piperidin-2-yl) phenyl)methanol;
(±)-5,7-dimethyl-4-((2-(4-(methylsulfonyl)phenyl)piperidin-1-yl)methyl)-1H-indole;
(±)-4-((2-(4-(2H-tetrazol-5-yl)phenyl)piperidin-1-yl) methyl)-5,7-dimethyl-1H-indole;
(±)-1-((5,7-dimethyl-1H-indol-4-yl)methyl)-2-phenylpiperidin-4-amine (diastereomer-1);
(±)-1-((5,7-dimethyl-1H-indol-4-yl)methyl)-2-phenylpiperidin-4-amine (diastereomer-2);
(±)-4-(1-((5,7-dimethyl-1H-indol-4-yl)methyl)piperidin-2-yl)benzamide;
(±)-4-(1-((5-chloro-7-methyl-1H-indol-4-yl)methyl)piperidin-2-yl)benzamide;
(±)-4-(rel-(2S,4S)-1-((5,7-dimethyl-1H-indol-4-yl)methyl)-4-methoxypiperidin-2-yl)benzamide;
(±)-4-(4-methoxy-1-((5-methoxy-7-methyl-1H-indol-4-yl) methyl)-4-methylpiperidin-2-yl)benzamide (single diastereomer);
(±)-4-(rel-(2S,4S)-1-((5,7-dimethyl-1H-indol-4-yl)methyl)-4-hydroxypiperidin-2-yl)benzoic acid;
(±)-4-(rel-(2S,4R)-1-((5,7-dimethyl-1H-indol-4-yl)methyl)-4-hydroxypiperidin-2-yl)benzoic acid;
(±)-4-(1-((5-chloro-7-methyl-1H-indol-4-yl)methyl)piperidin-2-yl)benzoic acid;
(±)-methyl 4-(rel-(2S,4S)-1-((5,7-dimethyl-1H-indol-4-yl) methyl)-4-methoxypiperidin-2-yl)benzoate;
(±)-methyl 4-(rel-(2S,4R)-1-((5,7-dimethyl-1H-indol-4-yl) methyl)-4-methoxypiperidin-2-yl)benzoate;

(−)-(S)-4-(1-((5-cyclopropyl-7-methyl-1H-indol-4-yl)
methyl)piperidin-2-yl)-2-fluorobenzoic acid;
(−)-(S)-4-(1-((5-cyclopropyl-7-methyl-1H-indol-4-yl)
methyl)piperidin-2-yl)benzoic acid;
(±)-4-(1-((5-cyclopropyl-7-methyl-1H-indol-4-yl)methyl)
pyrrolidin-2-yl)benzoic acid;
(−)-(S)-5-(1-((5-cyclopropyl-7-methyl-1H-indol-4-yl)
methyl)piperidin-2-yl)picolinic acid;
(−)-(S)-4-(1-((5-cyclopropyl-7-methyl-1H-indol-4-yl)
methyl)piperidin-2-yl)-3-methoxybenzoic acid;
(−)-(S)-4-(1-((5-methoxy-7-methyl-1H-indol-4-yl)methyl)
piperidin-2-yl)benzoic acid;
(±)-5-methoxy-7-methyl-4-((2-(pyridin-4-yl)piperidin-1-yl)
methyl)-1H-indole;
(±)-5-methoxy-7-methyl-4-((2-(pyridin-3-yl)piperidin-1-yl)
methyl)-1H-indole;
(+)-(S)-3-fluoro-4-(1-((5-methoxy-7-methyl-1H-indol-4-yl)
methyl)piperidin-2-yl)benzoic acid;
(−)-(R)-4-(4-((5-methoxy-7-methyl-1H-indol-4-yl)methyl)
morpholin-3-yl)benzoic acid;
(−)-(S)-6-(1-((5-methoxy-7-methyl-1H-indol-4-yl)methyl)
piperidin-2-yl)nicotinic acid;
(−)-4-((2S,4S)-1-((5-methoxy-7-methyl-1H-indol-4-yl)
methyl)-4-propoxypiperidin-2-yl)benzoic acid;
(−)-4-((2S,4S)-4-hydroxy-1-((5-methoxy-7-methyl-1H-indol-4-yl)methyl)piperidin-2-yl)benzoic acid;
(±)-4-(1-((5-methoxy-7-methyl-1H-indol-4-yl)methyl)piperidin-2-yl)-3-methylbenzoic acid;
(±)-4-(1-((5-methoxy-7-methyl-1H-indol-4-yl)methyl)-5-methylpiperidin-2-yl)benzoic acid (single diastereomer);
(±)-4-(rel-(2S,4R)-4-ethyl-1-((5-methoxy-7-methyl-1H-indol-4-yl)methyl)piperidin-2-yl)benzoic acid);
(±)-2-(4-(1-((5-methoxy-7-methyl-1H-indol-4-yl)methyl)
piperidin-2-yl)phenyl)acetic acid;
(±)-2-(3-(1-((5-methoxy-7-methyl-1H-indol-4-yl)methyl)
piperidin-2-yl)phenyl)acetic acid;
(±)-5-(rel-(2S,4S)-1-((5-cyclopropyl-7-methyl-1H-indol-4-yl)methyl)-4-methoxypiperidin-2-yl)picolinic acid;
(±)-2-(1-((5-methoxy-7-methyl-1H-indol-4-yl)methyl)piperidin-2-yl)thiazole-4-carboxylic acid;
(±)-2-(1-((5-methoxy-7-methyl-1H-indol-4-yl)methyl)piperidin-2-yl)-4-methylthiazole-5-carboxylic acid;
(±)-3-(1-((5,7-dimethyl-1H-indol-4-yl)methyl)piperidin-2-yl)benzoic acid;
(±)-4-(1-((5-methoxy-7-methyl-1H-indol-4-yl)methyl)azepan-2-yl)benzoic acid;
(−)-(S)-4-((2-(4-(1H-pyrazol-4-yl)phenyl)piperidin-1-yl)
methyl)-5-methoxy-7-methyl-1H-indole;
(−)-(S)-4-((2-(4-(1H-pyrazol-3-yl)phenyl)piperidin-1-yl)
methyl)-5-methoxy-7-methyl-1H-indole;
(±)-4-(1-((5-methoxy-7-methyl-1H-indol-4-yl)methyl)piperidin-2-yl)-1-naphthoic acid;
4-((2S)-1-(2,2,2-trifluoro-1-(5-methoxy-7-methyl-1H-indol-4-yl)ethyl)piperidin-2-yl)benzoic acid (diastereomer-1);
(±)-2-methoxy-4-(1-((5-methoxy-7-methyl-1H-indol-4-yl)
methyl)piperidin-2-yl)benzoic acid;
(±)-4-(6-((5-methoxy-7-methyl-1H-indol-4-yl)methyl)-6-azaspiro[2.5]octan-5-yl)benzoic acid;
(±)-4-(rel-(2S,4S)-4-ethyl-1-((5-methoxy-7-methyl-1H-indol-4-yl)methyl)piperidin-2-yl)benzoic acid;
(±)-2-(1-((5,7-dimethyl-1H-indol-4-yl)methyl)-2-phenylpiperidin-4-yl)acetonitrile (diastereomer-1);
(+)-4-((2S,4R)-1-((5-methoxy-7-methyl-1H-indol-4-yl)
methyl)-4-methylpiperidin-2-yl)benzoic acid;
(−)-4-((2R,4S)-1-((5-methoxy-7-methyl-1H-indol-4-yl)
methyl)-4-methylpiperidin-2-yl)benzoic acid;
(+)-4-((2R,4R)-4-methoxy-1-((5-methoxy-7-methyl-1H-indol-4-yl)methyl)piperidin-2-yl)benzoic acid;
(−)-4-((2S,4S)-4-methoxy-1-((5-methoxy-7-methyl-1H-indol-4-yl)methyl)piperidin-2-yl)benzoic acid;
(−)-5-(rel-(2S,4S)-4-ethoxy-1-((5-methoxy-7-methyl-1H-indol-4-yl)methyl)piperidin-2-yl)picolinic acid;
(+)-5-(rel-(2S,4S)-4-ethoxy-1-((5-methoxy-7-methyl-1H-indol-4-yl)methyl)piperidin-2-yl)picolinic acid;
(+)-4-(1-((5-methoxy-7-methyl-1H-indol-4-yl)methyl)-4,4-dimethylpiperidin-2-yl)benzoic acid;
(−)-4-(1-((5-methoxy-7-methyl-1H-indol-4-yl)methyl)-4,4-dimethylpiperidin-2-yl)benzoic acid;
(−)-4-(rel-(2S,4S)-4-ethoxy-1-((5-methoxy-7-methyl-1H-indol-4-yl)methyl)piperidin-2-yl)benzonitrile;
(+)-4-(rel-(2S,4S)-4-ethoxy-1-((5-methoxy-7-methyl-1H-indol-4-yl)methyl)piperidin-2-yl)benzamide;
(+)-4-(1-((5,7-dimethyl-1H-indol-4-yl)methyl)piperidin-2-yl)benzoic acid;
(−)-4-(1-((5,7-dimethyl-1H-indol-4-yl)methyl)piperidin-2-yl)benzoic acid;
(+)-4-((2S,4S)-(4-ethoxy-1-((5-methoxy-7-methyl-1H-indol-4-yl)methyl)piperidin-2-yl))benzoic acid;
(−)-4-((2R,4R)-(4-ethoxy-1-((5-methoxy-7-methyl-1H-indol-4-yl)methyl)piperidin-2-yl))benzoic acid;
(+)-4-(rel-(2S,4S)-1-((5,7-dimethyl-1H-indol-4-yl)methyl)-4-methoxypiperidin-2-yl)benzoic acid;
(−)-4-(rel-(2S,4S)-1-((5,7-dimethyl-1H-indol-4-yl)methyl)-4-methoxypiperidin-2-yl)benzoic acid;
(+)-4-(rel-(2S,4S)-1-((5,7-dimethyl-1H-indol-4-yl)methyl)-4-ethoxypiperidin-2-yl)benzoic acid;
(−)-4-(rel-(2S,4S)-1-((5,7-dimethyl-1H-indol-4-yl)methyl)-4-ethoxypiperidin-2-yl)benzoic acid;
(−)-4-(rel-(2S,4S)-1-((5-cyclopropyl-7-methyl-1H-indol-4-yl)methyl)-4-methoxypiperidin-2-yl)benzoic acid;
(+)-4-(rel-(2S,4S)-1-((5-cyclopropyl-7-methyl-1H-indol-4-yl)methyl)-4-methoxypiperidin-2-yl)benzoic acid;
(+)-4-(rel-(2S,4S)-1-((5-cyclopropyl-7-methyl-1H-indol-4-yl)methyl)-4-ethoxypiperidin-2-yl)benzoic acid;
(−)-4-(rel-(2S,4S)-1-((5-cyclopropyl-7-methyl-1H-indol-4-yl)methyl)-4-ethoxypiperidin-2-yl)benzoic acid;
(±)-4-(5-methoxy-1-((5-methoxy-7-methyl-1H-indol-4-yl)
methyl)piperidin-2-yl)benzoic acid (diastereomer-1);
(±)-4-(5-methoxy-1-((5-methoxy-7-methyl-1H-indol-4-yl)
methyl)piperidin-2-yl)benzamide (diastereomer-1);
(±)-4-(5-methoxy-1-((5-methoxy-7-methyl-1H-indol-4-yl)
methyl)piperidin-2-yl)benzoic acid (diastereomer-2);
(±)-4-(5-hydroxy-1-((5-methoxy-7-methyl-1H-indol-4-yl)
methyl)piperidin-2-yl)benzoic acid (diastereomer-1);
(±)-4-(5-hydroxy-1-((5-methoxy-7-methyl-1H-indol-4-yl)
methyl)piperidin-2-yl)benzoic acid (diastereomer-2);
(±)-1-((5,7-dimethyl-1H-indol-4-yl)methyl)-N-methyl-2-phenylpiperidin-4-amine-(diastereomer-1);
(±)-1-((5,7-dimethyl-1H-indol-4-yl)methyl)-N-methyl-2-phenylpiperidin-4-amine (diastereomer-2);
(±)-(4-(1-((5,7-dimethyl-1H-indol-4-yl)methyl)piperidin-2-yl)phenyl)methanamine;
(4-((2S,4S)-4-methoxy-1-((5-methoxy-7-methyl-1H-indol-4-yl)methyl)piperidin-2-yl)phenyl)methanol;
(±)-4-((2-(3-(2H-tetrazol-5-yl)phenyl)piperidin-1-yl)
methyl)-5,7-dimethyl-1H-indole;
(±)-3-(1-((5,7-dimethyl-1H-indol-4-yl)methyl)piperidin-2-yl)benzamide;
(±)-(3-(1-((5,7-dimethyl-1H-indol-4-yl)methyl)piperidin-2-yl)phenyl)methanol;
(±)-(4-(rel-(2S,4S)-(2-(4-(1H-tetrazol-5-yl)phenyl)-4-ethoxypiperidin-1-yl)methyl)-5-methoxy-7-methyl-1H-indole;

(+)-4-((2S,4S)-4-ethoxy-1-((5-methoxy-7-methyl-1H-indol-4-yl)methyl)piperidin-2-yl)-N-(methylsulfonyl)benzamide;

4-((2S,4S)-4-methoxy-1-((5-methoxy-7-methyl-1H-indol-4-yl)methyl)piperidin-2-yl)-N-methylbenzamide;

4-((2S,4S)-4-methoxy-1-((5-methoxy-7-methyl-1H-indol-4-yl)methyl)piperidin-2-yl)-N,N-dimethylbenzamide;

(4-((2S,4S)-4-methoxy-1-((5-methoxy-7-methyl-1H-indol-4-yl)methyl)piperidin-2-yl)phenyl)(morpholino)methanone;

N-(2-hydroxyethyl)-4-((2S,4S)-4-methoxy-1-((5-methoxy-7-methyl-1H-indol-4-yl)methyl)piperidin-2-yl)benzamide;

4-((2S,4S)-4-methoxy-1-((5-methoxy-7-methyl-1H-indol-4-yl)methyl)piperidin-2-yl)-N-(2-methoxyethyl)benzamide;

(±)-N-((4-(1-((5-cyclopropyl-7-methyl-1H-indol-4-yl)methyl)piperidin-2-yl)phenyl)sulfonyl)acetamide;

ethyl 4-((2S,4R)-1-((5-methoxy-7-methyl-1H-indol-4-yl)methyl)-4-methylpiperidin-2-yl)benzoate;

ethyl 4-((2S,4S)-4-ethoxy-1-((5-methoxy-7-methyl-1H-indol-4-yl)methyl)piperidin-2-yl)benzoate and salts, stereoisomers and tautomers thereof.

In another embodiment, pharmaceutical compositions are provided which comprise one or more pharmaceutically acceptable carriers and a therapeutically effective amount of a compound of any one of formulae I, II, III or IV, or a subformulae thereof.

In another embodiment, combinations, in particular pharmaceutical combinations, are provided which comprise a therapeutically effective amount of the compound any one of formulae I, II, III or IV or a subformulae thereof.

In another embodiment, methods of modulating complement alternative pathway activity in a subject are provided which methods comprise administering to the subject a therapeutically effective amount of any one of formulae I, II, III or IV, or a subformulae thereof.

In yet other embodiments, methods of treating a disorder or a disease in a subject mediated by complement activation, in particular mediated by activation of the complement alternative pathway, are provided, which methods comprise administering to the subject a therapeutically effective amount of the compound of any one of formulae I, II, III, IV, or a subformulae thereof.

In another embodiment, methods of treating age related macular degeneration in a subject are provided which methods comprise administering to the subject a therapeutically effective amount of the compound of any one of formulae I, II, III, IV, or a subformulae thereof.

In another aspect, the invention provides for the use of compounds of any one of formulae I, II, III, IV, or a subformulae thereof for use in the preparation of a medicament and more particularly for use in the manufacture of a medicament for the treatment of a disorder or disease in a subject mediated by complement activation or activation of the complement alternative pathway. In certain other aspects, the invention provides for the use of a compound according of any one of formulae I, II, III, IV, or a subformulae thereof in the treatment of age-related macular degeneration.

In one embodiment, the invention provides a combination, in particular a pharmaceutical combination, comprising a therapeutically effective amount of the compound according to the definition of formula (I), (Ia) or subformulae thereof or any one of the specifically disclosed compounds of the invention and one or more therapeutically active agents (preferably selected from those listed infra).

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkylene" refers to divalent alkyl group as defined herein above having 1 to 20 carbon atoms. It comprises 1 to 20 carbon atoms. Unless otherwise provided, alkylene refers to moieties having 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

As used herein, the term "haloalkyl" refers to an alkyl as defined herein, that is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

The term "aryl" refers to an aromatic hydrocarbon group having 6-20 carbon atoms in the ring portion. Typically, aryl is monocyclic, bicyclic or tricyclic aryl having 6-20 carbon atoms.

Furthermore, the term "aryl" as used herein, refers to an aromatic substituent which can be a single aromatic ring, or multiple aromatic rings that are fused together.

Non-limiting examples include phenyl, naphthyl or tetrahydronaphthyl, each of which may optionally be substituted by 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S—, nitro, cyano, carboxy, alkyl-O—C(O)—, carbamoyl, alkyl-S(O)—, sulfonyl, sulfonamido, phenyl, and heterocyclyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

As used herein, the term "heterocyclyl" or "heterocyclo" refers to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

The term "heterocyclyl" further refers to heterocyclic groups as defined herein substituted with 1 to 5 substituents independently selected from the groups consisting of the following:

(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "cycloalkyl" refers to saturated or unsaturated monocyclic, bicyclic or tricyclic hydrocarbon groups of 3-12 carbon atoms. Unless otherwise provided, cycloalkyl refers to cyclic hydrocarbon groups having between 3 and 9 ring carbon atoms or between 3 and 7 ring carbon atoms, each of which can be optionally substituted by one, or two, or three, or more substituents independently selected from the group consisting of alkyl, halo, oxo, hydroxy, alkoxy, alkyl-C(O)—, acylamino, carbamoyl, alkyl-NH—, (alkyl)$_2$N—, thiol, alkyl-S—, nitro, cyano, carboxy, alkyl-O—C(O)—, sulfonyl, sulfonamido, sulfamoyl, and heterocyclyl. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolylcarbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d] thiazolyl, 3-, 5-, or 8-pyrazino[2,3-d]pyridazinyl, 2-, 3-, 5-, or 6-imidazo[2,1-b] thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A heteroaryl group may be substituted with 1 to 5 substituents independently selected from the groups consisting of the following:

(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;

(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "halogen" or "halo" refers to fluoro, chloro, bromo, and iodo.

As used herein, the term "optionally substituted" unless otherwise specified refers to a group that is unsubstituted or is substituted by one or more, typically 1, 2, 3 or 4, suitable non-hydrogen substituents, each of which is independently selected from the group consisting of:
(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. The use of "rel" indicates that the diastereomeric orientation is known but the absolute stereochemistry is not. For example, the moniker "rel-2S,4S", as used herein, indicates the relative stereochemistry at the 2 and 4 positions is either 2S,4S or in the alternative 2R,4R. The absolute stereochemistry has not been determined but the optical rotation and/or chiral chromatography conditions will indicate which isomer is present. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line or retention time on chiral chromatography separation. Certain of the compounds described herein contain one or more asymmetric centers or axes and may thus give rise to enantiomers, diastereomers, and other stereoisomeric forms that may be defined, in terms of absolute stereochemistry, as (R)- or (S)-, or with the (+) or (−) sign. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, benzenesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of formula I in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sufonic acid, benzenesulfonic acid or mono-, di- or tri-$C_1$-$C_4$alkyl substituted benzene sufonic acid addition salt form.

In another aspect, the present invention provides (−)-(S)-4-(1-((5-cyclopropyl-7-methyl-1H-indol-4-yl)methyl)piperidin-2-yl)benzoic acid in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sufonic acid, benzenesulfonic acid or mono-, di- or tri-$C_1$-$C_4$alkyl substituted benzene sufonic acid addition salt form.

In another aspect, the present invention provides (−)-4-((2S,4S)-1-((5-methoxy-7-methyl-1H-indol-4-yl)methyl)-4-propoxypiperidin-2-yl)benzoic acid in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sufonic acid, benzenesulfonic acid or mono-, di- or tri-$C_1$-$C_4$alkyl substituted benzene sufonic acid addition salt form.

In another aspect, the present invention provides (+)-4-((2S,4R)-1-((5-methoxy-7-methyl-1H-indol-4-yl)methyl)-4-methylpiperidin-2-yl)benzoic acid in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sufonic acid, benzenesulfonic acid or mono-, di- or tri-$C_1$-$C_4$alkyl substituted benzene sufonic acid addition salt form.

In another aspect, the present invention provides (−)-4-((2S,4S)-4-methoxy-1-((5-methoxy-7-methyl-1H-indol-4-yl)methyl)piperidin-2-yl)benzoic acid in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sufonic acid, benzenesulfonic acid or mono-, di- or tri-$C_1$-$C_4$alkyl substituted benzene sufonic acid addition salt form.

In another aspect, the present invention provides (−)-5-(rel-(2S,4S)-4-ethoxy-1-((5-methoxy-7-methyl-1H-indol-4-yl)methyl)piperidin-2-yl)picolinic acid in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sufonic acid, benzenesulfonic acid or mono-, di- or tri-$C_1$-$C_4$alkyl substituted benzene sufonic acid addition salt form.

In another aspect, the present invention provides (−)-4-(1-((5-methoxy-7-methyl-1H-indol-4-yl)methyl)-4,4-dimethylpiperidin-2-yl)benzoic acid in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in C₁-C₄alkyl sufonic acid, benzenesulfonic acid or mono-, di- or tri-C₁-C₄alkyl substituted benzene sufonic acid addition salt form.

In another aspect, the present invention provides 4-((2S,4S)-(4-ethoxy-1-((5-methoxy-7-methyl-1H-indol-4-yl) methyl)piperidin-2-yl))benzoic acid ((+)—as TFA salt) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in C₁-C₄alkyl sufonic acid, benzenesulfonic acid or mono-, di- or tri-C₁-C₄alkyl substituted benzene sufonic acid addition salt form.

In another aspect, the present invention provides (−)-4-(rel-(2S,4S)-1-((5,7-dimethyl-1H-indol-4-yl)methyl)-4-methoxypiperidin-2-yl)benzoic acid in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in C₁-C₄alkyl sufonic acid, benzenesulfonic acid or mono-, di- or tri-C₁-C₄alkyl substituted benzene sufonic acid addition salt form.

In another aspect, the present invention provides 4-(rel-(2S,4S)-1-((5,7-dimethyl-1H-indol-4-yl)methyl)-4-ethoxypiperidin-2-yl)benzoic acid ((+)—as TFA salt) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in C₁-C₄alkyl sufonic acid, benzenesulfonic acid or mono-, di- or tri-C₁-C₄alkyl substituted benzene sufonic acid addition salt form.

In another aspect, the present invention provides (−)-4-(rel-(2S,4S)-1-((5-cyclopropyl-7-methyl-1H-indol-4-yl) methyl)-4-methoxypiperidin-2-yl)benzoic acid in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in C₁-C₄alkyl sufonic acid, benzenesulfonic acid or mono-, di- or tri-C₁-C₄alkyl substituted benzene sufonic acid addition salt form.

In another aspect, the present invention provides (+)-4-(rel-(2S,4S)-1-((5-cyclopropyl-7-methyl-1H-indol-4-yl) methyl)-4-ethoxypiperidin-2-yl)benzoic acid in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in C₁-C₄alkyl sufonic acid, benzenesulfonic acid or mono-, di- or tri-C₁-C₄alkyl substituted benzene sufonic acid addition salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}$H, $^{3}$H, $^{11}$C, $^{13}$C, $^{14}$C, $^{15}$N, $^{18}$F, $^{31}$P, $^{32}$P, $^{35}$S, $^{36}$Cl, $^{124}$I, $^{125}$I, respectively. The invention includes various isotopically labeled compounds as defined herein, for example those into which radioactive isotopes, such as $^{3}$H, $^{13}$C, and $^{14}$C, are present. Such isotopically labelled compounds are useful in metabolic studies (with $^{14}$C), reaction kinetic studies (with, for example $^{2}$H or $^{3}$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and salts thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^{2}$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In certain embodiments, selective deuteration of compounds of Formula (I) include deuteration of $R^1$, $R^3$, $R^5$ and/or $R^6$, for example when any of $R^1$, $R^3$, $R^5$ and/or $R^6$ are methyl, methoxy, or ethoxy, the alkyl residue is preferably deuterated, e.g. $CD_3$, $OCD_3$ or $OC_2D_5$. when $R^3$ is alkanoyl, e.g., $C(O)CD_3$.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

The compounds of the present invention may inherently or by design form solvates with solvents (including water). Therefore, it is intended that the invention embrace both solvated and unsolvated forms. The term "solvate" refers to a molecular complex of a compound of the present invention (including salts thereof) with one or more solvent molecules. Such solvent molecules are those commonly used in the pharmaceutical art, which are known to be innocuous to a recipient, e.g., water, ethanol, dimethylsulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder, or a disease or biological process (e.g., tissue regeneration and reproduction) (i) mediated by Factor B, or (ii) associated with Factor B activity, or (iii) characterized by activity (normal or abnormal) of the complement alternative pathway; or (2) reducing or inhibiting the activity of Factor B; or (3) reducing or inhibiting the expression of Factor B; or (4) reducing or inhibiting activation of the complement system and particularly reducing or inhibiting generation of C3a, iC3b, C5a or the membrane attack complex generated by activation of the complement alternative pathway. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Factor B and/or the complement alternative pathway; or at least partially reducing or inhibiting the expression of Factor B and/or the complement alternative pathway. The meaning of the term "a therapeutically effective amount" as illustrated in the above embodiment for Factor B and/or the complement alternative pathway.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis- (Z)- or trans- (E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high performance liquid chromatography (HPLC) or supercritical fluid chromatography (SFC) using a chiral adsorbent.

Furthermore, the compounds of the present invention, including their salts, can also be obtained in the form of their hydrates, or include other solvents used for their crystallization.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-)crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 250° C., including, for example, from approximately −80° C. to approximately 250° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

General Synthetic Aspects

The following Examples serve to illustrate the invention without limiting the scope thereof.

Typically, the compounds of formula (I) can be prepared according to the Schemes provided below.

Compounds such as A-5, wherein PG is a protecting group (preferably Boc or Ts), $R^a$ is halo or alkyl, and $R^b$ is alkoxy, and $G^a$ is hydrogen or fluoro can be prepared by the general method outlined in Scheme 1.

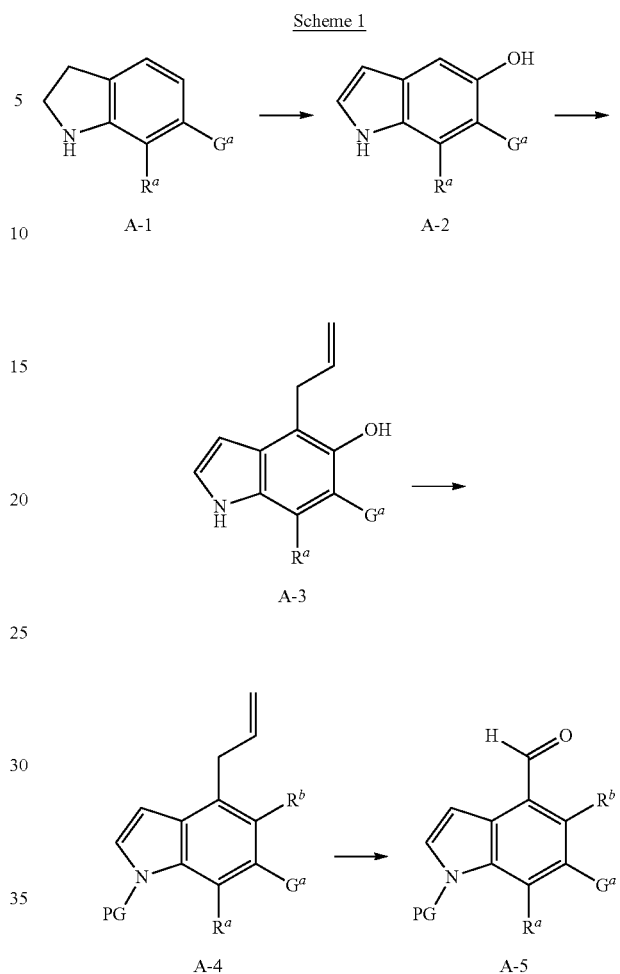

Scheme 1

Transformation of indoline A-1 to the corresponding 5-hydroxyindole A-2 can be accomplished by treatment with potassium nitrosodisulfonate preferably in a solvent mixture of acetone/aq. buffer at pH=7 either at 0° C. or at room temperature. The hydroxy group of A-2 can then be alkylated utilizing a Mitsunobu-type reaction with allyl alcohol in a suitable solvent such as toluene. The product can then be converted to C-allyl derivatives such as A-3 by thermally promoted sigmatropic rearrangement at temperatures between 200° C. and 250° C. without the use of solvent. Compound A-3 can then be reacted with alcohols (e.g. MeOH, BnOH) utilizing Mitsunobu-type conditions permitting differentiation at $R^b$. Subsequent protection of the nitrogen of the indole employing TsCl and an appropriate base, preferably NaH, or alternatively with Boc$_2$O in the presence of a catalytic amount of DMAP can afford compounds such as A-4. Isomerization of the double bond of A-4 can be accomplished via treatment with Pd(OAc)$_2$ in hexafluoroisopropyl alcohol (HFIPA). Cleavage of the olefin can then be effected by reaction with osmium tetraoxide and sodium periodate to afford A-5.

Alternatively, compounds such as A-5, wherein PG is a protecting group (preferably Boc), $R^a$ is alkyl, $R^b$ is alkoxyl, and $G^a$ is hydrogen can be also prepared by formylation of indole A-5a using Vilsmeier-type reagents such as N-(chloromethylene)-N-methylbenzenaminium chloride in acetonitrile at temperatures between 0° C. and room temperature as shown in Scheme 1b.

Scheme 1b

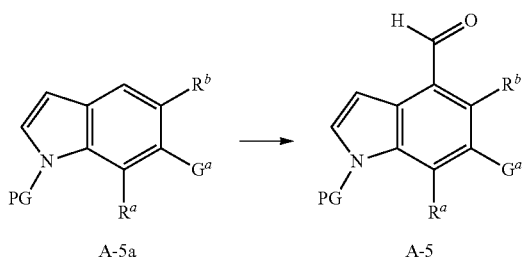

Compounds such as A-10, wherein is $X^a$ is Cl, Br, or SMe, can be prepared according to Scheme 2.

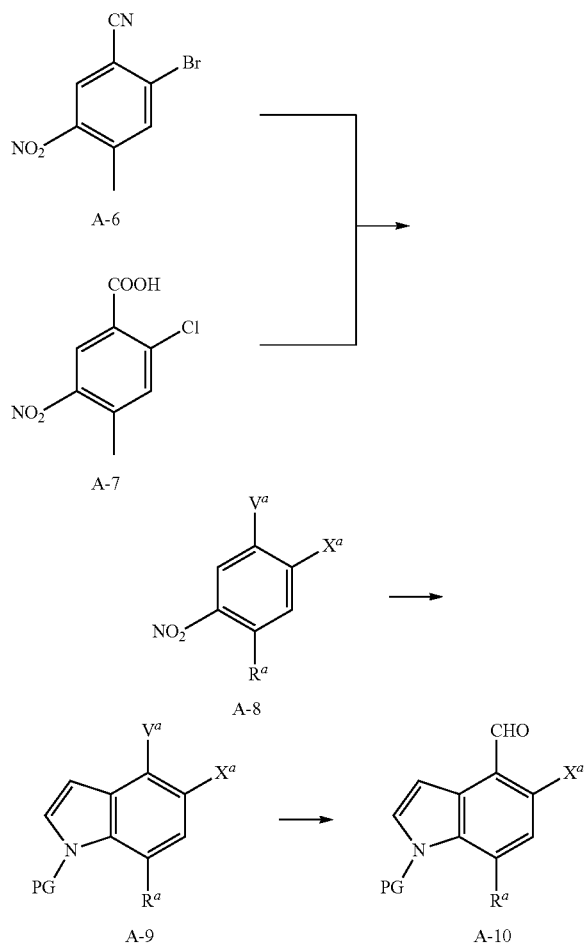

Nucleophilic aromatic substitution of A-6 (CAS: 1202858-65-8) can be achieved by sodium thiomethoxide in DMF at 60° C. to afford 8 ($X^a$=SMe). Alternatively, A-7 (CAS: 101580-96-5) can be transformed into A-8 ($X^a$=Cl, $V^a$=CH$_2$OTHP) by reduction employing 1,1,1-trichloro-2-methylpropan-2-yl carbonochloridate and NaBH$_4$, followed by protection of the resulting hydroxy with 3,4-dihydro-2H-pyran in the presence of TsOH. Transformation of A-8 ($V^a$ is either CN or CH$_2$-OTHP) to the indole A-9 can be achieved by Bartoli reaction using vinylmagnesium bromide in THF at temperatures ranging from −78° C. to room temperature, followed by protection of the indole. Protection can be effected by employing TsCl and an appropriate base preferably NaH, or alternatively protection can be accomplished with Boc$_2$O in the presence of a catalytic amount of DMAP. The aldehyde A-10 can be accessed when $V^a$=CN by reduction with DIBAL followed by acid hydrolysis, preferably employing aq. HCl. Alternatively, when $V^a$=CH$_2$OTHP, A-10 can be accessed by deprotection of the THP protecting group via acid mediated hydrolysis preferably employing TsOH in EtOH, followed by oxidation preferably using MnO$_2$ or SO$_3$-pyridine complex.

Compounds such as A-14, wherein $R^c$ is alkyl and $R^d$ is CH$_2$O-alkyl, or CH$_2$-phthaloyl, can be prepared according to Scheme 3.

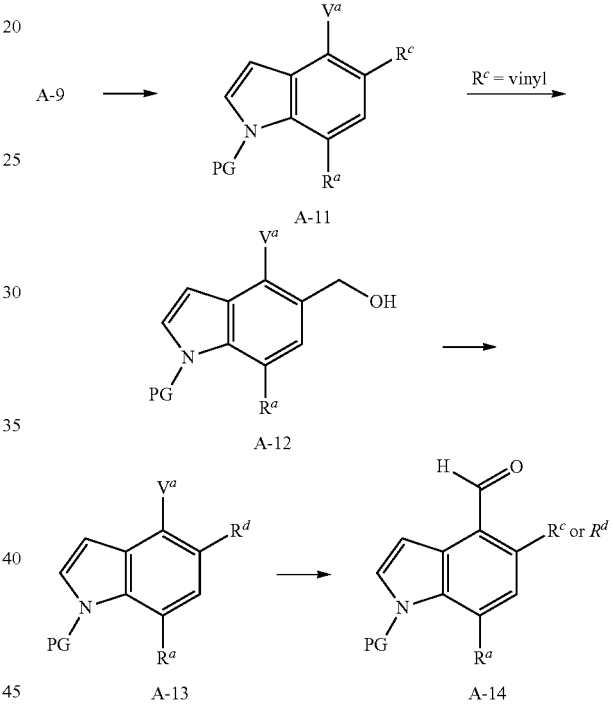

Indole A-9 ($X^a$=Cl or Br, $V^a$=CN or CH$_2$OTHP) can be transformed to A-11 wherein $R^c$=alkyl or vinyl utilizing a Suzuki-coupling with an appropriate boronate (such as alkyl trifluoroborates, or 2,4,6-trivinylcyclotriboroxane-pyridine complex). Alternatively a Negishi-type coupling employing an alkylzinc halide can be used in place of the Suzuki reaction. A-11 ($R^c$=vinyl) can be further transformed into A-12 by a dihydroxyation preferably employing ADmix-α, followed by oxidative cleavage using NaIO$_4$ and reduction of the resulting aldehyde with NaBH$_4$. Alkylation of the hydroxy group of A-12 can be achieved by deprotonation with an appropriate base, preferably NaH, and reaction with an appropriate electrophile such as MeI or SEM-Cl to afford A-13. Alternatively A-12 can undergo Mitsunobu reaction with phthalimide. Lastly, indoles of type A-13 can be converted to A-14 in accordance with Scheme 2 (i.e. A-9→A-10).

Aldehyde such as A-18 can be prepared as described in Scheme 4.

Scheme 4

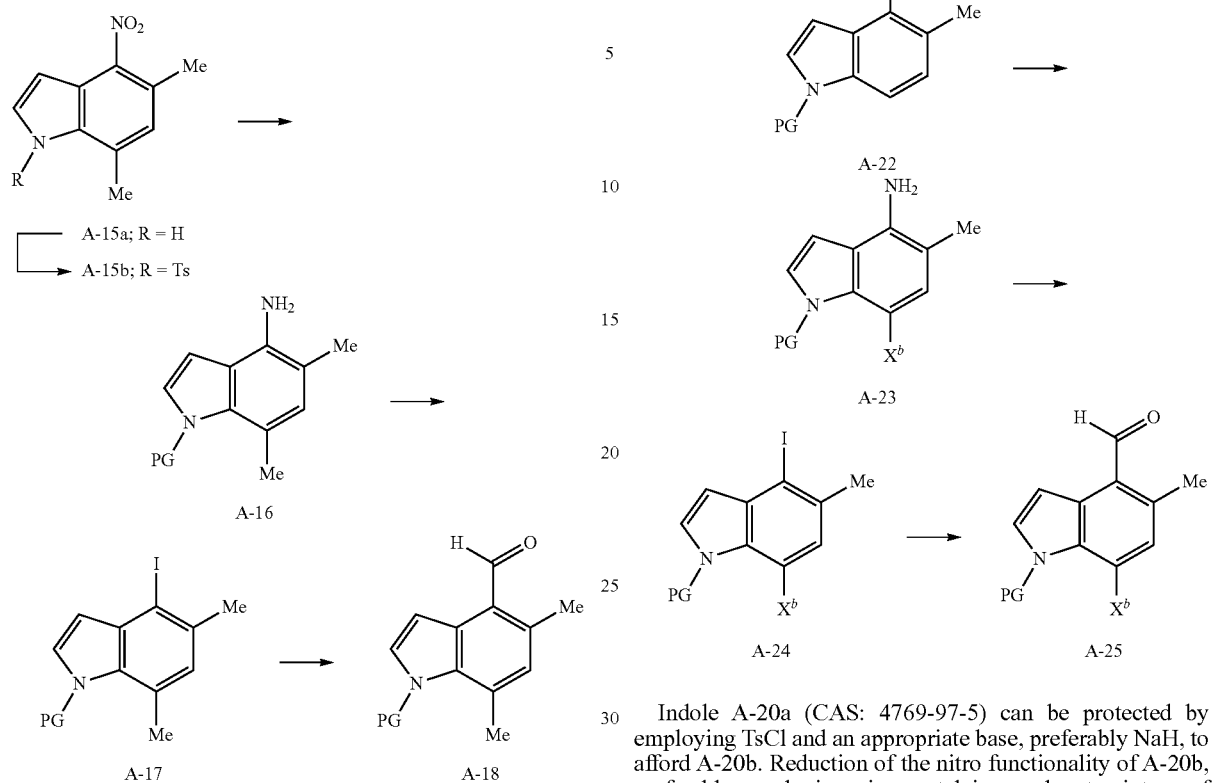

Indole A-15a (CAS: 1190314-35-2) can be protected by employing TsCl and an appropriate base, preferably NaH, to afford A-15b. Reduction of the nitro functionality, preferably by employing zinc metal in a solvent mixture of EtOAc/MeOH, can afford aniline A-16, which can be converted to iodide A-17 upon treatment with $NaNO_2$, followed by $I_2$. Treatment of A-17 with butyl lithium in the presence of DMF can provide the aldehyde A-18.

Compounds such A-25 where $X^b$=Cl, or Br, can be prepared by the sequence described in Scheme 5.

Indole A-20a (CAS: 4769-97-5) can be protected by employing TsCl and an appropriate base, preferably NaH, to afford A-20b. Reduction of the nitro functionality of A-20b, preferably employing zinc metal in a solvent mixture of EtOAc/MeOH, followed by bromination, preferably with NBS, can afford A-21. Boc protection of the aniline A-21 followed by Suzuki-coupling using potassium methyltrifluoroborate can afford A-22. Acid mediated deprotection of the Boc group of A-22, followed by halogenation using NBS or NCS can yield halides of type A-23. Transformation of the aniline A-23 to aldehyde A-25 can be accomplished in accordance with Scheme 4 (i.e. A-17→A-18).

Compounds such as B-5a, wherein $R^f$ is H, F, Cl, Br, SMe, or CN; and $R^g$=H or $C_1$-$C_4$ alkyl; and $L^a$ is an aryl group optionally substituted with —$R^f$; can be prepared by the general method outlined in Scheme 6.

Scheme 5

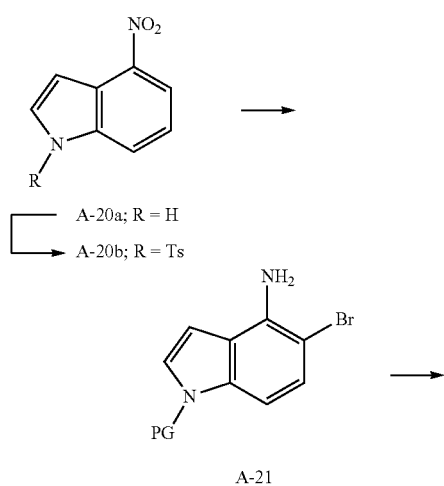

Scheme 6

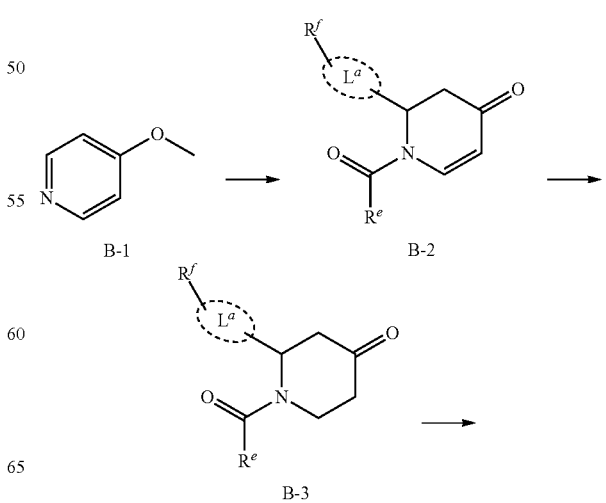

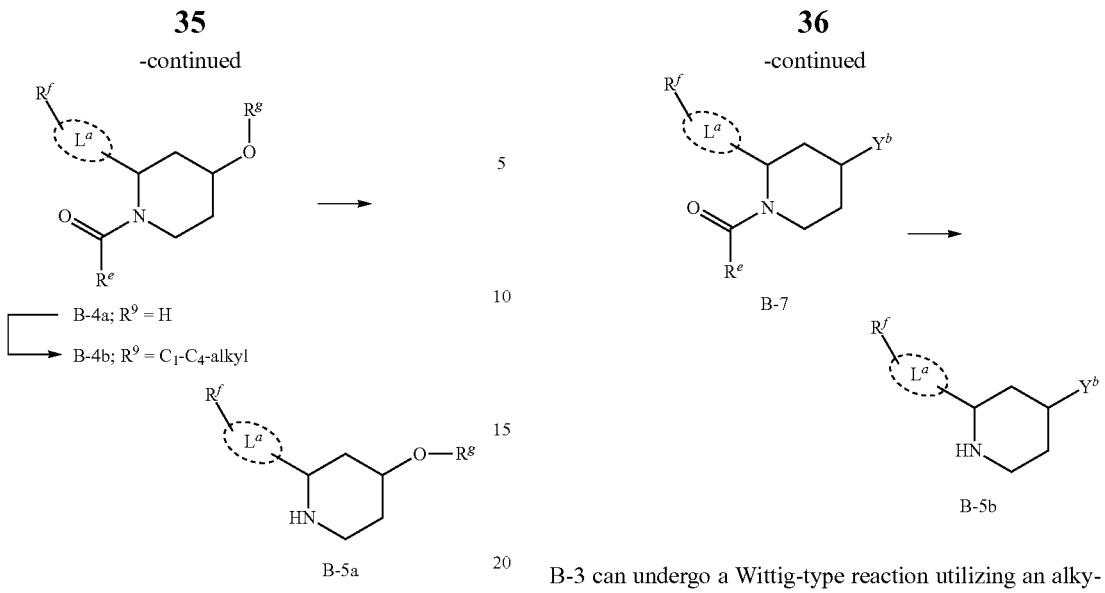

4-Methoxypyridine B-1 can be transformed to compound B-2, wherein $R^e$ is an alkoxy group (preferably —OPh, —OBn or —OtBu), by in situ N-acylation with a chloroformate such as benzyl or phenyl chloroformate, followed by addition of an arylmagnesium halide, and subsequent acid mediated hydrolysis, preferably employing aqueous HCl. Alternatively, B-2 when $R^e$=OtBu can be synthesized by the following sequence: reaction of B-1 with phenyl chloroformate; treatment with an aryl Grignard reagent to install $L^a$; treatment with KOtBu to convert the phenyl chloroformate to the Boc protecting group; and then acid mediated hydrolysis to reveal the ketone. The double bond of B-2 can then undergo reduction utilizing a suitable choice of reagents such as L-Selectride®, or a reducing metal such as zinc, to afford ketone B-3. The reduction may also be effected by the hydrogenation over Pd/C under a pressurized hydrogen atmosphere ranging up to 20 bar. B-3 can then be converted to the corresponding alcohol B-4a ($R^g$=H) employing a reducing reagent such as $NaBH_4$ or $LiBH_4$. Alkylation of B-4a can be achieved by reaction with an electrophile such as MeI or EtI in the presence of a base such as NaH in a suitable solvent such as DMF, to provide B-4b ($R^g$=$C_{1-4}$alkyl). Lastly, deprotection of B-4a and B-4b can furnish B-5a by employing conditions such as aqueous basic hydrolysis ($R^e$=OPh), catalytic hydrogenation ($R^e$=OBn), or acid treatment ($R^e$=OtBu).

Compounds such as B-5b, wherein $Y^b$ is $C_1$-$C_4$-alkyl, $CH_2OH$, $CH_2CN$ or NH—Cbz; can be prepared by the general method outlined in Scheme 7.

B-3 can undergo a Wittig-type reaction utilizing an alkylphosphonium halide such as methyltriphenylphosphonium bromide ($Y^a$=$CH_2$), ethyltriphenylphosphoniym bromide ($Y^a$=$CHCH_3$), or a Horner-Wadsworth-Emmons type reaction employing diethyl cyanomethylphosphonate ($Y^a$=CHCN) to furnish B-6. B-6, when $Y^a$=$CH_2$, can undergo hydroboration employing 9-BBN, followed by the treatment with hydrogen peroxide, to afford B-7 ($Y^b$=$CH_2OH$). In addition, hydrogenation of B-6, when $Y^a$=$CHCH_3$ or CHCN, can afford B-7 ($Y^b$=$CH_2CH_3$ or $CH_2CN$, respectively), which can be a mixture of diastereomer. Alternatively, compound B-7 (when $Y^b$=NHCbz) can be obtained by a condensation of B-3 with tert-butyl sulfinylamide in the presence of a dehydrating reagent, such as $Ti(OiPr)_4$ or $Zr(OtBu)_4$, followed by reduction of the sulfinylimine with $NaBH_4$. The resulting sulfinylamide can then be treated with an appropriate acid such as HCl in methanol to afford the corresponding primary amine, which can then be reacted with Cbz-Cl to provide B-7 ($Y^b$=NHCbz). Transformation from B-7 to B-5b can be achieved by the standard methods as mentioned above (e.g. B-4 to B-5a).

Alternatively, compounds such as B-11 and B-5c, wherein: $L^b$=$L^a$, or a heterocycle which is optionally substituted with $R^f$; $R^1$=—$CH_2$—, —CH(OTBDPS)—, —CH(OH)—, or —$C(Me)_2$-; and n=0 or 1; can be prepared according to Scheme 8a.

Scheme 8a

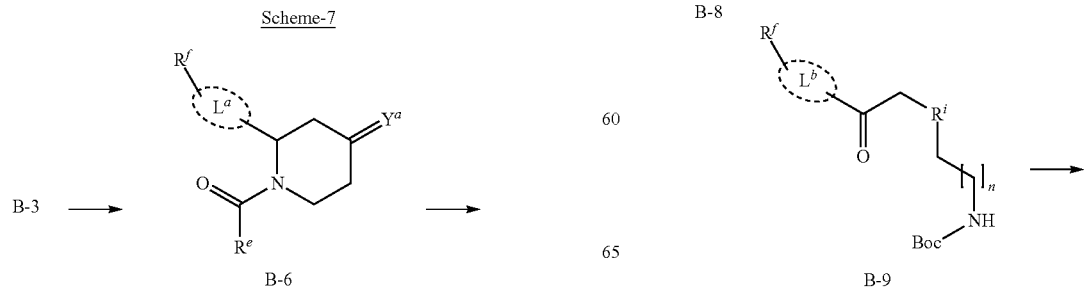

-continued

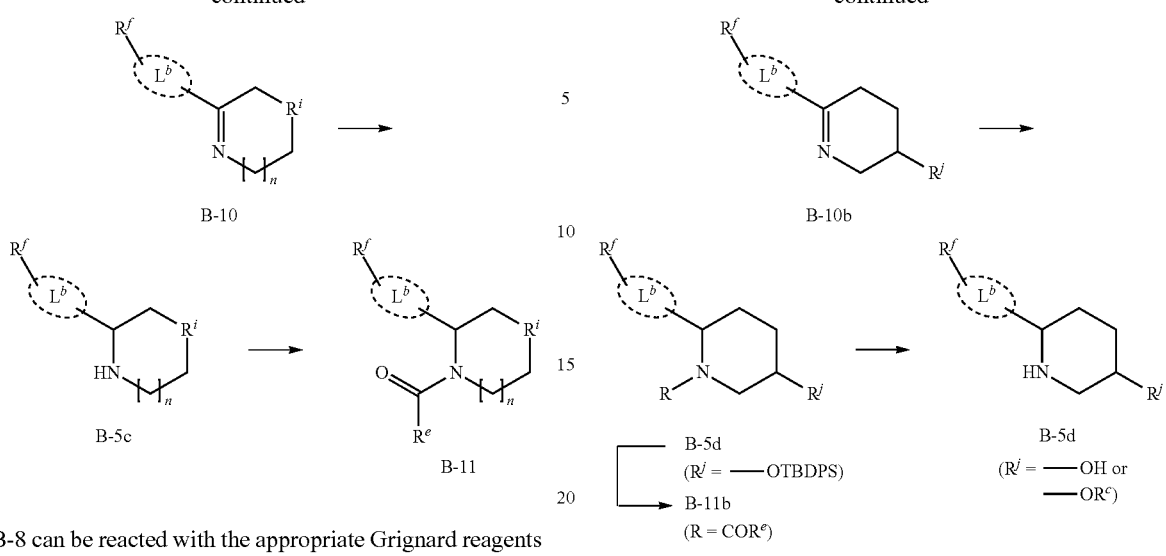

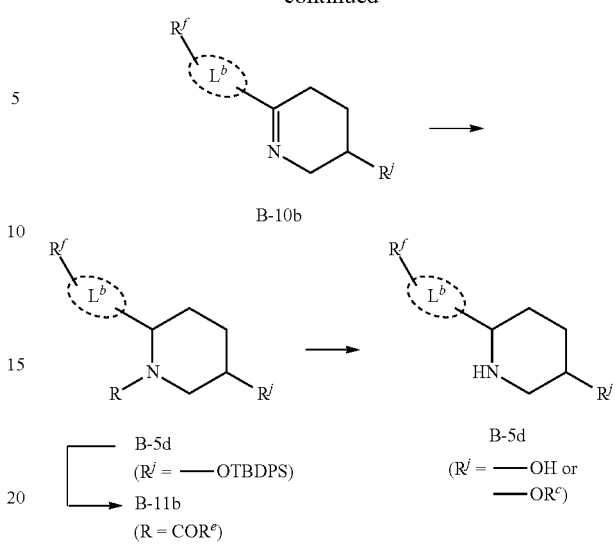

B-8 can be reacted with the appropriate Grignard reagents such as (4-(methylthio)phenyl)magnesium bromide, to furnish B-9. Deprotection of the Boc group of B-9 can be achieved by treatment with a suitable acid and solvent such as HCl in dioxane. Subsequent dehydration employing a reagent such as Ti(OiPr)$_4$ can afford the corresponding cyclic imine B-10. Alternatively, B-10 can be accessed directly by a treatment of B-9 with TMSOTf in the presence of 2,6-lutidine. B-10 can then be reduced employing reagents such as NaBH$_4$, to afford B-5c.

Compounds such as B-5c when $R^i$=—CH(OTBDPS)— can then be transformed to the corresponding alcohol (B-11 when $R^i$=—CH(OH)—) as follows: protection of the nitrogen with an appropriate group such as Boc or Cbz; deprotection of the TBDPS group by a treatment with nucleophilic fluoride anion preferably via the use of TBAF in THF or by hydrolysis with HCl in MeOH; and then by methods described in Scheme 6 (e.g. B-4a to B-5a) to liberate the amine.

Alternatively, compounds such as B-11b and B-5d, wherein: $R^j$=OTBDPS or OR$^g$; can be prepared according to Scheme 8b.

B-8b (when $R^j$=CH(OTBDPS)) can be reacted with the appropriate Grignard reagents such as (4-cyanophenyl)magnesium bromide, to furnish B-9b. Deprotection of the Boc group of B-9b, followed by the imine formation can be achieved by treatment with TMSOTf in the presence of 2,6-lutidine to afford B-5d ($R^j$=OTBDPS), which can then be transformed to B-11b. B-11b (when $R^j$=OTBDPS) can then be transformed to B-5d (where $R^j$=OH, or OR$^c$) by the standard methods described in Scheme 6.

Compounds such as B-4a or B-11 can be transformed to the corresponding diastereomer as shown in Scheme 9. Of note, the relative stereochemistry shown in Scheme 9 is intended for illustrative purposes only and does not specify a particular absolute configuration. Typically, reactions provide a mixture of diastereomers generally with one diastereomer in excess of the other.

Scheme 9

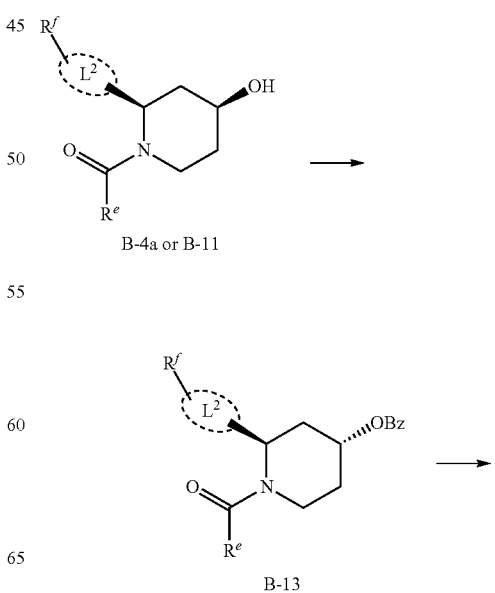

Scheme 8b

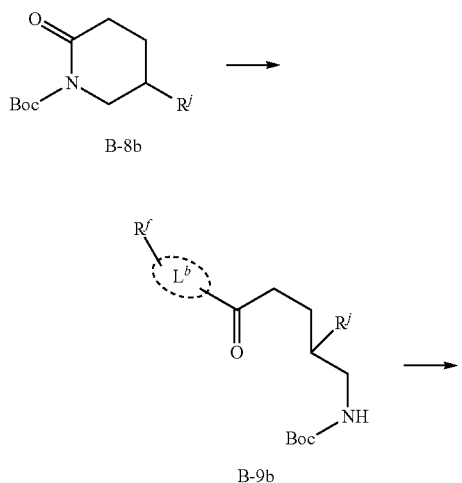

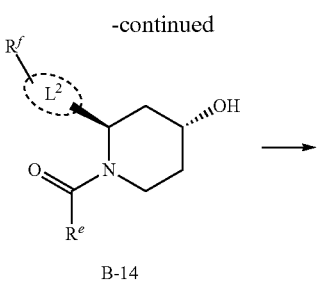

B-14

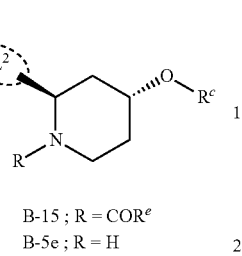

B-15 ; R = COR$^e$
B-5e ; R = H

Stereochemical inversion of the hydroxy of B-4a or B-11 can be achieved by reaction with a carboxylic acid such as benzoic acid under Mitsunobu-type reaction conditions in a suitable solvent, preferably in THF, to provide B-13. Subsequent saponification employing conditions such as $K_2CO_3$ in methanol can give B-14. B-14 can then be transformed to B-15, and then to amine B-5e employing similar methods as described in Scheme 6 (e.g. B-4a to B-5a).

Compounds such as B-5f; wherein $R^{f-2}$ is COO-alkyl; and $R^{i-2}$ is —CH(OR$^g$)— or —C(Me)$_2$-; can be prepared according to Scheme 10.

Scheme 10

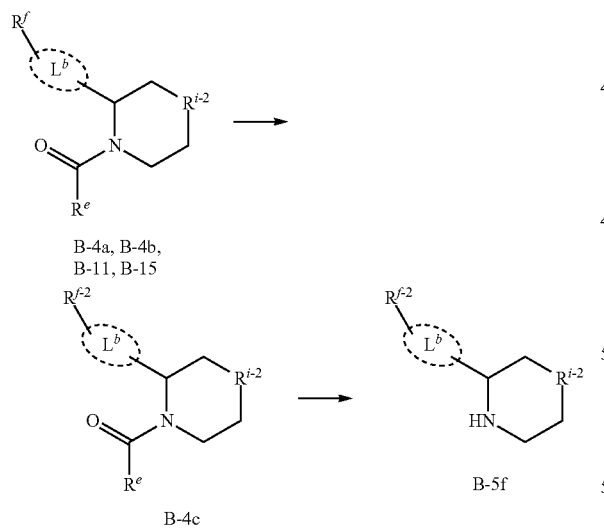

B-4a, B-4b, B-11, B-15

B-4c

B-5f

B-4a, B-4b, B-11, or B-15 when R$^f$=CN can undergo hydrolysis of the nitrile group by employing a source of hydroxide, preferably barium hydroxide, in a suitable solvent preferably a mixture of iPrOH/H$_2$O, at temperatures between 80° C. and 110° C. The subsequent acid can then be transformed to corresponding alkyl esters B-4c utilizing reagents such as trimethylsilyldiazomethane in a solvent mixture of toluene/methanol (R$^{f-2}$=CO$_2$Me), or via treatment with an anhydrous alcoholic solvent with an acid such as methanolic HCl. Alternatively B-4b, B-11, or B-15 when R$^f$=Cl or Br can be transformed to B-4c respectively by a carbonylation employing carbon monooxide in the presence of a base, such as triethylamine and a palladium catalysts with an appropriate ligand such as (rac-BINAP)PdCl$_2$ in a suitable solvent such as methanol. Deprotection of B-4c can be accomplished by applying methods as described in Scheme 6 to afford B-5f.

Compounds such as B-5g wherein R$^k$=alkyl, can be prepared according to Scheme 11.

Scheme 11

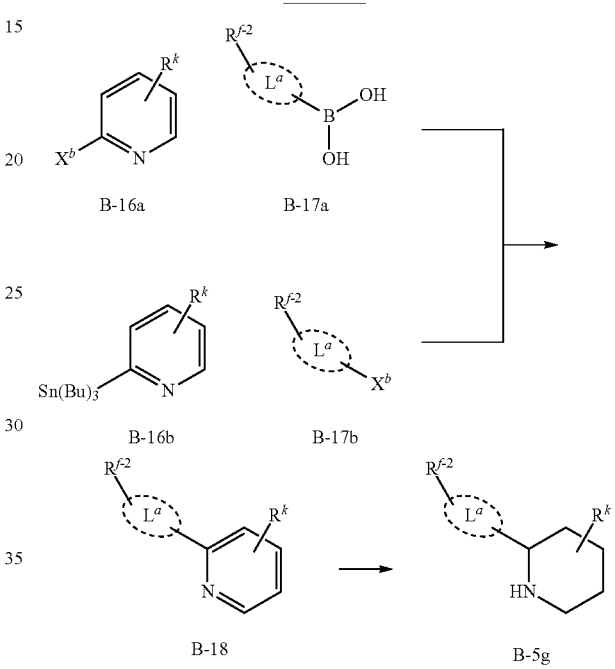

B-16a  B-17a

B-16b  B-17b

B-18  B-5g

Compounds of type B-16a (when X$^b$=Cl, Br or I) can be reacted with an appropriately substituted organoboronate (B-17a) utilizing Suzuki-type reaction conditions to provide B-18. Alternatively, B-18 can be prepared from compounds type B-16b and B-17b via Stille type coupling method. A reduction of the pyridine ring of B-18 can be accomplished by treatment with a catalyst such as PtO$_2$ under a hydrogen atmosphere in a suitable solvent such as methanol in the presence of an acid such as HCl, to afford piperidine B-5g.

Compounds such as B-5 h; can be prepared by the route depicted in Scheme 12 wherein R$^{m-1}$ and R$^{m-2}$ are independently selected from hydrogen or alkyl.

Scheme 12

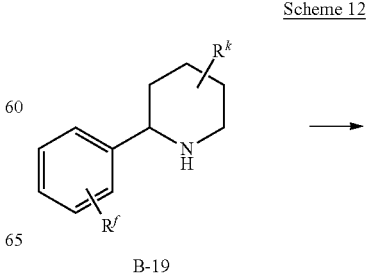

B-19

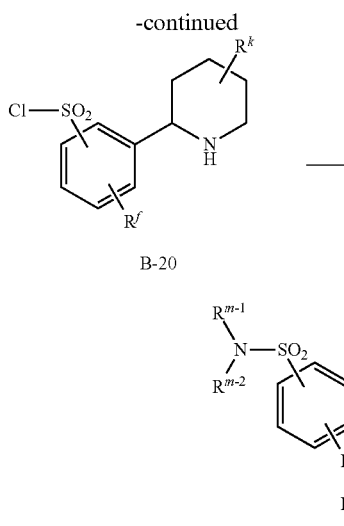

B-20

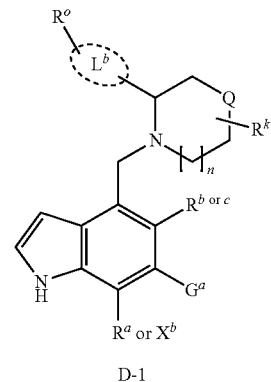

B-5h

Sulfonylation of compounds such as B-19 when $R^f$=H, Br, Cl, or F, can be accomplished by employing a reagent such as chlorosulfonic acid to afford B-20, which can subsequently be treated with a wide variety of primary ($R^{m-1}$—NH$_2$) and secondary amines ($R^{m-1}R^{m-2}$—NH) such as ammonia or methylamine, to furnish B-5 h.

Compounds such as C-2 wherein $R^n$=—$R^f$, $R^{f-2}$, or —SO$_2$NR$^{m-1}$R$^{m-2}$; and Q=R$^i$, R$^{i-2}$ or O; and R$^b$ and R$^c$ are independent groups respectively; can be prepared as outlined in Scheme 13.

aldehydes A-5, A-10, A-14, A-18 or A-25 can be coupled with the cyclic amines described above employing reductive alkylation conditions, e.g. treatment with sodium triacetoxyborohydride in DCE, to provide C-2.

Compounds such as D-1 wherein $R^o$=$R^n$, CONH$_2$, or COOH, can be prepared according to Scheme 14.

Scheme 14

C-2 →

D-1

Deprotection of PG (PG=Ts or Boc) in compound C-2 can be achieved by a treatment with a base such as KOH in a suitable solvent such as ethanol at temperatures ranging from 80 to 120° C. under microwave irradiation, to afford D-1. Deprotection of PG from C-2 when $R^o$=CN can also Scheme 13

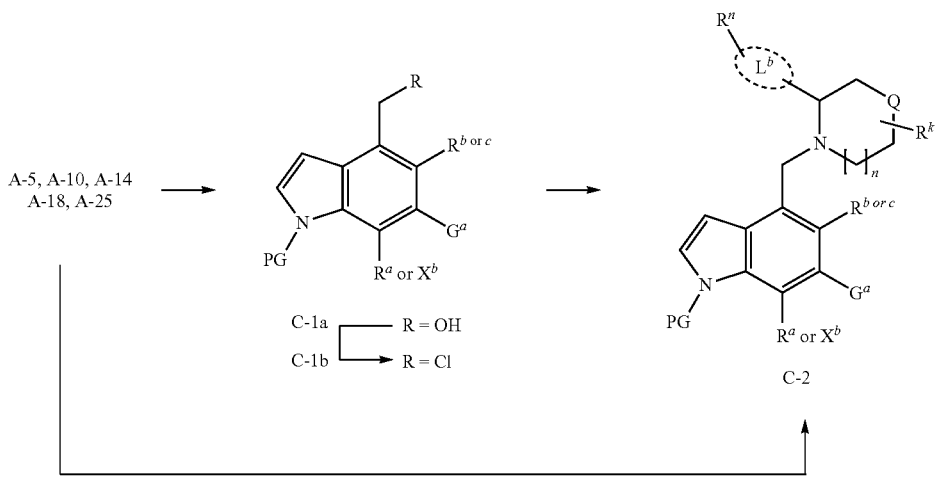

Indole aldehydes such as A-5, A-10, A-14, A-18 or A-25, can be reduced by a hydride donating reagent in a suitable solvent such as NaBH$_4$ in a mixture of methanol/THF, to provide C-1a. Subsequent, conversion of the resulting hydroxy to chloride C-1b can be accomplished by treatment with methanesulfonyl chloride and Et$_3$N, or by directly reacting with (chlormethylene)dimethylammonium chloride. C-1b can be reacted with a cyclic amine such as B-5a, B-5b, B-5c, B-5d, B-5e B-5f, B-5 g, B-5 h, or commercially available cyclic amines such as 4-(morpholin-3-yl)benzoic acid ester in the presence of a base such as potassium carbonate in a solvent such as DMSO at temperatures ranging from 0° C. to 100° C. to afford C-2. Alternatively, result in concomitant reaction of the nitrile to provide D-1 wherein $R^o$=—COOH or —CONH$_2$. Alternatively, transformation of C-2, when (PG=Boc), to D-1 can be accomplished by a treatment with a source of hydroxide such as KOH or LiOH in a suitable solvent system such as a mixture of THF/methanol/H$_2$O at temperatures ranging from room temperature to 100° C. In addition, treatment of C-2, when PG=Boc, with an appropriate acid such as TFA in a solvent such as CH$_2$Cl$_2$ at temperature preferably 0° C. can provide D-1.

Compounds such as D-1b wherein $R^p$=CH$_2$OH, CH$_2$NH$_2$, CONR$^{m-1}$R$^{m-2}$, or tetrazole, can be prepared according to Scheme 15.

Scheme 15

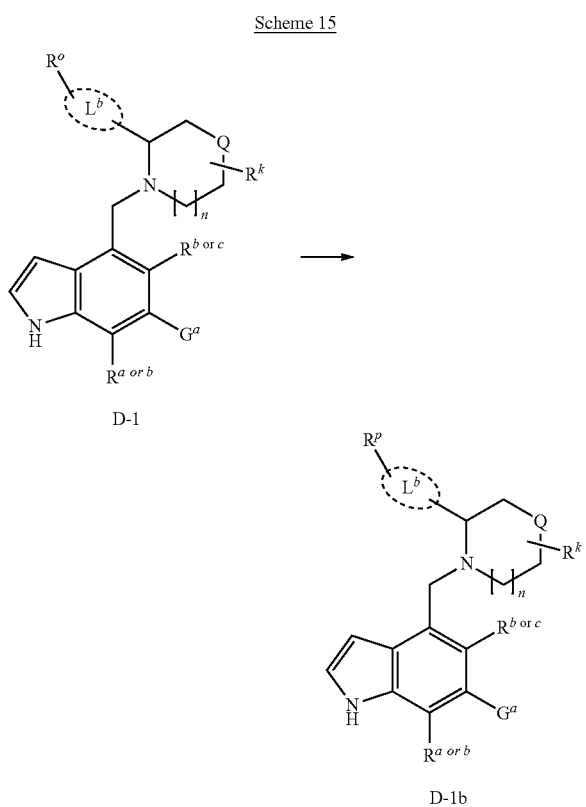

D-1

D-1b

D-1 when R°=COOR, COOH, or CN, can be further elaborated utilizing a reducing reagent such as LiAlH$_4$ in a suitable solvent such as THF at temperatures between 0 and 50° C., to provide D1-b (R$^p$=CH$_2$OH, CH$_2$NH$_2$). Alternatively, D-1, when R°=COOH, can also be coupled with a wide variety of primary and secondary amines (HNR$^{m-1}$R$^{m-2}$) such as methylamine, or sulfonamides such as methanesulfonamide by employing amide bond forming conditions of those that are well known to those skilled in the art, to provide amides of type D-1b. In addition, D-1 when R°=CN can be transformed to D-1b (R$^p$=tetrazole) by a treatment with azide containing reagents such as sodium azide in the presence of catalysts such as triethylamine hydrochloride in a suitable solvent such as chlorobenzene at elevated temperatures between 100° C. and 150° C.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure materials.

Compounds of the invention and intermediates can also be converted into each other according to methods generally known to those skilled in the art. All tautomeric forms are also intended to be included.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Ophthalmic formulations, eye ointments, powders, solutions, suspensions and the like, for topical administration are also contemplated as being within the scope of this invention.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Prophylactic and Therapeutic Uses

The compounds of formula I in free form or in pharmaceutically acceptable salt form, exhibit valuable pharmacological properties, e.g. Factor B modulating properties, complement pathway modulating properties and modulation of the complement alternative pathway properties, e.g. as indicated in in vitro and in vivo tests as provided in the next sections and are therefore indicated for therapy.

The present invention provides methods of treating a disease or disorder associated with increased complement activity by administering to a subject in need thereof an effective amount of the compounds of Formula (I) of the invention. In certain aspects, methods are provided for the treatment of diseases associated with increased activity of the C3 amplification loop of the complement pathway. In certain embodiments, methods of treating or preventing complement mediated diseases are provided in which the complement activation is induced by antibody-antigen interactions, by a component of an autoimmune disease, or by ischemic damage.

In a specific embodiment, the present invention provides a method of treating or preventing age-related macular degeneration (AMD) by administering to a subject in need thereof an effective amount of the compound of Formula (I) of the invention. In certain embodiments, patients who are currently asymptomatic but are at risk of developing a symptomatic macular degeneration related disorder are suitable for administration with a compound of the invention. The methods of treating or preventing AMD include, but are not limited to, methods of treating or preventing one or more symptoms or aspects of AMD selected from formation of ocular drusen, inflammation of the eye or eye tissue, loss of photoreceptor cells, loss of vision (including loss of visual acuity or visual field), neovascularization (including CNV), retinal detachment, photoreceptor degeneration, RPE degeneration, retinal degeneration, chorioretinal degeneration, cone degeneration, retinal dysfunction, retinal damage in response to light exposure, damage of the Bruch's membrane, and/or loss of RPE function.

The compound of Formula (I) of the invention can be used, inter alia, to prevent the onset of AMD, to prevent the progression of early AMD to advanced forms of AMD including neovascular AMD or geographic atrophy, to slow and/or prevent progression of geographic atrophy, to treat or prevent macular edema from AMD or other conditions (such as diabetic retinopathy, uveitis, or post surgical or non-surgical trauma), to prevent or reduce the loss of vision from AMD, and to improve vision lost due to pre-existing early or advanced AMD. It can also be used in combination with anti-VEGF therapies for the treatment of neovascular AMD patients or for the prevention of neovascular AMD. The present invention further provides methods of treating a complement related disease or disorder by administering to a subject in need thereof an effective amount of the compound(s) of the invention, wherein said disease or disorder is selected from uveitis, adult macular degeneration, diabetic retinopathy, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, and retinal vein occlusion.

In some embodiments, the present invention provides methods of treating a complement related disease or disorder by administering to a subject in need thereof an effective amount of the compounds of the invention. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration and neural regeneration. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome.

In a specific embodiment, the present invention provides methods of treating a complement related disease or disorder by administering to a subject in need thereof an effective amount of the compounds of the invention, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, anca vasculitis, cryoglobulinemia, systemic lupus, lupus erythematosus, psoriasis, multiple sclerosis, transplantation, diseases of the central nervous system such as Alzheimer's disease and other neurodegenerative conditions, atypicaly hemolytic uremic syndrome (aHUS), glomerulonephritis (including membrane proliferative glomerulonephritis), dense deposit disease, blistering cutaneous diseases (including bullous pemphigoid, pemphigus, and epidermolysis bullosa), ocular cicatrical pemphigoid or MPGN II.

In a specific embodiment, the present invention provides methods of treating glomerulonephritis by administering to a subject in need thereof an effective amount of a composition comprising a compound of the present invention. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH) by administering to a subject in need thereof an effective amount of a composition comprising an compound of the present invention with or without concomitent administration of a complement C5 inhibitor or C5 convertase inhibitor such as Soliris.

In a specific embodiment, the present invention provides methods of reducing the dysfunction of the immune and/or hemostatic systems associated with extracorporeal circulation by administering to a subject in need thereof an effective amount of a composition comprising an compound of the present invention. The compounds of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient. More particularly, such procedures include, but are not limited to, transplantation procedures including kidney, liver, lung or heart transplant procedures and islet cell transplant procedures.

In other embodiments, the compounds of the invention are suitable for use in the treatment of diseases and disorders associated with fatty acid metabolism, including obesity and other metabolic disorders.

In another embodiment, the compounds of the invention may be used in blood ampules, diagnostic kits and other equipment used in the collection and sampling of blood. The use of the compounds of the invention in such diagnostic kits may inhibit the ex vivo activation of the complement pathway associated with blood sampling.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by alternative complement pathway. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by the complement alternative pathway, wherein the medicament is prepared for administration with another therapeutic agent. The invention also provides the use of another therapeutic agent for treating a disease or condition mediated by the complement alternative pathway, wherein the medicament is administered with a compound of formula (I).

The invention also provides a compound of formula (I) for use in a method of treating a disease or condition mediated by the complement alternative pathway, wherein the compound of formula (I) is prepared for administration with another therapeutic agent. The invention also provides another therapeutic agent for use in a method of treating a disease or condition mediated by the complement alternative pathway and/or Factor B, wherein the other therapeutic agent is prepared for administration with a compound of formula (I). The invention also provides a compound of formula (I) for use in a method of treating a disease or condition mediated by the complement alternative pathway and/or Factor B, wherein the compound of formula (I) is administered with another therapeutic agent. The invention also provides another therapeutic agent for use in a method of treating a disease or condition mediated by the complement alternative pathway and/or Factor B, wherein the other therapeutic agent is administered with a compound of formula (I).

The invention also provides the use of a compound of formula (I) for treating a disease or condition mediated by the complement alternative pathway and/or Factor B, wherein the patient has previously (e.g. within 24 hours) been treated with another therapeutic agent. The invention also provides the use of another therapeutic agent for treating a disease or condition mediated by the complement alternative pathway and/or Factor B wherein the patient has previously (e.g. within 24 hours) been treated with a compound of formula (I).

The pharmaceutical compositions can be administered alone or in combination with other molecules known to have a beneficial effect on retinal attachment or damaged retinal tissue, including molecules capable of tissue repair and regeneration and/or inhibiting inflammation. Examples of useful, cofactors include complement inhibitors (such as inhibitors of Factor D, C5a receptor and antibody or Fabs against C5, C3, properidin, factor H, and the like), anti-VEGF agents (such as an antibody or FAB against VEGF, e.g., Lucentis or Avastin), basic fibroblast growth factor (bFGF), ciliary neurotrophic factor (CNTF), axokine (a mutein of CNTF), leukemia inhibitory factor (LIF), neurotrophin 3 (NT-3), neurotrophin-4 (NT-4), nerve growth factor (NGF), insulin-like growth factor II, prostaglandin E2, 30 kD survival factor, taurine, and vitamin A. Other useful cofactors include symptom-alleviating cofactors, including antiseptics, antibiotics, antiviral and antifungal agents and analgesics and anesthetics. Suitable agents for combination treatment with the compounds of the invention include agents known in the art that are able to modulate the activities of complement components.

A combination therapy regimen may be additive, or it may produce synergistic results (e.g., reductions in complement pathway activity more than expected for the combined use of the two agents). In some embodiments, the present invention provide a combination therapy for preventing and/or treating AMD or another complement related ocular disease as described above with a compound of the invention and an anti-angiogenic, such as anti-VEGF agent (including Lucentis Avastin and VEGF-R2 inhibitors including pazopanib, sutent, inifanib, and VEGF-R2 inhibitors disclosed in WO2010/066684) or photodynamic therapy (such as as verteporfin).

In some embodiments, the present invention provide a combination therapy for preventing and/or treating autoimmune disease as described above with a compound of the invention and a B-Cell or T-Cell modulating agent (for example cyclosporine or analogs thereof, rapamycin, RAD001 or analogs thereof, and the like). In particular, for multiple sclerosis therapy may include the combination of a compound of the invention and a second MS agent selected from fingolimod, cladribine, tysarbi, laquinimod, rebif, avonex and the like.

In one embodiment, the invention provides a method of modulating activity of the complement alternative pathway in a subject, wherein the method comprises administering to the subject a therapeutically effective amount of the compound according to the definition of formula (I). The invention further provides methods of modulating the activity of the complement alternative pathway in a subject by modulating the activity of Factor B, wherein the method comprises administering to the subject a therapeutically effective amount of the compound according to the definition of Formula (I).

In one embodiment, the invention provides a compound according to the definition of formula (I), (Ia), or any subformulae thereof, for use as a medicament.

In one embodiment, the invention provides the use of a compound according to the definition of formula (I), (Ia), or any subformulae thereof, for the treatment of a disorder or disease in a subject mediated by complement activation. In particular, the invention provides the use of a compound according to the definition of formula (I), (Ia), or any subformulae thereof, for the treatment of a disorder or disease mediated by activation of the complement alternative pathway.

In one embodiment, the invention provides the use of a compound according to the definition of formula (I), (Ia), or a subformulae thereof in the manufacture of a medicament for the treatment of a disorder or disease in a subject characterized by activation of the complement system. More particularly in the manufacture of a medicament for the treatment of a disease or disorder in a subject characterized by over activiation of the complement alternative pathway.

In one embodiment, the invention provides the use of a compound according to the definition of formula (I), (Ia), or subformulae thereof for the treatment of a disorder or disease in a subject characterized by activation of the complement system. More particularly, the invention provides uses of the compounds provided herein in the treatment of a disease or disorder characterized by over activation of the complement alternative pathway or the C3 amplification loop of the alternative pathway. In certain embodiments, the use is in the treatment of a disease or disorder is selected from retinal diseases (such as age-related macular degeneration).

The present invention provides use of the compounds of the invention for treating a disease or disorder associated with increased complement activity by administering to a subject in need thereof an effective amount of the compounds of Formula (I) of the invention. In certain aspects, uses are provided for the treatment of diseases associated with increased activity of the C3 amplification loop of the complement pathway. In certain embodiments, uses of treating or preventing complement mediated diseases are provided in which the complement activation is induced by antibody-antigen interactions, by a component of an autoimmune disease, or by ischemic damage.

In a specific embodiment, the present invention provides use of the compounds of the invention for treating or preventing age-related macular degeneration (AMD). In certain embodiments, patients who are currently asymptomatic but are at risk of developing a symptomatic macular degeneration related disorder are suitable for administration with a compound of the invention. The use in treating or preventing AMD include, but are not limited to, uses in treating or preventing one or more symptoms or aspects of AMD selected from formation of ocular drusen, inflammation of the eye or eye tissue, loss of photoreceptor cells, loss of vision (including loss of visual acuity or visual field), neovascularization (including CNV), retinal detachment, photoreceptor degeneration, RPE degeneration, retinal degeneration, chorioretinal degeneration, cone degeneration, retinal dysfunction, retinal damage in response to light exposure, damage of the Bruch's membrane, and/or loss of RPE function.

The compound of Formula (I) of the invention can be used, inter alia, to prevent the onset of AMD, to prevent the progression of early AMD to advanced forms of AMD including neovascular AMD or geographic atrophy, to slow and/or prevent progression of geographic atrophy, to treat or prevent macular edema from AMD or other conditions (such as diabetic retinopathy, uveitis, or post surgical or non-surgical trauma), to prevent or reduce the loss of vision from AMD, and to improve vision lost due to pre-existing early or advanced AMD. It can also be used in combination with anti-VEGF therapies for the treatment of neovascular AMD patients or for the prevention of neovascular AMD. The present invention further provides methods of treating a complement related disease or disorder by administering to a subject in need thereof an effective amount of the compound(s) of the invention, wherein said disease or disorder is selected from uveitis, adult macular degeneration, diabetic retinopathy, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, and retinal vein occlusion.

In some embodiments, the present invention provides uses for treating a complement related disease or disorder. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration and neural regeneration. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome.

In a specific embodiment, the present invention provides use of the compounds of the invention for treating a complement related disease or disorder, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, systemic lupus, lupus erythematosus, psoriasis, multiple sclerosis, transplantation, diseases of the central nervous system such as Alzheimer's disease and other neurodegenerative conditions, atypicaly hemolytic uremic syndrome (aHUS), glomerulonephritis (including membrane proliferative glomerulonephritis), blistering cutaneous diseases (including bullous pemphigoid, pemphigus, and epidermolysis bullosa), ocular cicatrical pemphigoid or MPGN II.

In a specific embodiment, the present invention provides use of the compounds of the invention for treating glomerulonephritis. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH) by administering to a subject in need thereof an effective amount of a composition comprising an compound of the present invention with or without concomitant administration of a complement C5 inhibitor or C5 convertase inhibitor such as Soliris.

In a specific embodiment, the present invention provides use of the compounds of the invention for reducing the dysfunction of the immune and/or hemostatic systems associated with extracorporeal circulation. The compounds of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient. More particularly, such procedures include, but are not limited to, transplantation procedures including kidney, liver, lung or heart transplant procedures and islet cell transplant procedures.

In one embodiment of the present invention, there is (−)-(S)-4-(1-((5-cyclopropyl-7-methyl-1H-indol-4-yl)methyl)piperidin-2-yl)benzoic acid for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In one embodiment of the present invention, there is (−)-4-((2S,4S)-1-((5-methoxy-7-methyl-1H-indol-4-yl)methyl)-4-propoxypiperidin-2-yl)benzoic acid for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In one embodiment of the present invention, there is (+)-4-((2S,4R)-1-((5-methoxy-7-methyl-1H-indol-4-yl)methyl)-4-methylpiperidin-2-yl)benzoic acid for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In one embodiment of the present invention, there is (−)-4-((2S,4S)-4-methoxy-1-((5-methoxy-7-methyl-1H-indol-4-yl)methyl)piperidin-2-yl)benzoic acid for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In one embodiment of the present invention, there is (−)-5-(rel-(2S,4S)-4-ethoxy-1-((5-methoxy-7-methyl-1H-indol-4-yl)methyl)piperidin-2-yl)picolinic acid for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In one embodiment of the present invention, there is (−)-4-(1-((5-methoxy-7-methyl-1H-indol-4-yl)methyl)-4,4-dimethylpiperidin-2-yl)benzoic acid for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In one embodiment of the present invention, there is 4-((2S,4S)-(4-ethoxy-1-((5-methoxy-7-methyl-1H-indol-4-yl)methyl)piperidin-2-yl))benzoic acid ((+)—as TFA salt) for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, postoperative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In one embodiment of the present invention, there is (−)-4-(rel-(2S,4S)-1-((5,7-dimethyl-1H-indol-4-yl)methyl)-4-methoxypiperidin-2-yl)benzoic acid for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, postoperative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In one embodiment of the present invention, there is 4-(rel-(2S,4S)-1-((5,7-dimethyl-1H-indol-4-yl)methyl)-4-ethoxypiperidin-2-yl)benzoic acid ((+)—as TFA salt) for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, postoperative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In one embodiment of the present invention, there is (−)-4-(rel-(2S,4S)-1-((5-cyclopropyl-7-methyl-1H-indol-4-yl)methyl)-4-methoxypiperidin-2-yl)benzoic acid for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In one embodiment of the present invention, there is (+)-4-(rel-(2S,4S)-1-((5-cyclopropyl-7-methyl-1H-indol-4-yl)methyl)-4-ethoxypiperidin-2-yl)benzoic acid for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

The following examples are intended to illustrate the invention and are not to be construed as being limitations thereon. Temperatures are given in degrees centigrade (° C.). If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Inter Alia the following in vitro tests may be used.

The following Examples, while representing preferred embodiments of the invention, serve to illustrate the invention without limiting its scope.

Abbreviations
9-BBN 9-Borabicyclo[3.3.1]nonane
Ac acetyl
AcOH acetic acid
APCI atmospheric-pressure chemical ionization
app apparent
aq. aqueous
atm atmosphere
BINAP 2,2'-Bis(diphenylphosphino)-1,1'-binaphthyl
Boc tertiary butyloxy carboxy
br. Broad
Bu butyl
BuOH butanol
Bz benzoyl
calcd. Calculated
Cbz carboxybenzyl
d doublet
dd doublet of doublets
DCE 1,2-dichloroethane
DEA diethylamine
DEAD diethyl azodicarboxylate
DIBAL-H diisobutylaluminium hydride
DIPEA N,N-diisopropylethylamine
DMAP 4,4-dimethylaminopyridine
DME 1,2-dimethoxyethane
DMF N,N-dimethylformamide
DMSO dimethylsulfoxide
dppf 1,1'-bis(diphenylphosphino)ferrocene
dppp 1,3-bis(diphenylphosphino)propane
EDC-HCl 1-ethyl-3-(3-dimethylaminopropyl)carbodiimide hydrochloride
ESI electrospray ionization
EtOAc ethyl acetate
Et ethyl
EtOH ethanol
g grams
h, hr hour(s)
HATU 2-(1H-7-azabenzotriazol-1-yl)-1,1,3,3-tetramethyl uronium hexafluorophosphate methanaminium
HC HPLC condition
HFIP 1,1,1,3,3,3-hexafluoro-2-propanol
HPLC high performance liquid chromatography
IPA, iPrOH 2-propanol
IR infrared spectroscopy
L liter(s)
M molar
MHz mega Hertz
m multiplet
Me methyl
MeI iodomethane
MeOH methanol
mg milligram(s)
min minutes
mL milliliter(s)
mmol millimoles
MS mass spectrometry
Ms methyanesulfonyl
m/z mass to charge ratio
N normal
NMR nuclear magnetic resonance
PBS phosphate buffered saline
Pd/C palladium on carbon
Ph phenyl
ppm parts per million
rac racemic
rel relative stereochemical information (e.g., trans or cis) and does not denote absolute stereochemistry of accompanying stereochemical information
r.t. room temperature
RP- reverse phase
s singlet
satd. saturated
SFC Supercritical Fluid Chromatography
$SO_3.Py$, $SO_3$-Py sulfur trioxide pyridine complex
t triplet
TBAF tetra-n-butylammonium fluoride
TBDPS tert-butyldiphenylsilyl
TBDPSCl, TBDPS-Cl tert-butyldiphenylsilyl chloride
TEA, $Et_3N$ triethylamine
tert- tertiary
TFA trifluoroacetic acid
TFE 2,2,2-trifluoroethanol
THF tetrahydrofuran
TMS trimethylsilyl
TMSOTf trimethylsilyl trifluoromethanesulfonate
TMSP sodium 3-trimethylsilylpropionate-2,2,3,3-$d_4$
$t_r$ retention time
Tris tris(hydroxymethyl)aminomethane
Ts p-toluenesulfonyl
TsOH p-toluenesulfonic acid
v/v volume per volume
w/v weight per volume The following examples are intended to illustrate the invention and are not to be construed as being limitations thereon. Unless otherwise stated, one or more tautomeric forms of compounds of the examples described hereinafter may be prepared in situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated. Optical rotations were measured in MeOH, using D line of a sodium lamp.

Proton NMR ($^1$H NMR) is conducted in deuterated solvent. In certain compounds disclosed herein, one or more $^1$H shifts overlap with residual proteo solvent signals; these signals have not been reported in the experimental provided hereinafter.

Multiple parent ion masses are reported for mass spectroscopy data when the compound of the invention contains one or more bromine atoms. Bromine exists as an approximately 1:1 molar ratio of $^{79}$Br:$^{81}$Br. Thus, a compound with a single bromine atom will exhibit two parent mass ions having a difference of 2 amu.

Following preparation methods were used for RP-HPLC.

HC-A:

Stationary phase: Waters SunFire™ Prep C18 OBD™ 5 µm, 30×100 mm

Mobile phase: gradient, water with 0.1% TFA/acetonitrile

HC-B

Stationary phase: Gemini® NX 5µ C18 110A 100×30 mm

Mobile phase: gradient, water with 0.1% (28% ammonium hydroxide)/acetonitrile

Absolute stereochemistry and/or optical rotations are provided for the embodiments of the invention where applicable. The invention contemplates all stereochemical forms of the compounds provided herein. Where absolute stereochemistry is provided the assessment was made via X-ray diffraction, and/or chemical correlation, and/or at least one chiral center was from a purchased commercial enantiopure (>15:1 er) starting material. In some instances compounds contain two or more chiral centers. The relative stereochemistry of these compounds was assessed via NMR studies and/or X-ray diffraction. In these cases the compounds are identified with the prefix "rel" followed by R/S nomenclature. Of note, in instances where "rel" is used the R/S only provides relative stereochemical information (e.g., trans or cis) and does not denote absolute stereochemistry. In some instances the relative stereochemistry of a diastereomeric pair was not determined and thus the individual diastereomers are identified by the retention time under delineated HPLC conditions and the monikers "diastereomer-1" or "diastereomer-2", or "single diastereomer" when only one isomer is isolated and/or available.

In the case of a racemic samples, including intermediates, enantiomers are separated by chromatography using a chiral stationary phase and are identified/differentiated either by HPLC retention time employing a chiral stationary phase and the monikers "enantiomer-1" or "enantiomer-2", and/or by a specific "+" or "−" sign referring to the rotation of polarized light when this data is available.

In instances when individual diastereomers, that are racemic, are identified but relative stereochemistry is not determined, then the compounds are designated with the symbol "(±)" along with the moniker "diastereomer-1" or "diastereomer-2", or "single diastereomer" if only one isomer is isolated and/or available.

In instances where a qualitative specific rotation is available, but relative stereochemistry is not determined, individual diastereomers are identified as "+" or "−" along with the designation "diastereomer-1" or "diastereomer-2", or "single diastereomer" when only one isomer is isolated and/or available.

In some instances examples possess an acidic functional group as such during final purification procedures samples may contain an undetermined mixture of the free acid along with potassium and/or lithium salts of the titled compound. Small changes in the amount of salt present may change the observed chemical shift or intensity for some peaks in the $^1$H NMR spectra.

Intermediate 1-1:

Intermediate 1-1-A;
5,7-dimethyl-4-nitro-1-tosyl-1H-indole

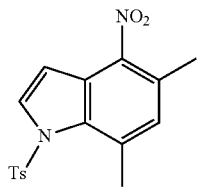 [SMILES: Cc1ccc(S(=O)(=O)n2ccc3c([N+](=O)[O-])c(C)cc(C)c32)cc1]

To a solution of 5,7-dimethyl-4-nitro-1H-indole (CAS; 1190314-35-2, 10 g, 52.6 mmol) in DMF (200 mL) was added portionwise NaH (3.2 g, 60% in mineral oil, 79 mmol) at 0° C., and then the mixture was stirred at room temperature for 0.5 h. The mixture was cooled down to 0° C. To the red suspension was added TsCl (15.0 g, 79 mmol) at 0° C., and then the mixture was stirred at room temperature for 22 h. At this point, the reaction was quenched with half saturated aq. KHSO$_4$. The mixture was diluted with H$_2$O, and then the whole mixture was stirred at room temperature for 1 h. The resulting solid was collected by filtration. The obtained brown solid was successively washed with H$_2$O, MeOH, and heptane. The solid was dried to give the title compound. MS (ESI+) m/z 345.1 (M+H).

Intermediate 1-1-B;
5,7-dimethyl-1-tosyl-1H-indol-4-amine

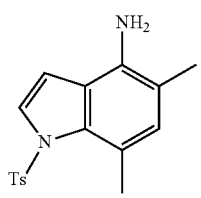 [SMILES: Cc1ccc(S(=O)(=O)n2ccc3c(N)c(C)cc(C)c32)cc1]

To a solution of 5,7-dimethyl-4-nitro-1-tosyl-1H-indole, Intermediate 1-1-A, (17 g, 49.4 mmol) in MeOH (50 mL)/EtOAc (300 mL) was added Zn (16.1 g, 247 mmol). The suspension was cooled down to 0° C. To the suspension was added dropwise AcOH (30 mL) over 30 min, and then the mixture was stirred at 0° C. for 0.5 h. The flask was removed from the ice bath, and the mixture left stirring at room temperature for 18.5 h. The reaction mixture was poured into a mixture of Celite®/5% aq. NaHCO$_3$/EtOAc, and then the basic mixture was vigorously stirred for 0.5 h. The mixture was filtered through Celite®. The layers were separated and the aqueous layer was extracted with EtOAc. The combined organic layers were washed with 5% aq. NaHCO$_3$, H$_2$O, and brine, dried over Na$_2$SO$_4$, and then filtered. Concentration of the filtrate gave the title compound, which was used without the need for further purification. MS (ESI+) m/z 315.1 (M+H).

Intermediate 1-1-C;
4-iodo-5,7-dimethyl-1-tosyl-1H-indole

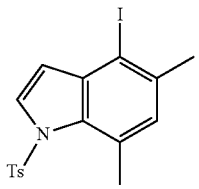 [SMILES: Cc1ccc(S(=O)(=O)n2ccc3c(I)c(C)cc(C)c32)cc1]

To a suspension of 5,7-dimethyl-1-tosyl-1H-indol-4-amine, Intermediate 1-1-B, (7.70 g, 24.5 mmol) in H$_2$O (80 mL)/EtOAc (150 mL) was added conc. aq. HCl (4.3 mL, 49.0 mmol) at 0° C., and then the mixture was stirred at 0° C. To the suspension was added dropwise a solution of NaNO$_2$ (2.0 g, 29.4 mmol) in H$_2$O (20 mL) over 15 min while keeping the temperature below 5° C. Once the addition was complete, the mixture was stirred at 0° C. for 1 h. To the mixture was added dropwise a solution of KI (12.2 g, 73.5 mmol) in H$_2$O (20 mL) over 15 min, and then the mixture was stirred at 0° C. for 1 hr. The reaction was quenched with half saturated Na$_2$S$_2$O$_3$, and then the whole mixture was stirred at room temperature for ca. 16 h. The mixture was diluted with EtOAc, and then the layers were partitioned. The organic layer was successively washed with H$_2$O and brine, dried over Na$_2$SO$_4$, and then filtered and concentrated. The resulting residue was purified by silica gel flash column chromatography [heptane/(30% EtOAc in CH$_2$Cl$_2$)=91/9 to 85/15)]. The resulting residue was triturated with Et$_2$O, and then the solid was collected by filtration to give the title compound. $^1$H NMR (400 MHz, DMSO-d$_6$) δ 7.92 (d, J=3.80 Hz, 1H), 7.61 (d, J=8.60 Hz, 2H), 7.40 (dd, J=0.50, 8.60 Hz, 2H), 7.04 (s, 1H), 6.72 (d, J=3.79 Hz, 1H), 2.41 (s, 3H), 2.37 (s, 3H), 2.34 (s, 3H).

Intermediate 1-1;
5,7-dimethyl-1-tosyl-1H-indole-4-carbaldehyde

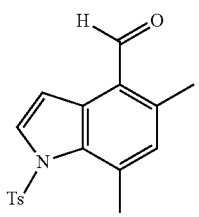 [SMILES: Cc1ccc(S(=O)(=O)n2ccc3c(C=O)c(C)cc(C)c32)cc1]

To a solution of 4-iodo-5,7-dimethyl-1-tosyl-1H-indole, Intermediate 1-1-C, (950 mg, 2.1 mmol) and DMF (0.33 mL, 4.2 mmol) in cyclopentyl methyl ether (22 mL), was added n-butyllithium in hexane (2.2 M, 1.3 mL, 2.8 mmol) at −78° C. After stirring for 1 h, additional n-butyllithium in hexane (2.2 M, 0.19 mL, 0.42 mmol) was added. After stirring for 15 min, the reaction was quenched with MeOH (2 mL) and 1M aq. NaHSO$_4$ (4.5 mL), and diluted with EtOAc and brine. The layers were separated and the aqueous layer was extracted with EtOAc. The organic layers were combined, washed with brine, dried over Na$_2$SO$_4$, filtered, and concentrated. The resulting residue was purified by silica gel flash column chromatography [(10% CH$_2$Cl$_2$/heptane)/(20% EtOAc/CH$_2$Cl$_2$)=100/0 to 50/50] to afford the title compound. MS (ESI+) m/z 328.2 (M+H).

Intermediate 1-2:

IntermediateInt-1-2-A;
5-bromo-7-methyl-1H-indole-4-carbonitrile

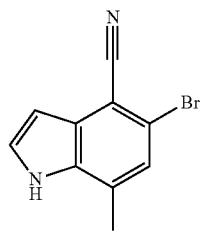

To a suspension of 1 M vinylmagnesium bromide in THF (249 mL, 249 mmol) was added 2-bromo-4-methyl-5-nitrobenzonitrile (15 g, 62.2 mmol) in THF (100 mL) dropwise while keeping the reaction temperature below −20° C. After completion of the addition, the mixture was placed at room temperature and stirred at for 1.5 h. The reaction mixture was then cooled to below −20° C. and quenched with MeOH while maintaining the internal reaction temperature below 0° C. To the mixture was added Celite®, and 5% aq. NaHCO$_3$ (50 mL). The mixture was diluted with CH$_2$Cl$_2$, and filtered through a SiO$_2$ pad, which was rinsed with a mixture of CH$_2$Cl$_2$/EtOAc (ca. 1/1). The filtrate was concentrated to give the title compound, which was used in the next reaction without the need for further purification. MS (ESI−) m/z 233.1, 235.1. (M−H).

Intermediate 1-2-B; 5-bromo-7-methyl-1-tosyl-1H-indole-4-carbonitrile

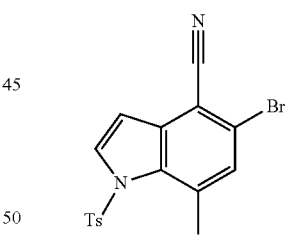

To a suspension of 5-bromo-7-methyl-1H-indole-4-carbonitrile, Intermediate 1-2-A, (11.99 g, 51 mmol), TsCl (14.58 g, 77 mmol), and triethylbenzylammonium chloride (1.162 g, 5.10 mmol) in CH$_2$Cl$_2$ (300 mL) was added NaOH (3.06 g, 77 mmol), and then the mixture was stirred at room temperature for 19 h. The reaction mixture was quenched with H$_2$O, and the mixture was vigorously stirred for 1 h. The mixture was further diluted with CH$_2$Cl$_2$ and the mixture was successively washed with H$_2$O and brine, and the organic layer then dried over Na$_2$SO$_4$, filtered, and concentrated. The resulting residue was triturated with MeOH and the solid was collected by filtration to afford the title compound, which was used in the next reaction without the need for further purification. MS (ESI−) m/z 387.2, 389.2. (M−H).

Intermediate 1-2-C; 5-bromo-7-methyl-1-tosyl-1H-indole-4-carbaldehyde

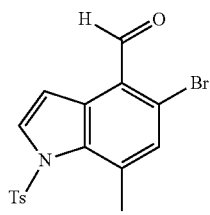 [SMILES: Cc1ccc(S(=O)(=O)n2ccc3c(C=O)c(Br)cc(C)c32)cc1]

To a solution of 5-bromo-7-methyl-1-tosyl-1H-indole-4-carbonitrile, Intermediate 1-2-B, (10 g, 25.7 mmol) in toluene (500 mL) at −78° C. was added 1 M DIBAL-H (38.5 mL, 38.5 mmol) in toluene over 10 min. The mixture was then stirred at −78° C. for ca. 75 minutes. The reaction was then quenched with MeOH at −78° C. To the mixture was then added 5 N aq. HCl (100 mL), and the reaction mixture was then placed at room temperature for 2 h at which time an excess of solid Na$^+$/K$^+$ tartrate (Rochelle's Salt) was added followed by H$_2$O (100 mL). The mixture was then vigorously stirred at room temperature for ca. 3 h and then diluted with EtOAc. The mixture was filtered through a plug of Celite®, and the filtrate was partitioned. The organic phase was successively washed with 5% aq. NaHCO$_3$, H$_2$O, and brine, dried over Na$_2$SO$_4$, filtered, and concentrated to furnish the title compound without the need for further purification. MS (ESI+) m/z 392.0; 394.0 (M+H).

Intermediate 1-2-D; 5-bromo-7-methyl-1H-indole-4-carbaldehyde

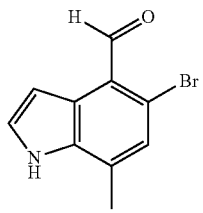

To a solution of 5-bromo-7-methyl-1-tosyl-1H-indole-4-carbaldehyde, Intermediate 1-2-C, (6.5 g, 16.57 mmol) in 1,4-dioxane (50 mL)/H$_2$O (5 mL) was added KOH (2 g, 35.6 mmol). The mixture was stirred at 100° C. for ca. 3 h. The reaction mixture was then diluted with CH$_2$Cl$_2$, and the mixture was washed with H$_2$O and brine, and the organic layer dried over Na$_2$SO$_4$, filtered, and concentrated to furnish the title compound without the need for further purification. MS (ESI−) m/z 235.9, 238.0 (M−H).

Intermediate 1-2-E; tert-butyl 5-bromo-4-formyl-7-methyl-1H-indole-1-carboxylate

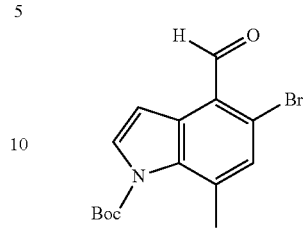

To a solution of 5-bromo-7-methyl-1H-indole-4-carbaldehyde, Intermediate 1-2-D, (3.6 g, 15.12 mmol) in CH$_3$CN was added Boc$_2$O (7.02 mL, 30.2 mmol), followed by DMAP (0.185 g, 1.512 mmol). The mixture was stirred at room temperature for ca. 1 h. Then the reaction was quenched with H$_2$O. The whole mixture was vigorously stirred for 0.5 h. The mixture was then diluted with CH$_2$Cl$_2$. The organic phase was then washed successively with H$_2$O and brine, dried over Na$_2$SO$_4$, filtered, and concentrated. The resulting residue was purified by silica gel flash column chromatography [heptane/30% EtOAc in CH$_2$Cl$_2$=85/15] to give the title compound. MS (ESI+) m/z 338.0, 340.0 (M+H)+.

Intermediate 1-2; tert-butyl 5-cyclopropyl-4-formyl-7-methyl-1H-indole-1-carboxylate

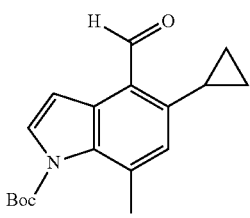 [SMILES: Cc1cc(C2CC2)c(C=O)c2ccn(C(=O)OC(C)(C)C)c12]

To a suspension of tert-butyl 5-bromo-4-formyl-7-methyl-1H-indole-1-carboxylate, Intermediate 1-2-E, (9.5 g, 14.05 mmol) in toluene (50 mL)/H$_2$O (20 mL) at room temperature was added Cs$_2$CO$_3$ (27.5 g, 84 mmol), potassium cyclopropyltetrafluoroborate (4.16 g, 28.1 mmol), and Ru-Phos (CAS: 787618-22-8) (2.62 g, 5.62 mmol), followed by Pd(OAc)$_2$ (0.631 g, 2.81 mmol). The whole mixture was then stirred at 100° C. for 2 h. The reaction mixture was cooled down to room temperature and diluted with CH$_2$Cl$_2$. The organic layer was washed successively with H$_2$O and brine, dried over Na$_2$SO$_4$, filtered and concentrated. The resulting residue was purified by silica gel flash column chromatography [heptane/(30% EtOAc in CH$_2$Cl$_2$)=82/18]. The resulting solid was triturated with heptane to furnish the title compound. MS (ESI+) m/z 300.3 (M+H)+.

Intermediate 1-3:

Intermediate 1-3-A; tert-butyl 5-methoxy-7-methyl-1H-indole-1-carboxylate

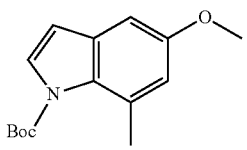 [SMILES: COc1cc(C)c2c(ccn2C(=O)OC(C)(C)C)c1]

To a solution of 5-methoxy-7-methyl-1H-indole (CAS: 61019-05-4, 9.69 g, 60.1 mmol) in CH$_2$Cl$_2$ (200 mL) at room temperature was added Boc$_2$O (19.54 ml, 84 mmol), DMAP (0.734 g, 6.01 mmol), and Et$_3$N (10.05 ml, 72.1 mmol). The mixture was then stirred for 16 h. The reaction was diluted with CH$_2$Cl$_2$ and saturated NH$_4$Cl. The aqueous phase was extracted three times with CH$_2$Cl$_2$. The organic phase was washed with brine, dried over Na$_2$SO$_4$, filtered, and concentrated. The resulting residue was purified by silica gel flash column chromatography (EtOAc/heptanes) to provide the title compound. MS (ESI+) m/z 262.2 (M+H).

Intermediate 1-3; tert-butyl 4-formyl-5-methoxy-7-methyl-1H-indole-1-carboxylate

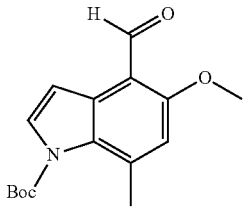 [SMILES: COc1cc(C)c2c(ccn2C(=O)OC(C)(C)C)c1C=O]

To a solution of N-methylformanilide (10.49 ml, 85 mmol) in CH$_2$Cl$_2$ (68 mL) at room temperature was added oxalyl chloride (7.44 ml, 85 mmol) dropwise over 30 min. The mixture was then stirred for 16 h at room temperature. The mixture was then added dropwise over 45 min to a solution of tert-butyl 5-methoxy-7-methyl-1H-indole-1-carboxylate, Intermediate 1-3-A, (16.99 g, 65 mmol) in CH$_2$Cl$_2$ (70 mL) at −14° C. The resulting mixture was stirred for 1.5 h at −14° C. The reaction was quenched with ice water and then extracted three times with CH$_2$Cl$_2$. The organic phase was then washed with brine, dried over Na$_2$SO$_4$, filtered, and concentrated. The resulting residue was purified by silica gel flash column chromatography (EtOAc/heptanes) to provide the title compound. MS (ESI+) m/z 290.1 (M+H).

Intermediate 1-4:

Intermediate 1-4-A; (2-chloro-4-methyl-5-nitrophenyl)methanol

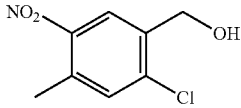

To a solution of 2-chloro-4-methyl-5-nitrobenzoic acid (CAS; 101580-96-5, 15 g, 69.6 mmol) and triethylamine (11.1 mL, 80 mmol) in THF (200 mL) was added 1,1,1-trichloro-2-methylpropan-2-yl carbonochloridate (19.2 g, 80 mmol) at 0° C., and then the mixture was stirred at 0° C. for 1 hr. The resulting white solid was filtered off through a plug of Celite®, which was rinsed with THF (20 mL). To the filtrate was added NaBH$_4$ (3.2 g, 83 mmol) at 0° C., followed by H$_2$O (50 mL). The mixture was stirred at 0° C. for 0.5 h, and then stirred at room temperature for 1.25 h. The reaction was quenched by half satd. aq. KHSO$_4$. The layers were separated and the aqueous layer was extracted with CH$_2$Cl$_2$. The combined organic layers were washed successively with H$_2$O and brine, dried over Na$_2$SO$_4$, and then filtered through a plug of SiO$_2$, which was rinsed with EtOAc. The residue was concentrated and then triturated with heptane. The resulting solid was collected by filtration to give the title compound. $^1$H NMR (400 MHz, CD$_3$CN) δ 8.11 (s, 1H), 7.47 (s, 1H), 4.68 (s, 2H), 2.53 (s, 3H).

Intermediate 1-4-B; 2-((2-chloro-4-methyl-5-nitrobenzyl)oxy)tetrahydro-2H-pyran

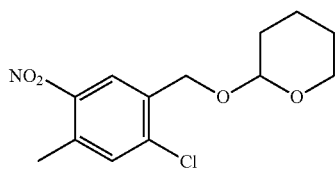 [SMILES: Cc1cc(Cl)c(COC2CCCCO2)cc1[N+](=O)[O-]]

To a solution of (2-chloro-4-methyl-5-nitrophenyl)methanol, Intermediate 1-4-A, (23 g, 114 mmol) and 3,4-dihydro-2H-pyran (20.9 mL, 228 mmol) in CH$_2$Cl$_2$ (500 mL) was added pyridinium p-toluenesulfonate (5.7 g, 22.8 mmol), and then the mixture was stirred at room temperature for 11 h. The reaction was quenched with 5% aq. NaHCO$_3$. The layers were separated and the aqueous layer was extracted with CH$_2$Cl$_2$. The combined organic layers were washed successively with H$_2$O and brine, dried over Na$_2$SO$_4$, filtered and concentrated. The resulting residue was purified by silica gel flash column chromatography (heptane/EtOAc=96/4) to give the title compound. $^1$H NMR (400 MHz, CD$_3$CN) δ 8.10 (s, 1H), 7.49 (s, 1H), 4.81 (d, J=13.64 Hz, 1H), 4.72-4.78 (m, 1H), 4.59 (d, J=13.64 Hz, 1H), 3.77-3.92 (m, 1H), 3.34-3.60 (m, 1H), 2.54 (s, 3H), 1.68-1.91 (m, 2H), 1.43-1.68 (m, 4H).

Intermediate 1-4-C; 5-chloro-7-methyl-4-(((tetrahydro-2H-pyran-2-yl)oxy)methyl)-1H-indole

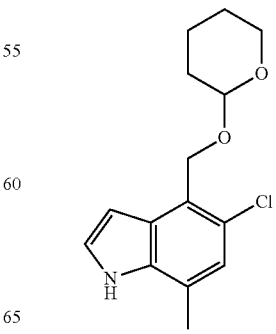

To a suspension of vinylmagnesium bromide (1M in THF, 200 mL, 200 mmol) was added dropwise 2-((2-chloro-4-methyl-5-nitrobenzyl)oxy)tetrahydro-2H-pyran, Intermediate 1-4-B, (14 g, 49.0 mmol) in THF (40 mL) below −20° C. After completion of the addition, the flask was removed from the ice bath. The mixture was then stirred at room temperature. After 2 h, the reaction mixture was cooled to below −20° C. The reaction was quenched with MeOH while maintaining the temperature below 0° C. The mixture was diluted with $CH_2Cl_2$ and $H_2O$. The mixture was filtered through a plug of Celite®, which was rinsed with $CH_2Cl_2$. The layers were separated and the organic phase was washed with $H_2O$ and brine, dried over $Na_2SO_4$, and then filtered. Concentration of the filtrate gave the title compound, which was used in the next reaction without any further purification. For the characterization purpose, the product was purified by silica gel flash column chromatography [heptane/(30% EtOAc in $CH_2Cl_2$)]=69/31] to afford the title compound. $^1$H NMR (400 MHz, $CD_3CN$) δ 9.43 (br. s., 1H), 7.29-7.36 (m, 1H), 6.99 (s, 1H), 6.58-6.70 (m, 1H), 5.05 (d, J=11.12 Hz, 1H), 4.84 (d, J=11.10 Hz, 1H), 4.67-4.77 (m, 1H), 3.89-4.03 (m, 1H), 3.46-3.60 (m, 1H), 2.47 (s, 3H), 1.59-1.75 (m, 2H), 1.43-1.59 (m, 4H).

Intermediate 1-4-D; 5-chloro-7-methyl-4-(((tetrahydro-2H-pyran-2-yl)oxy)methyl)-1-tosyl-1H-indole

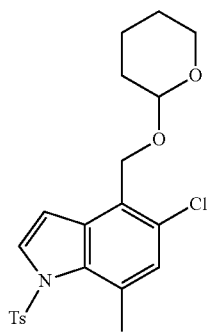 [SMILES: Cc1ccc(S(=O)(=O)n2ccc3c(COC4CCCCO4)c(Cl)cc(C)c32)cc1]

To a solution of 5-chloro-7-methyl-4-(((tetrahydro-2H-pyran-2-yl)oxy)methyl)-1H-indole, Intermediate 1-4-C, (8.95 g, 32 mmol) in $CH_2Cl_2$ (150 mL), at 0° C. was added NaOH (2.56 g, 64.0 mmol), followed by triethylbenzylammonium chloride (0.729 g, 3.20 mmol) and TsCl (12.20 g, 64.0 mmol). The mixture was then stirred at room temperature. After 17 h, additional NaOH (1.28 g, 32.0 mmol), and TsCl (6.10 g, 32.0 mmol) were added. The mixture was stirred at room temperature for 1.5 h. The reaction mixture was diluted with $H_2O$, and was vigorously stirred for 1 h. The mixture was diluted with $CH_2Cl_2$ and the organic layer was successively washed with $H_2O$ and brine, dried over $Na_2SO_4$, filtered, and then concentrated. The resulting residue was purified by silica gel flash column chromatography [heptane/(30% EtOAc in $CH_2Cl_2$)=82/18 then 79/21] to give the title compound. $^1$H NMR (400 MHz, $CD_3CN$) δ 7.84 (d, J=3.79 Hz, 1H), 7.67 (d, J=8.20 Hz, 1H), 7.59 (d, J=8.59 Hz, 1H), 7.48 (d, J=8.20 Hz, 1H), 7.33 (d, J=8.50 Hz, 1H), 7.13 (s, 1H), 6.97 (d, J=3.79 Hz, 1H), 4.97 (d, J=11.37 Hz, 1H), 4.76 (d, J=11.37 Hz, 1H), 4.61-4.70 (m, 1H), 3.79-3.91 (m, 1H), 3.40-3.52 (m, 1H), 2.53 (s, 3H), 2.36 (s, 3H), 1.58-1.75 (m, 2H), 1.38-1.58 (m, 4H).

Intermediate 1-4-E; (5-chloro-7-methyl-1-tosyl-1H-indol-4-yl)methanol

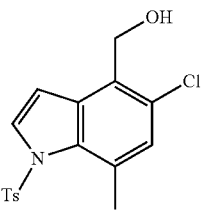 [SMILES: Cc1ccc(S(=O)(=O)n2ccc3c(CO)c(Cl)cc(C)c32)cc1]

A solution of 5-chloro-7-methyl-4-(((tetrahydro-2H-pyran-2-yl)oxy)methyl)-1-tosyl-1H-indole, Intermediate 1-4-D, (4.1 g, 9.5 mmol) and TsOH $H_2O$ (359 mg, 1.9 mmol) in EtOH (50 mL) was stirred at room temperature for 21 h. The reaction mixture was concentrated. The mixture was diluted with $CH_2Cl_2$. The organic phase was successively washed with 5% aq. $NaHCO_3$, $H_2O$ and brine, dried over $Na_2SO_4$, and then filtered. Concentration of the filtrate gave the title compound without the need for further purification. $^1$H NMR (400 MHz, $CD_3CN$) δ 7.84 (d, J=3.79 Hz, 1H), 7.59 (d, J=8.34 Hz, 2H), 7.33 (d, J=8.34 Hz, 2H), 7.10 (s, 1H), 7.00 (d, J=3.79 Hz, 1H), 4.84 (d, J=5.81 Hz, 2H), 3.14 (t, J=5.81 Hz, 1H), 2.52 (s, 3H), 2.37 (s, 3H).

Intermediate 1-4; 5-chloro-7-methyl-1-tosyl-1H-indole-4-carbaldehyde

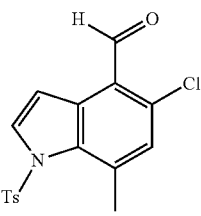 [SMILES: Cc1ccc(S(=O)(=O)n2ccc3c(C=O)c(Cl)cc(C)c32)cc1]

To a solution of (5-chloro-7-methyl-1-tosyl-1H-indol-4-yl)methanol, Intermediate 1-4-E, (3.3 g, 9.5 mmol) and N-ethyl-diisopropylamine (8.3 mL, 47.3 mmol) in $CH_2Cl_2$ (20 mL)/DMSO (1 mL) was added $SO_3$.Py (4.5 g, 28.4 mmol) at 0° C. The mixture was stirred at 0° C. for 2.5 h, and then stirred at room temperature for 15 h. The reaction was quenched by MeOH. The mixture was stirred for 1 h. The mixture was partially concentrated. The mixture was diluted with $H_2O$, and then the resulting solid was collected by filtration. The resulting residue was triturated with MeOH to give the title compound. $^1$H NMR (400 MHz, $CD_3CN$) δ 10.56 (s, 1H), 8.00 (d, J=3.80 Hz, 1H), 7.62 (d, J=3.80 Hz, 1H), 7.60 (d, J=8.60 Hz, 2H), 7.35 (d, J=8.60 Hz, 2H), 7.22 (s, 1H), 2.60 (s, 3H), 2.37 (s, 3H).

Intermediate 1-5:

Intermediate 1-5-A;
5,7-dimethyl-1H-indole-4-carbaldehyde

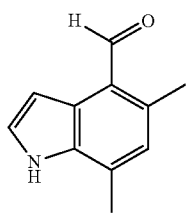

To a solution of 5,7-dimethyl-1-tosyl-1H-indole-4-carbaldehyde, Intermediate 1-1, (2 g, 6.11 mmol) in THF (6 mL) was added TBAF in THF (12 mL, 12 mmol). The mixture was then stirred at 60° C. for 4 h, and then cooled to room temperature. The mixture was then diluted with EtOAc. The organic phase was then washed successively with $H_2O$ (twice), and brine, dried over $Na_2SO_4$, filtered, and concentrated to afford the title compound, which was used in the next reaction without the need for further purification. MS (ESI+) m/z 174.3 (M+H).

Intermediate 1-5; tert-butyl
4-formyl-5,7-dimethyl-1H-indole-1-carboxylate

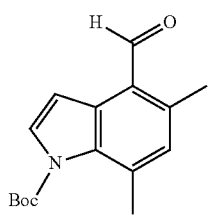 [SMILES: Cc1cc(C)c2c(ccn2C(=O)OC(C)(C)C)c1C=O]

The title compound was synthesized from 5,7-dimethyl-1H-indole-4-carbaldehyde, Intermediate 1-5-A, analogously to the preparation of Intermediate 1-2-E. MS (ESI+) m/z 274.4 (M+H).

Intermediate 1-6:

Intermediate 1-6-A; (5,7-dimethyl-1-tosyl-1H-indol-4-yl)methanol

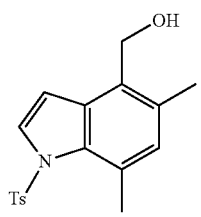 [SMILES: Cc1ccc(S(=O)(=O)n2ccc3c(CO)c(C)cc(C)c32)cc1]

To a solution of 5,7-dimethyl-1-tosyl-1H-indole-4-carbaldehyde, Intermediate 1-1, (3 g, 9.16 mmol) in THF (50 mL)/MeOH (50 mL) at room temperature was added $NaBH_4$ (1 g, 26.4 mmol). The mixture was then stirred at room temperature for 1.5 h, and then quenched with half satd. aq. $KHSO_4$. The mixture was then extracted with EtOAc/TFE (ca. 9/1). The organic layer was then washed successively with $H_2O$, and brine, dried over $Na_2SO_4$, and then concentrated to furnish the title compound without the need for further purification. MS (ESI−) m/z 328.2 (M−H), (ESI+) m/z 312.3 (M−OH).

Intermediate 1-6;
4-(chloromethyl)-5,7-dimethyl-1-tosyl-1H-indole

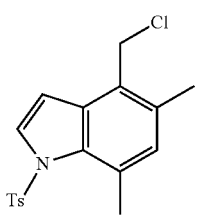

To a solution of (5,7-dimethyl-1-tosyl-1H-indol-4-yl)methanol, Intermediate 1-6-A, (3 g, 9.11 mmol) in $CH_2Cl_2$ (80 mL) at room temperature was added N-(chloromethylene)-N-methylmethanaminium chloride (CAS: 3724-43-4, 2 g, 15.62 mmol). The mixture was then stirred at room temperature for 0.75 h, and then was cooled to 0° C. The reaction was then quenched with 5% aq. $NaHCO_3$ at 0° C. The mixture was then extracted with $EtOAc/CH_2Cl_2$. The organic layer was washed successively with 0.2M aq. LiCl, and brine, dried over $Na_2SO_4$, and then concentrated. The resulting residue was triturated with $Et_2O$, and then the resulting solid was collected by filtration to afford the title compound. MS (ESI+) m/z 312.4 (M−Cl)$^+$.

Intermediate 1-7:

tert-Butyl 4-(chloromethyl)-5,7-dimethyl-1H-indole-1-carboxylate

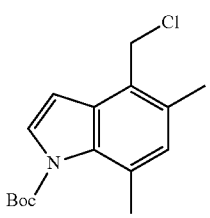 [SMILES: Cc1cc(C)c2c(ccn2C(=O)OC(C)(C)C)c1CCl]

The title compound was synthesized from tert-butyl 4-formyl-5,7-dimethyl-1H-indole-1-carboxylate, Intermediate 1-5, analogously to the preparation of Intermediate 1-6. 1H NMR (400 MHz, $CD_2Cl_2$) δ 7.50 (d, J=3.79 Hz, 1H), 6.87 (s, 1H), 6.56 (d, J=3.79 Hz, 1H), 4.80 (s, 2H), 2.49 (s, 3H), 2.36 (s, 3H), 1.54 (s, 9H).

Intermediate 1-8:

tert-Butyl 4-(chloromethyl)-5-cyclopropyl-7-methyl-1H-indole-1-carboxylate

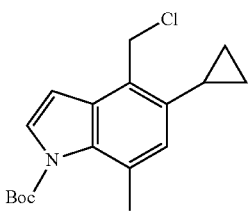 [SMILES: Cc1cc(C2CC2)c(CCl)c2ccn(C(=O)OC(C)(C)C)c12]

The title compound was synthesized from tert-butyl 5-cyclopropyl-4-formyl-7-methyl-1H-indole-1-carboxylate, Intermediate 1-2, analogously to the preparation of Intermediate 1-6. $^1$H NMR (400 MHz, CD$_3$CN) δ 7.63 (d, J=3.79 Hz, 1H), 6.81 (s, 1H), 6.72 (d, J=3.80 Hz, 1H), 5.13 (s, 2H), 2.53 (d, J=0.76 Hz, 3H), 2.11-2.16 (m, 1H), 1.60 (s, 9H), 0.93-1.03 (m, 2H), 0.67-0.74 (m, 2H).

Intermediate 1-9:

5-Chloro-4-(chloromethyl)-7-methyl-1-tosyl-1H-indole

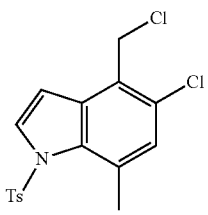 [SMILES: Cc1ccc(S(=O)(=O)n2ccc3c(CCl)c(Cl)cc(C)c32)cc1]

The title compound was synthesized from (5-chloro-7-methyl-1-tosyl-1H-indol-4-yl)methanol, Intermediate 1-4-E, analogously to the preparation of Intermediate 1-6. $^1$H NMR (400 MHz, CD3CN) δ 7.92 (d, J=3.79 Hz, 1H), 7.59 (d, J=8.60 Hz, 2H), 7.33 (d, J=8.60 Hz, 2H), 7.14 (s, 1H), 6.95 (d, J=3.79 Hz, 1H), 2.51 (s, 3H), 2.36 (s, 3H).

Intermediate 1-10 tert-Butyl 4-(hydroxymethyl)-5-methoxy-7-methyl-1H-indole-1-carboxylate

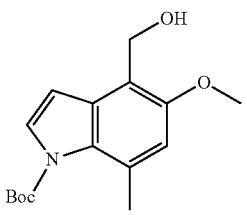 [SMILES: COc1cc(C)c2c(ccn2C(=O)OC(C)(C)C)c1CO]

To a solution of tert-butyl 4-formyl-5-methoxy-7-methyl-1H-indole-1-carboxylate, Intermediate 1-3, (1 g, 3.46 mmol) in MeOH (10 mL) at 0° C. was added NaBH$_4$ (0.3 g, 7.93 mmol). The mixture was then stirred at 0° C. for 5 h. The reaction mixture was diluted with H$_2$O. The mixture was then extracted twice with Et$_2$O. The organic layer was washed successively with H$_2$O, and brine, dried over Na$_2$SO$_4$, and then concentrated to afford the title compound, which was used in the next reaction without the needs of further purification. $^1$H NMR (400 MHz, CD$_3$CN) δ 7.57 (d, J=3.79 Hz, 1H), 6.82 (s, 1H), 6.68 (d, J=3.79 Hz, 1H), 4.72-4.77 (m, 2H), 3.84 (s, 3H), 2.56 (s, 3H), 1.60 (s, 9H).

Intermediate 2-1:

Intermediate 2-1-A; (±)-tert-butyl 4-hydroxy-2-phenylpiperidine-1-carboxylate (Diastereomeric Mixture)

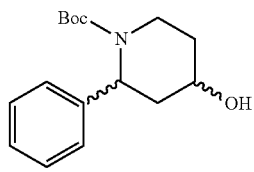

diastereomeric mixture

To a solution of tert-butyl 4-oxo-2-phenylpiperidine-1-carboxylate (CAS: 849928-30-9, 500 mg, 1.816 mmol) in THF (10 mL) at −78° C. was added L-Selectride® (2.2 mL, 2.2 mmol). The mixture was then stirred at −78° C. for ca. 1.75 h. The reaction was then quenched with 7N NH$_3$ in MeOH at −78° C., and then stirred at −78° C. for 5 min. To the mixture was then added satd. aq. NH$_4$Cl, and then stirred at room temperature for 1.5 h. The mixture was then extracted with EtOAc. The organic layer was washed successively with H$_2$O, and brine, dried over Na$_2$SO$_4$, filtered, and concentrated. The resulting residue was purified by silica gel flash column chromatography [heptane/(30% EtOAc in CH$_2$Cl$_2$)=82/18] to afford the title compound as a diastereomeric mixture, which was used in the next reaction without the need for further purification. MS (ESI+) m/z 278.4 (M+H).

Intermediate 2-1; (±)-2-phenylpiperidin-4-ol (Diastereomeric Mixture)

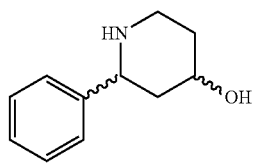

diastereomeric mixture

A mixture of (±)-tert-butyl 4-hydroxy-2-phenylpiperidine-1-carboxylate (diastereomeric mixture), Intermediate 2-1-A, (200 mg, 0.721 mmol) in 4M HCl in dioxane (2 mL) was stirred at room temperature for 1 h. The mixture was concentrated to afford a HCl salt of the title compound as a diastereomeric mixture, which was used in the next reaction without the need for further purification. MS (ESI−) m/z 211.1 (M−H).

Intermediate 2-2:

Intermediate 2-2-A; (±)-tert-butyl 4-methoxy-2-phenylpiperidine-1-carboxylate (Diastereomeric Mixture)

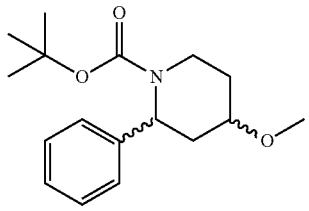

diastereomeric mixture

To a solution of (±)-tert-butyl 4-hydroxy-2-phenylpiperidine-1-carboxylate (diastereomeric mixture), Intermediate 2-1-A, (220 mg, 0.793 mmol) and MeI (100 µL, 1.6 mmol) in DMF (3 mL) at 0° C. was added NaH (70 mg, 1.750 mmol). The mixture was then stirred at 0° C. for 3 h, and then quenched with satd. aq. KHSO$_4$. The mixture was then stirred at the same temperature for 5 min.

The mixture was then extracted with Et$_2$O. The organic layer was washed successively with H$_2$O, and brine, dried over Na$_2$SO$_4$, filtered, and concentrated to afford the title compound as a diastereomeric mixture, which was used in the next reaction without the need for further purification. MS (ESI+) m/z 292.4 (M+H).

Intermediate 2-2; (±)-4-methoxy-2-phenylpiperidine (Diastereomeric Mixture)

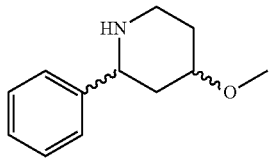

diastereomeric mixture

The title compound was synthesized from (±)-tert-butyl 4-methoxy-2-phenylpiperidine-1-carboxylate (diastereomeric mixture), Intermediate 2-2-A, analogously to the preparation of Intermediate 2-1. MS (ESI+) m/z 192.3 (M+H).

Intermediate 2-3:

Intermediate 2-3-A; (±)-tert-butyl 4-(cyanomethylene)-2-phenylpiperidine-1-carboxylate

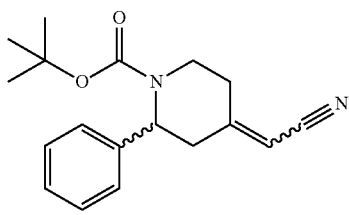 [SMILES: CC(C)(C)OC(=O)N1CCC(=CC#N)CC1c1ccccc1]

To a solution of diethyl cyanomethylphosphonate (1.2 g, 6.77 mmol) in THF (10 mL) at 0° C. was added NaH (60% in oil, 0.27 g, 6.75 mmol). The mixture was then stirred at 0° C. for ca. 1 h. The resulted suspension was diluted with THF (25 mL). To the suspension 0° C. was added a solution of tert-butyl 4-oxo-2-phenylpiperidine-1-carboxylate (CAS: 849928-30-9, 1.2 g, 4.36 mmol) in THF (10 mL). The mixture was then stirred at room temperature for 2 h. The reaction was then quenched with satd. aq. KHSO$_4$. The mixture was then extracted with Et$_2$O. The organic layer was washed successively with H$_2$O, and brine, dried over Na$_2$SO$_4$, filtered, and concentrated. The resulting residue was purified by SiO$_2$ flash column chromatography (heptane/EtOAc=78/22) to afford the title compound as a mixture of isomers. MS (ESI+) m/z 299.7 (M+H).

Intermediate 2-3-B; (±)-tert-butyl 4-(cyanomethyl)-2-phenylpiperidine-1-carboxylate (Diastereomer-1) and (±)-tert-butyl 4-(cyanomethyl)-2-phenylpiperidine-1-carboxylate (Diastereomer-2)

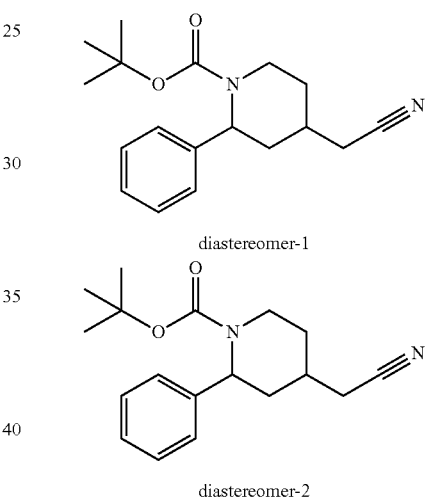

diastereomer-1 diastereomer-2

A suspension of (±)-tert-butyl 4-(cyanomethylene)-2-phenylpiperidine-1-carboxylate, Intermediate 2-3-A, (1 g, 3.35 mmol) and Pd/C (5%) (300 mg, 3.35 mmol) in MeOH (20 mL) was stirred at room temperature under H$_2$ atmosphere for 15.5 h. The H$_2$ gas was replaced with N$_2$. The catalyst was removed by filtration through a plug of Celite®, which was rinsed with MeOH. The filtrate was concentrated. The resulting residue was purified by silica gel flash column chromatography (heptane/EtOAc=80/20) to afford in respective elution order (±)-tert-butyl 4-(cyanomethyl)-2-phenylpiperidine-1-carboxylate (diastereomer-1) and (±)-tert-butyl 4-(cyanomethyl)-2-phenylpiperidine-1-carboxylate (diastereomer-2).

(diastereomer-1); $^1$H NMR (400 MHz, CD$_3$CN) δ 7.34-7.39 (m, 2H), 7.19-7.28 (m, 3H), 5.48 (br. s., 1H), 4.08 (d, J=13.39 Hz, 1H), 2.74 (br. dd, J=12.10, 12.60 Hz, 1H), 2.40-2.48 (m, 1H), 2.36 (d, J=6.10 Hz, 2H), 1.56-1.82 (m, 3H), 1.43 (br. s., 9H), 1.18-1.26 (m, 1H).

(diastereomer-2); $^1$H NMR (400 MHz, CD$_3$CN) δ 7.29-7.35 (m, 2H), 7.19-7.26 (m, 3H), 4.85 (dd, J=5.94, 9.73 Hz, 1H), 3.90-3.97 (m, 1H), 3.25-3.34 (m, 1H), 2.23-2.35 (m, 2H), 1.96-2.10 (m, 2H), 1.66-1.77 (m, 1H), 1.34-1.43 (m, 1H), 1.26 (s, 9H), 0.78-0.91 (m, 1H).

Intermediate 2-3; (±)-2-(2-phenylpiperidin-4-yl)acetonitrile (Diastereomer-1)

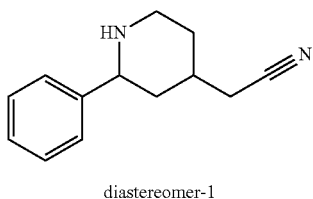 [SMILES: N#CCC1CCNC(c2ccccc2)C1]

diastereomer-1

The title compound was prepared from (±)-tert-butyl 4-(cyanomethyl)-2-phenylpiperidine-1-carboxylate (diastereomer-1), Intermediate 2-3-B, analogously to the preparation of Intermediate 2-1. MS (ESI+) m/z 201.3 (M+H).

Intermediate 2-4:

(±)-(2-(2-Phenylpiperidin-4-yl)acetonitrile (Diastereomer-2)

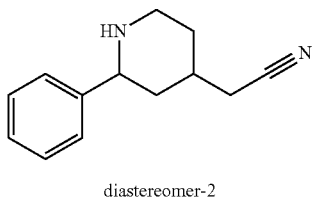 [SMILES: N#CCC1CCNC(c2ccccc2)C1]

diastereomer-2

The title compound was synthesized from (±)-tert-butyl 4-(cyanomethyl)-2-phenylpiperidine-1-carboxylate (diastereomer-2), Intermediate 2-3-B, analogously to the preparation of Intermediate 2-1. MS (ESI+) m/z 201.2 (M+H).

Intermediate 2-5:

Intermediate 2-5-A; (±)-tert-butyl 4-((tert-butylsulfinyl)imino)-2-phenylpiperidine-1-carboxylate

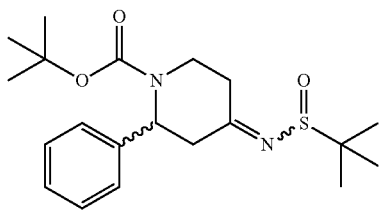 [SMILES: CC(C)(C)OC(=O)N1CCC(=NS(=O)C(C)(C)C)CC1c1ccccc1]

A mixture of (±)-tert-butyl 4-oxo-2-phenylpiperidine-1-carboxylate (CAS: 849928-30-9, 1 g, 3.63 mmol) and (±)-2-methylpropane-2-sulfinamide (0.6 g, 4.95 mmol) in Zr(O-tBu)$_4$ in toluene (15 mL, 7.50 mmol) was stirred at 100° C. for 1.75 h. The reaction mixture was cooled to room temperature, and diluted with CH$_2$Cl$_2$. To the mixture was then added Celite®, followed by 5% aq. NaHCO$_3$. The mixture was stirred for 0.25 h, and then filtered through a plug of Celite®. The filtrate was then extracted with CH$_2$Cl$_2$. The organic phase was then successively washed with 5% aq. NaHCO$_3$, H$_2$O, and brine, dried over Na$_2$SO$_4$, filtered, and concentrated to afford the title compound, which was used in the next reaction without the needs of further purification. MS (ESI+) m/z 379.4 (M+H).

Intermediate 2-5-B; (±)-tert-butyl 4-(1,1-dimethylethylsulfinamido)-2-phenylpiperidine-1-carboxylate

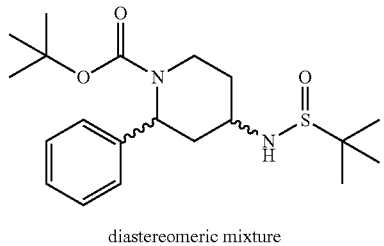 [SMILES: CC(C)(C)OC(=O)N1CCC(NS(=O)C(C)(C)C)CC1c1ccccc1]

diastereomeric mixture

To a solution of (±)-tert-butyl 4-((tert-butylsulfinyl)imino)-2-phenylpiperidine-1-carboxylate, Intermediate 2-5-A, (600 mg, 1.585 mmol) in MeOH (15 mL) at 0° C. was added NaBH$_4$ (600 mg, 15.86 mmol). The mixture was then stirred at room temperature for ca. 1 h, and then diluted with H$_2$O. The mixture was then extracted with EtOAc. The organic phase was successively washed with 5% aq. NaHCO$_3$, H$_2$O, and brine, dried over Na$_2$SO$_4$, filtered, and concentrated to afford the title compounds as a diastereomeric mixture, which was used in the next reaction without the need for further purification. MS (ESI+) m/z 381.4 (M+H).

Intermediate 2-5-C; (±)-tert-butyl 4-amino-2-phenylpiperidine-1-carboxylate

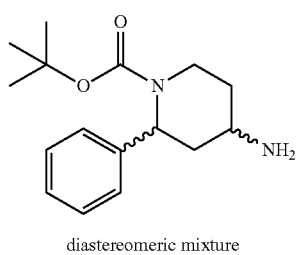 [SMILES: CC(C)(C)OC(=O)N1CCC(N)CC1c1ccccc1]

diastereomeric mixture

A solution of (±)-tert-butyl 4-(1,1-dimethylethylsulfinamido)-2-phenylpiperidine-1-carboxylate, Intermediate 2-5-B, (60 mg, 1.579 mmol) in 0.5M HCl in MeOH (20 mL) was stirred at room temperature for 0.5 h, and then quenched with 5% aq. NaHCO$_3$. The mixture was then extracted with CH$_2$Cl$_2$, and then was successively washed with 5% aq. NaHCO$_3$, H$_2$O, and brine, dried over Na$_2$SO$_4$, filtered, and concentrated to afford the title compounds as a diastereomeric mixture, which was used in the next reaction without the need for further purification. MS (ESI+) m/z 277.4 (M+H).

Intermediate 2-5-D; (±)-tert-butyl 4-(((benzyloxy)carbonyl)amino)-2-phenylpiperidine-1-carboxylate (Diastereomer-1) and (±)-tert-butyl 4-(((benzyloxy)carbonyl)amino)-2-phenylpiperidine-1-carboxylate (Diastereomer-2)

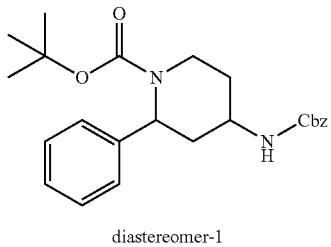

diastereomer-1

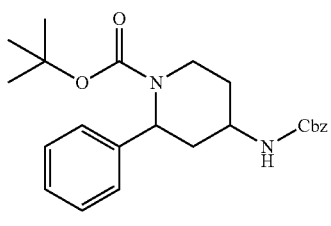

diastereomer-2

To a suspension of (±)-tert-butyl 4-amino-2-phenylpiperidine-1-carboxylate, Intermediate 2-5-C, (434 mg, 1.57 mmol) in CH$_2$Cl$_2$ (10 mL)/5% aq. NaHCO$_3$ (10 mL) was added Cbz-Cl (500 µL, 3.50 mmol). The mixture was then stirred at room temperature for 0.5 h. The reaction was quenched with N,N-dimethylethylenediamine (0.25 mL). The mixture was then stirred at room temperature for 0.5 h. The mixture was then extracted with EtOAc. The organic phase was then washed successively with H$_2$O, 1M HClaq, H$_2$O, 5% aq. NaHCO$_3$, and brine, dried over Na$_2$SO$_4$, filtered, and concentrated. The resulting residue was purified by silica gel flash column chromatography [heptane/(10% MeOH in EtOAc)=74/26] to afford in respective elution order (±)-tert-butyl 4-(((benzyloxy)carbonyl)amino)-2-phenylpiperidine-1-carboxylate (diastereomer-1) and (±)-tert-butyl 4-(((benzyloxy)carbonyl)amino)-2-phenylpiperidine-1-carboxylate (diastereomer-2).

(diastereomer-1); $^1$H NMR (400 MHz, CD$_3$CN) δ 7.17-7.41 (m, 10H), 5.61 (br. d, J=6.10 Hz, 1H), 5.49 (br. s., 1H), 5.02 (s, 2H), 4.06 (br. d, J=13.40 Hz, 1H), 3.41-3.53 (m, 1H), 2.75 (br. dd, J=12.90, 13.10 Hz, 1H), 2.60 (br. d, J=13.10 Hz, 1H), 1.71-1.79 (m, 1H), 1.60-1.71 (m, 1H), 1.43 (s, 9H), 1.28-1.40 (m, 1H).

(diastereomer-2); $^1$H NMR (400 MHz, CD$_3$CN) δ 7.10-7.46 (m, 10H), 5.01-5.17 (m, 2H), 4.92 (s, 2H), 3.89-4.00 (m, 1H), 3.72-3.82 (m, 1H), 3.21-3.32 (m, 1H), 2.19-2.30 (m, 1H), 2.04-2.11 (m, 1H), 1.95-2.01 (m, 1H), 1.50-1.59 (m, 1H), 1.32 (s, 9H).

Intermediate 2-5; (±)-benzyl (2-phenylpiperidin-4-yl)carbamate (Diastereomer-1)

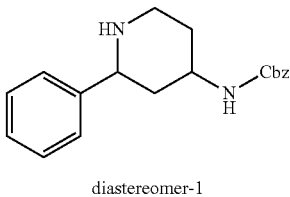 [SMILES: O=C(NC1CCNC(c2ccccc2)C1)OCc1ccccc1]

diastereomer-1

The title compound was synthesized from (±)-tert-butyl 4-(((benzyloxy)carbonyl)amino)-2-phenylpiperidine-1-carboxylate (diastereomer-1), Intermediate 2-5-D, analogously to the preparation of Intermediate 2-1. MS (ESI+) m/z 311.4 (M+H).

Intermediate 2-6:

(±)-Benzyl (2-phenylpiperidin-4-yl)carbamate (Diastereomer-2)

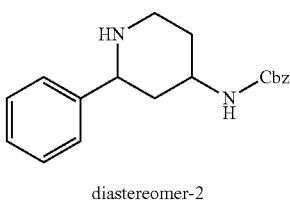 [SMILES: O=C(NC1CCNC(c2ccccc2)C1)OCc1ccccc1]

diastereomer-2

The title compound was synthesized from (±)-tert-butyl 4-(((benzyloxy)carbonyl)amino)-2-phenylpiperidine-1-carboxylate (diastereomer-2), Intermediate 2-5-D, analogously to the preparation of Intermediate 2-1. MS (ESI+) m/z 311.4 (M+H).

Intermediate 2-7:

Intermediate 2-7-A; (±)-tert-butyl 4-methylene-2-phenylpiperidine-1-carboxylate

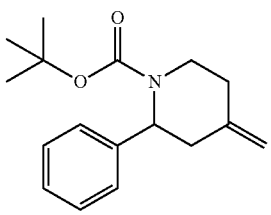 [SMILES: C=C1CCN(C(=O)OC(C)(C)C)C(c2ccccc2)C1]

To a solution of methyl triphenylphosphonium bromide (5 g, 14 mmol) in THF (30 mL) at −78° C. was added n-BuLi (2.5 M, 5.5 mL, 13.75 mmol). The mixture was then stirred at −78° C. for 5 min, and then stirred at 0° C. for 0.5 h. To the mixture at −78° C. was then added a solution of (±)-tert-butyl 4-oxo-2-phenylpiperidine-1-carboxylate (2 g, 7.26 mmol) in THF (10 mL). The mixture was stirred at room temperature for 15 h, and then stirred at 40° C. for 3 h. The reaction was quenched with MeOH (10 mL), and then diluted with Et$_2$O. The mixture was then filtered through a plug of Celite®, which was rinsed with Et$_2$O. The filtrate was concentrated. The resulting residue was purified by silica gel flash column chromatography (heptane/EtOAc=81/19) to afford the title compound. MS (ESI+) m/z 274.4 (M+H).

Intermediate 2-7-B; (±)-tert-butyl 4-(hydroxymethyl)-2-phenylpiperidine-1-carboxylate (Diastereomer-1) and (±)-tert-butyl 4-(hydroxymethyl)-2-phenylpiperidine-1-carboxylate (Diastereomer-2)

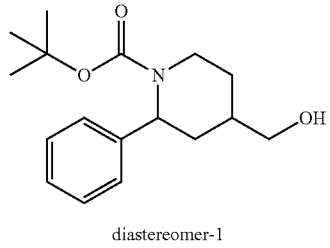

diastereomer-1

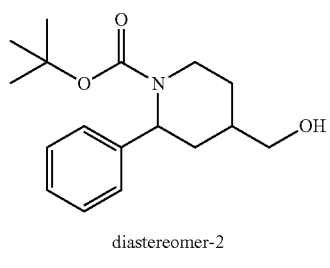

diastereomer-2

A mixture of (±)-tert-butyl 4-methylene-2-phenylpiperidine-1-carboxylate, Intermediate 2-7-A, (580 mg, 2.122 mmol) and 9-BBN in THF (12 mL, 6 mmol) was stirred at room temperature for 2.75 h. The mixture was then cooled to 0° C. To the mixture was then added H$_2$O$_2$ (1 mL, 32.6 mmol) dropwise. The mixture was then stirred at 0° C. for 0.5 h. The mixture was then diluted with EtOAc. The mixture was then washed successively with H$_2$O, aq. Na$_2$S$_2$O$_3$, H$_2$O, and brine, dried over Na$_2$SO$_4$, filtered, and concentrated. The resulting residue was purified by silica gel flash column chromatography (heptane/EtOAc=68/32) to afford, in respective elution order, (±)-tert-butyl 4-(hydroxymethyl)-2-phenylpiperidine-1-carboxylate (diastereomer-1) and (±)-tert-butyl 4-(hydroxymethyl)-2-phenylpiperidine-1-carboxylate (diastereomer-2).

(diastereomer-1); $^1$H NMR (400 MHz, CD$_3$CN) δ 7.32-7.38 (m, 2H), 7.18-7.26 (m, 3H), 5.44 (br. s., 1H), 4.24-4.37 (m, 1H), 4.05 (br. d, J=12.60 Hz, 1H), 3.27-3.34 (m, 1H), 2.67-2.80 (m, 1H), 2.38 (br. d, J=10.90 Hz, 1H), 1.47-1.85 (m, 18H), 1.41 (br. s, 12H), 1.02-1.15 (m, 1H).

(diastereomer-2); $^1$H NMR (400 MHz, CD$_3$CN) δ 7.26-7.35 (m, 2H), 7.14-7.26 (m, 3H), 4.78 (dd, J=6.06, 10.36 Hz, 1H), 3.88-3.98 (m, 1H), 3.28-3.37 (m, 1H), 3.18-3.27 (m, 2H), 2.58 (t, J=5.43 Hz, 1H), 1.97-2.06 (m, 1H), 1.69-1.89 (m, 2H), 1.49-1.61 (m, 1H), 1.28-1.39 (m, 1H), 1.26 (s, 9H).

Intermediate 2-7; (±)-(2-phenylpiperidin-4-yl)methanol (Diastereomer-1)

diastereomer-1

The title compound was synthesized from (±)-tert-butyl 4-(hydroxymethyl)-2-phenylpiperidine-1-carboxylate (diastereomer-1), Intermediate 2-7-B, analogously to the preparation of Intermediate 2-1. MS (ESI+) m/z 192.3 (M+H). Intermediate 2-8:

(±)-(2-Phenylpiperidin-4-yl)methanol (Diastereomer-2)

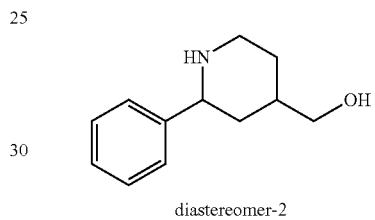

diastereomer-2

The title compound was synthesized from (±)-tert-butyl 4-(hydroxymethyl)-2-phenylpiperidine-1-carboxylate (diastereomer-2), Intermediate 2-7-B, analogously to the preparation of Intermediate 2-1. MS (ESI+) m/z 192.3 (M+H). Intermediate 2-9:

Intermediate 2-9-A; (±)-tert-butyl 2-(3-sulfamoylphenyl)piperidine-1-carboxylate and (±)-tert-butyl 2-(4-sulfamoylphenyl)piperidine-1-carboxylate

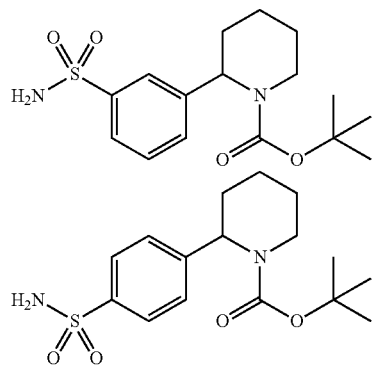

At 0° C., chlorosulfonic acid (0.536 mL, 8.00 mmol) was added dropwise to (±)-2-phenylpiperidine (0.322 g, 2 mmol). The reaction mixture was stirred at 60° C. for 0.5 h. The reaction mixture was then cooled to 0° C. To the mixture was then added dropwise 7N NH$_3$ in MeOH (30 mL) at 0° C. The mixture was then stirred at room temperature for 1 h, and then concentrated. The resulting residue was suspended in CH₃CN (20 mL). To the mixture were added Boc₂O (1.393 mL, 6.00 mmol) and DMAP (200 mg, 1.64 mmol). The mixture was stirred at 60° C. for 3 hr, and then concentrated. The resulting residue was then dissolved in H₂O, and extracted twice with EtOAc. The combined organic layers were dried over Na₂SO₄, filtered and concentrated. The resulting residue was purified by silica gel flash column chromatography (heptane/EtOAc=1/0 to 2/8) to afford the title compounds as a mixture of regioisomers, which was used in the next reaction without the need for further purification. MS (ESI−) m/z 339.4 (M−H).

Intermediate 2-9; (±)-3-(piperidin-2-yl)benzenesulfonamide and (±)-4-(piperidin-2-yl)benzenesulfonamide

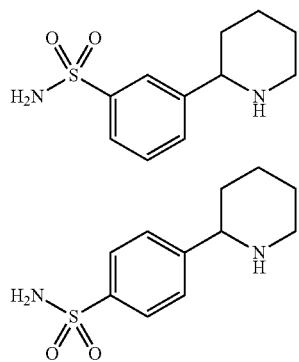

The title compounds (a mixture of regioisomer) were prepared from a mixture of (±)-tert-butyl 2-(3-sulfamoylphenyl)piperidine-1-carboxylate and (±)-tert-butyl 2-(3-sulfamoylphenyl)piperidine-1-carboxylate, Intermediate 2-9-A, analogously to the preparation of Intermediate 2-1. MS (ESI+) m/z 241.3 (M+H).

Intermediate 2-10:

(±)-N-methyl-3-(piperidin-2-yl)benzenesulfonamide and (±)-N-methyl-4-(piperidin-2-yl)benzenesulfonamide

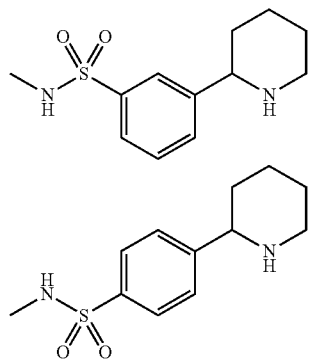

The title compounds (as a mixture of regioisomers) were synthesized analogously to the preparation of Intermediate 2-9 by using 33% MeNH₂ in EtOH in the place of 7N ammonia in MeOH. MS (ESI+) m/z 255.3 (M+H).

Intermediate 2-11:

Intermediate 2-11-A; (±)-phenyl 2-(4-fluorophenyl)-4-oxo-3,4-dihydropyridine-1(2H)-carboxylate

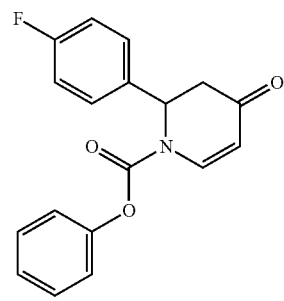 [SMILES: O=C1C=CN(C(=O)Oc2ccccc2)C(c2ccc(F)cc2)C1]

To a solution of 4-methoxypyridine (1.1 g, 10 mmol) in THF (20 mL) at −40° C. was added 4-fluorophenylmagnesium bromide in THF (1M, 11 mL, 11 mmol), followed by phenyl chloroformate (1.566 g, 10.00 mmol) in THF (10 mL) dropwise. The mixture was then stirred at the same temperature for 0.25 h, and then stirred at room temperature for ca. 15 h. The reaction was then quenched with 10% HCl (30 mL), and the whole mixture was stirred for 0.5 h. The reaction is diluted with brine and EtOAc, and the organic layer was then separated. The aqueous layer was extracted three times with EtOAc. The combined organic layers were washed with sat. aq. NaHCO₃, and dried over Na₂SO₄, filtered, and concentrated. The resulting residue was purified by silica gel flash column chromatography (heptane/EtOAc=1/0 to 1/1) to afford the title compound. MS (ESI+) m/z 277.4 (M+H).

Intermediate 2-11-B; (±)-phenyl 2-(4-fluorophenyl)-4-oxopiperidine-1-carboxylate

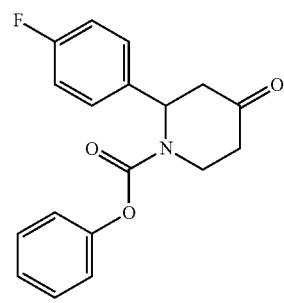 [SMILES: O=C1CCN(C(=O)Oc2ccccc2)C(c2ccc(F)cc2)C1]

A solution of (±)-phenyl 2-(4-fluorophenyl)-4-oxo-3,4-dihydropyridine-1(2H)-carboxylate, Intermediate 2-11-A, (1.090 g, 3.5 mmol) in MeOH (150 mL) was hydrogenated over 10% Pd/C cartridge at 10 bar in an H-cube®. The reaction mixture was concentrated to afford the title compound, which was used in the next reaction without the need for further purification. MS (ESI+) m/z 314.3 (M+H).

Intermediate 2-11-C; (±)-phenyl 2-(4-fluorophenyl)-4-hydroxypiperidine-1-carboxylate

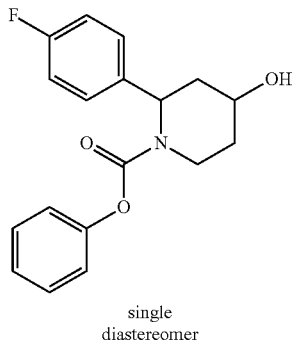 [SMILES: O=C(Oc1ccccc1)N1CCC(O)CC1c1ccc(F)cc1]

single diastereomer

To a solution of (±)-phenyl 2-(4-fluorophenyl)-4-oxopiperidine-1-carboxylate, Intermediate 2-11-B, (1.1 g, 3.51 mmol) in MeOH (20 mL) at room temperature, NaBH₄ (0.266 g, 7.02 mmol) was added. The reaction mixture was stirred at r.t. for 0.5 h, and then quenched with sat. aq. NH₄Cl. The mixture was partially concentrated. The resulting residue was then diluted with brine, and then extracted with EtOAc. The aqueous layer was extracted twice with EtOAc. The combined organic layers were dried over Na₂SO₄, filtered, and concentrated. The resulting residue was purified by silica gel flash column chromatography (heptane/EtOAc=1/0 to 4/6) to afford the title compound. MS (ESI+) m/z 316.4 (M+H).

Intermediate 2-11-D; (±)-phenyl 2-(4-fluorophenyl)-4-methoxypiperidine-1-carboxylate

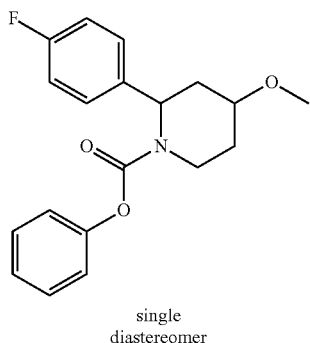 [SMILES: COC1CCN(C(=O)Oc2ccccc2)C(c2ccc(F)cc2)C1]

single diastereomer

To a solution of (±)-phenyl 2-(4-fluorophenyl)-4-hydroxypiperidine-1-carboxylate, Intermediate 2-11-C, (1.37 g, 4.34 mmol) in DMF (20 mL), was added NaH (0.261 g, 6.52 mmol). The reaction mixture was then stirred for 0.25 h at room temperature. To the mixture was then added methyl iodide (0.407 mL, 6.52 mmol). The mixture was stirred at room temperature for 1.5 h, and then quenched with satd. aq. NH4Cl. The reaction mixture was extracted with EtOAc. The organic layer was then concentrated. The resulting residue was purified by silica gel flash column chromatography (heptane/EtOAc=1/0 to 6/4) to afford the title compound as a single diastereomer. ¹H NMR (400 MHz, CD₂Cl₂) δ 7.30-7.37 (m, 4H), 7.16-7.21 (m, 1H), 7.00-7.08 (m, 4H), 5.33-5.38 (m, 1H), 4.10-4.18 (m, 1H), 3.60-3.66 (m, 1H), 3.44 (ddd, J=4.04, 12.22, 13.42 Hz, 1H), 3.11 (s, 3H), 2.39-2.46 (m, 1H), 2.12-2.20 (m, 1H), 1.81-1.98 (m, 2H); MS (ESI+) m/z 330.4 (M+H).

Intermediate 2-11; (±)-2-(4-fluorophenyl)-4-methoxypiperidine

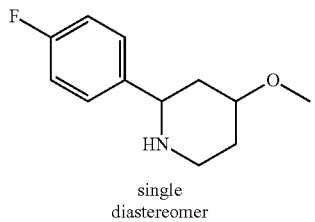

single diastereomer

To a solution of phenyl 2-(4-fluorophenyl)-4-methoxypiperidine-1-carboxylate, Intermediate 2-11-D, (290 mg, 0.88 mmol) in iPrOH (4 mL), KOH (400 mg) was added. The reaction is heated to 100° C. for 2 hr, and then cooled to room temperature. The reaction mixture was diluted with H₂O. The mixture was extracted four times with EtOAc. The combined organic layers were dried over Na₂SO₄, filtered, and concentrated to afford the title compound, which was used in the next reaction without the need for further purification. MS (ESI+) m/z 210.3 (M+H).

Intermediate 2-12:

Intermediate 2-12-A; (±)-benzyl 2-(4-cyanophenyl)-4-oxo-3,4-dihydropyridine-1(2H)-carboxylate

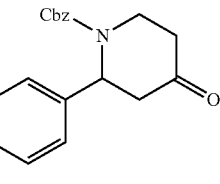

To a solution of 4-bromobenzonitrile (17 g, 93 mmol) in THF (50 mL) at room temperature was added isopropylmagnesium chloride lithium chloride complex solution (1.3M in THF, 70 mL, 91 mmol) dropwise over 0.25 h. The mixture was then stirred at room temperature for 2 h. The mixture was diluted with THF (300 mL), and then cooled to −5° C. To the mixture was then added 4-methoxypyridine (8.37 mL, 82 mmol), followed by Cbz-Cl (12 mL, 84 mmol) while maintain the internal temperature below 0° C. The mixture was then stirred at 0° C. for 1.5 h, and then stirred at room temperature for 16 h. The reaction was then quenched with 5M aq. HCl. The mixture was then stirred at room temperature for 0.5 h. The mixture was then diluted with EtOAc. The mixture was then washed with H₂O twice, 5% aq. NaHCO₃, and brine, dried over Na₂SO₄. The extract was then filtered through a plug of silica gel, which was rinsed with EtOAc. The filtrate was concentrated. The resulting residue was then triturated with Et₂O (ca. 100 mL). The resulted solid was collected by filtration to give the title compound. MS (ESI+) m/z 333.3 (M+H).

Intermediate 2-12-B; (±)-benzyl 2-(4-cyanophenyl)-4-oxopiperidine-1-carboxylate

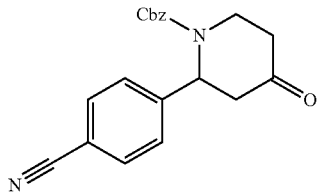 [SMILES: N#Cc1ccc(C2CC(=O)CCN2C(=O)OCc2ccccc2)cc1]

A suspension of (±)-benzyl 2-(4-cyanophenyl)-4-oxo-3,4-dihydropyridine-1(2H)-carboxylate, Intermediate 2-12-A, (13 g, 39.1 mmol) and zinc (5 g, 76 mmol) in AcOH (50 mL) was stirred at 100° C. for 1 h. The reaction mixture was cooled to room temperature. The mixture was filtered through a plug of Celite®, which was rinsed with Et$_2$O. The filtrate was diluted with Et$_2$O. The Et$_2$O layer was then washed successively with H$_2$O, 5% aq. NaHCO$_3$ (twice), H$_2$O (twice), and brine, dried over Na$_2$SO$_4$, filtered, and concentrated to furnish the title compound without the need for further purification. MS (ESI+) m/z 335.3 (M+H).

Intermediate 2-12-C; (±)-benzyl 2-(4-cyanophenyl)-4-hydroxypiperidine-1-carboxylate (Diastereomeric Mixture)

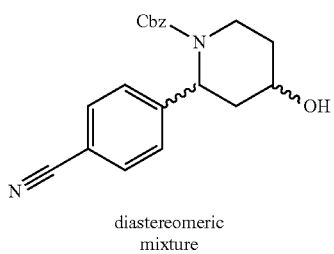 [SMILES: N#Cc1ccc(C2CC(O)CCN2C(=O)OCc2ccccc2)cc1]

diastereomeric mixture

To a solution of (±)-benzyl 2-(4-cyanophenyl)-4-oxopiperidine-1-carboxylate, Intermediate 2-12-B, (8 g, 23.93 mmol) in THF (100 mL) at room temperature was added LiBH$_4$ in THF (20 mL, 40.0 mmol) dropwise. The mixture was then stirred at room temperature for 0.5 h. The reaction was then quenched with half satd. aq. KHSO$_4$. The mixture was then extracted with EtOAc. The organic phase was then washed with brine, dried over Na$_2$SO$_4$, filtered, and concentrated to afford the title compounds as a diastereomeric mixture, which was used in the next reaction without the need for further purification. MS (ESI+) m/z 337.3 (M+H).

Intermediate 2-12-D; (±)-rel-(2S,4S)-benzyl 4-((tert-butyldiphenylsilyl)oxy)-2-(4-cyanophenyl)piperidine-1-carboxylate and (±)-rel-(2S,4R)-benzyl 4-((tert-butyldiphenylsilyl)oxy)-2-(4-cyanophenyl)piperidine-1-carboxylate

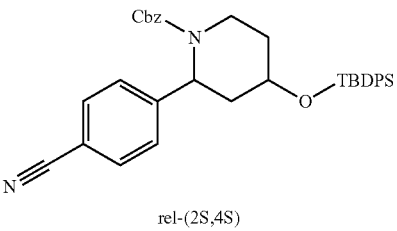

rel-(2S,4S)

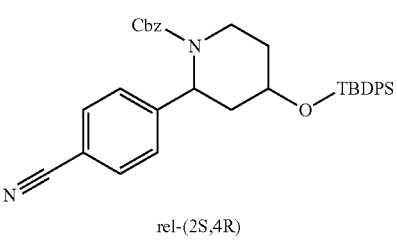

rel-(2S,4R)

To a solution of (±)-benzyl 2-(4-cyanophenyl)-4-hydroxypiperidine-1-carboxylate (diastereomeric mixture), Intermediate 2-12-C, (8.04 g, 23.9 mmol) in DMF (40 mL) at room temperature were added imidazole (5 g, 73.4 mmol) and TBDPS-Cl (8.5 mL, 33.1 mmol). The mixture was then stirred at room temperature for 20.5 h. The reaction was then quenched with MeOH. The mixture was then extracted with EtOAc. The organic phase was then washed successively with H$_2$O, 5% aq. NaHCO$_3$, and brine, dried over Na$_2$SO$_4$, filtered, and concentrated.

The resulting residue was purified by silica gel flash column chromatography (heptane/EtOAc=86/14) to afford in the respective elution order (±)-rel-(2S,4S)-benzyl 4-((tert-butyldiphenylsilyl)oxy)-2-(4-cyanophenyl)piperidine-1-carboxylate and (±)-rel-(2S,4R)-benzyl 4-((tert-butyldiphenylsilyl)oxy)-2-(4-cyanophenyl)piperidine-1-carboxylate.

(±)-rel-(2S,4S)-Benzyl 4-((tert-butyldiphenylsilyl)oxy)-2-(4-cyanophenyl)piperidine-1-carboxylate; $^1$H NMR (400 MHz, CD$_3$CN) δ 7.62-7.67 (m, 2H), 7.57-7.62 (m, 2H), 7.27-7.53 (m, 13H), 6.79-6.83 (m, 2H), 5.43 (br. d, J=4.50 Hz, 1H), 5.06-5.15 (m, 2H), 4.04-4.12 (m, 1H), 3.54-3.63 (m, 1H), 2.60 (dt, J=3.03, 13.64 Hz, 1H), 2.23-2.30 (m, 1H), 1.79-1.89 (m, 2H), 1.59 (ddt, J=5.05, 10.48, 12.82 Hz, 1H), 1.01 (s, 9H).

(±)-rel-(2S,4R)-Benzyl 4-((tert-butyldiphenylsilyl)oxy)-2-(4-cyanophenyl)piperidine-1-carboxylate; $^1$H NMR (400 MHz, CD$_3$CN) δ 7.60-7.64 (m, 2H), 7.22-7.47 (m, 17H), 5.37 (br. d, J=6.60 Hz, 1H), 5.02-5.12 (m, 2H), 4.16-4.21 (m, 1H), 3.99-4.06 (m, 1H), 3.49 (dt, J=3.03, 13.14 Hz, 1H), 2.34-2.41 (m, 1H), 2.01-2.08 (m, 1H), 1.47-1.56 (m, 1H), 1.35-1.41 (m, 1H), 0.73 (s, 9H).

Intermediate 2-12-E; (±)-rel-(2S,4S)-benzyl 2-(4-cyanophenyl)-4-hydroxypiperidine-1-carboxylate

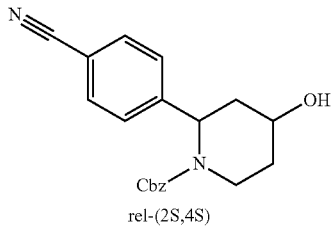 [SMILES: N#Cc1ccc(C2CC(O)CCN2C(=O)OCc2ccccc2)cc1]

rel-(2S,4S)

To a solution of TBAF in THF (1M, 20 mL, 20 mmol) was added (±)-rel-(2S,4S)-benzyl 4-((tert-butyldiphenylsilyl)oxy)-2-(4-cyanophenyl)piperidine-1-carboxylate, Intermediate 2-12-D, (3.5 g, 6.09 mmol). The mixture was then stirred at room temperature for 1.5 h, and then diluted with Et$_2$O. The mixture was then washed successively with H$_2$O, and brine, dried over Na$_2$SO$_4$, filtered, and concentrated to give the title compound. $^1$H NMR (400 MHz, CD$_3$CN) δ 7.64-7.73 (m, 2H), 7.37-7.42 (m, 2H), 7.28-7.36 (m, 5H), 5.57 (br. d, J=5.00 Hz, 1H), 5.09-5.18 (m, 2H), 4.12-4.19 (m, 1H), 3.45-3.55 (m, 1H), 2.89 (d, J=4.52 Hz, 1H), 2.82 (dt, J=3.06, 13.51 Hz, 1H), 2.45-2.53 (m, 1H), 1.71-1.84 (m, 2H), 1.31-1.44 (m, 1H).

Intermediate 2-12-F; (±)-rel-(2S,4S)-benzyl 2-(4-cyanophenyl)-4-methoxypiperidine-1-carboxylate

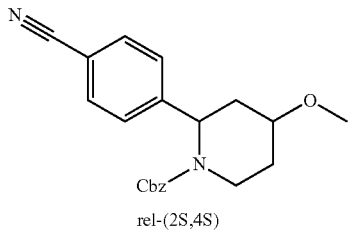 [SMILES: COC1CCN(C(=O)OCc2ccccc2)C(c2ccc(C#N)cc2)C1]

rel-(2S,4S)

The title compound was synthesized from (±)-rel-(2S,4S)-benzyl 2-(4-cyanophenyl)-4-hydroxypiperidine-1-carboxylate, Intermediate 2-12-E, analogously to the preparation of Intermediate 2-2-A. MS (ESI+) m/z 351.4 (M+H).

Intermediate 2-12-G; (±)-4-(rel-(2S,4S)-1-((benzyloxy)carbonyl)-4-methoxypiperidin-2-yl)benzoic acid

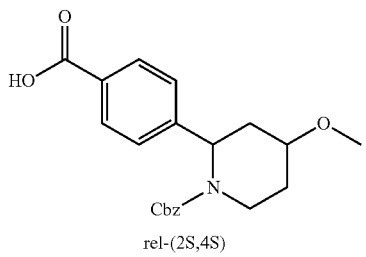 [SMILES: COC1CCN(C(=O)OCc2ccccc2)C(c2ccc(C(=O)O)cc2)C1]

rel-(2S,4S)

A mixture of (±)-rel-(2S,4S)-benzyl 2-(4-cyanophenyl)-4-methoxypiperidine-1-carboxylate, Intermediate 2-12-F, (9 g, 14.38 mmol) and Ba(OH)$_2$ hydrate (16 g, 57.3 mmol) in iPrOH/H$_2$O (15 mL/50 mL) was stirred at 80° C. for 15 h, and then 100° C. for 8 h. The reaction mixture was cooled to room temperature. The precipitate was filtered off through a plug of Celite®. The filtrate was then acidified by 5M aq. HCl (by pH ca. 3). The mixture was then extracted with EtOAc. The organic layer was washed successively with H$_2$O twice, and brine, dried over Na$_2$SO$_4$, filtered, and concentrated to afford the title compound. MS (ESI+) m/z 370.3 (M+H).

Intermediate 2-12-H; (±)-rel-(2S,4S)-benzyl 4-methoxy-2-(4-(methoxycarbonyl)phenyl)piperidine-1-carboxylate

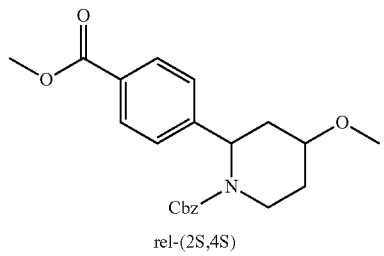

rel-(2S,4S)

To a solution of (±)-4-(rel-(2S,4S)-1-((benzyloxy)carbonyl)-4-methoxypiperidin-2-yl)benzoic acid, Intermediate 2-12-G, (10 g, 15.16 mmol) in MeOH (15 mL) was added HCl in MeOH, which was prepared by addition of SOCl$_2$ (6 mL, 82 mmol) in MeOH (15 mL). The mixture was then stirred at 40° C. for 1.75 h. The reaction mixture was then diluted with CH$_2$Cl$_2$. The organic phase was then washed successively with 5% aq. NaHCO$_3$ (twice), H$_2$O, and brine, dried over Na$_2$SO$_4$, filtered, and concentrated. The resulting residue was purified by silica gel flash column chromatography (heptane/EtOAc=68/32) to afford the title compound. MS (ESI+) m/z 384.3 (M+H).

Intermediate 2-12; (±)-methyl 4-(rel-(2S,4S)-4-methoxypiperidin-2-yl)benzoate

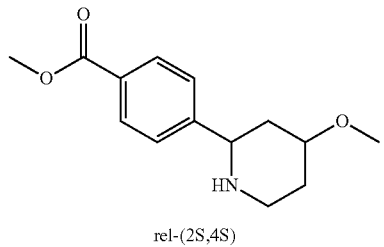

rel-(2S,4S)

A mixture of rel-(2S,4S)-benzyl methoxy-2-(4-(methoxycarbonyl)phenyl)piperidine-1-carboxylate, Intermediate 2-12-H, (6 g, 15.65 mmol) and Pd/C (5%) (1 g, 15.65 mmol) in MeOH (30 mL) was stirred at room temperature under H$_2$ atmosphere for 2 h. The H$_2$ gas was replaced with N$_2$. The catalyst was then removed by filtration through a plug of Celite®, which was rinsed with MeOH. The filtrate was then concentrated to afford the title compound. MS (ESI+) m/z 250.3 (M+H).

Intermediate 2-12b; (+)-methyl 4-(((2S,4S)-4-methoxypiperidin-2-yl))benzoate and (−)-methyl 4-(((2R,4R)-4-methoxypiperidin-2-yl))benzoate

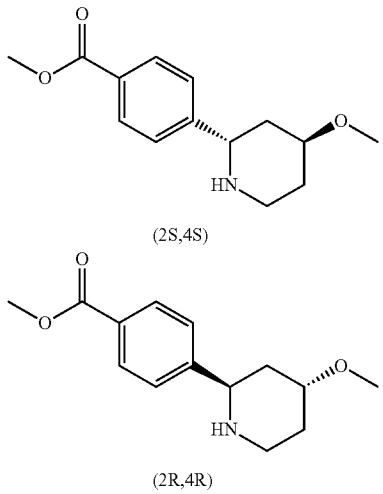

(2S,4S)

(2R,4R)

Resolution of the enantiomers of (±)-methyl 4-(rel-(2S,4S)-(4-methoxypiperidin-2-yl))benzoate, Intermediate 2-12, was achieved by chiral SFC using a CHIRALPAK® AS-H column with 5% (MeOH with 5 mM NH₄OH) in CO₂ to give (+)-methyl 4-((2S,4S)-4-methoxypiperidin-2-yl)benzoate (peak 1, t$_r$=2.8 min) and (−)-methyl 4-((2R,4R)-4-methoxypiperidin-2-yl)benzoate (peak 2, t$_r$=4.1 min). Absolute stereochemistry of (+)-methyl 4-((2S,4S)-4-methoxypiperidin-2-yl)benzoate was confirmed by X-ray single crystal diffraction.

Intermediate 2-13:

Intermediate 2-13-A; (−)-(2S,4S)-benzyl 2-(4-cyanophenyl)-4-hydroxypiperidine-1-carboxylate

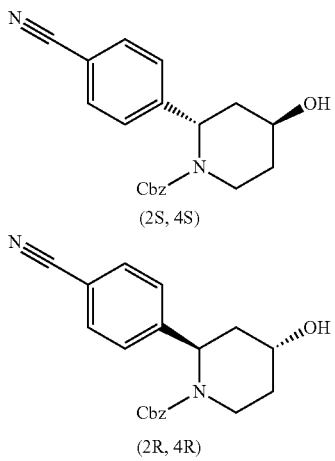

(2S, 4S)

(2R, 4R)

Resolution of the enantiomers of (±)-rel-(2S,4S)-benzyl 2-(4-cyanophenyl)-4-hydroxypiperidine-1-carboxylate, Intermediate 2-12-E, was achieved by chiral SFC using a CHIRALPAK® AD-H column with 25% (MeOH with 5 mM NH₄OH) in CO₂ to give (+)-(2R,4R)-benzyl 2-(4-cyanophenyl)-4-hydroxypiperidine-1-carboxylate (peak-1, t$_r$=2.8 min) and (−)-(2S,4S)-benzyl 2-(4-cyanophenyl)-4-hydroxypiperidine-1-carboxylate (peak-2, t$_r$=4.5 min).

Intermediate 2-13-B; (2S,4S)-benzyl 2-(4-cyanophenyl)-4-ethoxypiperidine-1-carboxylate

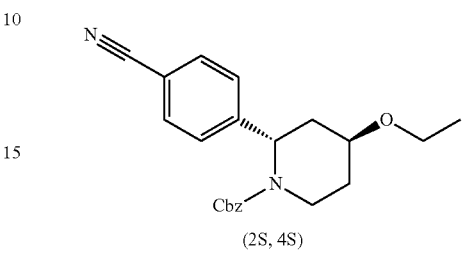

(2S, 4S)

To a solution of (−)-(2S,4S)-benzyl 2-(4-cyanophenyl)-4-hydroxypiperidine-1-carboxylate, Intermediate 2-13-A, (2 g, 5.95 mmol) in DMF (20 mL) at 0° C. was added EtI (1 mL, 12.37 mmol), followed by NaH (60% in oil, 400 mg, 10 mmol). The mixture was then stirred at 15° C. for 1.5 h. The reaction was quenched with MeOH. The mixture was then stirred for 0.25 h. The mixture was then diluted with half satd. aq. KHSO₄, and then extracted with EtOAc. The organic phase was then washed successively with H₂O, 0.5M aq. LiCl, and brine, dried over Na₂SO₄, filtered, and concentrated to furnish the title compound without further purification. MS (ESI+) m/z 365.3 (M+H).

Intermediate 2-13-C; 4-((2S,4S)-1-((benzyloxy)carbonyl)-4-ethoxypiperidin-2-yl)benzoic acid

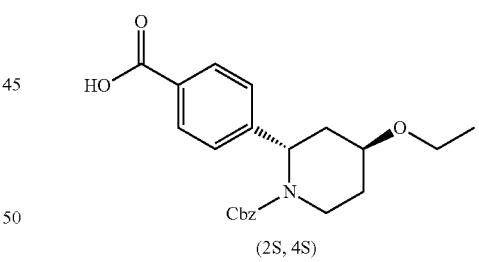

(2S, 4S)

A suspension of (2S,4S)-benzyl 2-(4-cyanophenyl)-4-ethoxypiperidine-1-carboxylate, Intermediate 2-13-B, (2.17 g, 5.95 mmol) and Ba(OH)2 hexahydrate (6 g, 21.5 mmol) in iPrOH/H₂O (15 mL/40 mL) was stirred at 100° C. for 20 h, and then cooled to room temperature. The reaction mixture was then acidified with half satd. aq. KHSO₄. The mixture was then extracted with EtOAc. The organic layer was washed successively with H₂O twice, and brine, dried over Na₂SO₄, filtered, and concentrated to furnish the title compound without further purification. MS (ESI+) m/z 384.3 (M+H).

Intermediate 2-13-D; (2S,4S)-benzyl 4-ethoxy-2-(4-(methoxycarbonyl)phenyl)piperidine-1-carboxylate

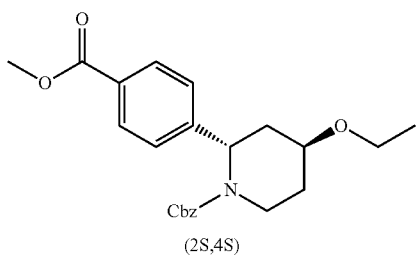 [SMILES: CCO[C@H]1CCN(C(=O)OCc2ccccc2)[C@H](c2ccc(C(=O)OC)cc2)C1]
(2S,4S)

To a solution of 4-((2S,4S)-1-((benzyloxy)carbonyl)-4-ethoxypiperidin-2-yl)benzoic acid, Intermediate 2-13-C (1.0 g, 2.68 mmol) in toluene (10 mL)/MeOH (3 mL) was added TMSCHN$_2$ in Et$_2$O (3 mL, 6 mmol) dropwise. The mixture was then stirred at room temperature for 0.5 h. The reaction was then quenched with AcOH. The mixture was then diluted with EtOAc. The organic phase was then washed successively with 5% aq. NaHCO$_3$ twice, H$_2$O, brine, dried over Na$_2$SO$_4$, filtered, and concentrated. The resulting residue was purified by silica gel flash column chromatography (heptane/EtOAc=66/34) to afford the title compound. MS (ESI+) m/z 398.3 (M+H).

Intermediate 2-13a; methyl 4-((2S,4S)-4-ethoxypiperidin-2-yl)benzoate

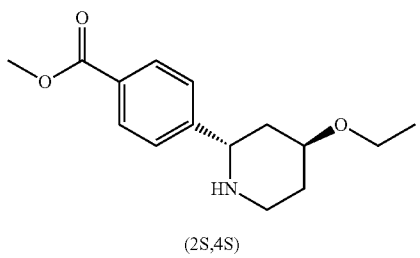 [SMILES: CCO[C@H]1CCN[C@H](c2ccc(C(=O)OC)cc2)C1]
(2S,4S)

A mixture of (2S,4S)-benzyl 4-ethoxy-2-(4-(methoxycarbonyl)phenyl)piperidine-1-carboxylate, Intermediate 2-13-D, (1.8 g, 4.53 mmol) and Pd/C (5%) (200 mg, 4.53 mmol) in MeOH (20 mL) was stirred at room temperature under H$_2$ atmosphere for 5 h. The H$_2$ gas was replaced to N$_2$. The catalyst was then removed by filtration through a plug of Celite®, which was rinsed with MeOH. The filtrate was then concentrated to furnish the title compound without further purification. MS (ESI+) m/z 264.3 (M+H).

Intermediate 2-13b; (±)-methyl 4-(rel-(2S,4S)-4-ethoxypiperidin-2-yl)benzoate

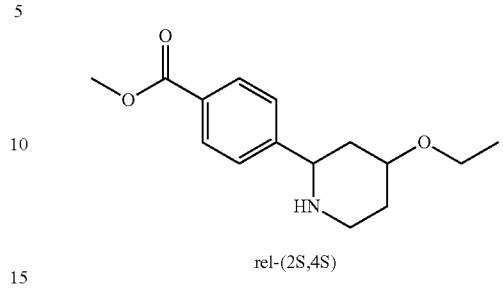
rel-(2S,4S)

The title compound was synthesized from (±)-rel-(2S,4S)-benzyl 2-(4-cyanophenyl)-4-hydroxypiperidine-1-carboxylate, Intermediate 2-12-E, by following methods sequence described in the synthesis of Intermediate 2-13-B, Intermediate 2-13-C, and then Intermediate 2-13-D. Analytical data; same as Intermediate 2-13.

Intermediate 2-14:

Intermediate 2-14-A; (±)-benzyl 2-(4-cyanophenyl)-4-hydroxy-4-methylpiperidine-1-carboxylate (Diastereomeric Mixture)

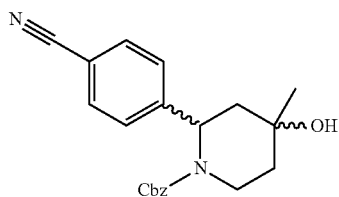 [SMILES: CC1(O)CCN(C(=O)OCc2ccccc2)C(c2ccc(C#N)cc2)C1]

To a mixture of CeCl$_3$ (516 mg, 2.093 mmol) and THF (10 mL) at 0° C. was added MeMgBr (3 M in Et$_2$O) (0.698 ml, 2.093 mmol). The mixture was then stirred at the same temperature for 3 h. To the mixture at 0° C. was then added a solution of (±)-benzyl 2-(4-cyanophenyl)-4-oxopiperidine-1-carboxylate, Intermediate 2-12-B, (500 mg, 1.495 mmol) in THF (6 mL). The mixture was then stirred at room temperature for ca. 16 h, and then quenched with satd. aq. NH$_4$Cl with 10% citric acid. The mixture was then extracted two times with EtOAc. The combined organic layers were then washed with brine, dried over Na$_2$O$_4$, filtered, and concentrated. The resulting residue was purified by silica gel flash column chromatography (heptane/EtOAc=1/0 to 0/1) to afford the title compound as a single diastereomer, which was used in the next reaction without the need for further purification. MS (ESI+) m/z 351.0 (M+H).

Intermediate 2-14-B; (±)-benzyl 2-(4-cyanophenyl)-4-methoxy-4-methylpiperidine-1-carboxylate (Single Diastereomer)

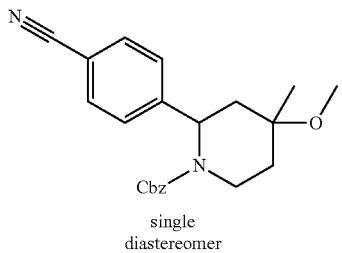 [SMILES: COC1(C)CCN(C(=O)OCc2ccccc2)C(c2ccc(C#N)cc2)C1]

single diastereomer

The title compound was synthesized from (±)-benzyl 2-(4-cyanophenyl)-4-hydroxy-4-methylpiperidine-1-carboxylate (single diastereomer), Intermediate 2-14-A, (70 mg, 0.200 mmol) analogously to the preparation of Intermediate 2-2-A. The product was characterized as follow; $^1$H NMR (400 MHz, CD$_3$CN) δ 7.65 (d, J=8.4 Hz, 2H), 7.39-7.35 (m, 3H), 7.35-7.24 (m, 4H), 5.38 (d, J=6.2 Hz, 1H), 5.14-5.08 (m, 2H), 4.10 (app. ddd, J=2.5, 5.0, 13.4 Hz, 1H), 3.33 (app. dt, J=3.1, 13.2 Hz, 1H), 2.64 (s, 3H), 2.41 (app. td, J=2.3, 14.6 Hz, 1H), 1.54 (app. dt, J=5.0, 13.4 Hz, 1H), 1.32-1.30 (m, 1H), 1.13 (s, 3H), 0.93-0.89 (m, 1H).

Intermediate 2-14; (±)-4-(4-methoxy-4-methylpiperidin-2-yl)benzonitrile (Single Diastereomer)

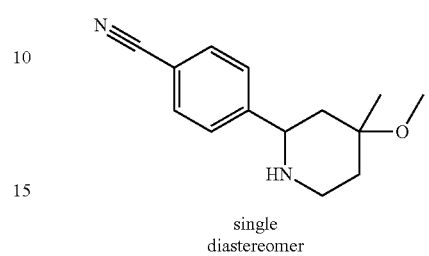

single diastereomer

The title compound was synthesized from (±)-benzyl 2-(4-cyanophenyl)-4-methoxy-4-methylpiperidine-1-carboxylate (single diastereomer), Intermediate 2-14-B, analogously to the preparation of Intermediate 2-12. MS (ESI+) m/z 231.0 (M+H).

Following intermediates were prepared from appropriate starting materials by similar methods described above.

| Intermediate | structure | chemical name starting material | MS (ESI+) (m/z) |
|---|---|---|---|
| 2-15-1 | ![structure] rel-(2S,4S) | (±)-4-(rel-(2S,4S)-4-hydroxypiperidin-2-yl) benzonitrile Intermediate 2-12-E | 203.3 (M + H) |
| 2-15-2 | ![structure] rel-(2S,4R) | (±)-4-(rel-(2S,4R)-4-hydroxypiperidin-2-yl) benzonitrile (±)-rel-(2S,4S)-isomer in Intermediate 2-12-D | 203.3 (M + H) |
| 2-15-3 | ![structure] rel-(2S,4S) | (±)-4-(rel-(2S,4S)-4-methoxypiperidin-2-yl) benzonitrile Intermediate 2-12-F | 217.3 (M + H) |
| 2-15-4 | ![structure] rel-(2S,4R) | (±)-4-(rel-(2S,4R)-4-methoxypiperidin-2-yl) benzonitrile (±)-rel-(2S,4S)-isomer in Intermediate 2-12-D | 217.3 (M + H) |

| Intermediate | structure | chemical name starting material | MS (ESI+) (m/z) |
|---|---|---|---|
| 2-15-5 | ![structure] rel-(2S,4S) | (±)-4-(rel-(2S,4S)-4-ethoxypiperidin-2-yl) benzonitrile Intermediate 2-12-E | 231.4 (M + H) |
| 2-15-6 | ![structure] (2S,4S) | methyl 4-((2S,4S)-4-propoxypiperidin-2-yl)benzoate (2S,4S)-isomer in Intermediate 2-13-A | 278.4 (M + H) |
| 2-15-7 | ![structure] (2S,4S) | methyl 4-((2S,4S)-4-hydroxypiperidin-2-yl) benzoate (2S,4S)-isomer in Intermediate 2-13-A | 236.3 (M + H) |

Intermediate 2-16:

Intermediate 2-16-A; methyl 4-(4-methylpyridin-2-yl)benzoate

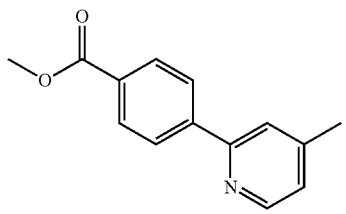

To a suspension of 2-chloro-4-methylpyridine (5 g, 39.2 mmol) and (4-(methoxycarbonyl)phenyl)boronic acid (8 g, 44.5 mmol) in toluene (50 mL) was added 2M aq. Na$_2$CO$_3$ (30 mL) followed by PdCl$_2$(dppf). CH$_2$Cl$_2$ adduct (4 g, 4.90 mmol). The whole mixture was then stirred at 100° C. for 17 h, and then cooled to room temperature. The reaction mixture was then diluted with Et$_2$O, and then separated. The organic layer was dried over Na$_2$SO$_4$, filtered, and concentrated. The resulting residue was purified by silica gel flash column chromatography (heptane/EtOAc=76/24) to afford the title compound. MS (ESI+) m/z 228.1 (M+H).

Intermediate 2-16; (±)-methyl 4-(rel-(2S,4R)-4-methylpiperidin-2-yl)benzoate

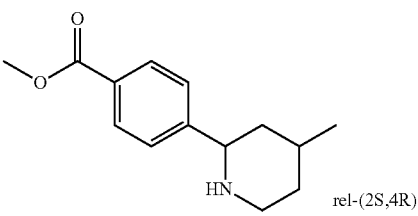

A mixture of methyl 4-(4-methylpyridin-2-yl)benzoate, Intermediate 2-16-A, (3 g, 13.20 mmol) and PtO$_2$ (500 mg, 13.20 mmol) in MeOH (50 mL)/1M HCl in MeOH (2 mL) was stirred at room temperature under H$_2$ atmosphere (50 psi) for 20 h. The H$_2$ gas was replaced with N$_2$. The catalyst was filtered through a plug of Celite®, which was rinsed with MeOH and concentrated. The resulting residue was then dissolved in CH$_2$Cl$_2$, and then washed with 5% aq. NaHCO$_3$ and brine, dried over Na$_2$SO$_4$, filtered, and then concentrated. The resulting residue was purified by silica gel flash column chromatography (0.5% Et$_3$N in CH$_2$Cl$_2$/MeOH=1/0 to 95/5) to afford the title compound isolated as a single diastereomer. $^1$H NMR (400 MHz, CD$_3$OD) δ 7.98 (d, J=8.30 Hz, 2H), 7.47 (d, J=8.30 Hz, 2H), 3.89 (s, 3H), 3.69-3.75 (m, 1H), 3.14-3.21 (m, 1H), 2.74-2.83 (m, 1H), 1.80-1.87 (m, 1H), 1.64-1.76 (m, 2H), 1.12-1.27 (m, 2H), 0.98 (d, J=6.36 Hz, 3H), MS (ESI+) m/z 234.3 (M+H).

Intermediate 2-17:

Intermediate 2-17-A; methyl 2-methoxy-4-(pyridin-2-yl)benzoate

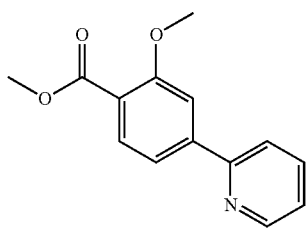 [SMILES: COC(=O)c1ccc(-c2ccccn2)cc1OC]

A mixture of methyl 4-bromo-2-methoxybenzoate (1 g, 4.07 mmol), 2-(tributylstannyl)pyridine (1.84 g, 5.01 mmol), CuI (155 mg, 0.81 mmol), and Pd(PPh$_3$)$_4$ (235 mg, 0.203 mmol) in DMF (8 mL) was stirred at 80° C. for 2 h, and then concentrated. The resulting residue was purified by silica gel flash column chromatography (heptane/EtOAc=8/2) to afford the title compound. MS (APCI+) m/z 244.1 (M+H).

Intermediate 2-17; (±)-methyl 2-methoxy-4-(piperidin-2-yl)benzoate

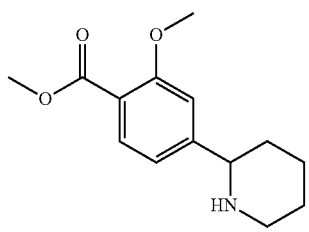 [SMILES: COC(=O)c1ccc(C2CCCCN2)cc1OC]

The title compound was synthesized form methyl 2-methoxy-4-(pyridin-2-yl)benzoate, Intermediate 2-17-A, analogously to the preparation of Intermediate 2-16. (APCI+) 250.2 (M+H).

Following intermediates were prepared from appropriate starting materials by similar methods described above.

| Intermediate | structure | chemical name<br>starting materials | MS<br>(m/z) |
|---|---|---|---|
| 2-18-1 | 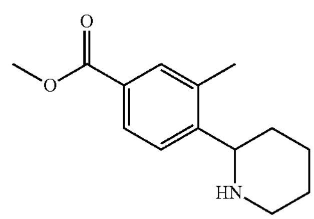 [SMILES: COC(=O)c1ccc(C2CCCCN2)c(C)c1] | (±)-methyl 3-methyl-4-(piperidin-2-yl)<br>benzoate<br>methyl 4-bromo-3-methylbenzoate<br>and 2-(tributylstannyl)pyridine | (APCI+)<br>234.0<br>(M +H) |
| 2-18-2 | single isomer isolated | (±)-methyl 4-(5-methylpiperidin-2-yl)<br>benzoate (single diastereomer)<br>(4-(methoxycarbonyl)phenyl)boronic acid<br>and 2-bromo-5-methylpyridine | (APCI+)<br>234.0<br>(M +H) |
| 2-18-3 | rel-(2S,4R) | (±)-methyl 4-(rel-(2S,4R)-4-<br>ethylpiperidin-2-yl)benzoate<br>2-bromo-4-ethylpyridine and<br>(4-(methoxycarbonyl)phenyl)boronic acid | (ESI+)<br>248.2<br>(M + H) |
| 2-18-4 | 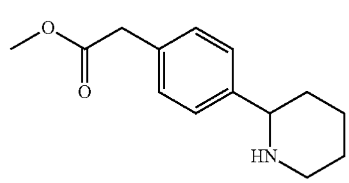 [SMILES: COC(=O)Cc1ccc(C2CCCCN2)cc1] | (±)-methyl 2-(4-(piperidin-2-yl)phenyl)<br>acetate<br>2-bromopyridine and<br>methyl 2-(4-(4,4,5,5-tetramethyl-1,3,2-<br>dioxaborolan-2-yl)phenyl)acetate | (APCI+)<br>234.1<br>(M + H) |

| Intermediate | structure | chemical name<br>starting materials | MS<br>(m/z) |
|---|---|---|---|
| 2-18-5 | 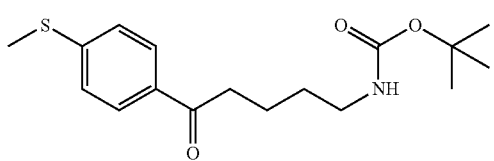 | (±)-methyl 2-(3-(piperidin-2-yl)phenyl)<br>acetate<br>2-bromopyridine and<br>methyl 2-(3-(4,4,5,5-tetramethyl-1,3,2-<br>dioxaborolan-2-yl)phenyl)acetate | (APCI+)<br>234.0<br>(M + H) |
| 2-18-6 | 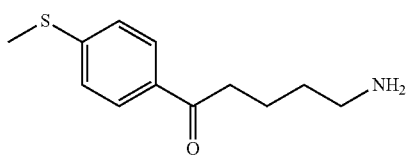 | (±)-methyl 4-(piperidin-2-yl)-1-<br>naphthoate<br>2-bromopyridine and<br>methyl 4-(4,4,5,5-tetramethyl-1,3,2-<br>dioxaborolan-2-yl)-1-naphthoate | (APCI+)<br>270.1<br>(M + H) |

Intermediate 2-19:

Intermediate 2-19-A; tert-butyl (5-(4-(methylthio)phenyl)-5-oxopentyl)carbamate

To a solution of tert-butyl 2-oxopiperidine-1-carboxylate (CAS: 85908-96-9, 4.98 g, 25 mmol) in THF (75 mL) at −78° C. under nitrogen, was added 0.5N (4-(methylthio)phenyl)magnesium bromide in THF (50 mL, 25 mmol) slowly over 10 min. The mixture was stirred at −78° C. for 0.5 h, and then the reaction was quenched with MeOH and half satd. aq. KHSO₄. The mixture was then extracted with EtOAc. The organic layer was concentrated. The resulting residue was purified by silica gel flash column chromatography (heptane/EtOAc=1/0 to 6/4) to afford the title compound. MS (ESI−) m/z 322.3 (M−H).

Intermediate 2-19-B; 5-amino-1-(4-(methylthio)phenyl)pentan-1-one

The title compound was prepared from tert-butyl (5-(4-(methylthio)phenyl)-5-oxopentyl)carbamate, Intermediate 2-19-A, analogously to the preparation of Intermediate 2-1. MS (ESI+) m/z 224.2 (M+H).

Intermediate 2-19-C; (±)-2-(4-(methylthio)phenyl)piperidine

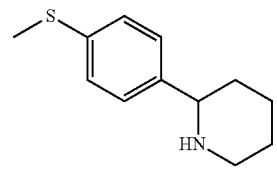

To the suspension of 5-amino-1-(4-(methylthio)phenyl)pentan-1-one, Intermediate 2-19-B, (3.9 g, 15 mmol) in toluene (50 mL), Ti(O-iPr)₄ (12.79 mL, 45.0 mmol) was added slowly. The mixture was stirred at r.t. for 15 min, then heated at 85° C. for 2.5 hr, and then cooled to 0° C. To the mixture was then added a suspension of NaBH₄ (2.27 g, 60 mmol) in MeOH (50 mL) dropwise. After completion of the addition, to the mixture was successively added H₂O, CH₂Cl₂, and Celite®. The mixture was then filtered through a plug of Celite®, which was rinsed with CH₂Cl₂. The organic layer was then separated. The aqueous layer was then extracted twice with CH₂Cl₂. The combined organic layers were dried over Na₂SO₄, filtered, and concentration to furnish the title compound without the need for further purification. MS (ESI+) m/z 208.3 (M+H).

Intermediate 2-19-D; (±)-tert-butyl 2-(4-(methylthio)phenyl)piperidine-1-carboxylate

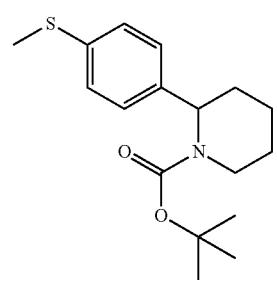 [SMILES: CSc1ccc(C2CCCCN2C(=O)OC(C)(C)C)cc1]

To a solution of (±)-2-(4-(methylthio)phenyl)piperidine, Intermediate 2-19-C, (3 g, 14.47 mmol) in acetonitrile (30 mL), Boc₂O (4.03 mL, 17.36 mmol) and DMAP (0.088 g, 0.723 mmol) were added. The reaction mixture was stirred at 45° C. for 0.5 h, and then concentrated. The resulting residue was purified by silica gel flash column chromatography (heptane/EtOAc=1/0 to 4/6) to afford the title compound. MS (ESI+) m/z 308.4 (M+H).

Intermediate 2-19-E; (±)-tert-butyl 2-(4-(methylsulfonyl)phenyl)piperidine-1-carboxylate

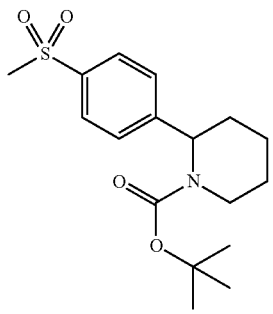 [SMILES: CC(C)(C)OC(=O)N1CCCCC1c1ccc(S(C)(=O)=O)cc1]

To a solution of (±)-tert-butyl 2-(4-(methylthio)phenyl)piperidine-1-carboxylate, Intermediate 2-19-D, (307 mg, 1 mmol) in EtOH (5 mL) at 0° C. was added a mixture of ammonium molybdate tetrahydrate (371 mg, 0.300 mmol) and 50% H₂O₂ in H₂O (1.4 mL) slowly. The mixture was then stirred at room temperature during over ca. 72 h. The reaction mixture was then diluted with H₂O and CH₂Cl₂, and then quenched with Na₂S₂O₃. The mixture was partitioned. The aqueous layer was extracted with CH₂Cl₂. The combined organic layers were dried over Na₂SO₄, filtered, and concentrated. The resulting residue was purified by silica gel flash column chromatography (heptane/EtOAc=1/0 to 0/1) to afford the title compound. MS (ESI+) m/z 340.4 (M+H).

Intermediate 2-19;
(±)-2-(4-(methylsulfonyl)phenyl)piperidine

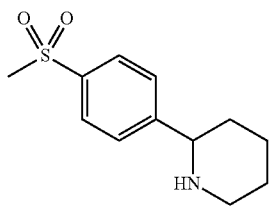 [SMILES: CS(=O)(=O)c1ccc(C2CCCCN2)cc1]

The title compound was prepared from (±)-tert-butyl 2-(4-(methylsulfonyl)phenyl)piperidine-1-carboxylate, Intermediate 2-19-E, analogously to the preparation of Intermediate 2-1. MS (ESI+) m/z 240.3 (M+H).

Intermediate 2-20:

Intermediate 2-20-A; (±)-4-((tert-butyldiphenylsilyl)oxy)piperidin-2-one

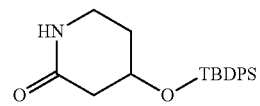

To a solution of (±)-4-hydroxypiperidin-2-one (7.5 g, 65.1 mmol) in DMF (60 mL) at room temperature were added imidazole (6 g, 88 mmol) and TBDPS-Cl (22 mL, 86 mmol). The mixture was then stirred at room temperature for 1.25 h. The mixture was then diluted with H₂O. The mixture was then extracted with EtOAc. The organic phase was then washed successively with H₂O, and brine, dried over Na₂SO₄, filtered, and concentrated to give the title compound, which was used in the next reaction without the need for further purification. MS (ESI+) m/z 354.3 (M+H).

Intermediate 2-20-B; (±)-tert-butyl 4-((tert-butyldiphenylsilyl)oxy)-2-oxopiperidine-1-carboxylate

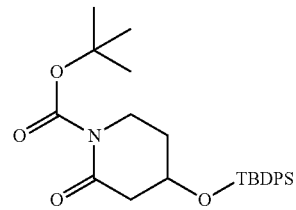

To a solution of (±)-4-((tert-butyldiphenylsilyl)oxy)piperidin-2-one, Intermediate 2-20-A, (23 g, 65 mmol) in CH₂Cl₂ (30 mL) at room temperature were added Boc₂O (21.28 mL, 92 mmol) and Et₃N (13 mL, 94 mmol), followed by DMAP (0.2 g, 1.637 mmol). The mixture was then stirred at room temperature for 7 h. The reaction was then quenched with H₂O. The mixture was then extracted with CH₂Cl₂. The organic phase was then washed successively with H₂O, and brine, dried over Na₂SO₄, filtered, and concentrated. The resulting residue was purified by silica gel column chromatography (heptane/EtOAc=77/23) to afford the title compound. MS (ESI+) m/z 454.4 (M+H).

Intermediate 2-20-C; (±)-tert-butyl (3-((tert-butyldiphenylsilyl)oxy)-5-(6-chloropyridin-3-yl)-5-oxopentyl)carbamate

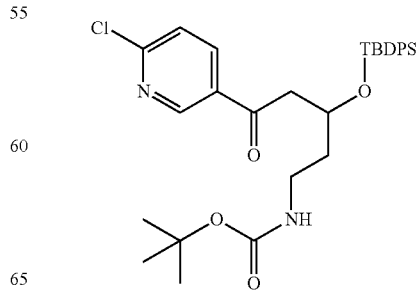

To a solution of 2-chloro-5-iodopyridine (14 g, 58.5 mmol) in THF (50 mL) at 0° C. was added isopropylmagnesium chloride lithium chloride complex in THF (1.3 M, 45 mL, 58.5 mmol). The mixture was then stirred at 0° C. for 1 h. To a solution of (±)-tert-butyl 4-((tert-butyldiphenylsilyl)oxy)-2-oxopiperidine-1-carboxylate, Intermediate 2-20-B, (20 g, 44.1 mmol) in THF (100 mL) at −78° C. was added the mixture above over 15 min. The mixture was then stirred at −78° C. for 10 min. The mixture was then warmed to 0° C., and then stirred for 1 h. The reaction was quenched with MeOH, followed by half satd. aq. KHSO₄. The mixture was warmed to room temperature. The mixture was then extracted with EtOAc. The organic layer was then washed successively with 5% aq. NaHCO₃ and brine, dried over Na₂SO₄, filtered, and concentrated to give the title compound, which was used in the next reaction without the need for further purification. MS (ESI+) m/z 567.2, 569.19 (M+H).

Intermediate 2-20-D; (±)-5-(rel-(2S,4R)-4-((tert-butyldiphenylsilyl)oxy)piperidin-2-yl)-2-chloropyridine

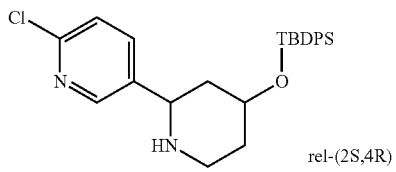

To a solution of (±)-tert-butyl (3-((tert-butyldiphenylsilyl)oxy)-5-(6-chloropyridin-3-yl)-5-oxopentyl)carbamate, Intermediate 2-20-C, (25 g, 44.1 mmol) in CH₂Cl₂ (200 mL) at 0° C. was added 2,6-lutidine (10 mL, 86 mmol), followed by TMSOTf (15 mL, 83 mmol). The mixture was then stirred at 0° C. for 2 h. To the mixture was added an additional amount of 2,6-lutidine (6 mL, 51.5 mmol), followed by TMSOTf (6 mL, 33.2 mmol). The mixture was then stirred at 0° C. for 1 h. The reaction was then quenched with MeOH (50 mL). The mixture was then stirred at the same temperature for 0.25 h. To the mixture was then added NaBH₄ (3 g, 79 mmol). The mixture was then stirred at 0° C. for 1 h. The reaction was then diluted with H₂O. The mixture was then extracted with CH₂Cl₂. The aqueous layer was extracted with CH₂Cl₂. The combined organic layers were then dried over Na₂SO₄, filtered, and concentrated to give the title compound as a single diastereomer, which was used in the next reaction without the need for further purification. MS (ESI+) m/z 451.1, 453.1 (M+H).

Intermediate 2-20-E; (±)-rel-(2S,4R)-benzyl 4-((tert-butyldiphenylsilyl)oxy)-2-(6-chloropyridin-3-yl)piperidine-1-carboxylate

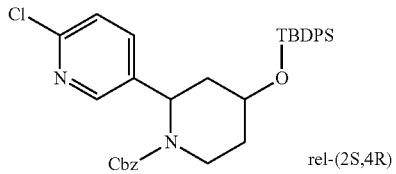

To a solution of (±)-rel-(2S,4R)-4-((tert-butyldiphenylsilyl)oxy)piperidin-2-yl)-2-chloropyridine, Intermediate 2-20-D, (19.85 g, 44 mmol) in CH₂Cl₂ (100 mL) at 0° C. was added Et₃N (10 mL, 72.1 mmol), followed by Cbz-Cl (10 mL, 70.0 mmol) over 0.25 h. The mixture was then stirred at 0° C. for 2 h. The reaction was then quenched with 1M NH₄OH. The mixture was then stirred at room temperature for 0.5 h and diluted with CH₂Cl₂. The organic phase was then washed successively with H₂O, and brine, dried over Na₂SO₄, filtered, and concentrated to give the title compound, which was used in the next reaction without the need for further purification. MS (ESI+) m/z 595.3, 587.2 (M+H).

Intermediate 2-20-F; (±)-rel-(2S,4R)-benzyl 2-(6-chloropyridin-3-yl)-4-hydroxypiperidine-1-carboxylate

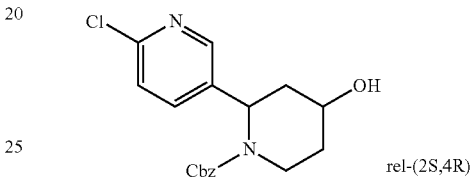

To a solution of (±)-rel-(2S,4R)-benzyl 4-((tert-butyldiphenylsilyl)oxy)-2-(6-chloropyridin-3-yl)piperidine-1-carboxylate, Intermediate 2-20-E, (25.7 g, 44 mmol) in MeOH (100 mL) was added a solution of HCl in MeOH, which was prepared by SOCl₂ (6.5 mL, 89 mmol) and MeOH (100 mL). The mixture was stirred at room temperature for 16 h, and then 2 h at 40° C. The mixture was diluted with CH₂Cl₂. The mixture was then washed successively with 5% aq. NaHCO₃, and brine, dried over Na₂SO₄, filtered, and concentrated. The resulting residue was purified by silica gel flash column chromatography (CH₂Cl₂/EtOAc=61/39 to 25/75) to afford the title compound. MS (ESI+) m/z 347.2, 349.0 (M+H).

Intermediate 2-20-G; (±)-rel-(2S,4S)-benzyl 4-(benzoyloxy)-2-(6-chloropyridin-3-yl)piperidine-1-carboxylate

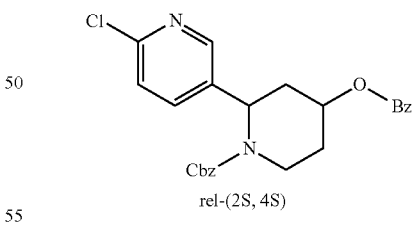

To a solution of (±)-rel-(2S,4R)-benzyl 2-(6-chloropyridin-3-yl)-4-hydroxypiperidine-1-carboxylate, Intermediate 2-20-F, (7 g, 20.18 mmol), benzoic acid (4.2 g, 34.4 mmol), and PPh₃ (8 g, 30.5 mmol) in THF (200 mL) at 0° C. was added DEAD (4.2 mL, 26.5 mmol) over 0.25 h. The mixture was then stirred at 0° C. for 1 h. The reaction was quenched with MeOH. The mixture was then absorbed on silica gel, which was purified by silica gel flash column chromatography [heptane/(30% EtOAc in CH₂Cl₂)=1/0 to 3/7] to afford the title compound. MS (ESI+) m/z 451.1, 453.0 (M+H).

Intermediate 2-20-H; (±)-rel-(2S,4S)-benzyl 2-(6-chloropyridin-3-yl)-4-hydroxypiperidine-1-carboxylate

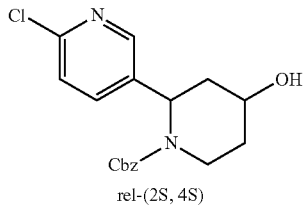 [SMILES: O=C(OCc1ccccc1)N1CCC(O)CC1c1ccc(Cl)nc1]

rel-(2S, 4S)

A suspension of (±)-rel-(2S,4S)-benzyl 4-(benzoyloxy)-2-(6-chloropyridin-3-yl)piperidine-1-carboxylate, Intermediate 2-20-G, (9.02 g, 20 mmol) and $K_2CO_3$ (5 g, 36.2 mmol) in MeOH (100 mL) was stirred at 60° C. for 1.5 h. The reaction mixture was cooled to room temperature. The mixture was diluted with $CH_2Cl_2$. The organic phase was then washed successively with $H_2O$ and brine, dried over $Na_2SO_4$, filtered, and concentrated. The resulting residue was purified by silica gel flash column chromatography ($CH_2Cl_2$/MeOH=93/7) to afford the title compound. $^1$H NMR (400 MHz, $CD_3CN$) δ 8.23-8.26 (m, 1H), 7.59 (ddd, J=0.92, 2.66, 8.41 Hz, 1H), 7.26-7.39 (m, 6H), 5.57 (br. d, J=4.90 Hz, 1H), 5.09-5.18 (m, 2H), 4.10-4.17 (m, 1H), 3.54-3.65 (m, 1H), 2.91 (d, J=4.65 Hz, 1H), 2.75-2.85 (m, 1H), 2.43-2.50 (m, 1H), 1.69-1.85 (m, 2H), 1.31-1.43 (m, 1H).

Intermediate 2-20-I; (±)-rel-(2S,4S)-benzyl 2-(6-chloropyridin-3-yl)-4-ethoxypiperidine-1-carboxylate

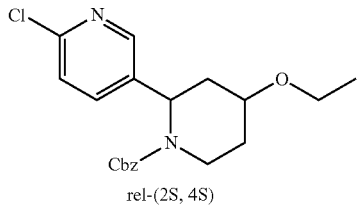 [SMILES: CCOC1CCN(C(=O)OCc2ccccc2)C(c2ccc(Cl)nc2)C1]

rel-(2S, 4S)

The title compound was synthesized from (±)-rel-(2S,4S)-benzyl 2-(6-chloropyridin-3-yl)-4-hydroxypiperidine-1-carboxylate, Intermediate 2-20-H, by using EtI in the place of MeI analogously to the preparation of Intermediate 2-2-A. MS (ESI+) m/z 375.1, 377.4 (M+H).

Intermediate 2-20-J; (±)-methyl 5-(rel-(2S,4S)-1-((benzyloxy)carbonyl)-4-ethoxypiperidin-2-yl)picolinate

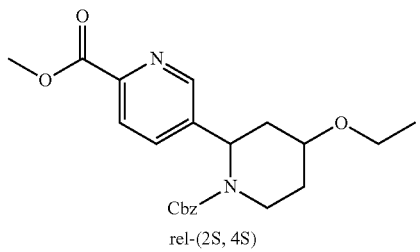 [SMILES: CCOC1CCN(C(=O)OCc2ccccc2)C(c2ccc(C(=O)OC)nc2)C1]

rel-(2S, 4S)

A solution of (±)-rel-(2S,4S)-benzyl 2-(6-chloropyridin-3-yl)-4-ethoxypiperidine-1-carboxylate, Intermediate 2-20-I, (1.8 g, 4.80 mmol) and $Et_3N$ (1.2 mL, 8.66 mmol) in MeOH (4 mL) was sparged with CO gas for 5 min in a vial. (rac)-BINAP (400 mg, 0.642 mmol) and $PdCl_2$ (100 mg, 0.564 mmol) was added to the mixture, and the vial was capped under CO atmosphere. The mixture was then stirred at 100° C. under the microwave irradiation for 1 hr. To the mixture was added additional amount of (rac)-BINAP (400 mg, 0.642 mmol), followed by $PdCl_2$ (100 mg, 0.564 mmol). The vial was filled with CO gas. The mixture was then stirred at 120° C. under the microwave irradiation for 1 hr. The reaction mixture was then diluted with $H_2O$. The mixture was then extracted with EtOAc. The organic phase was then washed with $H_2O$ and brine, dried over $Na_2SO_4$, filtered, and concentrated. The resulting residue was purified by silica gel flash column chromatography (heptane/EtOAc=55/45) to afford the title compound. MS (ESI+) m/z 399.2 (M+H).

Intermediate 2-20; (±)-methyl 5-(rel-(2S,4S)-4-ethoxypiperidin-2-yl)picolinate

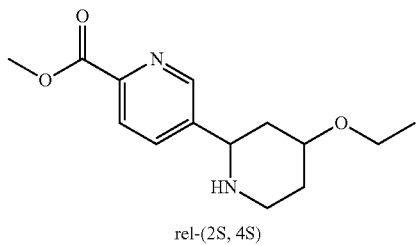 [SMILES: CCOC1CCNC(c2ccc(C(=O)OC)nc2)C1]

rel-(2S, 4S)

The title compound was synthesized from (±)-methyl 5-(rel-(2S,4S)-1-((benzyloxy)carbonyl)-4-ethoxypiperidin-2-yl)picolinate, Intermediate 2-20-J, analogously to the preparation of Intermediate 2-12. MS (ESI+) m/z 265.1 (M+H).

Intermediate 2-21:

Intermediate 2-21-A; (±)-tert-butyl 5-((tert-butyldiphenylsilyl)oxy)-2-oxopiperidine-1-carboxylate

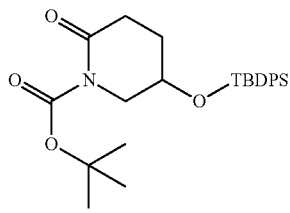

The title compound was synthesized from (±)-5-hydroxypiperidin-2-one (CAS: 19365-07-2) by following procedures described in the synthesis of Intermediate 2-20-A and then Intermediate 2-20-B. MS (ESI+) m/z 454.3 (M+H).

Intermediate 2-21-B; (±)-tert-butyl (2-((tert-butyldiphenylsilyl)oxy)-5-(4-cyanophenyl)-5-oxopentyl) carbamate

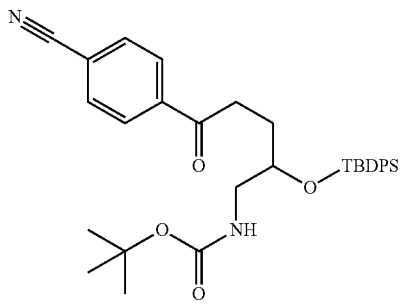

To a solution of iPrMgCl—LiCl complex solution in THF (15 mL, 19.50 mmol) in THF (15 mL) at −78° C. was added a solution of 4-bromobenzonitrile (4 g, 21.98 mmol) in THF (10 mL). The mixture was then stirred at room temperature for 1.5 h. To a solution of (±)-tert-butyl 5-((tert-butyldiphenylsilyl)oxy)-2-oxopiperidine-1-carboxylate, Intermediate 2-21-A, (6 g, 13.23 mmol) in THF (25 mL) at −78° C. was added the reaction mixture above over 15 min. The mixture was then stirred at −78° C. for 10 min, and then at 0° C. for 0.5 h. The reaction was then quenched with MeOH, followed by half satd. aq. KHSO₄. The mixture was then extracted with EtOAc. The organic layer was then washed successively with 5% aq. NaHCO₃ and brine, dried over Na₂SO₄, filtered, and concentrated. The resulting residue was used in the next reaction without the need for further purification. MS (ESI+) m/z 557.4 (M+H).

Intermediate 2-21-C; (±)-4-(5-((tert-butyldiphenylsilyl)oxy)piperidin-2-yl)benzonitrile (Diastereomeric Mixture)

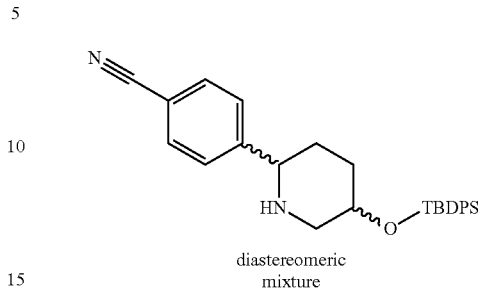

diastereomeric mixture

The title compounds was synthesized from (±)-tert-butyl (2-((tert-butyldiphenylsilyl)oxy)-5-(4-cyanophenyl)-5-oxopentyl)carbamate, Intermediate 2-21-B, analogously to the preparation of Intermediate 2-20-D. MS (ESI+) m/z 441.1 (M+H).

Intermediate 2-21-D; (±)-benzyl 5-((tert-butyldiphenylsilyl)oxy)-2-(4-cyanophenyl)piperidine-1-carboxylate (Diastereomer-1); and (±)-benzyl 5-((tert-butyldiphenylsilyl)oxy)-2-(4-cyanophenyl)piperidine-1-carboxylate (Diastereomer-2)

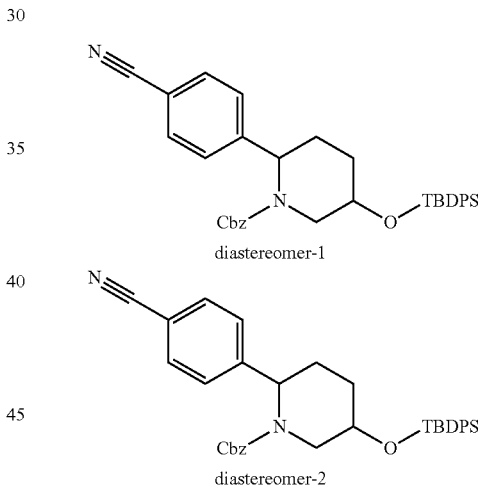

diastereomer-1 diastereomer-2

To a solution of (±)-4-(5-((tert-butyldiphenylsilyl)oxy)piperidin-2-yl)benzonitrile (diastereomeric mixture), Intermediate 2-21-C, (5.77 g, 13 mmol) in CH₂Cl₂ (100 mL) at 0° C. was added Et₃N (5 mL, 36.1 mmol), followed by Cbz-Cl (5 mL, 35.0 mmol) over 0.25 h. The mixture was then stirred at 0° C. for 2.5 h. The reaction was quenched with 28% NH₄OH. The mixture was diluted with CH₂Cl₂. The organic phase was then washed successively with H₂O, and brine, dried over Na₂SO₄, filtered, and concentrated. The resulting residue was purified by silica gel flash column chromatography (heptane/EtOAc=87/13) to afford, in respective elution order, (±)-benzyl 5-((tert-butyldiphenylsilyl)oxy)-2-(4-cyanophenyl)piperidine-1-carboxylate (diastereomer-1); and (±)-benzyl 5-((tert-butyldiphenylsilyl)oxy)-2-(4-cyanophenyl)piperidine-1-carboxylate (diastereomer-2).

(diastereomer-1); ¹H NMR (400 MHz, CD₃OD) δ 7.58-7.70 (m, 6H), 7.20-7.45 (m, 13H), 5.58 (br. d, J=2.00 Hz, 1H), 5.18 (d, J=11.98 Hz, 1H), 4.89-5.01 (m, 1H), 4.04 (br. d, J=13.90 Hz, 1H), 3.89 (br. s., 1H), 2.75 (dd, J=1.47, 14.06 Hz, 1H), 2.53-2.64 (m, 1H), 2.12-2.21 (m, 1H), 1.58-1.68 (m, 1H), 1.36-1.47 (m, 1H), 1.06 (s, 9H).

(diastereomer-2); $^1$H NMR (400 MHz, CD$_3$OD) δ 7.71 (d, J=8.31 Hz, 2H), 7.56-7.64 (m, 4H), 7.27-7.46 (m, 11H), 7.23 (br. s., 2H), 5.31 (br. d, J=2.70 Hz, 1H), 5.01-5.13 (m, 2H), 4.14 (br. d, J=10.80 Hz, 1H), 3.66-3.76 (m, 1H), 2.61 (dd, J=10.64, 12.84 Hz, 1H), 2.33 (d, J=14.31 Hz, 1H), 1.70-1.83 (m, 2H), 1.30-1.43 (m, 1H), 1.00 (s, 9H).

Intermediate 2-21-E; (±)-benzyl 2-(4-cyanophenyl)-5-hydroxypiperidine-1-carboxylate (Diastereomer-1)

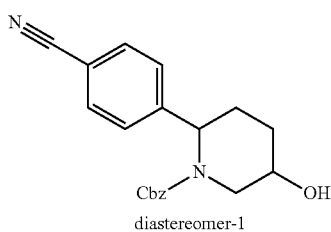 [SMILES: N#Cc1ccc(C2CCC(O)CN2C(=O)OCc2ccccc2)cc1]

diastereomer-1

The title compound was synthesized from (±)-benzyl 5-((tert-butyldiphenylsilyl)oxy)-2-(4-cyanophenyl)piperidine-1-carboxylate (diastereomer-1), Intermediate 2-21-D, analogously to the preparation of Intermediate 2-12-E. MS (ESI+) m/z 337.1 (M+H).

Intermediate 2-21-F; (±)-benzyl 2-(4-cyanophenyl)-5-methoxypiperidine-1-carboxylate (Diastereomer-1)

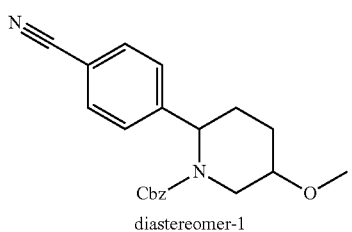 [SMILES: COC1CCC(c2ccc(C#N)cc2)N(C(=O)OCc2ccccc2)C1]

diastereomer-1

The title compound was synthesized from (±)-benzyl 2-(4-cyanophenyl)-5-hydroxypiperidine-1-carboxylate (diastereomer-1), Intermediate 2-21-E, analogously to the preparation of Intermediate 2-2-A. MS (ESI+) m/z 351.2 (M+H).

Intermediate 2-21; (±)-4-(5-methoxypiperidin-2-yl)benzonitrile (Diastereomer-1)

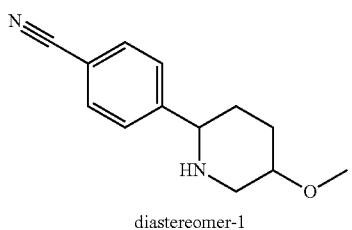 [SMILES: COC1CCC(c2ccc(C#N)cc2)NC1]

diastereomer-1

The title compound was synthesized from (±)-benzyl 2-(4-cyanophenyl)-5-methoxypiperidine-1-carboxylate (diastereomer-1), Intermediate 2-21-F, analogously to the preparation of Intermediate 2-12. MS (ESI+) m/z 217.1 (M+H).

Intermediate 2-22:

Intermediate 2-22-A; tert-butyl 4,4-dimethylpiperidine-1-carboxylate

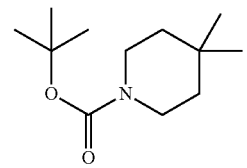

To a solution of 4,4-dimethylpiperidine hydrochloride (6 g, 40.1 mmol) and Boc$_2$O (12.77 mL, 55.0 mmol) in CH$_2$Cl$_2$ (100 mL) was added Et$_3$N (12 mL, 87 mmol). The mixture was then stirred at room temperature for 13 h. The reaction was quenched with H$_2$O. The mixture was then extracted with Et$_2$O. The mixture was then washed successively with 1M aq. HCl, 5% aq. NaHCO$_3$, and brine, dried over Na$_2$SO$_4$, filtered, and concentrated to afford the title compound, which was used in the next reaction without the need for further purification. $^1$H NMR (400 MHz, CDCl$_3$) δ 3.33-3.40 (m, 4H), 1.45 (s, 9H), 1.26-1.33 (m, 4H), 0.94 (s, 6H).

Intermediate 2-22-B; (±)-tert-butyl 4,4-dimethyl-2-oxopiperidine-1-carboxylate

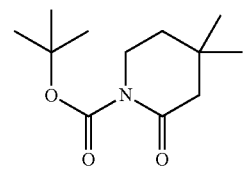 [SMILES: CC1(C)CCN(C(=O)OC(C)(C)C)C(=O)C1]

To a suspension of tert-butyl 4,4-dimethylpiperidine-1-carboxylate, Intermediate 2-22-A, (8.5 g, 40.0 mmol) and NaIO$_4$ (13 g, 60.8 mmol) in EtOAc (50 mL)/H$_2$O (100 mL) was added RuCl$_3$ (1 g, 4.82 mmol). The mixture was then stirred at room temperature for 4.5 h. To the mixture was then added additional amount of NaIO$_4$ (8 g, 37.4 mmol). The mixture was then stirred at room temperature for 2.5 h. The reaction mixture was then diluted with EtOAc. The mixture was then filtered through a plug of Celite®, which was rinsed with EtOAc. The organic phase was then washed successively with H$_2$O, 1% aq. Na$_2$S$_2$O$_3$, and brine, dried over Na$_2$SO$_4$, filtered, and concentrated. The resulting residue was absorbed onto silica gel. The silica gel was rinsed with Et$_2$O. The filtrate was then concentrated to afford the title compound. MS (ESI+) m/z 228.2 (M+H).

Intermediate 2-22-C; (±)-tert-butyl (5-(4-cyanophenyl)-3,3-dimethyl-5-oxopentyl)carbamate

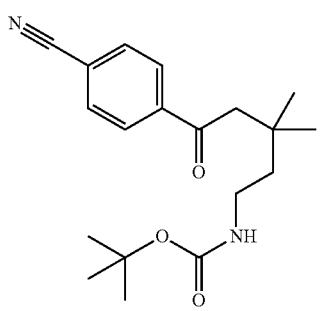 [SMILES: CC(C)(CCNC(=O)OC(C)(C)C)CC(=O)c1ccc(C#N)cc1]

The title compound was synthesized from (±)-tert-butyl 4,4-dimethyl-2-oxopiperidine-1-carboxylate, Intermediate 2-22-B, analogously to the preparation of Intermediate 2-21-B. MS (ESI+) m/z 331.2 (M+H).

Intermediate 2-22-D; (±)-4-(4,4-dimethylpiperidin-2-yl)benzonitrile

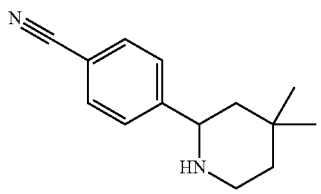 [SMILES: CC1(C)CCNC(c2ccc(C#N)cc2)C1]

The title compound was analogously synthesized form (±)-tert-butyl (5-(4-cyanophenyl)-3,3-dimethyl-5-oxopentyl)carbamate, Intermediate 2-22-C, by following methods described in the synthesis of Intermediate 2-19-B, and then Intermediate 2-19-C. MS (ESI+) m/z 215.3 (M+H).

Intermediate 2-22-E; (±)-benzyl 2-(4-cyanophenyl)-4,4-dimethylpiperidine-1-carboxylate

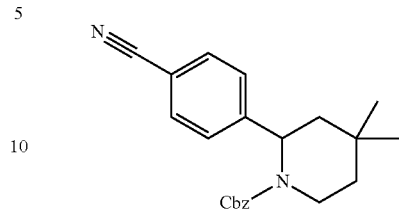

The title compound was synthesized from (±)-4-(4,4-dimethylpiperidin-2-yl)benzonitrile, Intermediate 2-22-D, analogously to the preparation of Intermediate 2-20-E. MS (ESI+) m/z 349.1 (M+H).

Intermediate 2-22; (±)-methyl 4-(4,4-dimethylpiperidin-2-yl)benzoate

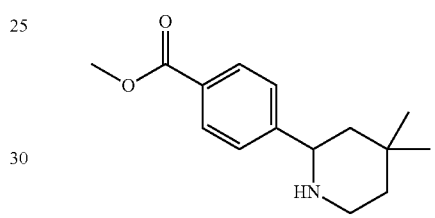

The title compound was synthesized from (±)-benzyl 2-(4-cyanophenyl)-4,4-dimethyl piperidine-1-carboxylate, Intermediate 2-22-E, by following procedures described in the synthesis of Intermediate 2-13-C, Intermediate 2-13-D, and then Intermediate 2-13. MS (ESI+) m/z 248.1 (M+H).

Following intermediates were prepared from appropriate starting materials by similar methods described above.

| Intermediate | structure | chemical name starting material | MS (m/z) |
|---|---|---|---|
| 2-23-1 | (structure shown) rel-(2S,4S) | (±)-methyl 5-(rel-(2S,4S)-4-methoxypiperidin-2-yl) picolinate Intermediate 2-20-H | (ESI+) 251.1 (M + H) |
| 2-23-2 | (structure shown) diastereomer-1 | (±)-4-(5-((tert-butyldiphenylsilyl)oxy) piperidin-2-yl)benzonitrile (diastereomer-1) diastereomer-1 described as Intermediate 2-21-D | (ESI+) 441.0 (M + H) |

| Intermediate | structure | chemical name starting material | MS (m/z) |
|---|---|---|---|
| 2-23-3 | 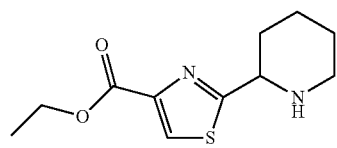 diastereomer-2 | (±)-4-(5-((tert-butyldiphenylsilyl)oxy) piperidin-2-yl)benzonitrile (diastereomer-2) diastereomer-2 described as Intermediate 2-21-D | (ESI+) 441.0 (M + H) |
| 2-23-4 | 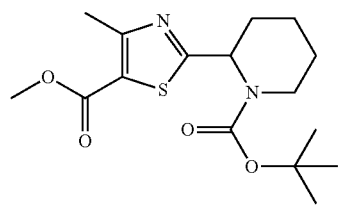 diastereomer-2 | (±)-4-(5-methoxypiperidin-2-yl)benzonitrile (diastereomer-2) diastereomer-2 described as Intermediate 2-21-D | (ESI+) 217.1 (M + H) |

Intermediate 2-24:

(±)-Ethyl 2-(piperidin-2-yl)thiazole-4-carboxylate

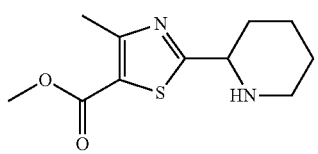 [SMILES: COC(=O)c1sc(C2CCCCN2)nc1C]

A mixture of (±)-tert-butyl 2-carbamothioylpiperidine-1-carboxylate (CAS: 569348-09-0, 99 mg, 0.405 mmol) and bromoethylpyruvate (79 mg, 0.405 mmol) in EtOH (3 mL) was stirred at room temperature for 4 days. The mixture was concentrated. The resulting residue was purified by silica gel flash column chromatography (heptane/EtOAc) to afford the title compound. MS (ESI+) m/z 241.3 (M+H).

Intermediate 2-25:

Intermediate 2-25-A; (±)-methyl 2-(1-(tert-butoxycarbonyl)piperidin-2-yl)-4-methylthiazole-5-carboxylate

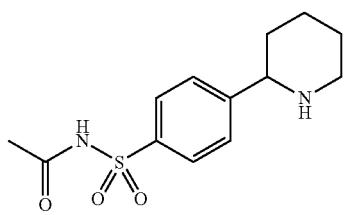 [SMILES: CC(=O)NS(=O)(=O)c1ccc(C2CCCCN2)cc1]

To a solution of (±)-tert-butyl 2-carbamothioylpiperidine-1-carboxylate (187 mg, 0.765 mmol) in EtOH (5 mL) at 50° C. was added methyl-2-chloroacetoacetate (138 mg, 0.918 mmol). The mixture was stirred at 70° C. for 16 h, and then concentrated. The resulting residue was then diluted with EtOAc. The EtOAc layer was then washed successively with satd. aq. NaHCO₃, and brine, dried over Na₂SO₄, filtered, and concentrated. The resulting residue was purified by flash column chromatography (heptane/EtOAc) to afford the title compound. MS (ESI+) m/z 340.9 (M+H).

Intermediate 2-25; (±)-methyl 4-methyl-2-(piperidin-2-yl)thiazole-5-carboxylate

To a solution of (±)-methyl 2-(1-(tert-butoxycarbonyl)piperidin-2-yl)-4-methylthiazole-5-carboxylate, Intermediate 2-25-A, (115 mg, 0.338 mmol) in CH₂Cl₂ (2 mL) was added TFA. The whole mixture was then stirred at room temperature for 1 h. The reaction mixture was diluted with EtOAc, and then washed successively with aq. NaHCO₃, brine, dried over Na₂SO₄, filtered, and concentrated to furnish the title compound without further purification. MS (ESI+) m/z 240.9 (M+H).

Intermediate 2-26:

(±)-N-((4-(piperidin-2-yl)phenyl)sulfonyl)acetamide

To a solution of a mixture of (±)-tert-butyl 2-(3-sulfamoylphenyl)piperidine-1-carboxylate and (±)-tert-butyl 2-(4-sulfamoylphenyl)piperidine-1-carboxylate, Intermediate 2-9-A, (0.11 g, 0.25 mmol) in CH₂Cl₂ (3 mL) at room temperature was added Et₃N (0.14 mL, 0.97 mmol), followed by Ac₂O (0.09 mL, 0.97 mmol). The mixture was then stirred for 20 min. The reaction mixture was then diluted with CH₂Cl₂ and satd. aq. NaHCO₃. The organic phase was then washed successively with brine, dried over Na₂SO₄, filtered, and concentrated. The resulting residue was used in the following step without any purification.

To a solution of the residue in CH₂Cl₂ (3 mL) at room temperature was added TFA (0.25 mL, 3.2 mmol. The mixture was then stirred at room temperature for 60 hr. The reaction mixture was concentrated to give the title compound as TFA salt, which was used in the next reaction without the need for further purification. MS (ESI+) m/z 283.1 (M+H).

Intermediate 2-27:

Intermediate 2-27-A; (±)-1-benzoyl-2-(4-bromophenyl)-2,3-dihydropyridin-4(1H)-one

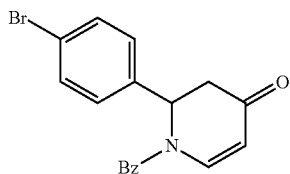

To a suspension of Mg (1.2 g, 50 mmol) in THF (50 mL) at room temperature was added iodine (50 mg), and then the mixture was stirred at room temperature for 5 min. To the mixture was then added 1,4-bibromobenzene (11.8 g, 50 mmol) portionwise, and the mixture was stirred at 70° C. for 2 h. The mixture was cooled to room temperature to furnish 4-bromophenylmagnesium bromide in THF.

To a solution of 4-methoxypyridine (1.52 g, 13.9 mmol) in THF (40 mL) at room temperature was added benzoyl chloride (1.6 mL, 13.9 mmol), followed by trimethylsilyl trifluoromethanesulfonate (3.06 g, 13.8 mmol). The mixture was then stirred at room temperature for 0.5 h, and then cooled to −78° C. To the mixture at −78° C. was then added the 4-bromophenylmagnesium brimide in THF, and then the mixture was stirred at the same temperature for 1 h. The mixture was then quenched with 2M HCl (50 mL). The mixture was then extracted with EtOAc. The organic layer was then dried over Na₂SO₄, filtered, and then concentrated. The resulting residue was purified by silica gel flash column chromatography (heptane/EtOAc=1/0 to 4/1) to afford the titled compound. MS (ESI+) m/z 357.8 (M+H).

Intermediate 2-27-B; (±)-tert-butyl 2-(4-bromophenyl)-4-oxo-3,4-dihydropyridine-1(2H)-carboxylate

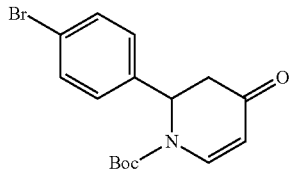 [SMILES: CC(C)(C)OC(=O)N1C=CC(=O)CC1c1ccc(Br)cc1]

A mixture of Intermediate 2-27-A (700 mg, 1.97 mmol) and 25% NaOMe in MeOH (5 mL) was stirred at room temperature for 2 h, and then diluted with H₂O. The mixture was then extracted with EtOAc. The organic phase was then dried over Na2SO4, filtered, and then concentrate. The resulting residue in THF (8 mL) were added Boc₂O (955 mg, 4.38 mmol) and Et₃N (0.5 mL, 3.28 mmol), followed by DMAP (130 mg, 1.06 mmol). The mixture was then stirred at room temperature for 1 h, and then concentrated. The resulting residue was purified by silica gel flash column chromatography (heptane/EtOAc=1/0 to 7/3) to afford the title compound. MS (ESI+) m/z 294.9 (M-tBu)⁺.

Intermediate 2-27-C; (±)-tert-butyl 2-(4-(methoxycarbonyl)phenyl)-4-oxo-3,4-dihydropyridine-1(2H)-carboxylate

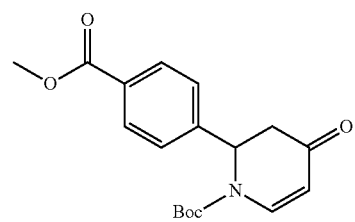 [SMILES: COC(=O)c1ccc(C2CC(=O)C=CN2C(=O)OC(C)(C)C)cc1]

A mixture of Intermediate 2-27-B (7.8 g, 22.2 mmol), iPr₂NEt (10 mL, 57.4 mmol), Pd(OAc)₂ (1.2 g, mmol, 5.34 mmol), and dppp (4.2 g, 10.2 mmol) in DMSO/MeOH (60 mL/60 mL) was stirred at 80° C. for 16 h under CO gas atmosphere (100 psi). The reaction mixture was diluted with H₂O. The mixture was then extracted with EtOAc. The organic layer was then concentrated. The resulting residue and Et3N (10 mL, 71 mmol) in THF (50 mL) was added Boc₂O (8 g, 36.7 mmol) in THF (10 mL), followed by catalytic amount of DMAP. The mixture was then stirred at room temperature for 2 h, and then concentrated. The resulting mixture was purified by silica gel flash column chromatography (heptane/EtOAc=1/0 to 4/1) to afford the titled compound. MS (ESI−) m/z 331.0 (M−H), (ESI+) m/z 231.95 (M-Boc)⁺.

Intermediate 2-27-D; (±)-tert-butyl 2-(4-(methoxycarbonyl)phenyl)-4-oxopiperidine-1-carboxylate

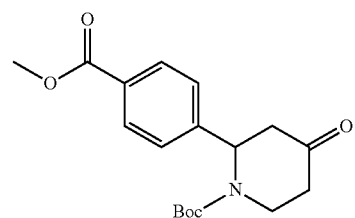 [SMILES: COC(=O)c1ccc(C2CC(=O)CCN2C(=O)OC(C)(C)C)cc1]

A mixture of Intermediate 2-27-C (4.5 g, 13.6 mmol) and Pd/C (10%, 800 mg) in MeOH (25 mL) was stirred at room temperature under H₂ atmosphere (40 psi) for 2 h. The H₂ gas was replaced to N₂, and then the catalyst was removed by filtration through a plug of Celite®, which was rinsed with MeOH. The filtrate was then concentrated. The resulting residue was purified by silica gel flash column chromatography (heptane/EtOAc=1/0 to 3/1) to afford the titled compound. MS (ESI−) m/z 333.1 (M−H).

Intermediate 2-27-E; (±)-tert-butyl 2-(4-(methoxy-carbonyl)phenyl)-4-methylenepiperidine-1-carboxy-late

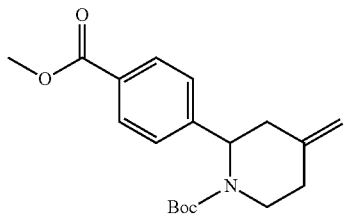

To a suspension of methyltriphenylphosphonium bromide (480 mg, 1.34 mmol) in THF (5 mL) at 0° C. was added KOtBu (153 mg, 1.36 mmol). The mixture was then stirred at the same temperature for 0.5 h. To the mixture was then added a solution of Intermediate 2-27-D (300 mg, 0.90 mmol) in THF (5 mL). The mixture was then stirred at room temperature for 16 h, and then quenched with H₂O. The mixture was then extracted with EtOAc. The organic phase was then dried over Na₂SO₄, filtered, and then concentrated. The resulting residue was purified by silica gel flash column chromatography (heptane/EtOAc=1/0 to 9/1) to afford the titled compound. ¹H NMR (300 MHz, CDCl₃) δ 7.98 (d, J=8.4 Hz, 2H), 7.36 (d, J=8.4 Hz, 2H), 5.53 (brd, J=3.8 Hz, 1H), 4.83 (br. s, 2H), 4.02-4.10 (m, 1H), 3.90 (s, 3H), 2.61-2.87 (m, 3H), 2.16-2.38 (m, 2H), 1.46 (s, 9H).

Intermediate 2-27; (±)-methyl 4-(6-azaspiro[2.5]octan-5-yl)benzoate

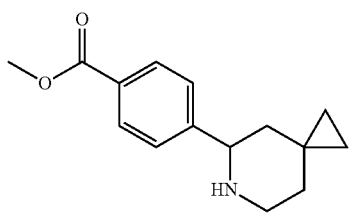 [SMILES: COC(=O)c1ccc(C2CC3(CCN2)CC3)cc1]

To a solution of diethylzinc (1M in hexane, 14 mmol) in CH₂Cl₂ (30 mL) at −40° C. was added diiodomethane (1.1 mL, 13.8 mmol). The mixture was then stirred at the same temperature for 0.5 h. To the mixture was then added a solution of Intermediate 2-27-E (1.52 g, 4.6 mmol) in CH₂Cl₂ (20 mL). The mixture was then stirred at room temperature for 16 h. The mixture was then quenched with H₂O/brine. The mixture was then extracted with CH₂Cl₂. The organic phase was then dried over Na₂SO₄, filtered, and concentrated. The resulting residue was purified by silica gel flash column chromatography (heptane/EtOAc=1/0 to 1/4) to afford the titled compound. MS (ESI+) m/z 246.0 (M+H).

Intermediate 2-28:

Intermediate 2-28-A; (±)-tert-butyl 4-ethylidene-2-(4-(methoxycarbonyl)phenyl)piperidine-1-carboxy-late

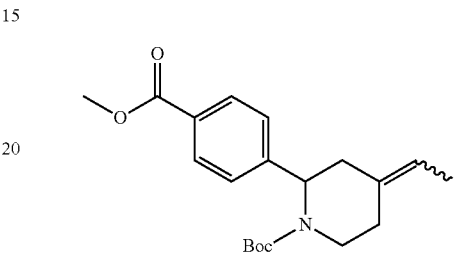

The title compound was synthesized from Intermediate 2-27-D (220 mg, 0.66 mmol) and ethyl triphenylphosphonium bromide (344 mg, 0.92 mmol) analogoulsy to the preparation of Intermediate 2-27-E. MS (ESI+) m/z 246.0 (M-tBu).

Intermediate 2-28-B; (±)-rel-(2S,4S)-tert-butyl 4-ethyl-2-(4-(methoxycarbonyl)phenyl)piperidine-1-carboxylate

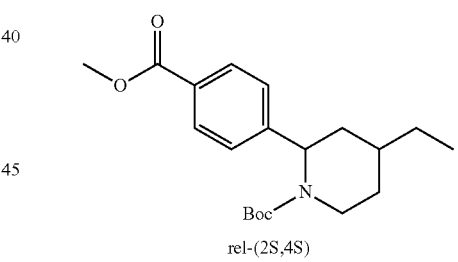

rel-(2S,4S)

A mixture of Intermediate 2-28-A (110 mg, 0.3 mmol) and Pd/C (10%, 30 mg) in MeOH (2 mL) was stirred at room temperature under H₂ atmosphere (50 psi) for 5 h. The H₂ gas was replaced to N₂, and then the catalyst was removed by filtration through a plug of Celite®, which was rinsed with MeOH. The filtrate was then concentrated. The resulting residue was purified by silica gel flash column chromatography (heptane/EtOAc=1/0 to 3/1) to afford the titled compound. ¹HNMR (300 MHz, CDCl₃) δ 8.00 (d, J=8.4 Hz, 2H), 7.27 (d, J=8.1 Hz, 2H), 5.49 (brs, 1H), 4.03-4.22 (m, 1H), 3.91 (s, 3H), 2.68-2.83 (m, 1H), 2.34 (br, d, J=14 Hz, 1H), 1.52-1.69 (m, 3H), 1.46 (s, 9H), 1.0-1.34 (m, 3H), 0.88 (t, J=7.1 Hz, 3H).

Intermediate 2-28; (±)-methyl 4-(rel-(2S,4S)-4-ethylpiperidin-2-yl)benzoate

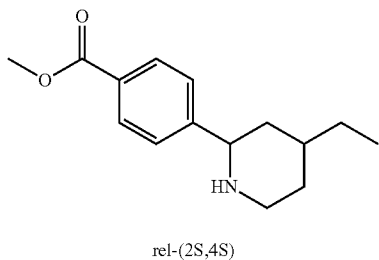 [SMILES: CCC1CCNC(c2ccc(C(=O)OC)cc2)C1]

rel-(2S,4S)

To a solution of Intermediate 2-28-B (40 mg, 0.115 mmol) in CH₂Cl₂/MeOH (1 mL/1 mL) at 0° C. was added 4M HCl in dioxane (2 mL). The mixture was then stirred at room temperature for 6 h. The mixture was then partially concentrated. The mixture was then diluted with H₂O. The mixture was then rendered basic by NaHCO₃ (pH-8). The mixture was then extracted with EtOAc. The organic phase was dried over Na₂SO₄, filtered, and concentrated to afford the title compound. ¹HNMR (300 MHz, CD₃OD) δ ppm: 7.97 (d, J=8.4 Hz, 2H), 7.47 (d, J=8.4 Hz, 2H), 3.94 (dd, J'=3 Hz, J''=7.4 Hz, 1H), 3.88 (s, 3H), 2.84-2.97 (m, 2H), 1.50-1.89 (m, 7H), 0.96 (t, J=8.0 Hz, 3H).

Intermediate 3-1:
(±)-1-((5,7-Dimethyl-1-tosyl-1H-indol-4-yl)methyl)-2-phenylpiperidin-4-ol (Diastereomeric Mixture)

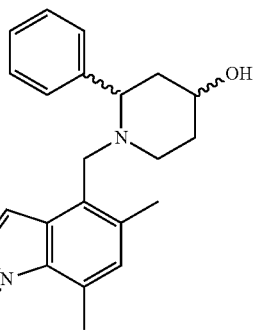

diastereomeric mixture

To a solution of (±)-2-phenylpiperidin-4-ol (diastereomeric mixture), Intermediate 2-1, (154 mg, 0.72 mmol) in DMSO (2 mL) was added K₂CO₃ (350 mg, 2.53 mmol). The mixture was then stirred for 10 min. To the mixture was then added 4-(chloromethyl)-5,7-dimethyl-1-tosyl-1H-indole, Intermediate 1-6, (170 mg, 0.489 mmol). The mixture was then stirred at 80° C. for 1 h. The reaction mixture was cooled to room temperature, and then poured into H₂O. The mixture was then extracted with EtOAc. The organic phase was washed successively with H₂O (twice) and brine, dried over K₂CO₃, filtered, and concentrated. The resulting residue was purified by silica gel flash column chromatography (heptane/EtOAc=75/25) to afford the title compound as a mixture of diastereomers, which was used in the next reaction without the need for further purification. MS (ESI+) m/z 489.4 (M+H).

Following intermediates were prepared from appropriate starting materials by similar methods described above.

| Intermediate | structure | chemical name starting material | MS (m/z) |
|---|---|---|---|
| 3-2-1 | (diastereomeric mixture) | (±)-4-((4-methoxy-2-phenylpiperidin-1-yl)methyl)-5,7-dimethyl-1-tosyl-1H-indole (diastereomeric mixture) Intermediate 1-6 and Intermediate 2-2 | (ESI+) 503.5 (M + H) |

-continued

| Intermediate | structure | chemical name starting material | MS (m/z) |
|---|---|---|---|
| 3-2-2 | diastereomer-1 | (±)-benzyl (1-((5,7-dimethyl-1-tosyl-1H-indol-4-yl)methyl)-2-phenylpiperidin-4-yl)carbamate (diastereomer-1) Intermediate 1-6 and Intermediate 2-5 | (ESI+) 622.6 (M + H) |
| 3-2-3 | diastereomer-2 | (±)-benzyl (1-((5,7-dimethyl-1-tosyl-1H-indol-4-yl)methyl)-2-phenylpiperidin-4-yl)carbamate (diastereomer-2) Intermediate 1-6 and Intermediate 2-6 | (ESI+) 622.6 (M + H) |
| 3-2-4 | 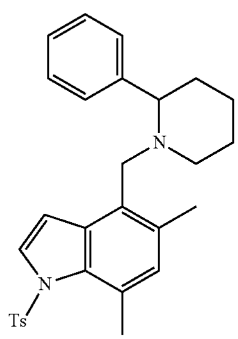 [SMILES: Cc1ccc(S(=O)(=O)n2ccc3c(CN4CCCCC4c4ccccc4)c(C)cc(C)c32)cc1] | (±)-5,7-dimethyl-4-((2-phenylpiperidin-1-yl)methyl)-1-tosyl-1H-indole Intermediate 1-6 and 2-phenylpiperidine | (ESI+) 473.2 (M + H) |
| 3-2-5 | diastereomer-1 | (±)-(1-((5,7-dimethyl-1-tosyl-1H-indol-4-yl)methyl)-2-phenylpiperidin-4-yl)methanol (diastereomer-1) Intermediate 1-6 and Intermediate 2-7 | (ESI+) 503.5 (M + H) |

| Intermediate | structure | chemical name / starting material | MS (m/z) |
|---|---|---|---|
| 3-2-6 | diastereomer-2 | (±)-(1-((5,7-dimethyl-1-tosyl-1H-indol-4-yl)methyl)-2-phenylpiperidin-4-yl)methanol (diastereomer-2) Intermediate 1-6 and Intermediate 2-8 | (ESI+) 503.5 (M + H) |
| 3-2-7 | (mixture of regioisomer) | (±)-4-(1-((5,7-dimethyl-1-tosyl-1H-indol-4-yl)methyl)piperidin-2-yl)benzenesulfonamide and (±)-3-(1-((5,7-dimethyl-1-tosyl-1H-indol-4-yl)methyl)piperidin-2-yl)benzenesulfonamide (mixture of regioisomer) Intermediate 1-6 and Intermediate 2-9 | (ESI+) 552.4 (M + H) |
| 3-2-8 | (mixture of regioisomer) | (±)-4-(1-((5,7-dimethyl-1-tosyl-1H-indol-4-yl)methyl)piperidin-2-yl)-N-methylbenzenesulfonamide and (±)-3-(1-((5,7-dimethyl-1-tosyl-1H-indol-4-yl)methyl)piperidin-2-yl)-N-methylbenzenesulfonamide Intermediate 1-6 and Intermediate 2-10 | (ESI+) 566.6 (M + H) |

-continued

| Intermediate | structure | chemical name starting material | MS (m/z) |
|---|---|---|---|
| 3-2-9 | 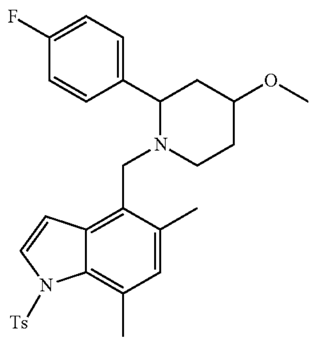 [SMILES: COC1CCN(Cc2c(C)cc(C)c3c2ccn3S(=O)(=O)c2ccc(C)cc2)C(c2ccc(F)cc2)C1] | (±)-4-((2-(4-fluorophenyl)-4-methoxypiperidin-1-yl)methyl)-5,7-dimethyl-1-tosyl-1H-indole Intermediate 1-6 and Intermediate 2-11 | (ESI+) 521.5 (M + H) |
| 3-2-10 | 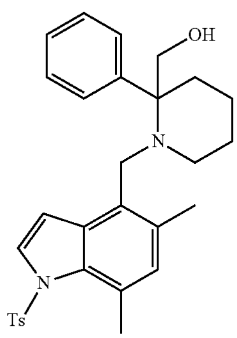 [SMILES: Cc1ccc(S(=O)(=O)n2ccc3c(CN4CCCCC4(CO)c4ccccc4)c(C)cc(C)c32)cc1] | (±)-(1-((5,7-dimethyl-1-tosyl-1H-indol-4-yl)methyl)-2-phenylpiperidin-2-yl)methanol Intermediate 1-6 and (2-phenylpiperidin-2-yl)methanol (CAS: 161499-35-0) | (ESI+) 503.3 (M + H) |
| 3-2-11 | 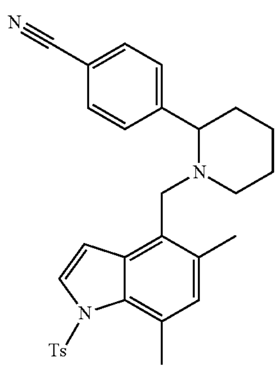 [SMILES: Cc1ccc(S(=O)(=O)n2ccc3c(CN4CCCCC4c4ccc(C#N)cc4)c(C)cc(C)c32)cc1] | (±)-4-(1-((5,7-dimethyl-1-tosyl-1H-indol-4-yl)methyl)piperidin-2-yl)benzonitrile Intermediate 1-6 and 4-(piperidin-2-yl)benzonitrile HCl (CAS: 1203685-85-1) | (ESI+) 498.5 (M + H) |
| 3-2-12 | 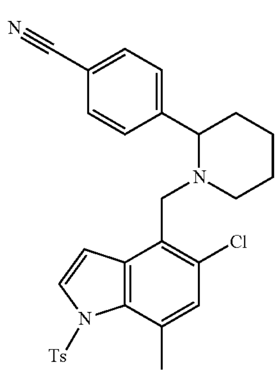 [SMILES: Cc1ccc(S(=O)(=O)n2ccc3c(CN4CCCCC4c4ccc(C#N)cc4)c(Cl)cc(C)c32)cc1] | (±)-4-(1-((5-chloro-7-methyl-1-tosyl-1H-indol-4-yl)methyl)piperidin-2-yl)benzonitrile Intermediate 1-9 and 4-(piperidin-2-yl)benzonitrile HCl | (ESI+) 518.4, 520.4 (M + H) |

| Intermediate | structure | chemical name starting material | MS (m/z) |
|---|---|---|---|
| 3-2-13 | 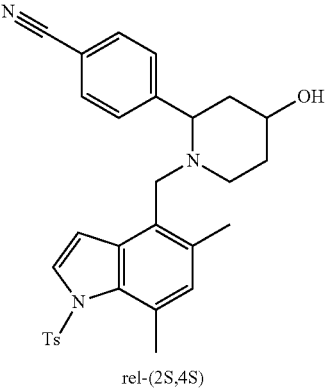 [SMILES: Cc1ccc(S(=O)(=O)n2ccc3c(CN4CCC(O)CC4c4ccc(C#N)cc4)c(C)cc(C)c32)cc1]<br>rel-(2S,4S) | (±)-4-(rel-(2S,4S)-1-((5,7-dimethyl-1-tosyl-1H-indol-4-yl)methyl)-4-hydroxypiperidin-2-yl)benzonitrile<br>Intermediate 1-6 and<br>Intermediate 2-15-1 | (ESI+)<br>514.5<br>(M + H) |
| 3-2-14 | 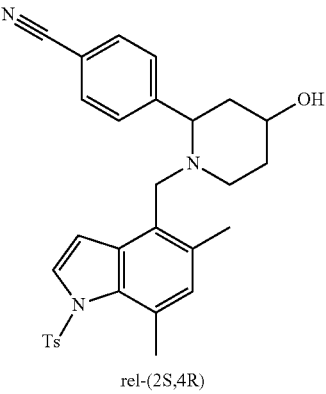 [SMILES: Cc1ccc(S(=O)(=O)n2ccc3c(CN4CCC(O)CC4c4ccc(C#N)cc4)c(C)cc(C)c32)cc1]<br>rel-(2S,4R) | (±)-4-(rel-(2S,4R)-1-((5,7-dimethyl-1-tosyl-1H-indol-4-yl)methyl)-4-hydroxypiperidin-2-yl)benzonitrile<br>Intermediate 1-6 and<br>Intermediate 2-15-2 | (ESI+)<br>514.5<br>(M + H) |
| 3-2-15 | 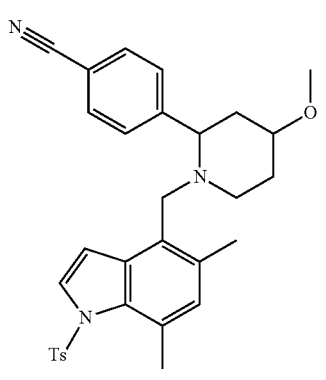<br>rel-(2S,4S) | (±)-4-(rel-(2S,4S)-1-((5,7-dimethyl-1-tosyl-1H-indol-4-yl)methyl)-4-methoxypiperidin-2-yl)benzonitrile<br>Intermediate 1-6 and<br>Intermediate 2-15-3 | (ESI+)<br>528.5<br>(M + H) |
| 3-2-16 | 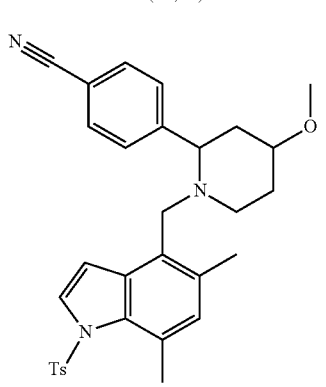<br>rel-(2S,4R) | (±)-4-(rel-(2S,4R)-1-((5,7-dimethyl-1-tosyl-1H-indol-4-yl)methyl)-4-methoxypiperidin-2-yl)benzonitrile<br>Intermediate 1-6 and<br>Intermediate 2-15-4 | (ESI+)<br>528.5<br>(M + H) |

-continued

| Intermediate | structure | chemical name starting material | MS (m/z) |
|---|---|---|---|
| 3-2-17 | rel-(2S,4R) | (±)-4-(rel-(2S,4S)-1-((5,7-dimethyl-1-tosyl-1H-indol-4-yl)methyl)-4-ethoxypiperidin-2-yl)benzonitrile<br>Intermediate 1-6 and<br>Intermediate 2-15-5 | (ESI+)<br>542.5<br>(M + H) |
| 3-2-18 | 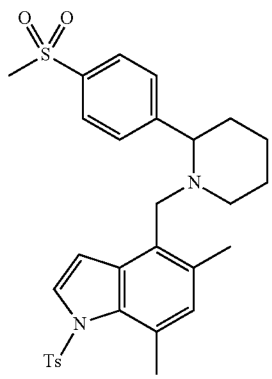 [SMILES: Cc1ccc(S(=O)(=O)n2ccc3c(CN4CCCCC4c4ccc(S(C)(=O)=O)cc4)c(C)cc(C)c32)cc1] | (±)-5,7-dimethyl-4-((2-(4-(methylsulfonyl)phenyl)piperidin-1-yl)methyl)-1-tosyl-1H-indole<br>Intermediate 1-6 and<br>Intermediate 2-19 | (ESI+)<br>551.5<br>(M + H) |
| 3-2-19 | 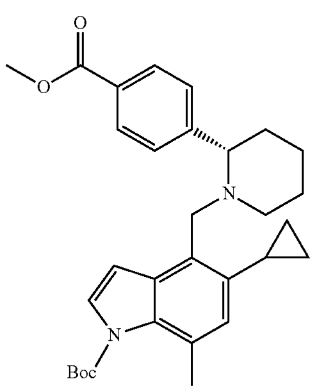 [SMILES: COC(=O)c1ccc([C@@H]2CCCCN2Cc2c(C3CC3)cc(C)c3c2ccn3C(=O)OC(C)(C)C)cc1] | (S)-tert-butyl 5-cyclopropyl-4-((4-(methoxycarbonyl)phenyl)piperidin-1-yl)methyl)-7-methyl-1H-indole-1-carboxylate<br>Intermediate 1-8 and<br>(S)-methyl 4-(piperidin-2-yl)benzoate HCl<br>(CAS: 1391547-09-3) | (ESI+)<br>503.5<br>(M + H) |
| 3-2-20 | 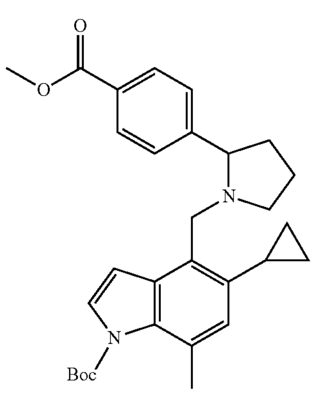 [SMILES: COC(=O)c1ccc(C2CCCN2Cc2c(C3CC3)cc(C)c3c2ccn3C(=O)OC(C)(C)C)cc1] | (±)-tert-butyl 5-cyclopropyl-4-((2-(4-(methoxycarbonyl)phenyl)pyrrolidin-1-yl)methyl)-7-methyl-1H-indole-1-carboxylate<br>Intermediate 1-8 and<br>methyl 4-(pyrrolidin-2-yl)benzoate<br>(CAS: 908334-13-4) | (ESI+)<br>489.5<br>(M + H) |

| Intermediate | structure | chemical name starting material | MS (m/z) |
|---|---|---|---|
| 3-2-21 | 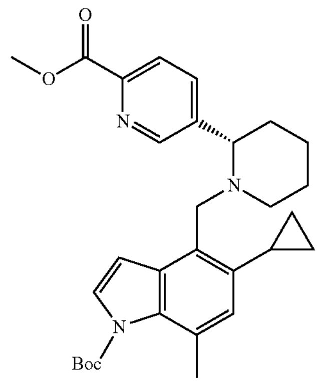 [SMILES: COC(=O)c1ccc([C@@H]2CCCCN2Cc2c(C3CC3)cc(C)c3c2ccn3C(=O)OC(C)(C)C)cn1] | (S)-tert-butyl 5-cyclopropyl-4-((2-(6-(methoxycarbonyl)pyridin-3-yl)piperidin-1-yl)methyl)-7-methyl-1H-indole-1-carboxylate<br>Intermediate 1-8 and<br>(S)-methyl 5-(2-piperidyl)pyridine-2-carboxylate (CAS: 1213606-12-2) | (ESI+)<br>504.5<br>(M + H) |
| 3-2-22 | 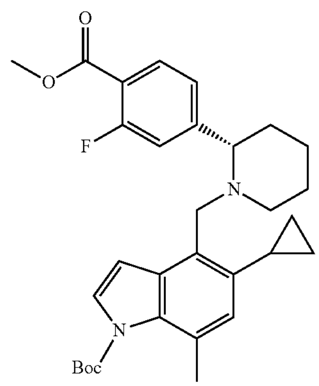 [SMILES: COC(=O)c1ccc([C@@H]2CCCCN2Cc2c(C3CC3)cc(C)c3c2ccn3C(=O)OC(C)(C)C)cc1F] | (S)-tert-butyl 5-cyclopropyl-4-((2-(3-fluoro-4-(methoxycarbonyl)phenyl)piperidin-1-yl)methyl)-7-methyl-1H-indole-1-carboxylate<br>Intermediate 1-8 and (S)-methyl 2-fluoro-4-(piperidin-2-yl)benzoate<br>(CAS: 1336571-41-5) | (ESI+)<br>521.5<br>(M + H) |
| 3-2-23 | 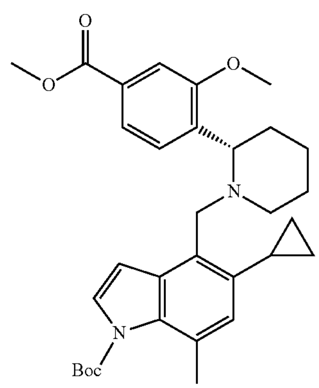 [SMILES: COC(=O)c1ccc([C@@H]2CCCCN2Cc2c(C3CC3)cc(C)c3c2ccn3C(=O)OC(C)(C)C)c(OC)c1] | (S)-tert-butyl 5-cyclopropyl-4-((2-(2-methoxy-4-(methoxycarbonyl)phenyl)piperidin-1-yl)methyl)-7-methyl-1H-indole-1-carboxylate<br>Intermediate 1-8 and<br>(S)-methyl 6-(-2-piperidyl)pyridine-3-carboxylate<br>(CAS: 1269996-93-1) | (ESI+)<br>533.5<br>(M + H) |
| 3-2-24 | rel-(2S,4S) | (±)-tert-butyl 4-(rel-(2S,4S)-(4-ethoxy-2-(4-(methoxycarbonyl)phenyl)piperidin-1-yl)methyl)-5,7-dimethyl-1H-indole-1-carboxylate<br>Intermediate 1-7 and<br>Intermediate 2-13b | (ESI+)<br>521.6<br>(M + H) |

| Intermediate | structure | chemical name starting material | MS (m/z) |
|---|---|---|---|
| 3-2-25 | (structure shown, rel-(2S,4S)) | (±)-tert-butyl 5-cyclopropyl-4-(rel-(2S,4S)-(4-methoxy-2-(4-(methoxycarbonyl)phenyl)piperidin-1-yl)methyl)-7-methyl-1H-indole-1-carboxylate Intermediate 1-8 and Intermediate 2-12 | (ESI+) 533.6 (M + H) |
| 3-2-26 | (structure shown, single regioisomer isolated) | (±)-tert-butyl 4-((2-(4-(N-acetylsulfamoyl)phenyl)piperidin-1-yl)methyl)-5-cyclopropyl-7-methyl-1H-indole-1-carboxylate Intermediate 1-8 and Intermediate 2-26 | (ESI+) 566.3 (M + H) |

Intermediate 3-3:

Intermediate 3-3-A; 1-((5,7-dimethyl-1-tosyl-1H-indol-4-yl)methyl)-2-(4-(hydroxymethyl)phenyl)pyridin-1-ium chloride

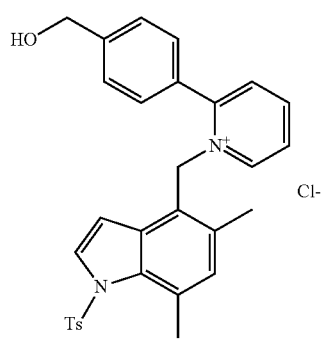 [SMILES: Cc1ccc(S(=O)(=O)n2ccc3c(C[n+]4ccccc4-c4ccc(CO)cc4)c(C)cc(C)c32)cc1 ; [Cl-]]

To a solution of (4-(pyridin-2-yl)phenyl)methanol (CAS: 98061-39-3, 70 mg, 0.378 mmol) in CH₃CN (0.5 mL) was added 4-(chloromethyl)-5,7-dimethyl-1-tosyl-1H-indole, Intermediate 1-6, (100 mg, 0.287 mmol). The mixture was then stirred at 70° C. for 23 h. The reaction mixture was concentrated to give the title compound, which was used in the next reaction without the need for further purification. MS (ESI+) m/z 497.5 (M)⁺.

Intermediate 3-3; (±)-(4-(1-((5,7-dimethyl-1-tosyl-1H-indol-4-yl)methyl)piperidin-2-yl)phenyl)methanol

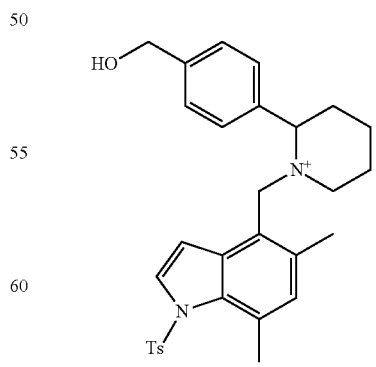

A mixture of 1-((5,7-dimethyl-1-tosyl-1H-indol-4-yl)methyl)-2-(4-(hydroxymethyl)phenyl)-pyridin-1-ium chloride, Intermediate 3-3-A, and PtO₂ (20 mg, 0.088 mmol) in MeOH (2 mL) was stirred at room temperature under H₂ atmosphere for ca. 4 h. The H₂ gas was replaced with N₂. The catalyst was then removed by filtration through a plug of Celite®, which was rinsed with MeOH. The filtrate was then concentrated, which was purified by silica gel flash column chromatography (heptane/EtOAc=4/1 to 1/1) to afford the title compound. MS (ESI+) m/z 503.5 (M+H).

Intermediate 4-1:

(±)-tert-Butyl 4-((4-(cyanomethyl)-2-phenylpiperidin-1-yl)methyl)-5,7-dimethyl-1H-indole-1-carboxylate (Diastereomer-1)

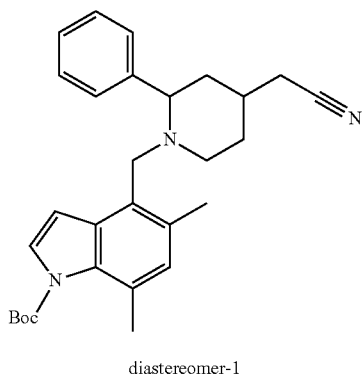 [SMILES: Cc1cc(C)c2c(ccn2C(=O)OC(C)(C)C)c1CN1CCC(CC#N)CC1c1ccccc1]

diastereomer-1

To a mixture of (±)-2-(2-phenylpiperidin-4-yl)acetonitrile (diastereomer-1), Intermediate 2-3, (46.7 mg, 0.233 mmol) and Ti(OiPr)₄ (1 mL, 3.38 mmol) was added tert-butyl 4-formyl-5,7-dimethyl-1H-indole-1-carboxylate, Intermediate 1-5, (55 mg, 0.201 mmol). The mixture was then stirred at 90° C. for 1 h. The reaction mixture was cooled to room temperature, and then diluted with CH₂Cl₂ (ca. 2 mL). The mixture was then poured into a suspension of NaBH₄ (500 mg, 13.22 mmol) in MeOH (20 mL) at 0° C. dropwise. The mixture was then stirred at room temperature for 1 h. The mixture was then diluted with CH₂Cl₂, and added Celite® and H₂O. The mixture was filtered through a plug of Celite®, which was rinsed with CH₂Cl₂. The organic phase was successively washed with H₂O, and brine, dried over Na₂SO₄, filtered, and concentrated to furnish the title compound without any purification MS (ESI+) m/z 458.5 (M+H).

Intermediate 4-2:

(±)-tert-Butyl 4-((4-(cyanomethyl)-2-phenylpiperidin-1-yl)methyl)-5,7-dimethyl-1H-indole-1-carboxylate (Diastereomer-2)

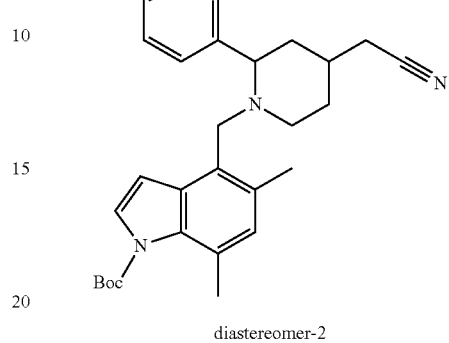

diastereomer-2

The title compound was synthesized from (±)-2-(2-phenylpiperidin-4-yl)acetonitrile (diastereomer-2), Intermediate 2-4, and tert-butyl 4-formyl-5,7-dimethyl-1H-indole-1-carboxylate, Intermediate 1-5, analogously to the preparation of Intermediate 4-2. MS (ESI+) m/z 458.5 (M+H).

Intermediate 4-3:

(±)-tert-Butyl 4-(rel-(2S,4S)-(4-ethoxy-2-(4-(methoxycarbonyl)phenyl)piperidin-1-yl)methyl)-5-methoxy-7-methyl-1H-indole-1-carboxylate

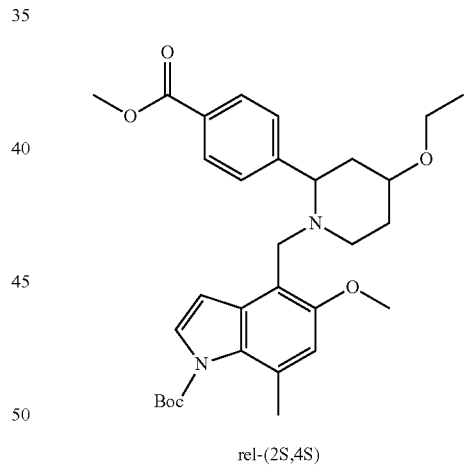

rel-(2S,4S)

To a solution of tert-butyl 4-formyl-5-methoxy-7-methyl-1H-indole-1-carboxylate, Intermediate 1-3, (1.5 g, 5.18 mmol) and (±)-methyl 4-(rel-(2S,4S)-4-ethoxypiperidin-2-yl)benzoate, Intermediate 2-13b, (1.185 g, 4.5 mmol) in DCE (20 mL) was added NaBH(OAc)₃ (3 g, 14.15 mmol). The mixture was then stirred at room temperature for 20 h. The reaction mixture was then diluted with EtOAc. The mixture was then washed successively with 5% aq. NaHCO₃, H₂O, and brine, dried over Na₂SO₄, filtered, and concentrated to afford the title compound, which was used in the next reaction without the needs of further purification. MS (ESI+) m/z 537.4 (M+1).

Following intermediates were prepared from appropriate starting materials by similar methods described above.

| Intermediate | structure | chemical name starting material | MS (m/z) |
|---|---|---|---|
| 4-4-1 | 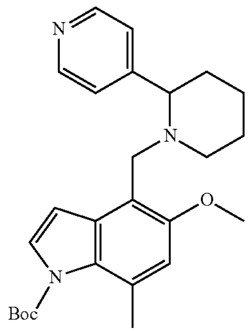 [SMILES: COc1cc(C)c2c(ccn2C(=O)OC(C)(C)C)c1CN1CCCCC1c1ccncc1] | (±)-tert-butyl 5-methoxy-7-methyl-4-((2-(pyridin-4-yl)piperidin-1-yl)methyl)-1H-indole-1-carboxylate Intermediate 1-3 and (±)-2-(4-pyridinyl)piperidine (CAS: 143924-51-0) | (APCI) 436.1 (M + H) |
| 4-4-2 | 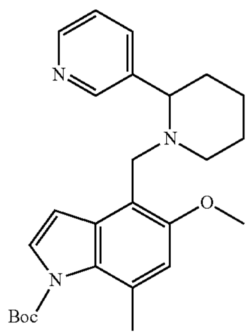 [SMILES: COc1cc(C)c2c(ccn2C(=O)OC(C)(C)C)c1CN1CCCCC1c1cccnc1] | (±)-tert-butyl 5-methoxy-7-methyl-4-((2-(pyridin-3-yl)piperidin-1-yl)methyl)-1H-indole-1-carboxylate Intermediate 1-3 and (±)-2-(3-pyridinyl)piperidine (CAS: 13078-04-1) | (APCI) 436.1 (M + H) |
| 4-4-3 | 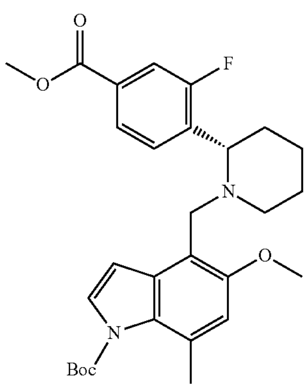 | (S)-tert-butyl 4-((2-(2-fluoro-4-(methoxycarbonyl)phenyl)piperidin-1-yl)methyl)-5-methoxy-7-methyl-1H-indole-1-carboxylate Intermediate 1-3 and (S)-methyl 4-((2-piperidyl))-3-fluorobenzoate (CAS: 1213320-08-1) | (APCI) 511.2 (M + H) |
| 4-4-4 | 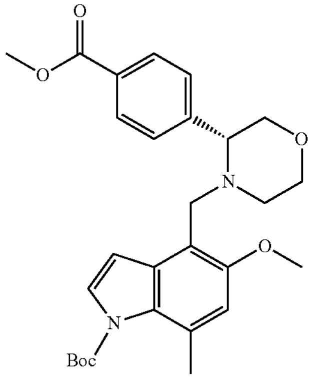 | (R)-tert-butyl 5-methoxy-4-((3-(4-(methoxycarbonyl)phenyl)morpholino)methyl)-7-methyl-1H-indole-1-carboxylate Intermediate 1-3 and (R)-methyl 4-(morpholin-3-yl)benzoate (CAS: 1213450-66-8) | (ESI+) 495.2 (M + H) |

| Intermediate | structure | chemical name / starting material | MS (m/z) |
|---|---|---|---|
| 4-4-5 | 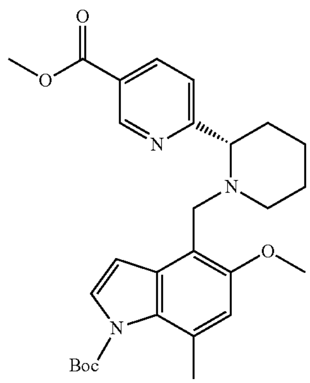 | (S)-tert-butyl 5-methoxy-4-((2-(5-(methoxycarbonyl)pyridin-2-yl)piperidin-1-yl)methyl)-7-methyl-1H-indole-1-carboxylate<br>Intermediate 1-3 and<br>(S)-methyl 6-(2-piperidyl)pyridine-3-carboxylate<br>(CAS: 1269996-93-1) | (ESI+)<br>495.2<br>(M + H) |
| 4-4-6 | 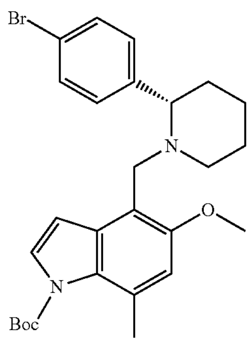 [SMILES: COc1cc(C)c2c(ccn2C(=O)OC(C)(C)C)c1CN1CCCC[C@H]1c1ccc(Br)cc1] | (S)-tert-butyl 4-((2-(4-bromophenyl)piperidin-1-yl)methyl)-5-methoxy-7-methyl-1H-indole-1-carboxylate<br>Intermediate 1-3 and<br>(S)-2-(4-bromophenyl)piperidine | (APCI+)<br>513.2,<br>515.1<br>(M + H) |
| 4-4-7 | 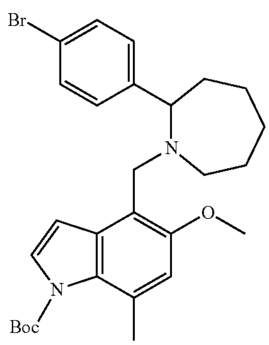 [SMILES: COc1cc(C)c2c(ccn2C(=O)OC(C)(C)C)c1CN1CCCCCC1c1ccc(Br)cc1] | (±)-tert-butyl 4-((2-(4-bromophenyl)azepan-1-yl)methyl)-5-methoxy-7-methyl-1H-indole-1-carboxylate<br>Intermediate 1-3 and<br>2-(4-bromophenyl)azepane<br>(CAS: 383129-24-6) | (APCI+)<br>527.2<br>(M + H) |
| 4-4-8 | 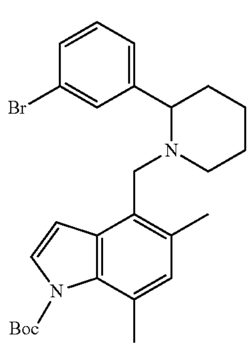 [SMILES: Cc1cc(C)c2c(ccn2C(=O)OC(C)(C)C)c1CN1CCCCC1c1cccc(Br)c1] | (±)-tert-butyl 4-((2-(3-bromophenyl)piperidin-1-yl)methyl)-5,7-dimethyl-1H-indole-1-carboxylate<br>Intermediate 1-3 and<br>2-(3-bromophenyl)piperidine<br>(CAS: 383128-74-3) | (APCI+)<br>497.0<br>(M + H |

| Intermediate | structure | chemical name starting material | MS (m/z) |
|---|---|---|---|
| 4-4-9 | 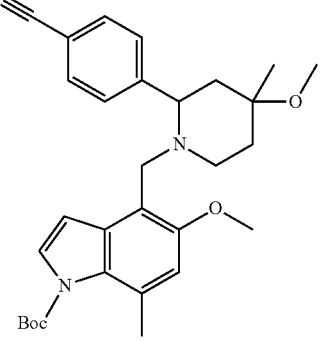 diastereomer-1 | (±)-tert-butyl 4-((2-(4-cyanophenyl)-4-methoxy-4-methylpiperidin-1-yl)methyl)-5-methoxy-7-methyl-1H-indole-1-carboxylate (single diastereomer) Intermediate 1-3 and Intermediate 2-14 | MS (ESI+) m/z 504.2 (M + H) |
| 4-4-10 | 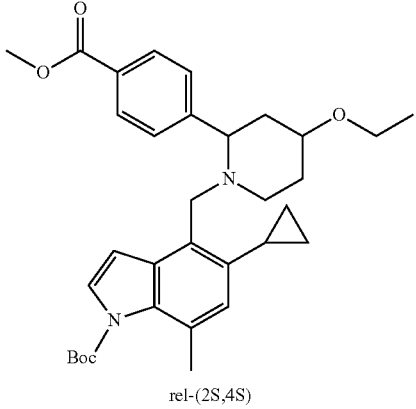 [SMILES: CCOC1CCN(Cc2c(C3CC3)cc(C)c3c2ccn3C(=O)OC(C)(C)C)C(c2ccc(C(=O)OC)cc2)C1] rel-(2S,4S) | (±)-tert-butyl 5-cyclopropyl-4-(rel-(2S,4S)-(4-ethoxy-2-(4-(methoxycarbonyl)phenyl)piperidin-1-yl)methyl)-7-methyl-1H-indole-1-carboxylate Intermediate 1-2 and Intermediate 2-13b | (ESI+) 547.3 (M + H) |
| 4-4-11 | 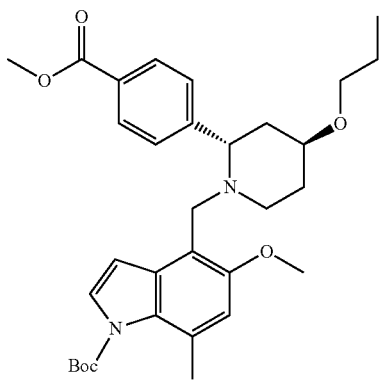 rel-(2S,4S) | tert-butyl 5-methoxy-4-((2S,4S)-(2-(4-(methoxycarbonyl)phenyl)-4-propoxypiperidin-1-yl)methyl)-7-methyl-1H-indole-1-carboxylate Intermediate 1-3 and Intermediate 2-15-6 | (ESI+) 551.4 (M + H) |

| Intermediate | structure | chemical name starting material | MS (m/z) |
|---|---|---|---|
| 4-4-12 | (structure shown) rel-(2S,4S) | tert-butyl 4-((2S,4S)-(4-hydroxy-2-(4-(methoxycarbonyl)phenyl)piperidin-1-yl)methyl)-5-methoxy-7-methyl-1H-indole-1-carboxylate<br>Intermediate 1-3 and<br>Intermediate 2-15-7 | (ESI+) 509.4 (M + H) |
| 4-4-13 | (structure shown) | (±)-tert-butyl 5-methoxy-4-((2-(4-(methoxycarbonyl)-2-methylphenyl)piperidin-1-yl)methyl)-7-methyl-1H-indole-1-carboxylate<br>Intermediate 1-3 and<br>Intermediate 2-18-1 | (APCI+) 507.2 (M + H) |
| 4-4-14 | (structure shown) single diastereomer | (±)-tert-butyl 5-methoxy-4-((2-(4-(methoxycarbonyl)phenyl)-5-methylpiperidin-1-yl)methyl)-7-methyl-1H-indole-1-carboxylate (single diastereomer)<br>Intermediate 1-3 and<br>Intermediate 2-18-2 | (APCI+) 507.4 (M + H) |

-continued

| Intermediate | structure | chemical name starting material | MS (m/z) |
|---|---|---|---|
| 4-4-15 | rel-(2S,4R) | (±)-tert-butyl 4-((rel-(2S,4R)-4-ethyl-2-(4-(methoxycarbonyl)phenyl)piperidin-1-yl)methyl)-5-methoxy-7-methyl-1H-indole-1-carboxylate Intermediate 1-3 and Intermediate 2-18-3 | (ESI+) 521.4 (M + H) |
| 4-4-16 | 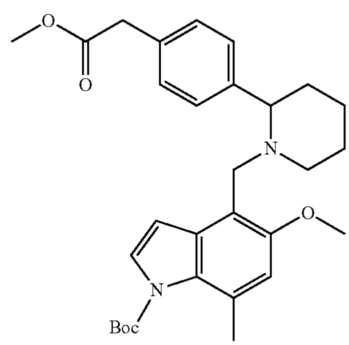 | (±)-tert-butyl 5-methoxy-4-((2-(4-(2-methoxy-2-oxoethyl)phenyl)piperidin-1-yl)methyl)-7-methyl-1H-indole-1-carboxylate Intermediate 1-3 and Intermediate 2-18-4 | (APCI+) 507.3 (M + 1) |
| 4-4-17 | 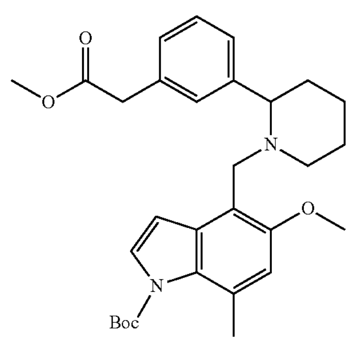 | (±)-tert-butyl 5-methoxy-4-((2-(3-(2-methoxy-2-oxoethyl)phenyl)piperidin-1-yl)methyl)-7-methyl-1H-indole-1-carboxylate Intermediate 1-3 and Intermediate 2-18-5 | (APCI+) 507.2 (M + 1) |
| 4-4-18 | rel-(2S,4S) | (±)-tert-butyl 5-cyclopropyl-4-(rel-(2S,4S)-(4-methoxy-2-(6-(methoxycarbonyl)pyridin-3-yl)piperidin-1-yl)methyl)-7-methyl-1H-indole-1-carboxylate Intermediate 1-2 and Intermediate 2-23-1 | (ESI+) 534.3 (M + 1) |

-continued

| Intermediate | structure | chemical name starting material | MS (m/z) |
|---|---|---|---|
| 4-4-19 | diastereomer-1 | (±)-tert-butyl 4-((2-(4-cyanophenyl)-5-methoxypiperidin-1-yl)methyl)-5-methoxy-7-methyl-1H-indole-1-carboxylate (diastereomer-1) Intermediate 1-3 and Intermediate 2-21 | (ESI+) 490.4 (M + H) |
| 4-4-20 | diastereomer-2 | (±)-tert-butyl 4-((2-(4-cyanophenyl)-5-methyl-1H-indole-1-carboxylate (diastereomer-2) Intermediate 1-3 and Intermediate 2-23-4 | (ESI+) 490.0 (M + H) |
| 4-4-21 | diastereomer-1 | (±)-tert-butyl 4-((5-((tert-butyldiphenylsilyl)oxy)-2-(4-cyanophenyl)piperidin-1-yl)methyl)-5-methoxy-7-methyl-1H-indole-1-carboxylate (diastereomer-1) Intermediate 1-3 and Intermediate 2-23-2 | (ESI+) 714.4 (M + H) |
| 4-4-22 | diastereomer-2 | (±)-tert-butyl 4-((5-((tert-butyldiphenylsilyl)oxy)-2-(4-cyanophenyl)piperidin-1-yl)methyl)-5-methoxy-7-methyl-1H-indole-1-carboxylate (diastereomer-2) Intermediate 1-3 and Intermediate 2-23-3 | (ESI+) 714.4 (M + H) |

| Intermediate | chemical name starting material | MS (m/z) |
|---|---|---|
| 4-4-23 | (±)-ethyl 2-(1-((1-(tert-butoxycarbonyl)-5-methoxy-7-methyl-1H-indol-4-yl)methyl)piperidin-2-yl)thiazole-4-carboxylate<br>Intermediate 1-3 and<br>Intermediate 2-24 | (ESI+)<br>514.1<br>(M + H) |
| 4-4-24 | (±)-methyl 2-(1-((1-(tert-butoxycarbonyl)-5-methoxy-7-methyl-1H-indol-4-yl)methyl)piperidin-2-yl)-4-methylthiazole-5-carboxylate<br>Intermediate 1-3 and<br>Intermediate 2-25 | (ESI+)<br>514.1<br>(M + H) |
| 4-4-25 | (S)-tert-butyl 5-methoxy-4-((2-(4-(methoxycarbonyl)phenyl)piperidin-1-yl)methyl)-7-methyl-1H-indole-1-carboxylate<br>Intermediate 1-3 and<br>(S)-methyl 4-(piperidin-2-yl)benzoate<br>(CAS: 1213455-84-5) | (ESI+)<br>493.5<br>(M + H) |
| 4-4-26 | (±)-tert-butyl 5-methoxy-4-((2-(3-methoxy-4-(methoxycarbonyl)phenyl)piperidin-1-yl)methyl)-7-methyl-1H-indole-1-carboxylate<br>Intermediate 1-3 and<br>Intermediate 2-17 | (ESI+)<br>523.3<br>(M + 1) |

| Intermediate | structure | chemical name starting material | MS (m/z) |
|---|---|---|---|
| 4-4-27 | 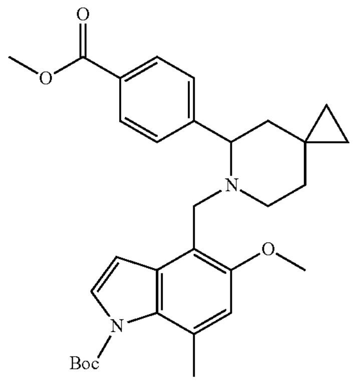 [SMILES: COC(=O)c1ccc(C2CC3(CCN2Cc2c(OC)cc(C)c4c2ccn4C(=O)OC(C)(C)C)CC3)cc1] | (±)-tert-butyl 5-methoxy-4-((5-(4-(methoxycarbonyl)phenyl)-6-azaspiro[2.5]octan-6-yl)methyl)-7-methyl-1H-indole-1-carboxylate Intermediate 1-3 and Intermediate 2-27 | (APCI+) 519.1 (M + 1) |
| 4-4-28 | rel-(2S,4S) | (±)-tert-butyl 4-((rel-(2S,4S)-4-ethyl-2-(4-(methoxycarbonyl)phenyl)piperidin-1-yl)methyl)-5-methoxy-7-methyl-1H-indole-1-carboxylate Intermediate 1-3 and Intermediate 2-28 | (APCI+) 521.1 (M + 1) |

Intermediate 4-5:

(±)-tert-Butyl 4-((2-(4-cyanophenyl)-5-hydroxypiperidin-1-yl)methyl)-5-methoxy-7-methyl-1H-indole-1-carboxylate (Diastereomer-1)

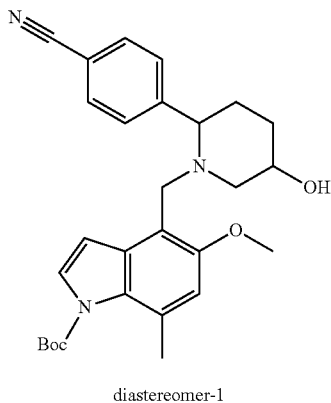 [SMILES: COc1cc(C)c2c(ccn2C(=O)OC(C)(C)C)c1CN1CC(O)CCC1c1ccc(C#N)cc1]

diastereomer-1

The title compound was synthesized from (±)-tert-butyl 4-((5-((tert-butyldiphenylsilyl)oxy)-2-(4-cyanophenyl)piperidin-1-yl)methyl)-5-methoxy-7-methyl-1H-indole-1-carboxylate (diastereomer-1), Intermediate 4-4-21 (diastereomer-1), analogously to the preparation of Intermediate 2-12-E. MS (ESI+) m/z 476.4 (M+H).

Intermediate 4-6:

(±)-tert-Butyl 4-((2-(4-cyanophenyl)-5-hydroxypiperidin-1-yl)methyl)-5-methoxy-7-methyl-1H-indole-1-carboxylate (Diastereomer-2)

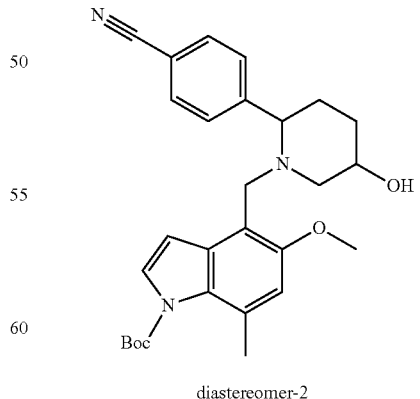

diastereomer-2

The title compound was synthesized from (±)-tert-butyl 4-((5-((tert-butyldiphenylsilyl)oxy)-2-(4-cyanophenyl)piperidin-1-yl)methyl)-5-methoxy-7-methyl-1H-indole-1-car- Intermediate 4-7:

(±)-tert-Butyl 4-((2-(3-cyanophenyl)piperidin-1-yl)methyl)-5,7-dimethyl-1H-indole-1-carboxylate

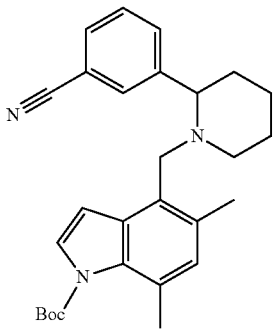 [SMILES: Cc1cc(C)c2c(ccn2C(=O)OC(C)(C)C)c1CN1CCCCC1c1cccc(C#N)c1]

To a solution of (±)-tert-butyl 4-((2-(3-bromophenyl)piperidin-1-yl)methyl)-5,7-dimethyl-1H-indole-1-carboxylate, Intermediate 4-4-8, (200 mg, 0.402 mmol) and zinc cyanide (10.16 mg, 0.087 mmol) in DMF (1.5 mL) was added Pd(PPh$_3$)$_4$ (50 mg, 0.043 mmol). The mixture was then stirred at 80° C. for 6 h, and then cooled to room temperature. The mixture was diluted with EtOAc. The organic phase was then washed successively with H$_2$O (twice), and brine, dried over Na$_2$SO$_4$, filtered, and concentrated. The resulting residue was purified by silica gel flash column chromatography (heptane/EtOAc) to afford the title compound. MS (APCI+) m/z 444.1 (M+H).

Intermediate 4-8:

(±)-Methyl 3-(1-((5,7-dimethyl-1H-indol-4-yl)methyl)piperidin-2-yl)benzoate

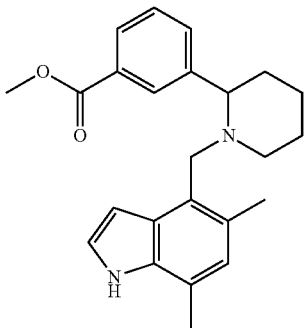 [SMILES: COC(=O)c1cccc(C2CCCCN2Cc2c(C)cc(C)c3[nH]ccc23)c1]

To a solution of (±)-tert-butyl 4-((2-(3-bromophenyl)piperidin-1-yl)methyl)-5,7-dimethyl-1H-indole-1-carboxylate, Intermediate 4-4-8, (580 mg, 1.166 mmol), Et$_3$N (1 mL, 7.21 mmol), and Pd(OAc)$_2$ (52.4 mg, 0.233 mmol) in DMSO (18 mL)/MeOH (18 mL) was added 1,3-bis(diphenylphosphino)propane (192 mg, 0.466 mmol). The mixture was then stirred at 80° C. under carbon monoxide atmosphere (100 psi) for ca. 16 h. The reaction mixture was diluted with EtOAc. The mixture was then washed successively with H$_2$O (twice) and brine, dried over Na$_2$SO$_4$, filtered, and concentrated. The resulting residue was purified by silica gel flash column chromatography (heptane/EtOAc) to afford the title compound. MS (APCI+) m/z 377.1 (M+H).

Intermediate 4-9:

(±)-tert-Butyl 5-methoxy-4-((2-(4-(methoxycarbonyl)phenyl)azepan-1-yl)methyl)-7-methyl-1H-indole-1-carboxylate

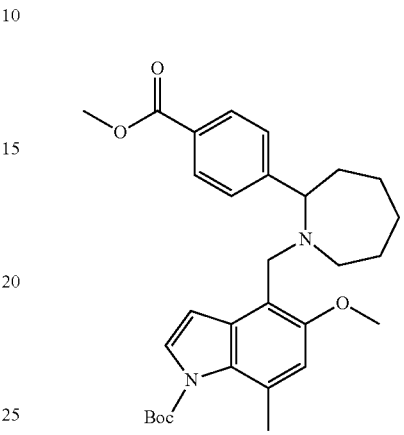

The title compound was synthesized from (±)-tert-butyl 4-((2-(4-bromophenyl)azepan-1-yl)methyl)-5-methoxy-7-methyl-1H-indole-1-carboxylate, Intermediate 4-4-7, analogously to the preparation of Intermediate 4-8. MS (APCI+) m/z 507.2 (M+1)

Intermediate 4-10:

(S)-tert-Butyl 4-((2-(4-(1H-pyrazol-4-yl)phenyl)piperidin-1-yl)methyl)-5-methoxy-7-methyl-1H-indole-1-carboxylate

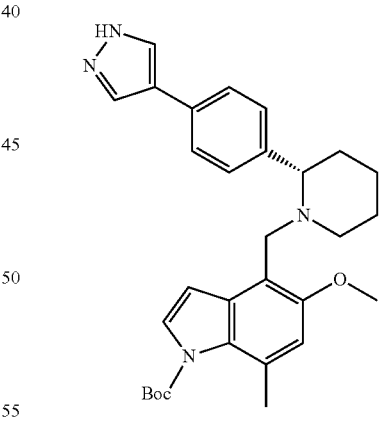

To a suspension of (S)-tert-butyl 4-((2-(4-bromophenyl)piperidin-1-yl)methyl)-5-methoxy-7-methyl-1H-indole-1-carboxylate, Intermediate 4-4-6 (153 mg, 0.298 mmol), 4-(4,4,5,5-tetramethyl-1,3,2-dioxaborolan-2-yl)-1H-pyrazole (89 mg, 0.46 mmol), and K$_2$CO$_3$ (124 mg, 0.9 mmol) in dioxane (8 mL)/H$_2$O (2 mL) was added Pd(PPh$_3$)$_4$ (30 mg, 0.026 mmol). The mixture was then stirred at 90° C. for ca. 16 h. The reaction mixture was then cooled down to room temperature, and then diluted with EtOAc. The mixture was then washed successively with 5% aq. NaHCO$_3$, H$_2$O, and brine, dried over Na$_2$SO$_4$, filtered, and concentrated. The resulting residue was purified by silica gel flash column chromatography (heptane/EtOAc=1/0 to 1/1) to afford the title compound. MS (ESI+) m/z 501.3 (M+H). Intermediate 4-11:

(S)-tert-Butyl 4-((2-(4-(1H-pyrazol-3-yl)phenyl)piperidin-1-yl)methyl)-5-methoxy-7-methyl-1H-indole-1-carboxylate

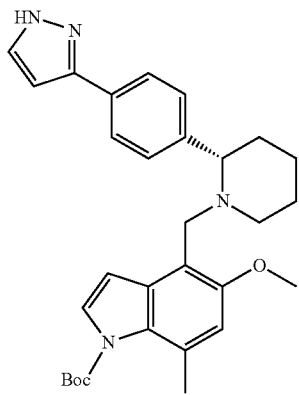 [SMILES: COc1cc(C)c2c(ccn2C(=O)OC(C)(C)C)c1CN1CCCC[C@H]1c1ccc(-c2cc[nH]n2)cc1]

The title compound was synthesized from (S)-tert-butyl 4-((2-(4-bromophenyl)piperidin-1-yl)methyl)-5-methoxy-7-methyl-1H-indole-1-carboxylate, Intermediate 4-4-6, and 3-(4,4,5,5-tetramethyl-1,3,2-dioxaborolan-2-yl)-1H-pyrazole analogously to the preparation of Intermediate 4-10. MS (ESI+) m/z 501.3 (M+H).

Intermediate 4-12:

(±)-tert-Butyl 5-methoxy-4-((2-(4-(methoxycarbonyl)naphthalen-1-yl)piperidin-1-yl)methyl)-7-methyl-1H-indole-1-carboxylate

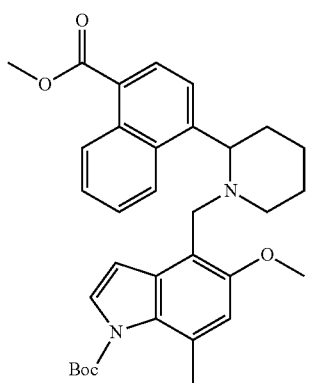 [SMILES: COC(=O)c1ccc(C2CCCCN2Cc2c(OC)cc(C)c3c2ccn3C(=O)OC(C)(C)C)c2ccccc12]

To a solution of tert-butyl 4-(hydroxymethyl)-5-methoxy-7-methyl-1H-indole-1-carboxylate, Intermediate 1-10, (50 mg, 0.172 mmol) in DMSO (1 mL) at room temperature was added cyanuric chloride (63 mg, 0.344 mmol). The mixture was then stirred at room temperature for 2 h, and then quenched with $H_2O$. The mixture was then extracted with EtOAc. The organic layer was washed successively with $H_2O$ and brine, dried over $Na_2SO_4$, filtered, and then concentrated. The resulting residue was dissolved in DMF (3 mL). To the DMF solution was added (±)-methyl 4-(piperidin-2-yl)-1-naphthoate HCl salt, Intermediate 2-18-6, (79 mg, 0.26 mmol) and $iPr_2NEt$ (0.13 mL, 0.777 mmol), followed by potassium iodide (21.6 mg, 0.13 mmol). The mixture was then stirred at room temperature for 4 days. The reaction mixture was then diluted with EtOAc. The organic phase was washed successively with $H_2O$ and brine, dried over $Na_2SO_4$, filtered, and concentrated. The resulting residue was purified by silica gel flash column chromatography (heptane/EtOAc=1/0 to 8/2) to afford the title compound. MS (APCI+) m/z 543.2 (M+H).

Intermediate 4-13 and Intermediate 4-14:

Intermediate 4-13-A; (±)-tert-butyl 5-methoxy-7-methyl-4-(2,2,2-trifluoro-1-hydroxyethyl)-1H-indole-1-carboxylate

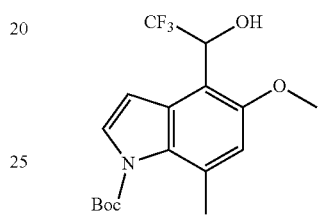

To a solution of tert-butyl 4-formyl-5-methoxy-7-methyl-1H-indole-1-carboxylate, Intermediate 1-3, (1.34 g, 4.6 mmol) and trimethyl(trifluoromethyl)silane (900 mg, 4.88 mmol) in THF (10 mL) was added TBAF (1M in THF, 92 uL, 0.09 mmol) at −20° C. The mixture was then stirred at room temperature for 2 h, and then concentrated. The resulting residue was purifies by silica gel flash column chromatography (heptane/EtOAc=1/0 to 8/2) to afford the title compound. $^1$H NMR (300 MHz, CDCl$_3$) δ 7.54 (d, J=3.0 Hz, 1H), 6.79 (s, 1H), 6.58 (d, J=3.0 Hz, 1H), 5.30-5.46 (m, 1H), 4.63 (br. d, J=5.4 Hz, 1H), 3.93 (br. s., 3H), 2.63 (s, 3H), 1.62 (s, 9H).

Intermediate 4-13; methyl 4-(2S)-(1-(2,2,2-trifluoro-1-(5-methoxy-7-methyl-1H-indol-4-yl)ethyl)piperidin-2-yl)benzoate (Diastereomer-1): and Intermediate 4-14; methyl 4-(2S)-(1-(2,2,2-trifluoro-1-(5-methoxy-7-methyl-1H-indol-4-yl)ethyl)piperidin-2-yl)benzoate (Diastereomer-2)

diastereomer-1

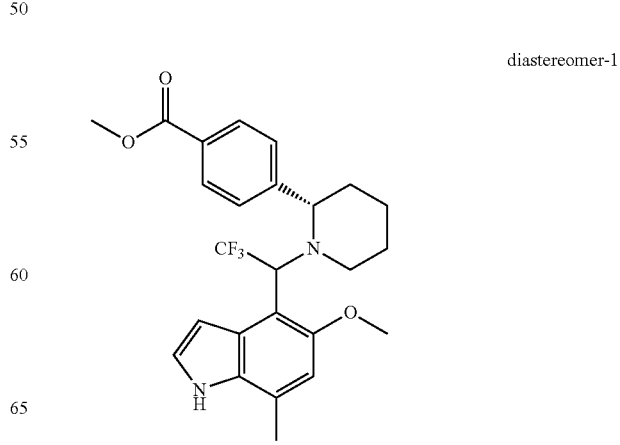

-continued diastereomer-2

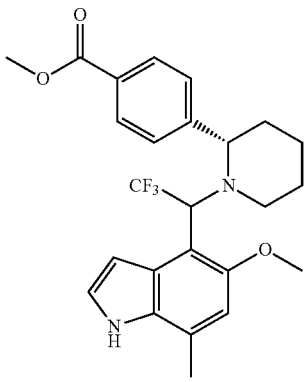

To a solution of (±)-tert-butyl 5-methoxy-7-methyl-4-(2,2,2-trifluoro-1-hydroxyethyl)-1H-indole-1-carboxylate, Intermediate 4-13-A, (350 mg, 0.974 mmol) in CH$_2$Cl$_2$ (5 mL) at 0° C. was added Et$_3$N (162 uL, 1.169 mmol), followed by MsCl (91 uL, 1.169 mmol). The mixture was then stirred at room temperature for 16 h. The mixture was then diluted with CH$_2$Cl$_2$. The mixture was then washed successively with 5% aq. NaHCO$_3$, H$_2$O, and brine, dried over Na$_2$SO$_4$, filtered, and concentrated. To a solution of the resulting residue in CH$_3$CN (5 mL) was added Et$_3$N (1 mL, 7.21 mmol), followed by methyl (S)-4-(piperidin-2-yl)benzoate (125 mg, 0.487 mmol). The mixture was then stirred at 130° C. for 16 h in the sealed tube. The reaction mixture was then concentrated. The resulting residue was purified by RP-HPLC (stationary phase; Xbridge™ C-18: mobile phase; 0.05% TFA in H$_2$O/CH$_3$CN: gradient; 5% to 90% B in 40 min) to afford, in respective elution order, tert-butyl 5-methoxy-7-methyl-4-(2,2,2-trifluoro-1-((S)-2-(4-(methoxycarbonyl)phenyl)piperidin-1-yl)ethyl)-1H-indole-1-carboxylate (diastereomer-1, t$_r$=23.8 min) as Intermediate 4-13, MS (APCI–) m/z 459.16 (M–H); and tert-butyl 5-methoxy-7-methyl-4-(2,2,2-trifluoro-1-((S)-2-(4-(methoxycarbonyl)phenyl)piperidin-1-yl)ethyl)-1H-indole-1-carboxylate (diastereomer-2, t$_r$=26.1 min) as Intermediate 4-14, MS (APCI–) m/z 459.15 (M–H).

Intermediate 4-15:

(±)-4-((2-(4-(2H-tetrazol-5-yl)phenyl)piperidin-1-yl)methyl)-5,7-dimethyl-1-tosyl-1H-indole diastereomer-1

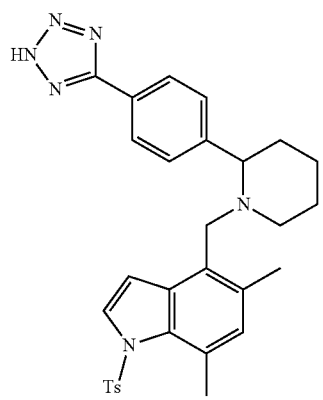

A mixture of (±)-4-(1-((5,7-dimethyl-1-tosyl-1H-indol-4-yl)methyl)piperidin-2-yl)benzonitrile, Intermediate 3-2-11, (80 mg, 0.161 mmol), sodium azide (15.68 mg, 0.241 mmol), and triethylamine hydrochloride (33.2 mg, 0.241 mmol) in chlorobenzene (2 mL) was stirred at 110° C. for 1 hr, and then at 130° C. for 5 hr. To the mixture were added additional amounts of sodium azide (29 mg) and triethylamine hydrochloride (63 mg) at room temperature. The mixture was then stirred at 130° C. for 3 hr, and then cooled to room temperature. The mixture was then diluted with H$_2$O, and then acidified with 1 mL of AcOH. The mixture was then extracted three times with EtOAc. The combined organic layers were then dried over Na$_2$SO$_4$, filtered, and then concentrated. The resulting residue was purified by silica gel flash column chromatography [heptane/(5% MeOH in EtOAc=1/0 to 0/1) to afford the title compound. MS (ESI+) m/z 541.5 (M+H).

Intermediate 5-1:

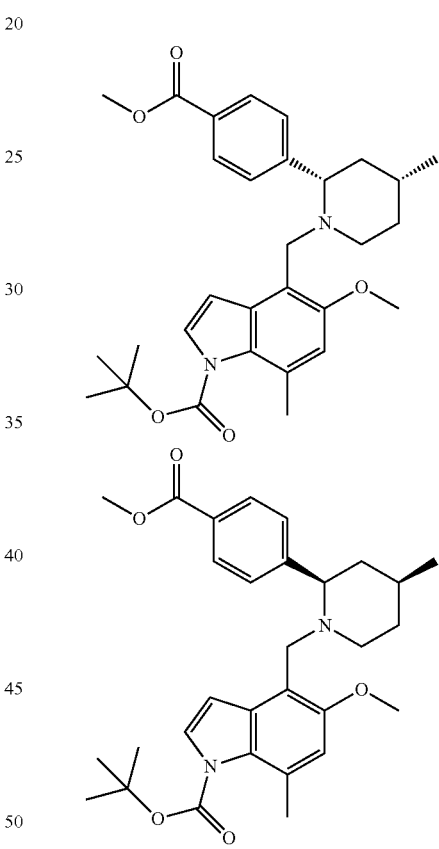

Intermediate 5-1a; (±)-tert-butyl 5-methoxy-4-((rel-(2S,4R)-2-(4-(methoxycarbonyl)phenyl)-4-methylpiperidin-1-yl)methyl)-7-methyl-1H-indole-1-carboxylate To a solution of tert-butyl 4-formyl-5-methoxy-7-methyl-1H-indole-1-carboxylate, Intermediate 1-3, (1.8 g, 6.22 mmol) and (±)-methyl 4-(rel-(2S,4R)-4-methylpiperidin-2-yl)benzoate, Intermediate 2-16, (1.2 g, 5.14 mmol) in DCE (15 mL) was added NaBH(OAc)$_3$ (3 g, 14.15 mmol). The mixture was then stirred at room temperature for 14 h. The reaction mixture was diluted with EtOAc. The mixture was then washed successively with 5% aq. NaHCO$_3$, H$_2$O, and brine, dried over Na$_2$SO$_4$, filtered, and concentrated. The resulting residue was purified by silica gel flash column chromatography (heptane/EtOAc=91/1) to afford the title compound. (ESI+) m/z 507.1 (M+H).

Intermediate 5-1b; tert-butyl 5-methoxy-4-(((2S,4R)-2-(4-(methoxycarbonyl)phenyl)-4-methylpiperidin-1-yl)methyl)-7-methyl-1H-indole-1-carboxylate and tert-butyl 5-methoxy-4-(((2R,4S)-2-(4-(methoxycarbonyl)phenyl)-4-methylpiperidin-1-yl)methyl)-7-methyl-1H-indole-1-carboxylate Resolution of the enantiomers of Intermediate 5-1a was achieved by chiral SFC using a CHIRALPAK® IA column with 20% iPrOH in $CO_2$ to give tert-butyl 5-methoxy-4-(((2S,4R)-2-(4-(methoxycarbonyl)phenyl)-4-methylpiperidin-1-yl)methyl)-7-methyl-1H-indole-1-carboxylate (peak-1, $t_r$=4.1 min) and tert-butyl 5-methoxy-4-(((2R,4S)-2-(4-(methoxycarbonyl)phenyl)-4-methylpiperidin-1-yl)methyl)-7-methyl-1H-indole-1-carboxylate (peak-2, $t_r$=5.8 min).

Intermediate 5-2:

Intermediate 5-2a; (±)-tert-butyl 5-methoxy-4-(rel-(2S,4S)-(4-methoxy-2-(4-(methoxycarbonyl)phenyl)piperidin-1-yl)methyl)-7-methyl-1H-indole-1-carboxylate

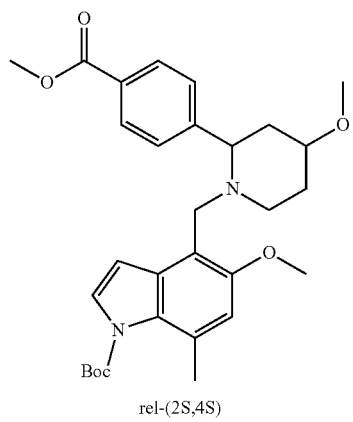

rel-(2S,4S)

To a solution of tert-butyl 4-formyl-5-methoxy-7-methyl-1H-indole-1-carboxylate, Intermediate 1-3, (120 mg, 0.415 mmol) and (±)-methyl 4-(rel-(2S,4S)-4-methoxypiperidin-2-yl)benzoate, Intermediate 2-12, (100 mg, 0.401 mmol) in DCE (2 mL) was added $NaB(OAc)_3H$ (400 mg, 1.887 mmol). The mixture was then stirred at room temperature for 17 h. The mixture was then diluted with $CH_2Cl_2$. The mixture was then washed successively with 5% aq. $NaHCO_3$, $H_2O$, and brine, dried over $Na_2SO_4$, filtered, and concentrated. The resulting residue was purified by flash column chromatography on aminopropyl-functionalized silica gel (heptane/EtOAc=94/6) to afford the title compound. MS (ESI+) m/z 523.4 (M+H).

Intermediate 5-2b; tert-butyl 5-methoxy-4-((2R,4R)-(4-methoxy-2-(4-(methoxycarbonyl)phenyl)piperidin-1-yl)methyl)-7-methyl-1H-indole-1-carboxylate: and tert-butyl 5-methoxy-4-((2S,4S)-(4-methoxy-2-(4-(methoxycarbonyl)phenyl)piperidin-1-yl)methyl)-7-methyl-1H-indole-1-carboxylate

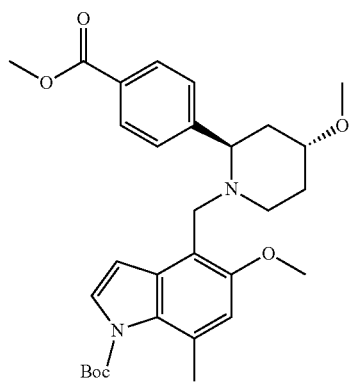

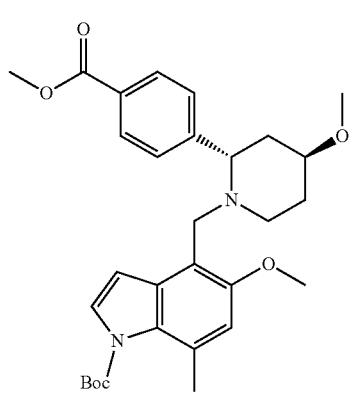

Resolution of the enantiomers of Intermediate 5-2a was achieved by chiral SFC using a CHIRALPAK® AD-H column with 15% (5 mM $NH_4OH$ in MeOH) in $CO_2$ to afford tert-butyl 5-methoxy-4-((2R,4R)-(4-methoxy-2-(4-(methoxycarbonyl)phenyl)piperidin-1-yl)methyl)-7-methyl-1H-indole-1-carboxylate (peak-1, $t_r$=2.8 min) and tert-butyl 5-methoxy-4-((2S,4S)-(4-methoxy-2-(4-(methoxycarbonyl)phenyl)piperidin-1-yl)methyl)-7-methyl-1H-indole-1-carboxylate (peak-2, $t_r$=5.5 min).

The following compounds were prepared from appropriate starting materials by similar methods described above:

| Intermediate | structure | chemical name<br>starting material<br>Conditions for the enantiomer separation | MS (m/z) |
|---|---|---|---|
| 5-3-1a | *(structure shown, rel-(2S,4S))* | (±)-tert-butyl 4-(rel-(2S,4S)-(4-ethoxy-2-(6-(methoxycarbonyl)pyridin-3-yl)piperidin-1-yl)methyl)-5-methoxy-7-methyl-1H-indole-1-carboxylate<br>Intermediate 1-3 and<br>Intermediate 2-20 | ESI+<br>538.0<br>(M + H) |
| 5-3-1b | Resolution of the enantiomers of Intermediate 5-3-1a was achieved by chiral SFC using a (R,R) Whelk-O ® 1 column with 40% MeOH in $CO_2$ to afford tert-butyl 4-(rel-(2S,4S)-(4-ethoxy-2-(6-(methoxycarbonyl)pyridin-3-yl)piperidin-1-yl)methyl)-5-methoxy-7-methyl-1H-indole-1-carboxylate (enantiomer-1) (peak-1, $t_r$ = 4.9 min) and tert-butyl 4-(rel-(2S,4S)-(4-ethoxy-2-(6-(methoxycarbonyl)pyridin-3-yl)piperidin-1-yl)methyl)-5-methoxy-7-methyl-1H-indole-1-carboxylate (enantiomer-2) (peak-2, $t_r$ = 6.0 min). | | |
| 5-3-2a | *(structure shown)* | (±)-tert-butyl 5-methoxy-4-((2-(4-(methoxycarbonyl)phenyl)-4,4-dimethylpiperidin-1-yl)methyl)-7-methyl-1H-indole-1-carboxylate<br>Intermediate 1-3 and<br>Intermediate 2-22 | ESI+<br>521.3<br>(M + H) |
| 5-3-2b | Resolution of the enantiomers of Intermediate 5-3-2a was achieved by chiral SFC using a CHIRALPAK ® AD column with 20% (5 mM $NH_4OH$ in MeOH) in $CO_2$ to afford tert-butyl 5-methoxy-4-((2-(4-(methoxycarbonyl)phenyl)-4,4-dimethylpiperidin-1-yl)methyl)-7-methyl-1H-indole-1-carboxylate (enantiomer-1) (peak-1, $t_r$ = 2.4 min) and tert-butyl 5-methoxy-4-((2-(4-(methoxycarbonyl)phenyl)-4,4-dimethylpiperidin-1-yl)methyl)-7-methyl-1H-indole-1-carboxylate (enantiomer-2) (peak-2, $t_r$ = 4.4 min). | | |

-continued

| Intermediate | structure | chemical name<br>starting material<br>Conditions for the enantiomer separation | MS (m/z) |
|---|---|---|---|
| 5-3-3a | (structure shown) | (±)-tert-butyl 4-(rel-(2S,4S)-(2-(4-cyanophenyl)-4-ethoxypiperidin-1-yl)methyl)-5-methoxy-7-methyl-1H-indole-1-carboxylate<br>Intermediate 1-3 and<br>Intermediate 2-13b | ESI+<br>504.5<br>(M + H) |

5-3-3b Resolution of the enantiomers of Intermediate 5-3-3a was achieved by chiral SFC using a CHIRALPAK® AD-H column with 20% (10 mM NH$_4$OH in MeOH) in CO$_2$ to afford tert-butyl 4-(rel-(2S,4S)-(2-(4-cyanophenyl)-4-ethoxypiperidin-1-yl)methyl)-5-methoxy-7-methyl-1H-indole-1-carboxylate)enantiomer-1) (peak-1, t$_r$ = 1.7 min) and tert-butyl 4-(rel-(2S,4S)-(2-(4-cyanophenyl)-4-ethoxypiperidin-1-yl)methyl)-5-methoxy-7-methyl-1H-indole-1-carboxylate (enantiomer-2) (peak-2, t$_r$ = 3.4 min).

Intermediate 6-1:

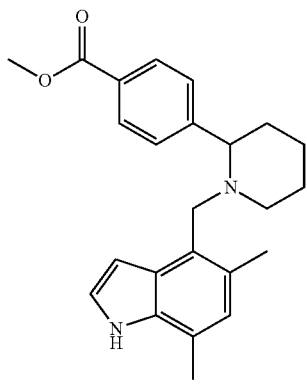 [SMILES: COC(=O)c1ccc(C2CCCCN2Cc2c(C)cc(C)c3[nH]ccc23)cc1]

Intermediate 6-1a; (±)-methyl 4-(1-((5,7-dimethyl-1H-indol-4-yl)methyl)piperidin-2-yl)benzoate A mixture of (±)-4-(1-((5,7-dimethyl-1-tosyl-1H-indol-4-yl)methyl)piperidin-2-yl)benzonitrile, Intermediate 3-2-11, (550 mg, 1.105 mmol) and KOH (500 mg, 8.91 mmol) in EtOH (8 mL) was stirred at 130° C. under the microwave irradiation for 2.5 hr. The reaction mixture was acidified by satd. aq. citric acid. The mixture was then extracted with CH$_2$Cl$_2$/TFE (ca. 9/1) two times. The combined organic layers were then dried over Na$_2$SO$_4$, filtered, and concentrated. The resulting residue was dissolved in toluene/MeOH (50 mL/15 mL). To the mixture at 0° C. was added trimethylsilyldiazomethane Et$_2$O (2M, 5 ml, 10 mmol). The mixture was then stirred at 0° C. for 1.5 h. The reaction was then quenched with acetic acid. The mixture was then diluted with EtOAc. The mixture was then washed successively with 5% aq. NaHCO$_3$ twice, H$_2$O, and brine, dried over Na$_2$SO$_4$, filtered, and then concentrated. The resulting residue was purified by silica gel column chromatography (heptane/EtOAc=76/24) to afford the title compound. MS (ESI+) m/z 377.5 (M+H).

Intermediate 6-1b;

Resolution of the enantiomers of (±)-methyl 4-(1-((5,7-dimethyl-1H-indol-4-yl)methyl)piperidin-2-yl)benzoate, Intermediate 6-1a, was achieved by chiral SFC using a CHIRALCEL® OJ-H column with 30% (0.2% DEA in MeOH) in CO$_2$ to give methyl 4-(1-((5,7-dimethyl-1H-indol-4-yl)methyl)piperidin-2-yl)benzoate (enantiomer-1) (peak-1, t$_r$=2.6 min) and methyl 4-(1-((5,7-dimethyl-1H-indol-4-yl)methyl)piperidin-2-yl)benzoate (enantiomer-2) (peak-2, t$_r$=4.1 min).

Intermediate 6-2:

Intermediate 6-2a; (±)-methyl 4-(rel-(2S,4S)-4-ethoxy-1-((5-methoxy-7-methyl-1H-indol-4-yl)methyl)piperidin-2-yl)benzoate

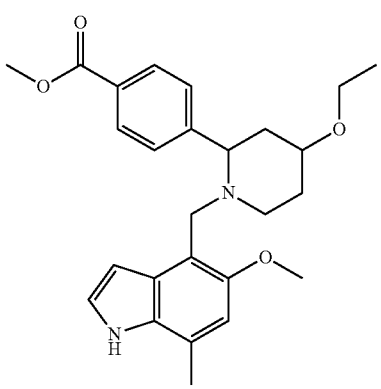

rel-(2S,4S)

A mixture of (±)-tert-butyl 4-((rel-(2S,4S)-4-ethoxy-2-(4-(methoxycarbonyl)phenyl)piperidin-1-yl)methyl)-5-methoxy-7-methyl-1H-indole-1-carboxylate, Intermediate 4-3, (310 mg, 0.578 mmol) in MeOH (15 mL) and K₂CO₃ (639 mg, 4.62 mmol) was stirred for 3 h under the reflux condition, and then concentrated. The resulting residue was then diluted with satd. aq. citric acid. The mixture was then extracted three times with EtOAc. The combined organic layers were then dried over Na₂SO₄, filtered, and then concentrated. The resulting residue in toluene (15 mL) and MeOH (5 mL) was added trimethylsilyldiazomethane (2M in Et₂O, 2 mL, 2 mmol) dropwise. The mixture was stirred at room temperature for 0.25 h. The reaction was then quenched with AcOH at 0° C. The reaction mixture was diluted with 5% aq. NaHCO₃. The mixture was then extracted three times with EtOAc. The combined organic layers were concentrated. The resulting residue was purified by silica gel flash column chromatography (heptane/EtOAc=1/0 to 1/7) to afford the title compound. MS (ESI+) m/z 437.5 (M+H).

Intermediate 6-2b; methyl 4-((2S,4S)-4-ethoxy-1-((5-methoxy-7-methyl-1H-indol-4-yl)methyl)piperidin-2-yl)benzoate and methyl 4-((2R,4R)-4-ethoxy-1-((5-methoxy-7-methyl-1H-indol-4-yl)methyl)piperidin-2-yl)benzoate

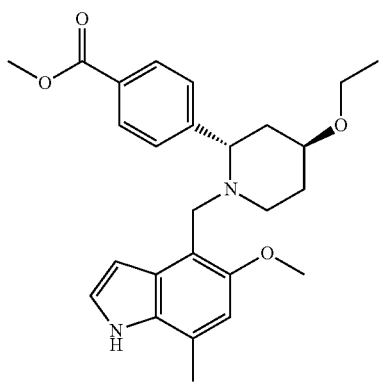

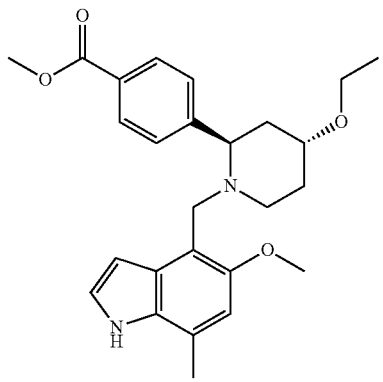

Resolution of the enantiomers of (±)-methyl 4-(rel-(2S,4S)-4-ethoxy-1-((5-methoxy-7-methyl-1H-indol-4-yl)methyl)piperidin-2-yl)benzoate, Intermediate 6-2a, was achieved by chiral SFC using a CHIRALPAK® AD-H column with 35% (5 mM NH₄OH in iPrOH) in CO₂ to afford methyl 4-((2S,4S)-4-ethoxy-1-((5-methoxy-7-methyl-1H-indol-4-yl)methyl)piperidin-2-yl)benzoate (peak-1, $t_r$=1.9 min) and methyl 4-((2R,4R)-4-ethoxy-1-((5-methoxy-7-methyl-1H-indol-4-yl)methyl)piperidin-2-yl)benzoate (peak-2, $t_r$=3.4 min).

The following compounds were prepared from the appropriate intermediate by similar methods as described in the examples above:

| Intermediate | Structure | chemical name<br>starting material<br>Conditions for the enantiomer separation | MS (m/z) |
|---|---|---|---|
| 6-2-2a | rel-(2S,4S) | (±)-methyl 4-(rel-(2S,4S)-1-((5,7-dimethyl-1H-indol-4-yl)methyl)-4-ethoxypiperidin-2-yl)benzoate<br>Intermediate 3-2-24 | ESI+<br>421.8<br>(M + H) |

6-2-2b  Resolution of the enantiomers of (±)-methyl 4-(rel-(2S,4S)-1-((5,7-dimethyl-1H-indol-4-yl)methyl)-4-ethoxypiperidin-2-yl)benzoate was achieved by chiral SFC using a CHIRALPAK ® AD-H column with 40% (5 mM NH₄OH in iPrOH) in CO₂ to afford methyl 4-

| Intermediate | Structure / Conditions for the enantiomer separation | chemical name starting material | MS (m/z) |
|---|---|---|---|
| | (rel-(2S,4S)-1-((5,7-dimethyl-1H-indol-4-yl)methyl)-4-ethoxypiperidin-2-yl)benzoate (enantiomer-1) (peak-1, t$_r$ = 1.7 min) and methyl 4-(rel-(2S,4S)-1-((5,7-dimethyl-1H-indol-4-yl)methyl)-4-ethoxypiperidin-2-yl)benzoate (enantiomer-2) (peak-2, t$_r$ = 4.4 min). | | |
| 6-2-3a | *structure shown* rel-(2S,4S) | (±)-methyl 4-(rel-(2S,4S)-1-((5-cyclopropyl-7-methyl-1H-indol-4-yl)methyl)-4-methoxypiperidin-2-yl)benzoate Intermediate 3-2-25 | ESI+ 433.4 (M + H) |
| 6-2-3b | Resolution of the enantiomers of (±)-methyl 4-(rel-(2S,4S)-1-((5-cyclopropyl-7-methyl-1H-indol-4-yl)methyl)-4-methoxypiperidin-2-yl)benzoate was achieved by chiral SFC using a CHIRALCEL ® OJ-H column with 30% (5 mM NH$_4$OH in MeOH) in CO$_2$ to give methyl 4-(rel-(2S,4S)-1-((5-cyclopropyl-7-methyl-1H-indol-4-yl)methyl)-4-methoxypiperidin-2-yl)benzoate (enantiomer-1) (peak-1, t$_r$ = 2.0 min) and methyl 4-(rel-(2S,4S)-1-((5-cyclopropyl-7-methyl-1H-indol-4-yl)methyl)-4-methoxypiperidin-2-yl)benzoate (enantiomer-2) (peak-2, t$_r$ = 4.3 min). | | |
| 6-2-4a | *structure shown* rel-(2S,4S) | (±)-methyl 4-(rel-(2S,4S)-1-((5-cyclopropyl-7-methyl-1H-indol-4-yl)methyl)-4-ethoxypiperidin-2-yl)benzoate Intermediate 4-4-10 | ESI+ 447.5 (M + H) |
| 6-2-4b | Resolution of the enantiomers of (±)-methyl 4-(rel-(2S,4S)-1-((5-cyclopropyl-7-methyl-1H-indol-4-yl)methyl)-4-ethoxy piperidin-2-yl)benzoate was achieved by chiral SFC using a CHIRALPAK ® AD-H column with 40% (5 mM NH$_4$OH in iPrOH) in CO$_2$ to give methyl 4-(rel-(2S,4S)-1-((5-cyclopropyl-7-methyl-1H-indol-4-yl)methyl)-4-ethoxypiperidin-2-yl)benzoate (enantiomer-1) (peak-1, t$_r$ = 1.3 min) and methyl 4-(rel-(2S,4S)-1-((5-cyclopropyl-7-methyl-1H-indol-4-yl)methyl)-4-ethoxypiperidin-2-yl)benzoate (enantiomer-2) (peak-2, t$_r$ = 2.9 min). | | |

Example-1

(±)-1-((5,7-Dimethyl-1H-indol-4-yl)methyl)-2-phenylpiperidin-4-ol (Diastereomer-1)

diastereomer-1

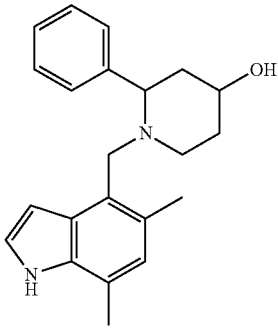

A mixture of (±)-1-((5,7-dimethyl-1-tosyl-1H-indol-4-yl)methyl)-2-phenylpiperidin-4-ol (diastereomeric mixture), Intermediate 3-1, (200 mg, 0.409 mmol), KOH (100 mg, 1.782 mmol), and isoamylamine (200 μL, 1.721 mmol) in EtOH (5 mL) was stirred at 100° C. under the microwave irradiation for 1 hr. The reaction mixture was diluted with $CH_2Cl_2$. The mixture was filtered through a plug of silica gel, which was rinsed with a mixture of $CH_2Cl_2$/MeOH (ca. 6/1). The filtrate was concentrated. The resulting residue was purified by silica gel flash column chromatography ($CH_2Cl_2$/MeOH=93/7 to 85/15) to afford, in respective elution order, (±)-1-((5,7-dimethyl-1H-indol-4-yl)methyl)-2-phenylpiperidin-4-ol (diastereomer-1) as Example-1 and diastereomer-2. $^1$H NMR (400 MHz, $CD_3CN$) δ 9.12 (br. s., 1H), 7.53 (d, J=7.33 Hz, 2H), 7.38 (dd, J=7.33, 7.80 Hz, 2H), 7.26-7.32 (m, 1H), 7.16 (dd, J=2.80, 3.03 Hz, 1H), 6.71 (s, 1H), 6.56 (dd, J=2.02, 3.03 Hz, 1H), 3.63 (d, J=12.13 Hz, 1H), 3.53-3.60 (m, 1H), 3.14-3.19 (m, 1H), 3.12 (d, J=12.13 Hz, 1H), 2.80 (br. s., 1H), 2.59-2.65 (m, 1H), 2.38 (s, 3H), 2.25 (s, 3H), 1.96-2.05 (m, 1H), 1.87-1.91 (m, 1H), 1.68-1.75 (m, 1H), 1.56-1.67 (m, 1H), 1.21-1.34 (m, 1H); HRMS calcd. for $C_{22}H_{27}N_2O$ (M+H)$^+$ 335.2123, found 335.2119.

Example-2 diastereomer-2

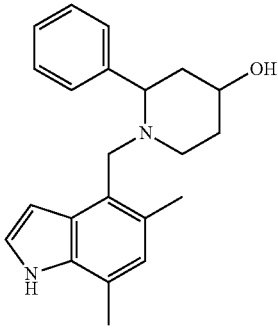

Example-2a; (±)-1-((5,7-dimethyl-1H-indol-4-yl)methyl)-2-phenylpiperidin-4-ol (Diastereomer-2)

The title compound was isolated as the diastereomer-2 in the preparation of Example-1. $^1$H NMR (400 MHz, $CD_3CN$) δ 9.09 (br. s., 1H), 7.54 (d, J=7.30 Hz, 2H), 7.37 (dd, J=7.30, 7.80 Hz, 2H), 7.23-7.32 (m, 1H), 7.12-7.21 (m, 1H), 6.71 (s, 1H), 6.55-6.63 (m, 1H), 3.91-4.00 (m, 1H), 3.66 (d, J=12.13 Hz, 1H), 3.53 (br. d, J=8.80 Hz, 1H), 3.23 (br. d, J=10.90 Hz, 1H), 2.64 (br. s., 1H), 2.31-2.48 (m, 5H), 2.27 (s, 3H), 1.84-1.91 (m, 1H), 1.68-1.78 (m, 1H), 1.43-1.66 (m, 2H); HRMS calcd. for $C_{22}H_{27}N_2O$ (M+H)$^+$ 335.2123, found 335.2123.

Example-2b, (+) and (+1-((5,7-dimethyl-1H-indol-4-yl)methyl)-2-phenylpiperidin-4-ol (Diastereomer-2)

Resolution of the enantiomers of (±)-1-((5,7-dimethyl-1H-indol-4-yl)methyl)-2-phenylpiperidin-4-ol (diastereomer-2), Example-2a, was achieved by chiral SFC using a CHIRALPAK® AD-H column with 30% (10 mM $NH_4OH$ in MeOH) in $CO_2$ to afford, in respective order, (+)-1-((5,7-dimethyl-1H-indol-4-yl)methyl)-2-phenylpiperidin-4-ol (diastereomer-2) (peak-1, $t_r$=1.6 min) and (−)-1-((5,7-dimethyl-1H-indol-4-yl)methyl)-2-phenylpiperidin-4-ol (diastereomer-2) (peak-2, $t_r$=3.0 min).

Example-3

(±)-1-((5,7-Dimethyl-1H-indol-4-yl)methyl)-2-phenylpiperidin-4-ol (Diastereomer-1)

diastereomer-1

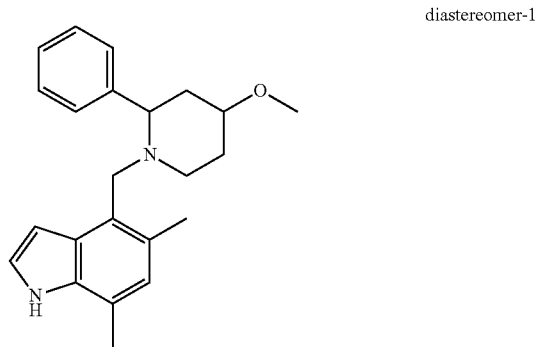 [SMILES: COC1CCN(Cc2c(C)cc(C)c3[nH]ccc23)C(c2ccccc2)C1]

The title compound was synthesized from (±)-4-((4-methoxy-2-phenylpiperidin-1-yl)methyl)-5,7-dimethyl-1-tosyl-1H-indole (diastereomeric mixture), Intermediate 3-2-1, by similar manner to the preparation of Example-1. Separation of the diastereomers were achieved by silica gel flash column chromatography [heptane/(10% MeOH in EtOAc)=77/23] to afford, in respective elution order, Example-3 (diastereomer-1), and diastereomer-2. $^1$H NMR (400 MHz, $CD_3CN$) δ 9.09 (br. s., 1H), 7.54 (d, J=7.20 Hz, 2H), 7.38 (dd, J=7.20, 7.80 Hz, 2H), 7.26-7.31 (m, 1H), 7.16 (dd, J=2.80, 3.00 Hz, 1H), 6.71 (s, 1H), 6.54-6.57 (m, 1H), 3.62 (d, J=12.13 Hz, 1H), 3.19-3.29 (m, 4H), 3.10-3.18 (m, 2H), 2.64 (td, J=3.54, 11.87 Hz, 1H), 2.38 (s, 3H), 2.25 (s, 3H), 2.02-2.10 (m, 1H), 1.97-2.02 (m, 1H), 1.79-1.90 (m, 1H), 1.55 (dd, J=11.40, 12.13 Hz, 1H), 1.14-1.25 (m, 1H); HRMS calcd. for $C_{23}H_{29}N_2O$ (M+H)$^+$ 349.2280, found 349.2278.

Example-4

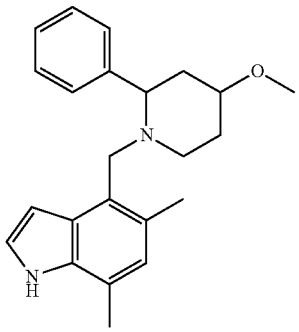

Example-4a; (±)-4-((4-methoxy-2-phenylpiperidin-1-yl)methyl)-5,7-dimethyl-1H-indole (Diastereomer-2)

The title compound was isolated as the diastereomer-2 in the preparation of Example-3. $^1$H NMR (400 MHz, CD$_3$CN) δ 9.08 (br. s., 1H), 7.54 (d, J=7.33 Hz, 2H), 7.37 (dd, J=7.33, 7.80 Hz, 2H), 7.25-7.30 (m, 1H), 7.14-7.17 (m, 1H), 6.70 (s, 1H), 6.58 (dd, J=2.02, 3.03 Hz, 1H), 3.63 (d, J=12.13 Hz, 1H), 3.45-3.50 (m, 1H), 3.41 (dd, J=3.41, 11.24 Hz, 1H), 3.27 (s, 3H), 3.19 (d, J=12.13 Hz, 1H), 2.38 (s, 3H), 2.32-2.37 (m, 1H), 2.21-2.31 (m, 4H), 1.78-1.91 (m, 2H), 1.70-1.77 (m, 1H), 1.45-1.54 (m, 1H); HRMS calcd. for C$_{23}$H$_{29}$N$_2$O (M+H)$^+$ 349.2280, found 349.2276.

Example-4b; (+) and (−)-4-((4-methoxy-2-phenylpiperidin-1-yl)methyl)-5,7-dimethyl-1H-indole (Diastereomer-2)

Resolution of the enantiomers of (±)-4-((4-methoxy-2-phenylpiperidin-1-yl)methyl)-5,7-dimethyl-1H-indole (diastereomer-2), Example-4a, was achieved by chiral SFC using a CHIRALPAK® IB column with 30% (10 mM NH$_4$OH in iPrOH) in CO$_2$ to afford, in respective elution order, (+)-4-((4-methoxy-2-phenylpiperidin-1-yl)methyl)-5,7-dimethyl-1H-indole (diastereomer-2) (peak-1, t$_r$=3.1 min) and (+4-((4-methoxy-2-phenylpiperidin-1-yl)methyl)-5,7-dimethyl-1H-indole (diastereomer-2)(peak-2, t$_r$=4.3 min).

The following Examples were synthesized from appropriate starting materials by applying similar methods described in the examples above:

| Example | Chemical name / Chemical structure | starting materials / NMR; HRMS |
|---|---|---|
| 5-1 | (±)-5,7-dimethyl-4-((2-phenylpiperidin-1-yl)methyl)-1H-indole<br>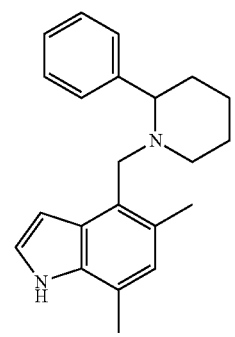 [SMILES: Cc1cc(C)c2[nH]ccc2c1CN1CCCCC1c1ccccc1] | Intermediate 3-2-4<br>$^1$H NMR (400 MHz, CD$_2$Cl$_2$) δ ppm 8.04 (br. s., 1 H), 7.53 (d, J = 7.1 Hz, 2 H), 7.36 (app.t, J = 7.3 Hz, 2 H), 7.26 (app.t, J = 7.2 Hz, 1 H), 7.16 (br. s., 1 H), 6.74 (s, 1 H), 6.68 (br. s., 1 H), 3.72 (d, J = 12.4 Hz, 1 H), 3.15 (d, J = 12.4 Hz, 1 H), 3.00-3.10 (m, 1 H), 2.72 (d, J = 10.9 Hz, 1 H), 2.40 (s, 3 H), 2.31 (s, 3 H), 1.94 (t, J = 11.4 Hz, 1 H), 1.65-1.79 (m, 3 H), 1.26-1.47 (m, 3 H); HRMS calcd. for C$_{22}$H$_{27}$N$_2$ (M + H)$^+$ 318.2096, found 318.2105. |
| 5-2 | (±)-1-((5,7-dimethyl-1H-indol-4-yl)methyl)-2-phenyl-piperidin-4-yl)methanol (diastereomer-1)<br>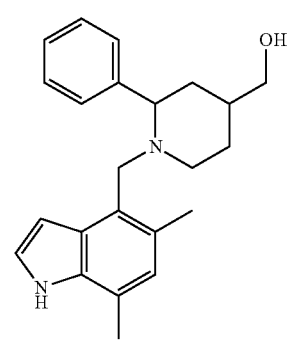diastereomer-1 | Intermediate 3-2-5<br>$^1$H NMR (TFA salt, 400 MHz, D$_2$O) δ 7.47-7.67 (m, 5H), 7.25 (d, J = 3.03 Hz, 1H), 6.78 (s, 1H), 6.12 (br. s., 1H), 4.40 (br. dd, J = 2.90, 12.30 Hz, 1H), 4.23 (d, J = 13.60 Hz, 1H), 4.07 (d, J = 13.60 Hz, 1H), 3.39 (d, J = 6.32 Hz, 2H), 3.33-3.38 (m, 1H), 3.18-3.29 (m, 1H), 2.32 (s, 3H), 2.05-2.13 (m, 1H), 1.91-2.03 (m, 4H), 1.77-1.89 (m, 2H), 1.24-1.38 (m, 1H); HRMS calcd. for C$_{23}$H$_{29}$N$_2$O (M + H)$^+$ 349.2280, found 349.2265. |

| Chemical name | |
|---|---|
| Example | Chemical structure | starting materials NMR; HRMS |

5-3 (±)-1-((5,7-dimethyl-1H-indol-4-yl)methyl)-2-phenyl-piperidin-4-yl)methanol (diastereomer-2)

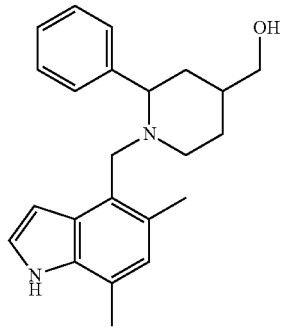

diastereomer-2

Intermediate 3-2-6
$^1$H NMR (TFA salt, 400 MHz, D$_2$O) δ 7.49-7.63 (m, 5H), 7.26 (d, J = 3.03 Hz, 1H), 6.78 (s, 1H), 6.12 (br. s., 1H), 4.46 (dd, J = 2.65, 13.26 Hz, 1H), 4.20 (d, J = 13.40 Hz, 1H), 4.10 (d, J = 13.40 Hz, 1H), 3.77 (d, J = 7.83 Hz, 2H), 3.15-3.29 (m, 2H), 2.26-2.40 (m, 4H), 1.95-2.14 (m, 5H), 1.70-1.90 (m, 2H); HRMS calcd. for C$_{23}$H$_{29}$N$_2$O (M + H)$^+$ 349.2280, found 349.2270.

5-4 (±)-4-(1-((5,7-dimethyl-1H-indol-4-yl)methyl)piperidin-2-yl)benzenesulfonamide

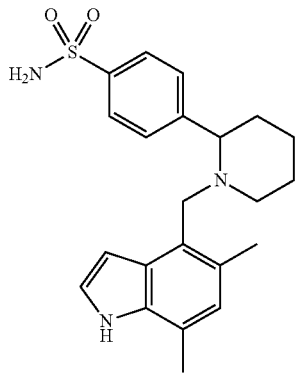 [SMILES: Cc1cc(C)c2[nH]ccc2c1CN1CCCCC1c1ccc(S(N)(=O)=O)cc1]

Intermediate 3-2-7
(isolated as a single regioisomer) $^1$H NMR (400 MHz, CD$_2$Cl$_2$) δ 8.11 (br. s., 1H), 7.91 (d, J = 8.46 Hz, 2H), 7.75 (br. d, J = 8.10 Hz, 2H), 7.22 (dd, J = 2.70, 2.80 Hz, 1H), 6.79 (s, 1H), 6.66-6.74 (m, 1H), 4.84 (br. s., 2H), 3.71 (d, J = 12.25 Hz, 1H), 3.26 (d, J = 12.38 Hz, 1H), 3.22 (dd, J = 2.91, 10.74 Hz, 1H), 2.74-2.83 (m, 1H), 2.45 (s, 3H), 2.36 (s, 3H), 1.96-2.05 (m, 1H), 1.64-1.85 (m, 3H), 1.38-1.54 (m, 2H), 1.37 (d, J = 4.55 Hz, 1H); HRMS calcd. for C$_{22}$H$_{28}$N$_3$O$_s$S (M + H)$^+$ 398.1902, found 398.1893.

5-5 (±)-3-(1-((5,7-dimethyl-1H-indol-4-yl)methyl)piperidin-2-yl)benzenesulfonamide

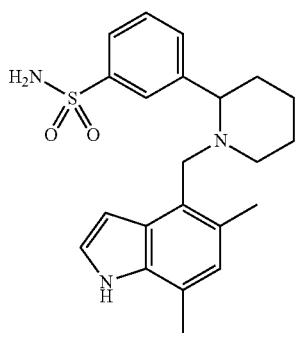 [SMILES: Cc1cc(C)c2[nH]ccc2c1CN1CCCCC1c1cccc(S(N)(=O)=O)c1]

Intermediate 3-2-7
(isolated as a single regioisomer) $^1$H NMR (TFA salt, 400 MHz, CD$_3$OD) δ 10.79 (br. s., 1H), 8.21 (s, 1H), 8.11 (td, J = 1.47, 7.80 Hz, 1H), 7.87 (br. d, J = 7.80 Hz, 1H), 7.77-7.82 (m, 1H), 7.30-7.33 (m, 1H), 6.83 (s, 1H), 6.34 (d, J = 3.03 Hz, 1H), 4.58-4.65 (m, 1H), 4.26-4.35 (m, 2H), 3.54 (br. d, J = 11.40 Hz, 1H), 3.36-3.41 (m, 1H), 2.45 (s, 3H), 2.10-2.22 (m, 5H), 1.76-2.02 (m, 4H); HRMS calcd. for C$_{22}$H$_{28}$N$_3$O$_s$S (M + H)$^+$ 398.1902, found 398.1884.

| Chemical | |
|---|---|
| Example | Chemical name |
| | Chemical structure |
| | starting materials |
| | NMR; HRMS |

5-6  (±)-4-(1-((5,7-dimethyl-1H-indol-4-yl)methyl)piperidin-2-yl)-N-methylbenzenesulfonamide

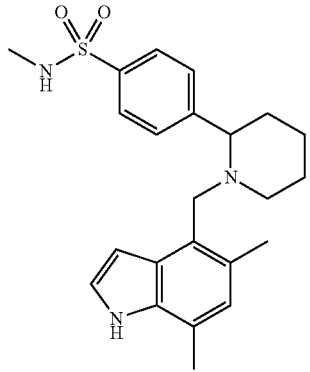 [SMILES: CNS(=O)(=O)c1ccc(C2CCCCN2Cc2c(C)cc(C)c3[nH]ccc23)cc1]

Intermediate 3-2-8
(isolated as a single regioisomer) ¹H NMR (TFA salt, 400 MHz, CD₃OD) δ 8.05 (d, J = 8.59 Hz, 2H), 7.86 (d, J = 8.46 Hz, 2H), 7.32 (d, J = 3.16 Hz, 1H), 6.83 (s, 1H), 6.34 (d, J = 3.03 Hz, 1H), 4.58-4.64 (m, 1H), 4.34 (d, J = 13.40 Hz, 1H), 4.27 (d, J = 13.40 Hz, 1H), 3.50-3.60 (m, 1H), 3.33-3.42 (m, 1H), 2.58 (s, 3H), 2.45 (s, 3H), 2.08-2.21 (m, 5H), 1.73-2.04 (m, 4H); HRMS calcd. for $C_{23}H_{30}N_3O_2S$ $(M + H)^+$ 412.2059, found 412.2048.

5-7  (±)-3-(1-((5,7-dimethyl-1H-indol-4-yl)methyl)piperidin-2-yl)-N-methylbenzenesulfonamide

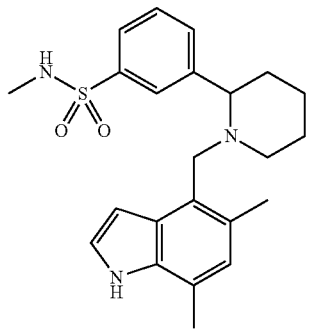 [SMILES: CNS(=O)(=O)c1cccc(C2CCCCN2Cc2c(C)cc(C)c3[nH]ccc23)c1]

Intermediate 3-2-8
(isolated as a single regioisomer) ¹H NMR (400 MHz, CD₃OD) δ 10.80 (br. s., 1H), 8.18 (s, 1H), 8.00-8.06 (m, 1H), 7.90 (br. d, J = 7.70 Hz, 1H), 7.83 (app. t, J = 7.70 Hz, 1H), 7.31 (dd, J = 2.80, 2.90 Hz, 1H), 6.83 (s, 1H), 6.32-6.38 (m, 1H), 4.59-4.66 (m, 1H), 4.34 (d, J = 13.30 Hz, 1H), 4.28 (d, J = 13.30 Hz, 1H), 3.54 (br. d, J = 12.80 Hz, 1H), 3.35-3.42 (m, 1H), 2.61 (s, 3H), 2.45 (s, 3H), 2.11-2.20 (m, 5H), 1.75-2.02 (m, 4H); HRMS calcd. for $C_{23}H_{30}N_3O_2S$ $(M + H)^+$ 412.2059, found 412.2048.

5-8  (±)-4-((2-(4-fluorophenyl)-4-methoxypiperidin-1-yl)methyl)-5,7-dimethyl-1H-indole

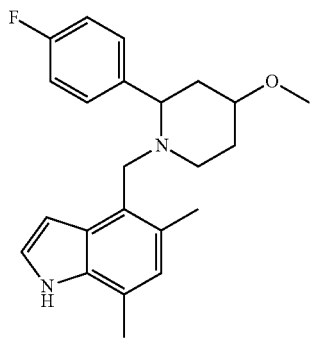 [SMILES: COC1CCN(Cc2c(C)cc(C)c3[nH]ccc23)C(c2ccc(F)cc2)C1]

Intermediate 3-2-9
¹H NMR (400 MHz, CD₂Cl₂) δ 8.08 (br. s., 1 H), 7.44-7.57 (m, 2 H), 7.17 (t, J = 2.8 Hz, 1 H), 7.07 (t, J = 8.8 Hz, 2 H), 6.75 (s, 1 H), 6.62 (dd, J = 3.2, 2.1 Hz, 1 H), 3.68 (d, J = 12.4 Hz, 1 H), 3.28 (s, 3 H), 3.19-3.26 (m, 1 H), 3.08-3.17 (m, 2 H), 2.74 (dt, J = 11.9, 3.5 Hz, 1 H), 2.41 (s, 3 H), 2.28 (s, 3 H), 2.04-2.15 (m, 1 H), 1.98 (td, J = 12.3, 2.3 Hz, 1 H), 1.80-1.90 (m, 1 H), 1.50-1.64 (m, 2 H), 1.23-1.39 (m, 1 H); HRMS calcd. for $C_{23}H_{28}FN_2O$ $(M + H)^+$ 367.2186, found 367.2174.

| Chemical name |
|---|
| Example | Chemical structure | starting materials<br>NMR; HRMS |

5-9  (±)-(1-((5,7-dimethy-1H-indol-4-yl)methyl)-2-phenylpiperidin-2-yl)methanol

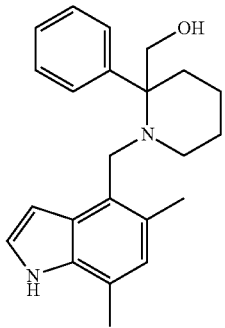 [SMILES: Cc1cc(C)c2[nH]ccc2c1CN1CCCCC1(CO)c1ccccc1]

Intermediate 3-2-10
$^1$H NMR (400 MHz, DMSO-$d_6$) δ 10.78 (br. s., 1 H), 7.71 (d, J = 7.6 Hz, 2 H), 7.31 (t, J = 7.7 Hz, 2 H), 7.15-7.24 (m, 2 H), 6.66-6.71 (m, 1 H), 6.64 (s, 1 H), 4.62 (t, J = 4.7 Hz, 1 H), 3.90-4.07 (m, 3 H), 3.80-3.89 (m, 2 H), 2.37 (s, 3 H), 2.29 (s, 3 H), 1.98-2.13 (m, 1 H), 1.71-1.85 (m, 1 H), 1.52-1.67 (m, 2 H), 1.41-1.51 (m, 1 H), 1.26-1.36 (m, 1 H), 1.05-1.20 (m, 1 H)

5-10  (±)-(4-(1-((5,7-dimethyl-1H-indol-4-yl)methyl)piperidin-2-yl)phenyl)methanol

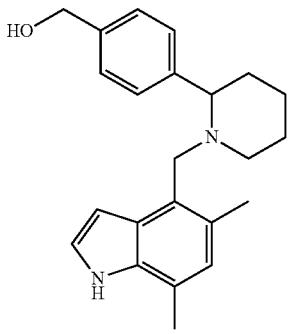 [SMILES: Cc1cc(C)c2[nH]ccc2c1CN1CCCCC1c1ccc(CO)cc1]

Intermediate 3-3
$^1$H NMR (TFA salt, 400 MHz, CD$_3$CN) δ 9.45 (br. s., 1H), 9.10 (br. s., 1H), 7.71-7.89 (m, 2H), 7.50 (d, J = 8.34 Hz, 2H), 7.29 (app. t, J = 2.91 Hz, 1H), 6.80 (s, 1H), 6.37-6.46 (m, 1H), 4.64 (s, 2H), 4.26-4.33 (m, 1H), 4.24 (d, J = 13.50 Hz, 1H), 4.01-4.12 (m, 1H), 3.34 (d, J = 12.38 Hz, 1H), 3.03-3.17 (m, 1H), 2.42 (s, 3H), 2.30-2.39 (m, 1H), 2.13 (s, 3H), 1.96-2.05 (m, 2H), 1.83-1.90 (m, 1H), 1.71-1.79 (m, 1H), 1.66 (td, J = 3.74, 13.23 Hz, 1H); HRMS calcd. for $C_{23}H_{29}N_2O$ (M + H)$^+$ 349.2280, found 349.2278.

5-11  (±)-5,7-dimethyl-4-((2-(4-(methylsulfonyl)phenyl)piperidin-1-yl)methyl)-1H-indole

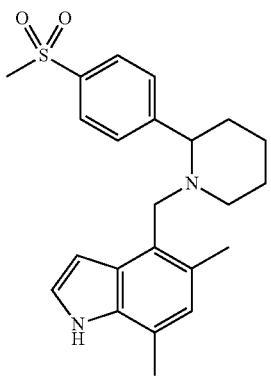 [SMILES: Cc1cc(C)c2[nH]ccc2c1CN1CCCCC1c1ccc(S(C)(=O)=O)cc1]

Intermediate 3-2-18
$^1$H NMR (400 MHz, CD$_2$Cl$_2$) δ 8.12 (br. s., 1H), 7.91 (d, J = 8.34 Hz, 2H), 7.78 (d, J = 8.08 Hz, 2H), 7.22 (dd, J = 2.80, 3.00 Hz, 1H), 6.78 (s, 1H), 6.70 (dd, J = 2.27, 3.03 Hz, 1H), 3.70 (d, J = 12.38 Hz, 1H), 3.27 (d, J = 12.38 Hz, 1H), 3.20-3.24 (m, 1H), 3.06 (s, 3H), 2.74-2.82 (m, 1H), 2.44 (s, 3H), 2.35 (s, 3H), 1.96-2.05 (m, 1H), 1.75 ?+0 1.85 (m, 2H), 1.64-1.75 (m, 1H), 1.38-1.53 (m, 3H); HRMS calcd. for $C_{23}H_{29}N_2O_2S$ (M + H)$^+$ 397.1950, found 397.1936.

-continued

| Chemical Example structure | Chemical name starting materials NMR; HRMS |
|---|---|
| 5-12 | (±)-4-((2-(4-(2H-tetrazol-5-yl)phenyl)piperidin-1-yl)methyl)-5,7-dimethyl-1H-indole |

Intermediate 4-15
$^1$H NMR (TFA salt, 400 MHz, CD$_3$OD) δ 10.80 (br. s., 1H), 8.28 (d, J = 8.34 Hz, 2H), 7.86 (d, J = 8.34 Hz, 2H), 7.32 (dd, J = 2.80, 2.90 Hz, 1H), 6.83 (s, 1H), 6.35-6.40 (m, 1H), 4.57-4.63 (m, 1H), 4.31-4.40 (m, 2H), 3.55 (br. d, J = 12.50 Hz, 1H), 3.36-3.42 (m, 1H), 2.45 (s, 3H), 2.11-2.25 (m, 5H), 1.77-2.04 (m, 4H); HRMS calcd. for C$_{23}$H$_{27}$N$_6$ (M + H)$^+$ 387.2297, found 387.2281.

Example-6

(±)-1-((5,7-Dimethyl-1H-indol-4-yl)methyl)-2-phenylpiperidin-4-amine (Diastereomer-1)

Example-7

(±)-1-((5,7-Dimethyl-1H-indol-4-yl)methyl)-2-phenylpiperidin-4-amine (Diastereomer-2)

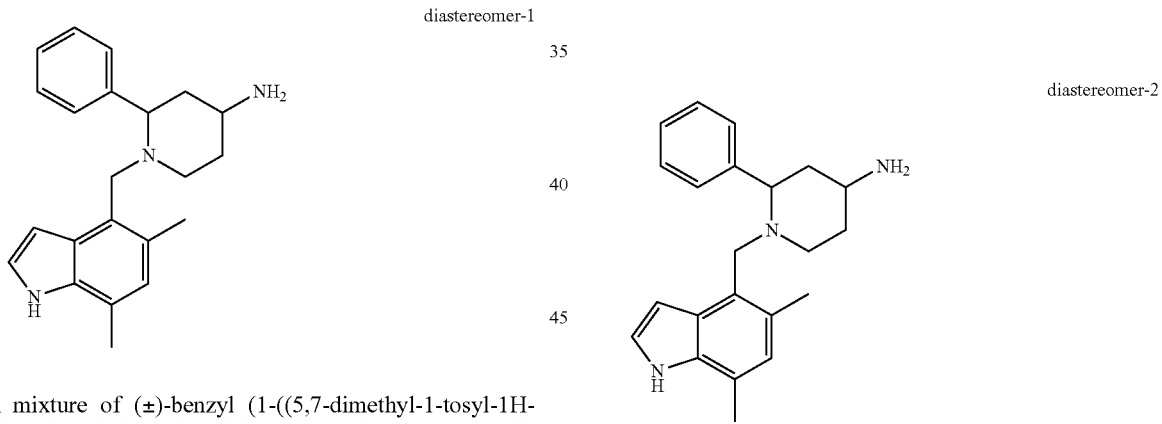

diastereomer-1 diastereomer-2

A mixture of (±)-benzyl (1-((5,7-dimethyl-1-tosyl-1H-indol-4-yl)methyl)-2-phenylpiperidin-4-yl)carbamate (diastereomer-1), Intermediate 3-2-2, (100 mg, 0.161 mmol) and KOH (100 mg, 1.782 mmol) in EtOH (5 mL)/H$_2$O (0.7 mL) was stirred at 130° C. under the microwave irradiation for 0.5 h. The reaction mixture was diluted with CH$_2$Cl$_2$. The mixture was filtered through a plug of silica gel, which was rinsed with a mixture of CH$_2$Cl$_2$/MeOH (ca. 6/1). The combined organic layers were concentrated. The resulting residue was purified by RP-HPLC (HC-A) to afford the title compound. $^1$H NMR (400 MHz, CD$_3$OD) δ 7.54 (br. d, J=7.30 Hz, 2H), 7.36 (dd, J=7.30, 7.60 Hz, 2H), 7.25-7.31 (m, 1H), 7.15 (d, J=3.03 Hz, 1H), 6.68 (s, 1H), 6.55 (d, J=3.03 Hz, 1H), 3.77 (d, J=12.38 Hz, 1H), 3.55 (dd, J=2.91, 11.49 Hz, 1H), 3.30 (d, J=12.38 Hz, 1H), 3.17-3.22 (m, 1H), 2.64 (td, J=3.92, 12.38 Hz, 1H), 2.46 (dt, J=2.78, 12.51 Hz, 1H), 2.40 (s, 3H), 2.26 (s, 3H), 2.04-2.12 (m, 1H), 1.78-1.88 (m, 1H), 1.71-1.78 (m, 1H), 1.48-1.56 (m, 1H); HRMS calcd. for C$_{22}$H$_{28}$N$_3$ (M+H)$^+$ 334.2283, found 334.2272.

The title compound was synthesized from (±)-benzyl (1-((5,7-dimethyl-1-tosyl-1H-indol-4-yl)methyl)-2-phenylpiperidin-4-yl)carbamate (diastereomer-2), Intermediate 3-2-3, analogously to the preparation of Example-6. $^1$H NMR (400 MHz, CD$_3$OD) δ 7.53 (br. d, J=7.10 Hz, 2H), 7.37 (dd, J=7.10, 8.10 Hz, 2H), 7.26-7.32 (m, 1H), 7.14 (d, J=3.15 Hz, 1H), 6.67 (s, 1H), 6.50 (d, J=3.15 Hz, 1H), 3.71 (d, J=12.10 Hz, 1H), 3.17 (dd, J=2.65, 11.49 Hz, 1H), 3.13 (d, J=12.10 Hz, 1H), 2.75-2.87 (m, 2H), 2.40 (s, 3H), 2.23 (s, 3H), 2.08 (dt, J=2.53, 12.25 Hz, 1H), 1.88-1.95 (m, 1H), 1.68-1.76 (m, 1H), 1.57-1.68 (m, 1H), 1.29-1.41 (m, 1H); HRMS calcd. for C$_{22}$H$_{28}$N$_3$ (M+H)$^+$ 334.2283, found 334.2271.

Example-8

(±)-4-(1-((5,7-Dimethyl-1H-indol-4-yl)methyl)piperidin-2-yl)benzamide

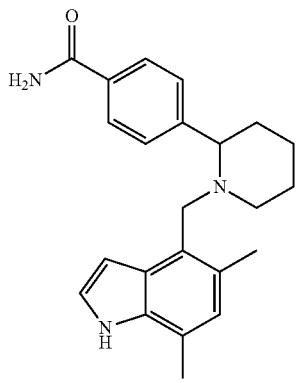 [SMILES: Cc1cc(C)c2[nH]ccc2c1CN1CCCCC1c1ccc(C(N)=O)cc1]

A mixture of (±)-4-(1-((5,7-dimethyl-1-tosyl-1H-indol-4-yl)methyl)piperidin-2-yl)benzonitrile, Intermediate 3-2-11, (100 mg, 0.201 mmol) and KOH (100 mg, 1.782 mmol) in EtOH (2 mL) was stirred at 100° C. under the microwave irradiation for 1 hr. The reaction mixture was then acidified with AcOH by pH=ca. 6. The resulted mixture was directly purified by RP-HPLC (HC-A) to afford (±)-4-(1-((5,7-dimethyl-1H-indol-4-yl)methyl)piperidin-2-yl)benzamide as Example-8, and the corresponding carboxylic acid. $^1$H NMR (TFA salt, 400 MHz, D$_2$O) δ 7.81 (d, J=8.34 Hz, 2H), 7.60 (br. d, J=7.80 Hz, 2H), 7.20 (d, J=3.03 Hz, 1H), 6.68-6.73 (m, 1H), 6.08 (br. s., 1H), 4.32-4.39 (m, 1H), 4.12 (d, J=13.60 Hz, 1H), 4.06 (d, J=13.60 Hz, 1H), 3.28 (d, J=12.13 Hz, 1H), 3.08-3.17 (m, 1H), 2.25 (s, 3H), 1.89-2.03 (m, 5H), 1.74-1.82 (m, 1H), 1.65-1.74 (m, 1H), 1.45-1.62 (m, 2H); HRMS calcd. for C$_{23}$H$_{28}$N$_3$O (M+H)$^+$ 362.2232, found 362.2221.

The following Examples were synthesized from appropriate starting materials by applying similar methods described in the examples above:

| Example | Chemical name / Chemical structure | Starting material / NMR and HRMS |
|---|---|---|
| 9-1 | (±)-4-(1-((5-chloro-7-methyl-1H-indol-4-yl)methyl)piperidin-2-yl)benzamide | Intermediate 3-2-12<br>$^1$H NMR (TFA salt, 400 MHz, CD$_3$OD) δ 11.20 (br. s., 1H), 8.07 (d, J = 8.40 Hz, 2H), 7.75 (d, J = 8.34 Hz, 2H), 7.41-7.46 (m, 1H), 7.04 (s, 1H), 6.44 (br. s., 1H), 4.58 (dd, J = 4.55, 10.86 Hz, 1H), 4.37-4.46 (m, 2H), 3.49-3.55 (m, 1H), 3.38-3.46 (m, 1H), 2.49 (s, 3H), 2.07-2.24 (m, 2H), 1.72-2.03 (m, 4H); HRMS calcd. for C$_{22}$H$_{25}$N$_3$OCl (M + H)$^+$ 382.1686, found 382.1679. |
| 9-2 | (±)-4-(rel-(2S,4S)-1-((5,7-dimethyl-1H-indol-4-yl)methyl)-4-methoxypiperidin-2-yl)benzamide | Intermediate 3-2-15<br>$^1$H NMR (TFA salt, 400 MHz, CD$_3$CN) δ 10.82 (br. s., 1H), 8.10 (br. d, J = 8.10 Hz, 2H), 7.76 (br. d, J = 8.30 Hz, 2H), 7.32 (br. s., 1H), 6.83 (s, 1H), 6.36 (br. s., 1H), 4.40 (d, J = 13.30 Hz, 1H), 4.27 (d, J = 13.30 Hz, 1H), 3.74 (br. s., 1H), 3.54-3.65 (m, 1H), 3.45 (s, 3H), 3.36-3.42 (m, 1H), 2.45 (s, 3H), 2.27-2.35 (m, 2H), 2.08-2.20 (m, 4H), 1.88-1.99 (m, 1H); HRMS calcd. for C$_{24}$H$_{30}$N$_3$O$_2$ (M + H)$^+$ 392.2338, found 392.2328. |

Example-10

(±)-4-(4-Methoxy-1-((5-methoxy-7-methyl-1H-indol-4-yl)methyl)-4-methylpiperidin-2-yl)benzamide (Single Diastereomer)

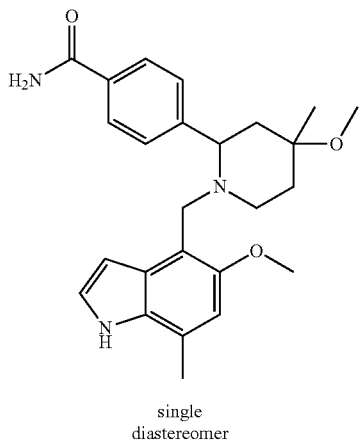 [SMILES: COc1cc(C)c2[nH]ccc2c1CN1CCC(C)(OC)CC1c1ccc(C(N)=O)cc1]

single diastereomer

A mixture of Ba(OH)$_2$ (97 mg, 0.347 mmol) and (±)-tert-butyl 4-((2-(4-cyanophenyl)-4-methoxy-4-methylpiperidin-1-yl)methyl)-5-methoxy-7-methyl-1H-indole-1-carboxylate (single diastereomer), Intermediate 4-4-9, (35 mg, 0.069 mmol) in iPrOH/H$_2$O (2 mL/2 mL) was stirred at 100° C. for 2 h under the microwave irradiation. The reaction mixture was then acidified with AcOH until pH around 7. The resulting mixture was purified by RP-HPLC (HC-B) to afford the title compound. $^1$H NMR (400 MHz, CD$_3$OD) δ 7.93 (d, J=7.7 Hz, 2H), 7.67 (d, J=7.7 Hz, 2H), 7.19 (d, J=2.6 Hz, 1H), 6.68 (s, 1H), 6.43 (d, J=2.9 Hz, 1H), 3.76 (s, 3H), 3.43-3.39 (m, 2H), 3.21-3.16 (m, 3H), 2.95 (br. s., 1H), 2.45 (s, 3H), 2.26 (br. s., 1H), 1.88-1.68 (m, 3H), 1.67-1.57 (m, 1H), 1.37 (s, 3H); HRMS calcd. for C$_{25}$H$_{31}$N$_3$O$_3$ (M+H)$^+$ 422.2444, found 422.2459.

Example-11

(±)-4-(rel-(2S,4S)-1-((5,7-dimethyl-1H-indol-4-yl)methyl)-4-hydroxypiperidin-2-yl)benzoic acid

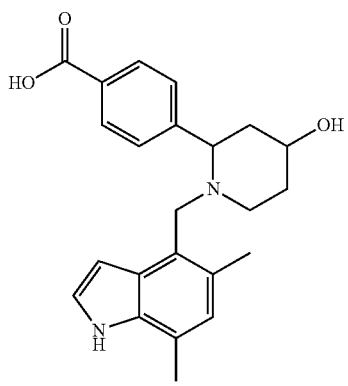

rel-2S,4S

A mixture of (±)-4-(rel-(2S,4S)-1-((5,7-dimethyl-1-tosyl-1H-indol-4-yl)methyl)-4-hydroxypiperidin-2-yl)benzonitrile, Intermediate 3-2-13, (144 mg, 0.28 mmol), KOH (100 mg, 1.782 mmol), and isoamylamine (100 μL, 0.860 mmol) in EtOH (2 mL) was stirred at 130° C. under the microwave irradiation for 2.5 hr. The reaction mixture was then acidified by AcOH by pH around 6. The mixture was purified by RP HPLC (HC-A) to afford the title compound. $^1$H NMR (TFA salt, 400 MHz, D$_2$O) δ 8.02 (br. d, J=8.60 Hz, 2H), 7.65 (br. d, J=7.80 Hz, 2H), 7.26 (d, J=3.03 Hz, 1H), 6.77 (s, 1H), 6.17 (br. s., 1H), 4.72-4.79 (m, 1H), 4.15-4.21 (m, 3H), 3.46-3.57 (m, 1H), 3.15-3.26 (m, 1H), 2.27-2.39 (m, 4H), 2.05-2.14 (m, 1H), 2.01 (s, 3H), 1.71-1.94 (m, 2H); HRMS calcd. for C$_{23}$H$_{27}$N$_2$O$_3$ (M+H)$^+$ 379.2022, found 379.2012.

Example-12

(±)-4-(rel-(2S,4R)-1-((5,7-dimethyl-1H-indol-4-yl)methyl)-4-hydroxypiperidin-2-yl)benzoic acid

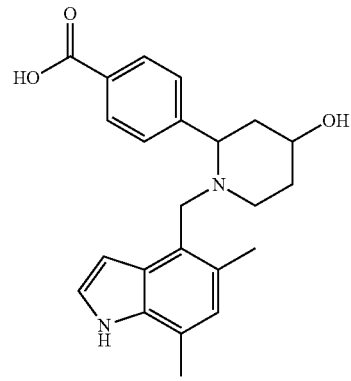

rel-2S,4R

The title compound was synthesized from (±)-4-(rel-(2S,4R)-1-((5,7-dimethyl-1-tosyl-1H-indol-4-yl)methyl)-4-hydroxypiperidin-2-yl)benzonitrile, Intermediate 3-2-14, analogously to the preparation of Example-11. H NMR (400 MHz, D$_2$O) δ 8.07 (d, J=8.60 Hz, 2H), 7.65 (br. d, J=7.60 Hz, 2H), 7.23 (d, J=3.03 Hz, 1H), 6.71 (s, 1H), 6.07 (br. s., 1H), 4.53 (dd, J=2.65, 12.76 Hz, 1H), 3.95-4.12 (m, 3H), 3.32-3.41 (m, 1H), 3.20-3.32 (m, 1H), 2.25-2.33 (m, 4H), 1.98-2.12 (m, 2H), 1.94 (br. s, 3H), 1.51-1.69 (m, 1H); HRMS calcd. for C$_{23}$H$_{27}$N$_2$O$_3$ (M+H)$^+$ 379.2022, found 379.2014.

Example-13

(±)-4-(1-((5-Chloro-7-methyl-1H-indol-4-yl)methyl)piperidin-2-yl)benzoic acid

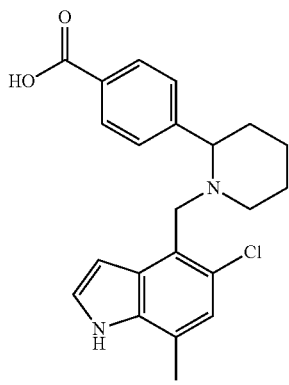 [SMILES: Cc1cc(Cl)c(CN2CCCCC2c2ccc(C(=O)O)cc2)c2cc[nH]c12]

The title compound was synthesized from (±)-4-(1-((5-chloro-7-methyl-1-tosyl-1H-indol-4-yl)methyl)piperidin-2-yl)benzonitrile, Intermediate 3-2-12, analogously to the preparation of Example-11. $^1$H NMR (TFA salt, 400 MHz, CD$_3$OD) δ 8.21 (d, J=8.34 Hz, 2H), 7.76 (d, J=8.34 Hz, 2H), 7.44 (d, J=3.03 Hz, 1H), 7.04 (s, 1H), 6.44 (d, J=3.03 Hz, 1H), 4.59 (dd, J=4.80, 10.36 Hz, 1H), 4.41 (s, 2H), 3.49-3.55 (m, 1H), 3.38-3.46 (m, 1H), 2.49 (s, 3H), 2.08-2.22 (m, 2H), 1.69-2.02 (m, 4H); HRMS calcd. for C$_{22}$H$_{24}$N$_2$O$_2$Cl (M+H)$^+$ 383.1526, found 383.1525.

Example-14

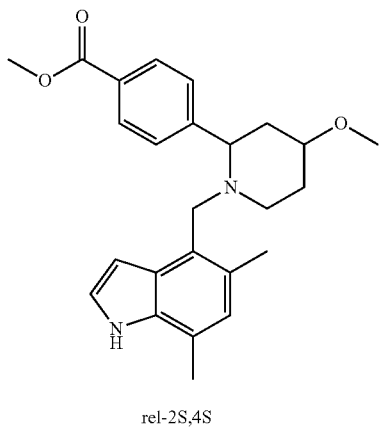

rel-2S,4S

Example-14a; (±)-methyl 4-(rel-(2S,4S)-1-((5,7-dimethyl-1H-indol-4-yl)methyl)-4-methoxypiperidin-2-yl)benzoate A mixture of (±)-4-(rel-(2S,4S)-1-((5,7-dimethyl-1-tosyl-1H-indol-4-yl)methyl)-4-methoxypiperidin-2-yl)benzonitrile, Intermediate 3-2-15, (320 mg, 0.606 mmol), KOH (400 mg, 7.13 mmol), and isoamylamine (0.5 mL, 4.30 mmol) in EtOH (5 mL) was stirred at 130° C. under the microwave irradiation for 2.5 hr. The reaction mixture was diluted with H$_2$O. The mixture was then acidified by half satd. aq. citric acid. The mixture was then extracted three times with CH$_2$Cl$_2$/TFE (ca. 9/1). The combined organic layers were then dried over Na$_2$SO$_4$, filtered, and concentrated. The resulting residue was dissolved in toluene (4 mL)/MeOH (1 mL). To the mixture was then added trimethylsilyldiazomethane in Et$_2$O (1 mL, 2 mmol) dropwise. The mixture was then stirred at room temperature for 2 h. The reaction was quenched with AcOH. The mixture was then diluted with EtOAc. The organic phase was then washed successively with 5% aq. NaHCO$_3$ twice, H$_2$O, brine, dried over Na$_2$SO$_4$, filtered, and concentrated. The resulting residue was purified by silica gel flash column chromatography (heptane/EtOAc=67/33) to afford the title compound. $^1$H NMR (400 MHz, CD$_3$CN) δ 9.09 (br. s., 1H), 7.99 (d, J=8.34 Hz, 2H), 7.65 (br. d, J=8.10 Hz, 2H), 7.17 (app. t, J=2.78 Hz, 1H), 6.71 (s, 1H), 6.57 (dd, J=2.02, 3.03 Hz, 1H), 3.85 (s, 3H), 3.60 (d, J=12.10 Hz, 1H), 3.45-3.54 (m, 2H), 3.21-3.29 (m, 4H), 2.34-2.40 (m, 4H), 2.23-2.33 (m, 4H), 1.86-1.91 (m, 1H), 1.79-1.85 (m, 1H), 1.70-1.78 (m, 1H), 1.45-1.56 (m, 1H); HRMS calcd. for C$_{25}$H$_{31}$N$_2$O$_3$ (M+H)$^+$ 407.2335, found 407.2326.

Example-14b; (+) and (−)-methyl 4-(rel-(2S,4S)-1-((5,7-dimethyl-1H-indol-4-yl)methyl)-4-methoxypiperidin-2-yl)benzoate Resolution of the enantiomers of (±)-methyl 4-(rel-(2S,4S)-1-((5,7-dimethyl-1H-indol-4-yl)methyl)-4-methoxypiperidin-2-yl)benzoate was achieved by chiral SFC using a CHIRALCEL® OJ-H column with 30% (10 mM NH$_4$OH in MeOH) in CO$_2$ to afford methyl 4-(rel-(2S,4S)-1-((5,7-dimethyl-1H-indol-4-yl)methyl)-4-methoxypiperidin-2-yl)benzoate (enantiomer-1) (peak-1, t$_r$=2.4 min) and methyl 4-(rel-(2S,4S)-1-((5,7-dimethyl-1H-indol-4-yl)methyl)-4-methoxypiperidin-2-yl)benzoate (enantiomer-2) (peak-2, t$_r$=3.4 min).

Example-15

(±)-Methyl 4-(rel-(2S,4R)-1-((5,7-dimethyl-1H-indol-4-yl)methyl)-4-methoxypiperidin-2-yl)benzoate

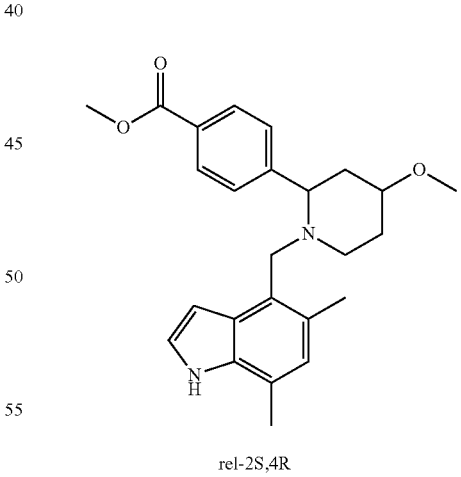

rel-2S,4R

The title compound was synthesized from (±)-4-(rel-(2S,4R)-1-((5,7-dimethyl-1-tosyl-1H-indol-4-yl)methyl)-4-methoxypiperidin-2-yl)benzonitrile, Intermediate 3-2-16, analogously to the preparation of Example-14. $^1$H NMR (400 MHz, CD$_3$CN) δ 9.03 (br. s., 1H), 7.92 (d, J=8.59 Hz, 2H), 7.57 (br. d, J=8.08 Hz, 2H), 7.09 (app. t, J=2.78 Hz, 1H), 6.63 (s, 1H), 6.46 (dd, J=2.02, 3.03 Hz, 1H), 3.77 (s, 3H), 3.50 (d, J=12.25 Hz, 1H), 3.12-3.22 (m, 5H), 3.09 (d, J=12.25 Hz, 1H), 2.52-2.62 (m, 1H), 2.30 (s, 3H), 2.17 (s, 3H), 1.89-2.03 (m, 2H), 1.73-1.82 (m, 1H), 1.38-1.49 (m, 1H), 1.06-1.20 (m, 1H); HRMS calcd. for $C_{25}H_{31}N_2O_3$ $(M+H)^+$ 407.2335, found 407.2334.

Example-16

(−)-(S)-4-(1-((5-cyclopropyl-7-methyl-1H-indol-4-yl)methyl)piperidin-2-yl)-2-fluorobenzoic acid

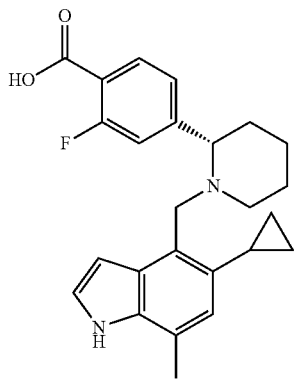 [SMILES: Cc1cc(C2CC2)c(CN2CCCC[C@H]2c2ccc(C(=O)O)c(F)c2)c2cc[nH]c12]

A mixture of (S)-tert-butyl 5-cyclopropyl-4-((2-(3-fluoro-4-(methoxycarbonyl)phenyl)piperidin-1-yl)methyl)-7-methyl-1H-indole-1-carboxylate, Intermediate 3-2-22, (370 mg, 0.711 mmol) and LiOH in $H_2O$ (2 mL, 2 mmol) in THF (1 mL)/MeOH (1 mL) was stirred at 70° C. for 6.5 h. The reaction mixture was cooled down to room temperature. The mixture was then acidified with AcOH. The mixture was then partially concentrated. The resulting residue was purified by RP-HPLC (HC-B) to afford the title compound. $^1$H NMR (400 MHz, $D_2O$) δ 7.77 (app. t, J=7.83 Hz, 1H), 7.42-7.53 (m, 2H), 7.41 (d, J=3.28 Hz, 1H), 6.74 (s, 1H), 6.36 (br. s., 1H), 4.50 (br. d, J=12.60 Hz, 1H), 4.09-4.37 (m, 2H), 3.41 (br. d, J=11.90 Hz, 1H), 3.11 (br. s., 1H), 2.44 (s, 3H), 2.09 (br. s, 2H), 1.90-1.98 (m, 1H), 1.79-1.89 (m, 1H), 1.62-1.79 (m, 3H), 0.91 (br. s., 1H), 0.76 (br. s., 1H), 0.49 (br. s., 1H), 0.21 (br. s., 1H); HRMS calcd. for $C_{25}H_{28}N_2O_2F$ $(M+H)^+$ 407.2135, found 407.2124.

The following examples were synthesized from the appropriate starting material by applying similar methods described in the examples above:

| Example | Chemical structure | Chemical name<br>Starting material<br>NMR and HRMS |
|---|---|---|

17-1 (−)-(S)-4-(1-((5-cyclopropyl-7-methyl-1H-indol-4-yl)methyl)piperidin-2-yl)benzoic acid Intermediate 3-2-19
$^1$H NMR (400 MHz, $D_2O$) δ 7.78 (br. d, J = 8.00 Hz, 2H), 7.48 (br. d, J = 8.00 Hz, 2H), 7.18 (d, J = 2.90 Hz, 1H), 6.49 (s, 1H), 6.20 (br. d, J = 2.90 Hz, 1H), 3.99-4.19 (m, 1H), 3.55-3.85 (m, 2H), 3.07 (br. d, J = 11.10 Hz, 1H), 2.66 (br. s, 1H), 2.23 (s, 3H), 1.79 (br. s., 2H), 1.64-1.74 (m, 1H), 1.47-1.63 (m, 2H), 1.32-1.46 (m, 2H), 0.59-0.72 (m, 1H), 0.45-0.59 (m, 1H), 0.07-0.21 (m, 1H), 0.22-0.03 (m, 1H); HRMS calcd. for $C_{25}H_{29}N_2O_2$ (M + H)$^+$ 389.2229, found 389.2216.

17-2 (±)-4-(1-((5-cyclopropyl-7-methyl-1H-indol-4-yl)methyl)pyrrolidin-2-yl)benzoic acid Intermediate 3-2-20
$^1$H NMR (400 MHz, $D_2O$) δ 7.88 (d, J = 8.20 Hz, 2H), 7.50 (d, J = 8.20 Hz, 2H), 7.37 (d, J = 3.28 Hz, 1H), 6.64 (s, 1H), 6.30 (br. s., 1H), 4.54 (d, J = 13.39 Hz, 1H), 4.41 (d, J = 7.07 Hz, 2H), 3.50 (d, J = 7.58 Hz, 1H), 3.40 (br. s., 1H), 2.47-2.65 (m, 1H), 2.39 (s, 3H), 1.99-2.32 (m, 3H), 1.54 (br. s., 1H), 0.75-0.88 (m, 1H), 0.61-0.74 (m, 1H), 0.46 (br. s., 1H), 0.12-0.33 (m, 1H); HRMS calcd. for $C_{24}H_{27}N_2O_2$ (M + H)$^+$ 375.2073, found 375.2071.

| Chemical name |
|---|
| Chemical Example structure / Starting material / NMR and HRMS |

17-3  (−)-(S)-5-(1-((5-cyclopropyl-7-methyl-1H-indol-4-yl)methyl)piperidin-2-yl)picolinic acid

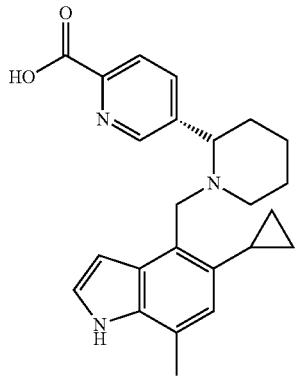

Intermediate 3-2-21
$^1$H NMR (600 MHz, CD$_3$OD) δ 8.66 (s, 1H), 7.81-8.07 (m, 2H), 7.16 (d, J = 3.12 Hz, 1H), 6.56 (d, J = 3.10 Hz, 1H), 6.52 (s, 1H), 3.89 (d, J = 12.29 Hz, 1H), 3.41 (d, J = 12.30 Hz, 1H), 3.22-3.27 (m, 1H), 2.92 (d, J = 11.28 Hz, 1H), 2.39 (s, 3H), 1.99-2.22 (m, 2H), 1.66-1.89 (m, 3H), 1.51-1.65 (m, 2H), 1.36-1.50 (m, 1H), 0.77-0.89 (m, 1H), 0.64-0.74 (m, 1H), 0.49-0.59 (m, 1H), 0.11-0.19 (m, 1H). HRMS calcd. for C$_{24}$H$_{28}$N$_3$O$_2$ (M + H)$^+$ 390.2182, found 390.2168.

17-4  (−)-(S)-4-(1-((5-cyclopropyl-7-methyl-1H-indol-4-yl)methyl)piperidin-2-yl)-3-methoxybenzoic acid

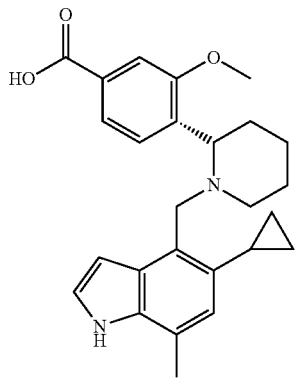

Intermediate 3-2-23
$^1$H NMR (HCl salt, 400 MHz, CD$_3$COCD$_3$) δ 9.99 (br. s., 1H), 7.83 (d, J = 7.80 Hz, 1H), 7.74 (dd, J = 1.30, 8.00 Hz, 1H), 7.71 (d, J = 1.34 Hz, 1H), 7.20-7.31 (m, 1H), 6.76 (dd, J = 2.02, 3.12 Hz, 1H), 6.57 (s, 1H), 3.95-4.03 (m, 4H), 3.85 (dd, J = 3.18, 10.51 Hz, 1H), 3.45 (d, J = 12.23 Hz, 1H), 2.90 (d, J = 11.74 Hz, 2H), 2.43 (s, 3H), 2.28-2.38 (m, 1H), 1.62-1.82 (m, 3H), 1.35-1.60 (m, 3H), 0.80-0.92 (m, 1H), 0.62-0.79 (m, 2H), 0.19-0.29 (m, 1H); HRMS calcd. for C$_{26}$H$_{31}$N$_2$O$_3$ (M + H)$^+$ 419.2335, found 419.2318.

17-5  (−)-(S)-4-(1-((5-methoxy-7-methyl-1H-indol-4-yl)methyl)piperidin-2-yl)benzoic acid

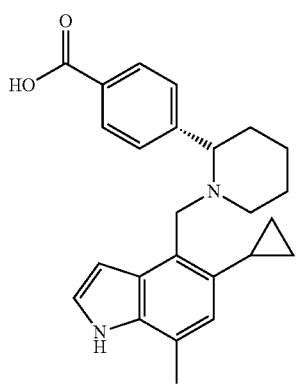

Intermediate 4-4-25
$^1$H NMR (400 MHz, D$_2$O) δ 7.81 (d, J = 8.20 Hz, 2H), 7.44 (d, J = 8.20 Hz, 2H), 7.15 (d, J = 3.03 Hz, 1H), 6.55 (s, 1H), 6.06 (d, J = 3.03 Hz, 1H), 3.70-3.92 (m, 2H), 3.46 (s, 3H), 3.41 (d, J = 12.63 Hz, 1H), 3.02 (br. d, J = 11.90 Hz, 1H), 2.49-2.74 (m, J = 11.00, 11.00 Hz, 1H), 2.23 (s, 3H), 1.62-1.85 (m, 3H), 1.25-1.62 (m, 3H); HRMS calcd. for C$_{23}$H$_{27}$N$_2$O$_3$ (M + H)$^+$ 379.2022, found 379.2021.

| Chemical name | |
|---|---|
| Chemical Example structure | Starting material NMR and HRMS |

17-6    (±)-5-methoxy-7-methy-4-((2-(pyridin-4-yl)piperidin-1-yl)methyl)-1H-indole

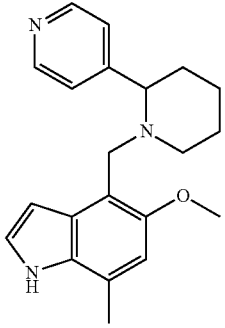 [SMILES: COc1cc(C)c2[nH]ccc2c1CN1CCCCC1c1ccncc1]

Intermediate 4-4-1
$^1$H NMR (400 MHz, CD$_2$Cl$_2$) δ 8.55 (d, J = 4.55 Hz, 2H), 8.10 (br. s., 1H), 7.50 (br. s., 2H), 7.21 (dd, J = 2.50, 2.80 Hz, 1H), 6.69 (s, 1H), 6.55-6.66 (m, 1H), 3.76 (s, 3H), 3.69 (d, J = 11.90 Hz, 1H), 3.25 (d, J = 12.13 Hz, 1H), 3.11 (d, J = 10.36 Hz, 1H), 2.87 (d, J = 10.86 Hz, 1H), 2.45 (s, 3H), 1.90-2.13 (m, 1H), 1.68-1.82 (m, 2H), 1.50-1.68 (m, 2H), 1.30-1.50 (m, 2H); HRMS calcd. for C$_{21}$H$_{26}$N$_3$O (M + H)$^+$ 336.2076, found 336.2067.

17-7    (±)-5-methoxy-7-methy-4-((2-(pyridin-3-yl)piperidin-1-yl)methyl)-1H-indole

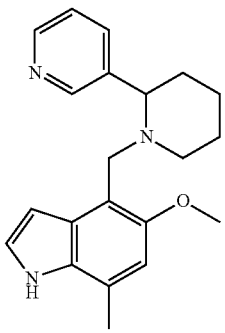 [SMILES: COc1cc(C)c2[nH]ccc2c1CN1CCCCC1c1cccnc1]

Intermediate 4-4-2
$^1$H NMR (400 MHz, CD$_2$Cl$_2$) δ 8.69 (s, 1H), 8.48 (dd, J = 1.30, 4.60 Hz, 1H), 8.04 (br. s., 1H), 7.91 (d, J = 7.58 Hz, 1H), 7.30 (dd, J = 4.60, 7.58 Hz, 1H), 7.20 (dd, J = 2.50, 3.03 Hz, 1H), 6.68 (s, 1H), 6.58 (dd, J = 2.02, 3.03 Hz, 1H), 3.75 (s, 3H), 3.68 (d, J = 12.13 Hz, 1H), 3.23 (d, J = 12.13 Hz, 1H), 3.14 (dd, J = 2.53, 11.12 Hz, 1H), 2.89 (d, J = 11.87 Hz, 1H), 2.45 (s, 3H), 1.94-2.12 (m, 1H), 1.70-1.84 (m, 2H), 1.49-1.69 (m, 2H), 1.25-1.48 (m, 2H); HRMS calcd. for C$_{23}$H$_{30}$N$_3$O$_2$S (M + H)$^+$ 412.2059, found 412.2072.

17-8    (+)-(S)-3-fluoro-4-(1-((5-methoxy-7-methyl-1H-indol-4-yl)methyl)piperidin-2-yl)benzoic acid

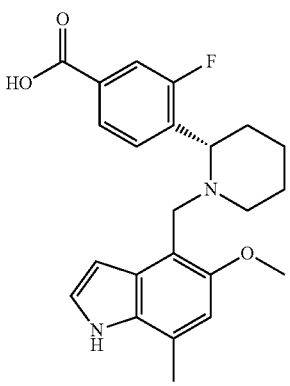 [SMILES: COc1cc(C)c2[nH]ccc2c1CN1CCCC[C@H]1c1ccc(C(=O)O)cc1F]

Intermediate 4-4-3
$^1$H NMR (HCl salt, 400 MHz, D$_2$O) δ 7.82 (br. d, J = 7.60 Hz, 1H), 7.72 (br. d, J = 11.10 Hz, 1H), 7.61 (br. dd, J = 7.10, 7.30 Hz, 1H), 7.29 (d, J = 3.03 Hz, 1H), 6.55 (s, 1H), 6.18 (d, J = 3.03 Hz, 1H), 4.63 (br. s., 1H), 3.88 (br. d, J = 12.90 Hz, 1H), 3.78 (br. d, J = 12.90 Hz, 1H), 3.57 (s, 3H), 3.37 (br. d, J = 11.80 Hz, 1H), 3.08-3.24 (m, 1H), 2.32 (s, 3H), 2.06 (br. s., 2H), 1.86-1.97 (m, 1H), 1.83 (br. d, J = 9.10 Hz, 1H), 1.55-1.75 (m, 2H); HRMS calcd. for C$_{23}$H$_{26}$N$_2$O$_3$F (M + H)$^+$ 397.1927, found 397.1916.

| Chemical name |
|---|
| Chemical Example structure / Starting material / NMR and HRMS |

17-9  (−)-(R)-4-(4-((5-methoxy-7-methyl-1H-indol-4-yl)methyl)morpholin-3-yl)benzoic acid

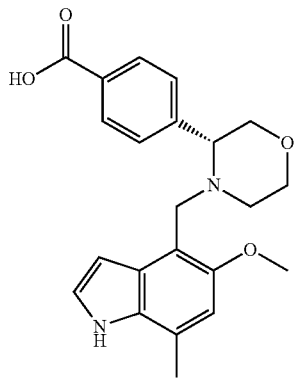 [SMILES: COc1cc(C)c2[nH]ccc2c1CN1CCOC[C@H]1c1ccc(C(=O)O)cc1]

Intermediate 4-4-4
$^1$H NMR (400 MHz, CD$_3$OD) δ 8.01 (d, J = 8.46 Hz, 2H), 7.59 (br. d, J = 7.30 Hz, 2H), 7.18 (d, J = 3.16 Hz, 1H), 6.68 (s, 1H), 6.44 (d, J = 3.16 Hz, 1H), 3.76-3.84 (m, 5H), 3.74 (s, 1H), 3.65-3.70 (m, 1H), 3.45-3.52 (m, 1H), 3.39-3.45 (m, 1H), 3.33-3.37 (m, 2H), 2.73 (s, 1H), 2.45 (s, 3H), 2.34-2.42 (m, 1H); HRMS calcd. for C$_{22}$H$_{25}$N$_2$O$_4$ (M + H)$^+$ 381.1809, found 381.1797.

17-10  (−)-(S)-6-(1-((5-methoxy-7-methyl-1H-indol-4-yl)methyl)piperidin-2-yl)nicotinic acid

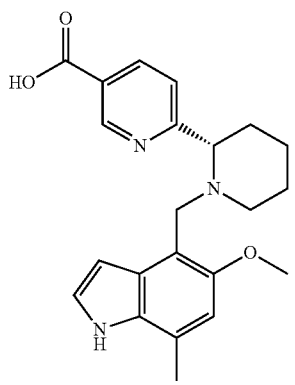 [SMILES: COc1cc(C)c2[nH]ccc2c1CN1CCCC[C@H]1c1ccc(C(=O)O)cn1]

Intermediate 4-4-5
$^1$H NMR (HCl salt, 400 MHz, D$_2$O) δ 8.91 (d, J = 2.02 Hz, 1H), 8.16 (dd, J = 2.10, 8.08 Hz, 1H), 7.41 (d, J = 8.08 Hz, 1H), 7.25 (d, J = 3.03 Hz, 1H), 6.49 (s, 1H), 6.16 (br. s., 1H), 4.35 (br. d, J = 9.30 Hz, 1H), 3.76-3.85 (m, 1H), 3.67-3.75 (m, 1H), 3.64 (s, 3H), 3.39 (br. d, J = 10.60 Hz, 1H), 3.00-3.20 (m, 1H), 2.29 (s, 3H), 2.02 (d, J = 12.88 Hz, 1H), 1.79-1.92 (m, 3H), 1.56-1.75 (m, 2H); HRMS calcd. for C$_{22}$H$_{26}$N$_3$O$_3$ (M + H)$^+$ 380.1974, found 380.1960.

17-11  (−)-4-((2S,4S)-1-((5-methoxy-7-methyl-1H-indol-4-yl)methyl)-4-propoxypiperidin-2-yl)benzoic acid

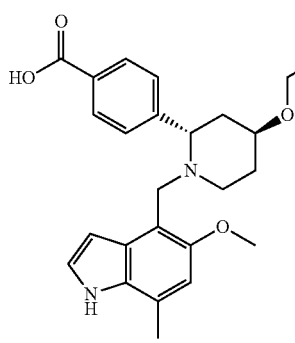

(2S,4S)

Intermediate 4-4-11
$^1$H NMR (400 MHz, D$_2$O) δ 8.06 (d, J = 8.07 Hz, 2H), 7.62 (d, J = 8.07 Hz, 2H), 7.32 (d, J = 2.93 Hz, 1H), 6.60 (s, 1H), 6.18 (br. s., 1H), 4.54 (br. d, J = 9.20 Hz, 1H), 3.84-3.95 (m, 2H), 3.74 (d, J = 12.96 Hz, 1H), 3.59 (s, 3H), 3.52 (t, J = 6.66 Hz, 2H), 3.27-3.38 (m, 1H), 3.21 (br. d, J = 10.90 Hz, 1H), 2.36 (s, 3H), 2.15-2.32 (m, 2H), 1.98-2.08 (m, 1H), 1.80-1.94 (m, 1H), 1.60-1.72 (m, 2H), 0.98 (t, J = 7.27 Hz, 3H); HRMS calcd. for C$_{26}$H$_{33}$N$_2$O$_4$ (M + H)$^+$ 437.2240, found 437.2436.

| Chemical Example | Chemical name structure | Starting material NMR and HRMS |
|---|---|---|

17-12 (−)-4-((2S,4S)-4-hydroxy-1-((5-methoxy-7-methyl-1H-indol-4-yl)methyl)piperidin-2-yl)benzoic acid (2S,4S)

Intermediate 4-4-12
$^1$H NMR (400 MHz, CD$_3$OD) δ 7.99 (d, J = 8.31 Hz, 2H), 7.55 (br. d, J = 7.70 Hz, 2H), 7.16 (d, J = 3.18 Hz, 1H), 6.67 (s, 1H), 6.41 (d, J = 3.18 Hz, 1H), 4.02 (br. s., 1H), 3.81 (d, J = 11.86 Hz, 1H), 3.75 (s, 3H), 3.66 (dd, J = 2.81, 11.62 Hz, 1H), 3.23 (d, J = 11.86 Hz, 1H), 2.76 (d, J = 11.37 Hz, 1H), 2.55-2.65 (m, 1H), 2.45 (s, 3H), 1.86-1.96 (m, 1H), 1.75-1.86 (m, 2H), 1.61 (d, J = 14.06 Hz, 1H); HRMS calcd. for C$_{23}$H$_{27}$N$_2$O$_4$ (M + H)$^+$ 395.1971, found 395.1967.

17-13 (±)-4-(1-((5-methoxy-7-methyl-1H-indol-4-yl)methyl)piperidin-2-yl)-3-methylbenzoic acid Intermediate 4-4-13
$^1$H NMR (HCl salt, 400 MHz, D$_2$O) δ 7.94 (d, J = 8.13 Hz, 1H), 7.88 (s, 1H), 7.59 (d, J = 8.13 Hz, 1H), 7.25 (d, J = 3.06 Hz, 1H), 6.49 (s, 1H), 6.09 (d, J = 3.06 Hz, 1H), 4.43-4.57 (m, 1H), 3.65 (d, J = 12.70 Hz, 1H), 3.50-3.59 (m, 4H), 3.22-3.33 (m, 1H), 3.05-3.19 (m, 1H), 2.48 (s, 3H), 2.28 (s, 3H), 1.74-2.02 (m, 4H), 1.65 (br. s., 2H); HRMS calcd. for C$_{24}$H$_{29}$N$_2$O$_3$ (M + H)$^+$ 393.2178, found 393.2172.

17-14 (±)-4-(1-((5-methoxy-7-methyl-1H-indol-4-yl)methyl)-5-methylpiperidin-2-yl)benzoic acid
(single diastereomer)

single diastereomer

Intermediate 4-4-14
$^1$H NMR (HCl salt, 400 MHz, D$_2$O) δ 7.93 (d, J = 8.38 Hz, 2H), 7.56 (d, J = 8.38 Hz, 2H), 7.32 (d, J = 3.10 Hz, 1H), 6.70 (s, 1H), 6.20 (br. d, J = 2.80 Hz, 1H), 4.37 (br. d, J = 9.70 Hz, 1H), 4.18 (d, J = 13.20 Hz, 1H), 4.05 (d, J = 13.20 Hz, 1H), 3.76 (s, 3H), 3.31 (dd, J = 3.00, 12.65 Hz, 1H), 3.16 (dd, J = 2.51, 12.65 Hz, 1H), 2.41 (s, 3H), 2.22-2.33 (m, 2H), 1.88-2.08 (m, 2H), 1.72 (dd, J = 3.00, 13.88 Hz, 1H), 1.06 (d, J = 7.21 Hz, 3H); HRMS calcd. for C$_{24}$H$_{29}$N$_2$O$_3$ (M + H)$^+$ 393.2178, found 393.2176.

| Chemical name |
|---|
| Chemical Example structure |
| Starting material NMR and HRMS |

17-15 (±)-4-(rel-(2S,4R)-4-ethyl-1-((5-methoxy-7-methyl-1H-indol-4-yl)methyl)piperidin-2-yl)benzoic acid

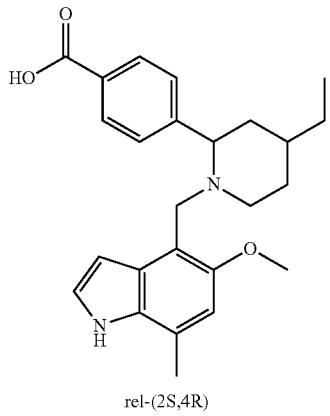 [SMILES: CCC1CCN(Cc2c(OC)cc(C)c3[nH]ccc23)C(c2ccc(C(=O)O)cc2)C1]

rel-(2S,4R)

Intermediate 4-4-15
$^1$H NMR (400 MHz, D$_2$O) δ 8.02 (br. d, J = 8.20 Hz, 2H), 7.62 (br. d, J = 7.70 Hz, 2H), 7.35 (d, J = 3.18 Hz, 1H), 6.73 (s, 1H), 6.18-6.28 (m, 1H), 4.13 (br. s., 1H), 4.02 (d, J = 12.84 Hz, 1H), 3.59-3.78 (m, 4H), 3.29 (br. d, J = 12.50 Hz, 1H), 2.89-3.03 (m, 1H), 2.42 (s, 3H), 2.03-2.14 (m, 1H), 1.79-1.89 (m, 1H), 1.57-1.71 (m, 2H), 1.20-1.41 (m, 3H), 0.87 (t, J = 7.46 Hz, 3H); HRMS calcd. for C$_{25}$H$_{31}$N$_2$O$_3$ (M + H)$^+$ 407.2335, found 407.2358.

17-16 (±)-2-(4-(1-((5-methoxy-7-methyl-1H-indol-4-yl)methyl)piperidin-2-yl)phenyl)acetic acid

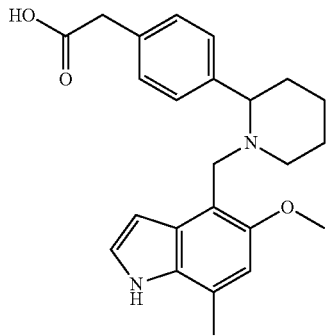 [SMILES: COc1cc(C)c2[nH]ccc2c1CN1CCCCC1c1ccc(CC(=O)O)cc1]

Intermediate 4-4-16
$^1$H NMR (HCl salt, 400 MHz, CD$_3$OD) δ 7.46-7.59 (m, 4H), 7.31 (d, J = 3.18 Hz, 1H), 6.76 (s, 1H), 6.29 (d, J = 3.18 Hz, 1H), 4.33-4.43 (m, 2H), 4.10 (d, J = 12.72 Hz, 1H), 3.75 (s, 3H), 3.67 (s, 2H), 3.49-3.57 (m, 1H), 3.20-3.27 (m, 1H), 2.50 (s, 3H), 2.04-2.14 (m, 2H), 1.90-1.99 (m, 1H), 1.68-1.90 (m, 3H); HRMS calcd. for C$_{24}$H$_{29}$N$_2$O$_3$ (M + H)$^+$ 393.2178, found 393.2181.

17-17 (±)-2-(3-(1-((5-methoxy-7-methyl-1H-indol-4-yl)methyl)piperidin-2-yl)phenyl)acetic acid

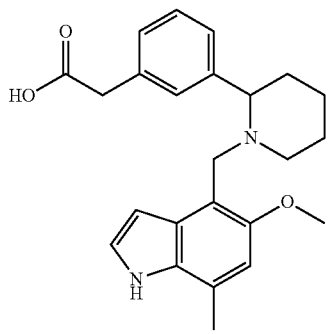 [SMILES: COc1cc(C)c2[nH]ccc2c1CN1CCCCC1c1cccc(CC(=O)O)c1]

Intermediate 4-4-17
$^1$H NMR (HCl salt, 400 MHz, CD$_3$OD) δ 7.53 (s, 1H), 7.37-7.50 (m, 3H), 7.31 (d, J = 3.06 Hz, 1H), 6.75 (s, 1H), 6.25 (br. s, 1H), 4.24-4.45 (m, 2H), 4.10 (d, J = 12.72 Hz, 1H), 3.76 (s, 3H), 3.58 (s, 2H), 3.41-3.52 (m, 1H), 3.17-3.25 (m, 1H), 2.50 (s, 3H), 2.01-2.20 (m, 2H), 1.63-2.00 (m, 4H); HRMS calcd. for C$_{24}$H$_{29}$N$_2$O$_3$ (M + H)$^+$ 393.2178, found 393.2175.

| Chemical name | |
|---|---|
| Chemical Example structure | Starting material NMR and HRMS |

17-18 (±)-5-(rel-(2S,4S)-1-((5-cyclopropyl-7-methyl-1H-indol-4-yl)methyl)-4-methoxypiperidin-2-yl)picolinic acid

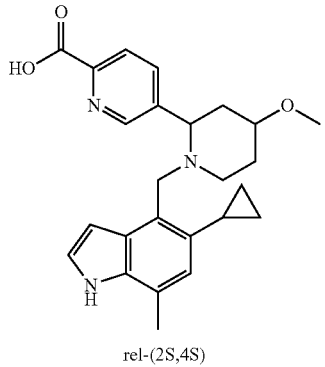 [SMILES: COC1CCN(Cc2c(C3CC3)cc(C)c3[nH]ccc23)C(c2ccc(C(=O)O)nc2)C1]

rel-(2S,4S)

Intermediate 4-4-18
$^1$H NMR (400 MHz, D$_2$O) δ 8.67 (s, 1H), 8.06 (br. d, J = 8.10 Hz, 1H), 7.94 (br. d, J = 8.10 Hz, 1H), 7.37 (d, J = 2.90 Hz, 1H), 6.67 (s, 1H), 6.48 (d, J = 2.81 Hz, 1H), 4.05 (br. d, J = 11.60 Hz, 1H), 3.81-3.93 (m, 1H), 3.77 (br. s., 1H), 3.59-3.73 (m, 1H), 3.41 (s, 3H), 2.86-2.98 (m, 1H), 2.70-2.84 (m, 1H), 2.41 (s, 3H), 1.91-2.17 (m, 3H), 1.72-1.84 (m, 2H), 0.80-0.91 (m, 1H), 0.68-0.79 (m, 1H), 0.26-0.38 (m, 1H), 0.06-0.18 (m, 1H); HRMS calcd. for C$_{25}$H$_{30}$N$_3$O3 (M + H)$^+$ 420.2287, found 420.2281.

17-19 (±)-2-(1-((5-methoxy-7-methyl-1H-indol-4-yl)methyl)piperidin-2-yl)thiazole-4-carboxylic acid

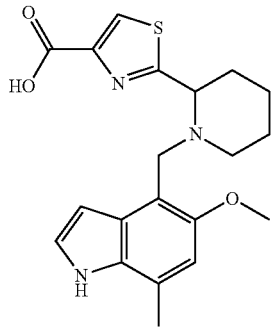 [SMILES: COc1cc(C)c2[nH]ccc2c1CN1CCCCC1c1nc(C(=O)O)cs1]

Intermediate 4-4-23
$^1$H NMR (400 MHz, CD$_3$OD) δ 8.00 (s, 1H), 7.19 (d, J = 3.16 Hz, 1H), 6.68 (s, 1H), 6.53 (d, J = 3.16 Hz, 1H), 3.84 (d, J = 12.00 Hz, 1H), 3.70-3.79 (m, 4H), 3.45 (d, J = 11.87 Hz, 1H), 3.33-3.38 (m, 1H), 2.96-3.05 (m, 1H), 2.46 (s, 3H), 2.16-2.25 (m, 1H), 1.97 (d, J = 11.24 Hz, 1H), 1.75-1.84 (m, 2H), 1.40-1.62 (m, 2H); HRMS calcd. for C$_{20}$H$_{24}$N$_3$O$_3$S (M + H)$^+$ 386.1533, found 386.1514.

17-20 (±)-2-(1-((5-methoxy-7-methyl-1H-indol-4-yl)methyl)piperidin-2-yl)-4-methylthiazole-5-carboxylic acid

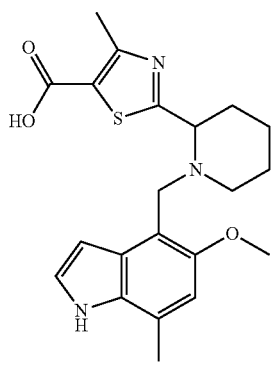 [SMILES: COc1cc(C)c2[nH]ccc2c1CN1CCCCC1c1nc(C)c(C(=O)O)s1]

Intermediate 4-4-24
$^1$H NMR (600 MHz, DMSO-d$_6$) δ 10.84(s, 1 H) 7.27 (t, J = 2.75 Hz, 1 H) 6.66 (s, 1 H) 6.65 (dd, J = 2.89, 2.06 Hz, 1 H) 3.75 (d, J = 12.10 Hz, 1 H) 3.71 (s, 3 H) 3.57-3.63 (m, 1 H) 3.53 (d, J = 12.10 Hz, 1 H) 2.71-2.81 (m, 1 H) 2.57 (s, 3 H) 2.42 (s, 3 H) 2.08 (t, J = 10.36 Hz, 1 H) 1.91 (dd, J = 9.22, 4.72 Hz, 1 H) 1.59-1.71 (m, 2 H) 1.52 (d, J = 12.84 Hz, 1 H) 1.25-1.42 (m, 2 H); HRMS calcd. for C$_{21}$H$_{26}$N$_3$O$_3$S (M + H)$^+$ 400.1702, found 400.1687.

| Chemical Example | Chemical structure | Chemical name<br>Starting material<br>NMR and HRMS |
|---|---|---|
| 17-21 | | (±)-3-(1-((5,7-dimethyl-1H-indol-4-yl)methyl)piperidin-2-yl)benzoic acid |
| | 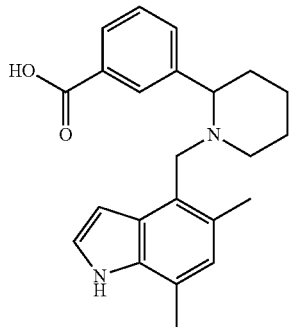 [SMILES: Cc1cc(C)c2[nH]ccc2c1CN1CCCCC1c1cccc(C(=O)O)c1] | Intermediate 4-8<br>$^1$H NMR (HCl salt, 400 MHz, DMSO-d$_6$) δ 10.82 (br. s., 1H), 8.06 (br. s., 1H), 7.80 (d, J = 7.33 Hz, 1H), 7.62 (br. d, J = 8.10 Hz, 1H), 7.33-7.49 (m, 1H), 7.19 (t, J = 2.80 Hz, 1H), 6.62 (s, 1H), 6.42-6.55 (m, 1H), 3.54 (d, J = 12.13 Hz, 1H), 3.06-3.16 (m, 2H), 2.62 (br. d, J = 11.40 Hz, 1H), 2.36 (s, 3H), 2.21 (s, 3H), 1.86-1.96 (m, N 1H), 1.54-1.75 (m, 3H), 1.48 (d, J = 8.59 Hz, 1H), 1.26-1.41 (m, 2H), HRMS calcd. for C$_{23}$H$_{27}$N$_2$O$_2$ (M + H)$^+$ 363.2073, found 363.2075. |
| 17-22 | | (±)-4-(1-((5-methoxy-7-methyl-1H-indol-4-yl)methyl)azepan-2-yl)benzoic acid |
| | 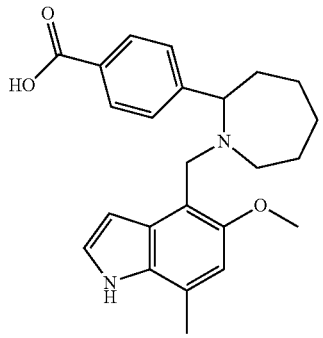 [SMILES: COc1cc(C)c2[nH]ccc2c1CN1CCCCCC1c1ccc(C(=O)O)cc1] | Intermediate 4-9<br>$^1$H NMR (HCl salt, 400 MHz, CD$_3$OD) δ 8.11 (d, J = 8.40 Hz, 2H), 7.59 (br. d, J = 8.30 Hz, 2H), 7.27 (d, J = 3.06 Hz, 1H), 6.69 (s, 1H), 6.06 (d, J = 3.18 Hz, 1H), 4.45-4.58 (m, 2H), 4.41 (d, J = 12.80 Hz, 1H), 3.58 (s, 3H), 3.44 (d, J = 6.97 Hz, 1H), 3.33-3.39 (m, 1H), 2.48 (s, 3H), 2.36-2.54 (m, 1H), 2.19-2.35 (m, 1H), 1.92-2.14 (m, 4H), 1.71-1.87 (m, 1H), 1.46-1.64 (m, 1H); HRMS calcd. for C$_{24}$H$_{29}$N$_2$O$_3$ (M + H)$^+$ 393.2178, found 393.2172. |
| 17-23 | | (−)-(S)-4-((2-(4-(1H-pyrazol-4-yl)phenyl)piperidin-1-yl)methyl)-5-methoxy-7-methyl-1H-indole |
| | 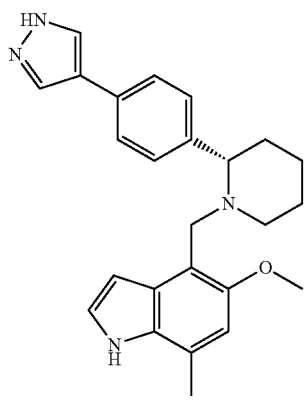 [SMILES: COc1cc(C)c2[nH]ccc2c1CN1CCCC[C@H]1c1ccc(-c2cn[nH]c2)cc1] | Intermediate 4-10<br>$^1$H NMR (400 MHz, DMSO-d$_6$) δ 12.88 (br. s., 1H), 10.77 (br. s., 1H), 8.16 (br. s., 1H), 7.91 (br. s., 1H), 7.60 (d, J = 8.31 Hz, 2H), 7.49 (br. d, J = 7.70 Hz, 2H), 7.23 (dd, J = 2.70, 2.80 Hz, 1H), 6.64 (s, 1H), 6.49-6.53 (m, 1H), 3.70 (s, 3H), 3.62 (d, J = 12.00 Hz, 1H), 3.17 (d, J = 11.98 Hz, 1H), 3.05 (br. dd, J = 2.00, 10.50 Hz, 1H), 2.76 (br. d, J = 10.40 Hz, 1H), 2.41 (s, 3H), 1.87-1.96 (m, 1H), 1.64-1.74 (m, 2H), 1.53-1.62 (m, 1H), 1.43-1.53 (m, 1H), 1.29-1.39 (m, 2H); HRMS calcd. for C$_{25}$H$_{28}$N$_4$O (M − H) 401.2328, found 401.2343. |

| Chemical name | |
|---|---|
| Chemical Example structure | Starting material NMR and HRMS |

17-24  (−)-(S)-4-((2-(4-(1H-pyrazol-3-yl)phenyl)piperidin-1-yl)methyl)-5-methoxy-7-methyl-1H-indole

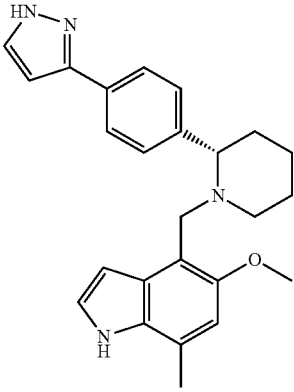 [SMILES: COc1cc(C)c2[nH]ccc2c1CN1CCCC[C@H]1c1ccc(-c2cc[nH]n2)cc1]

Intermediate 4-11
$^1$H NMR (400 MHz, CD$_3$COCD$_3$) δ 12.08 (br. s., 1H), 9.92 (br. s., 1H), 7.87 (br. d, J = 8.30 Hz, 2H), 7.68 (br. s., 1H), 7.63 (br. d, J = 7.80 Hz, 2H), 7.24 (app.t, J = 2.81 Hz, 1H), 6.66-6.72 (m, 3H), 3.80 (d, J = 12.10 Hz, 1H), 3.77 (s, 3H), 3.30 (d, J = 12.10 Hz, 1H), 3.13 (dd, J = 2.63, 10.70 Hz, 1H), 2.91 (br. d, J = 11.74 Hz, 1H), 2.76 (s, 3H), 2.44 (s, 3H), 1.95-2.02 (m, 1H), 1.72-1.80 (m, 2H), 1.63-1.72 (m, 1H), 1.50-1.56 (m, 1H), 1.37-1.50 (m, 2H); HRMS calcd. for C$_{25}$H$_{28}$N$_4$O (M − H) 401.2328, found 401.2334.

17-25  (±)-4-(1-((5-methoxy-7-methyl-1H-indol-4-yl)methyl)piperidin-2-yl)-1-naphthoic acid

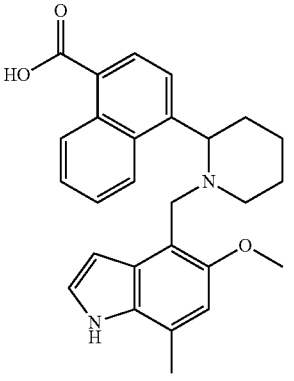 [SMILES: COc1cc(C)c2[nH]ccc2c1CN1CCCCC1c1ccc(C(=O)O)c2ccccc12]

Intermediate 4-12
$^1$H NMR (rotamer exists, 400 MHz, DMSO-d$_6$) δ 10.77 (br. s., 1H), 8.90 (br. s., 1H), 8.36 (br. m), 7.82-8.14 (br. m), 7.51 (br. s., 2H), 7.23 (m, 1H), 6.25-6.76 (m), 4.07 (br. s), 3.53-3.76 (m), 3.22 (br. s.), 2.86 (br. s., 1H), 2.40 (s, 3H), 2.03-2.21 (m, 1H), 1.73 (br. s., 2H), 1.33-1.61 (m, 4H); HRMS calcd. for C$_{27}$H$_{29}$N$_2$O$_3$ (M + H)$^+$ 429.2178, found 429.2180.

17-26  4-((2S)-1-(2,2,2-trifluoro-1-(5-methoxy-7-methyl-1H-indol-4-yl)ethyl)piperidin-2-yl)benzoic acid (diastereomer-1)

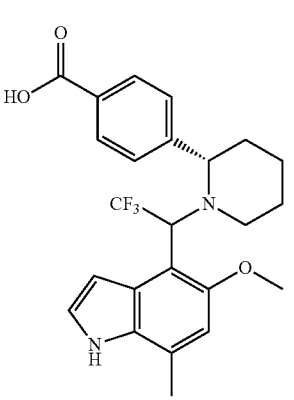

diastereomer-1

Intermediate 4-13
$^1$H NMR (400 MHz, CD$_3$COCD$_3$) δ 10.12 (br. s., 1H), 8.03 (d, J = 8.32 Hz, 2H), 7.64 (d, J = 8.32 Hz, 2H), 7.30 (app. t, J = 2.90 Hz, 1H), 6.82 (s, 1H), 6.56-6.62 (m, 1H), 5.36 (q, J = 10.39 Hz, 1H), 4.01-4.08 (m, 1H), 3.80 (s, 3H), 3.37-3.46 (m, 1H), 3.00-3.10 (m, 1H), 2.50 (d, J = 0.73 Hz, 3H), 1.55-1.81 (m, 4H), 1.41-1.52 (m, 1H), 1.21-1.33 (m, 1H); HRMS calcd. for C$_{24}$H$_{26}$F$_3$N$_2$O$_3$ (M + H) 447.1896, found 447.1895.

| Chemical name | |
|---|---|
| Chemical Example structure | Starting material NMR and HRMS |

17-27 4-((2S)-1-(2,2,2-trifluoro-1-(5-methoxy-7-methyl-1H-indol-4-yl)ethyl)piperidin-2-yl)benzoic acid (diastereomer-2)

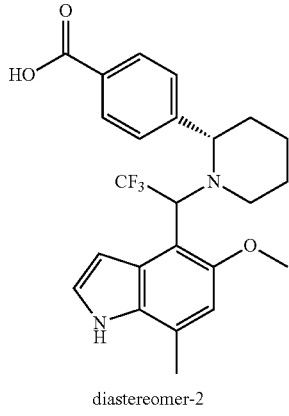 [SMILES: COc1cc(C)c2[nH]ccc2c1C(N1CCCC[C@H]1c1ccc(C(=O)O)cc1)C(F)(F)F]

diastereomer-2

Intermediate 4-14
$^1$H NMR (400 MHz, CD$_3$COCD$_3$) δ 10.16 (br. s., 1H), 8.09 (d, J = 8.19 Hz, 2H), 7.70 (d, J = 8.19 Hz, 2H), 7.34 (br. s., 1H), 6.86 (s, 1H), 6.66 (br. s., 1H), 5.07-5.25 (m, 1H), 3.64 (br. s., 3H), 3.51-3.61 (m, 2H), 2.53 (s, 3H), 1.94-2.03 (m, 1H), 1.45-1.74 (m, 5H), 1.02-1.18 (m, 1H); HRMS calcd. for C$_{24}$H$_{26}$F$_3$N$_2$O$_3$ (M + H) 447.1896, found 447.1921.

17-28 (±)-2-methoxy-4-(1-((5-methoxy-7-methyl-1H-indol-4-yl)methyl)piperidin-2-yl)benzoic acid

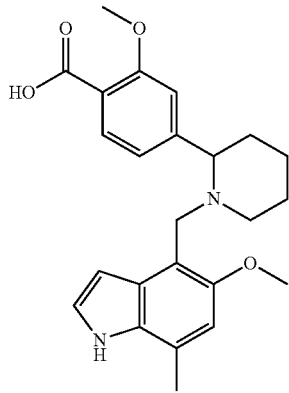 [SMILES: COc1cc(C2CCCCN2Cc2c(OC)cc(C)c3[nH]ccc23)ccc1C(=O)O]

Intermediate 4-4-26
$^1$H NMR (HCl salt, 400 MHz, D$_2$O) δ 7.63 (d, J = 7.70 Hz, 1H), 7.34 (d, J = 2.87 Hz, 1H), 7.17-7.28 (m, 2H), 6.68 (s, 1H), 6.18 (d, J = 2.87 Hz, 1H), 4.33 (br. dd, J = 3.40, 11.60 Hz, 1H), 4.10 (d, J = 12.96 Hz, 1H), 3.92 (s, 3H), 3.87 (d, J = 12.96 Hz, 1H), 3.65 (s, 3H), 3.40 (d, J = 12.35 Hz, 1H), 3.09-3.21 (m, 1H), 2.40 (s, 3H), 1.99-2.16 (m, 2H), 1.78-1.97 (m, 2H), 1.61-1.75 (m, 2H); HRMS calcd. for C$_{24}$H$_{29}$N$_2$O$_4$ (M + H)$^+$ 409.2127, found 409.2116.

17-29 (±)-4-(6-((5-methoxy-7-methyl-1H-indol-4-yl)methyl)-6-azaspiro[2.5]octan-5-yl)benzoic acid

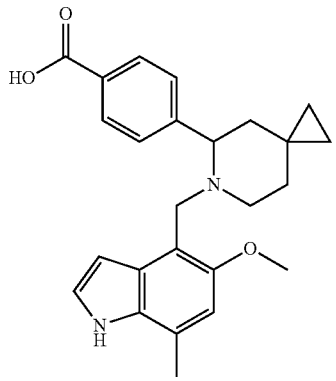 [SMILES: COc1cc(C)c2[nH]ccc2c1CN1CCC2(CC2)CC1c1ccc(C(=O)O)cc1]

Intermediate 4-4-27
$^1$H NMR (400 MHz, CD$_3$OD) δ 8.11 (d, J = 8.20 Hz, 2H), 7.61 (d, J = 8.20 Hz, 2H), 7.30 (d, J = 3.06 Hz, 1H), 6.75 (s, 1H), 6.33 (br. s., 1H), 4.46-4.62 (m, 1H), 4.36 (br. d, J = 12.70 Hz, 1H), 4.14 (d, J = 12.72 Hz, 1H), 3.75 (s, 3H), 3.44-3.58 (m, 1H), 3.33-3.42 (m, 1H), 2.52-2.64 (m, 1H), 2.50 (s, 3H), 2.21-2.39 (m, 1H), 1.25-1.35 (m, 1H), 1.02-1.14 (m, 1H), 0.45-0.68 (m, 4H). HRMS calc. for C$_{25}$H$_{27}$N$_2$O$_3$ (M − H) 403.2016, found 403.2019.

| Chemical Example structure | Chemical name Starting material NMR and HRMS |
|---|---|
| 17-30 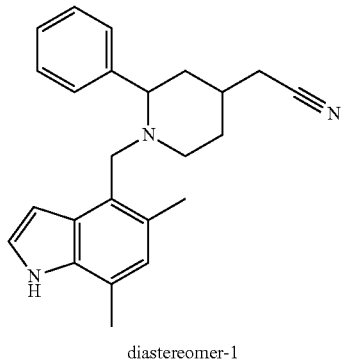 rel-(2S,4S) | (±)-4-(rel-(2S,4S)-4-ethyl-1-((5-methoxy-7-methyl-1H-indol-4-yl)methyl)piperidin-2-yl)benzoic acid<br><br>Intermediate 4-4-28<br>$^1$H NMR (400 MHz, CD$_3$OD) δ 8.13 (d, J = 8.07 Hz, 2H), 7.62 (br. d, J = 7.80 Hz, 2H), 7.31 (d, J = 3.06 Hz, 1H), 6.76 (s, 1H), 6.32 (br. s., 1H), 4.50-4.65 (m, 1H), 4.34 (d, J = 12.59 Hz, 1H), 4.17 (d, J = 12.60 Hz, 1H), 3.76 (s, 3H), 3.34-3.43 (m, 2H), 2.50 (s, 3H), 2.23-2.38 (m, 1H), 1.94-2.17 (m, 2H), 1.84-1.94 (m, 1H), 1.67-1.83 (m, 3H), 1.02 (t, J = 7.34 Hz, 3H). HRMS calc. for C$_{25}$H$_{31}$N$_2$O$_3$ (M + H) 407.2329, found 407.2312. |

Example-18

(±)-2-(1-((5,7-Dimethyl-1H-indol-4-yl)methyl)-2-phenylpiperidin-4-yl)acetonitrile (Diastereomer-1)

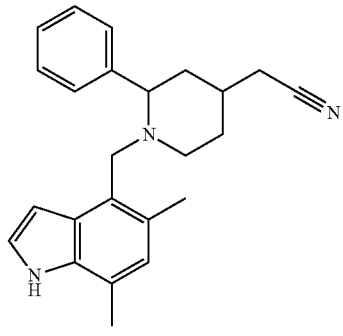

diastereomer-1

A mixture of (±)-tert-butyl 4-((4-(cyanomethyl)-2-phenylpiperidin-1-yl)methyl)-5,7-dimethyl-1H-indole-1-carboxylate (diastereomer-1), Intermediate 4-1, (95 mg, 0.208 mmol) and Cs$_2$CO$_3$ (300 mg, 0.921 mmol) in MeOH (5 mL) was stirred at 60° C. for 2 h, and then cooled to room temperature. The reaction mixture was diluted with CH$_2$Cl$_2$. The mixture was then washed successively with H$_2$O and brine, dried over Na$_2$SO$_4$, filtered, and concentrated. The resulting residue was purified by silica gel flash column chromatography [CH$_2$Cl$_2$/(10% MeOH in EtOAc)=92/8] to afford the title compound. $^1$H NMR (400 MHz, CD$_3$CN) δ 9.10 (br. s., 1H), 7.52 (d, J=7.30 Hz, 2H), 7.36 (dd, J=7.30, 7.60 Hz, 2H), 7.23-7.30 (m, 1H), 7.18 (app. t, J=2.80 Hz, 1H), 6.72 (s, 1H), 6.59 (br. dd, J=2.30, 2.50 Hz, 1H), 3.73 (d, J=12.13 Hz, 1H), 3.41-3.48 (m, 1H), 3.37 (d, J=12.13 Hz, 1H), 2.61 (d, J=8.08 Hz, 2H), 2.45-2.54 (m, 1H), 2.37-2.40 (m, 3H), 2.21-2.32 (m, 4H), 2.15-2.20 (m, 1H), 2.00-2.07 (m, 1H), 1.61-1.78 (m, 2H), 1.48-1.58 (m, 1H); HRMS calcd. for C$_{24}$H$_{28}$N$_3$ (M+H)$^+$ 358.2283, found 358.2278.

Example-19

(±)-2-(1-((5,7-Dimethyl-1H-indol-4-yl)methyl)-2-phenylpiperidin-4-yl)acetonitrile (Diastereomer-2)

diastereomer-2

The title compound was synthesized from (±)-tert-butyl 4-((4-(cyanomethyl)-2-phenylpiperidin-1-yl)methyl)-5,7-dimethyl-1H-indole-1-carboxylate (diastereomer-2), Intermediate 4-2, analogously to the preparation of Example-18. $^1$H NMR (400 MHz, CD$_3$CN) δ 9.09 (br. s., 1H), 7.54 (d, J=7.21 Hz, 2H), 7.39 (dd, J=7.21, 8.10 Hz, 2H), 7.27-7.33 (m, 1H), 7.17 (dd, J=2.80, 3.15 Hz, 1H), 6.71 (s, 1H), 6.57 (dd, J=2.15, 3.15 Hz, 1H), 3.66 (d, J=12.38 Hz, 1H), 3.16 (d, J=12.38 Hz, 2H), 2.65-2.71 (m, 1H), 2.38 (s, 3H), 2.31 (dd, J=1.64, 6.44 Hz, 2H), 2.26 (s, 3H), 1.98-2.05 (m, 1H), 1.78-1.87 (m, 2H), 1.61-1.69 (m, 1H), 1.45-1.56 (m, 1H), 1.12-1.24 (m, 1H); MS (ESI+) m/z 358.3 (M+H).

Example-20

Example-20a; (+)-4-((2S,4R)-1-((5-methoxy-7-methyl-1H-indol-4-yl)methyl)-4-methylpiperidin-2-yl)benzoic acid

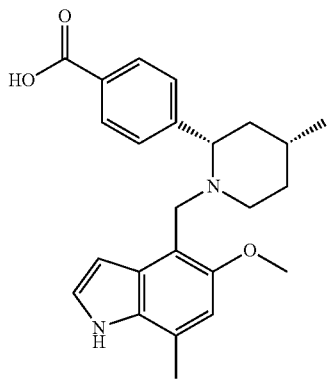 [SMILES: COc1cc(C)c2[nH]ccc2c1CN1CC[C@@H](C)C[C@H]1c1ccc(C(=O)O)cc1]

A mixture of tert-butyl 5-methoxy-4-(((2S,4R)-2-(4-(methoxycarbonyl)phenyl)-4-methylpiperidin-1-yl)methyl)-7-methyl-1H-indole-1-carboxylate, Intermediate 5-1 b peak-1 ($t_r$=4.1 min), (600 mg, 1.184 mmol) and LiOH in H$_2$O (4 mL, 4.00 mmol) in THF (3 mL)/MeOH (4 mL) was stirred at 80° C. for 6 h. The mixture was cooled to room temperature. The reaction mixture was diluted with H$_2$O. The mixture was washed twice with CH$_2$Cl$_2$. The aqueous layer was then acidified with citric acid by pH=ca. 6. The mixture was then saturated with NaCl. The mixture was then extracted three times with EtOAc/TFE (ca. 9/1). The organic layer was then dried over Na$_2$SO$_4$, filtered, and then concentrated. The resulting residue was purified by RP-HPLC (HC-B) to afford the title compound. $^1$H NMR (400 MHz, CD$_3$OD) δ 8.12 (d, J=8.10 Hz, 2H), 7.59 (d, J=7.83 Hz, 2H), 7.30 (d, J=2.93 Hz, 1H), 6.75 (s, 1H), 6.30 (br. d, J=2.70 Hz, 1H), 4.25-4.50 (m, 2H), 3.98-4.13 (m, 1H), 3.75 (s, 3H), 3.44-3.54 (m, 1H), 3.24-3.28 (m, 1H), 2.50 (s, 3H), 2.04 (br. d, J=14.50 Hz, 1H), 1.89-1.99 (m, 1H), 1.65-1.89 (m, 2H), 1.43-1.58 (m, 1H), 1.01 (d, J=6.24 Hz, 3H); HRMS calcd. for C$_{24}$H$_{29}$N$_2$O$_3$ (M+H)$^+$ 393.2178, found 393.2190.

Example-20b; (−)-4-((2R,4S)-1-((5-methoxy-7-methyl-1H-indol-4-yl)methyl)-4-methylpiperidin-2-yl)benzoic acid

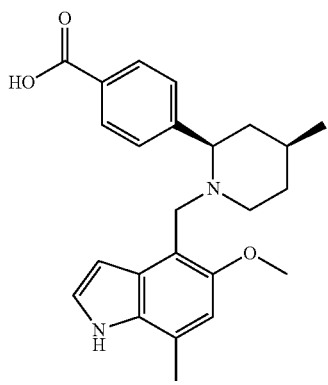 [SMILES: COc1cc(C)c2[nH]ccc2c1CN1CC[C@H](C)C[C@@H]1c1ccc(C(=O)O)cc1]

The title compound was synthesized from tert-butyl 5-methoxy-4-(((2R,4S)-2-(4-(methoxycarbonyl)phenyl)-4-methylpiperidin-1-yl)methyl)-7-methyl-1H-indole-1-carboxylate, Intermediate 5-1b peak-2 ($t_r$=5.8 min), analogously to the preparation of Example-20a. Analytical data; same as Example-20a.

Example-20c; 4-((2S,4R)-1-((5-methoxy-7-methyl-1H-indol-4-yl)methyl)-4-methylpiperidin-2-yl)benzoic acid phosphate salt

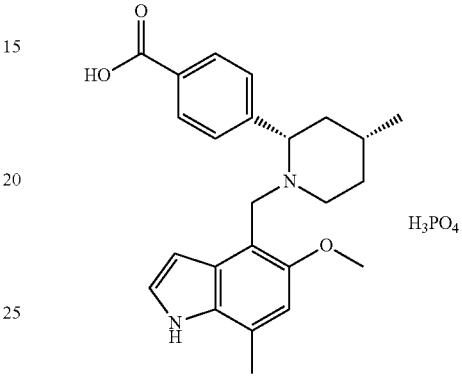

To a suspension of (+)-4-((2S,4R)-1-((5-methoxy-7-methyl-1H-indol-4-yl)methyl)-4-methylpiperidin-2-yl)benzoic acid (122 mg, 0.311 mmol) in 1.2 mL of a 1:9 mixture of methanol and acetonitrile was added H$_3$PO$_4$ (35.8 mg, 0.311 mmol, 85% aqueous) in 1.2 mL of 1:9 mixture of methanol and acetonitrile. The mixture was sonicated for 10 min. The mixture was then heated to 55° C. over 15 min and held at that temperature for 30 min. The mixture was cooled to 5° C. over 2 h and allowed to stir at 5° C. for 1 h. The mixture was then heated to 55° C. over 15 min and the process was repeated 3 additional times. The mixture was warmed to rt and filtered, washing with 10 mL of a 1:1 mixture of acetonitrile:methyl tert-butyl ether and the solid collected was dried to give the title compound. $^1$H NMR (400 MHz, Methanol-d$_4$) δ 8.22 (d, J=8.0 Hz, 2H), 7.71 (d, J=8.0 Hz, 2H), 7.35 (d, J=3.2 Hz, 1H), 6.79 (s, 1H), 6.35 (d, J=3.2 Hz, 1H), 4.55 (d, J=11.9 Hz, 1H), 4.38 (d, J=12.7 Hz, 1H), 4.16 (d, J=12.7 Hz, 1H), 3.78 (s, 3H), 3.56 (d, J=12.7 Hz, 1H), 3.38 (m, 1H), 2.53 (s, 3H), 2.10 (d, J=14.9 Hz, 1H), 1.99 (s, 1H), 1.90 (d, J=14.5 Hz, 1H), 1.78 (q, J=12.9 Hz, 1H), 1.55 (d, J=13.4 Hz, 1H), 1.05 (d, J=6.4 Hz, 3H). X-ray powder diffraction:

| Angle 2-Theta ° | d value Angstrom | Intensity Count | Intensity % % |
|---|---|---|---|
| 7.7 | 11.509 | 1522 | 27 |
| 9.1 | 9.677 | 5560 | 100 |
| 10.9 | 8.111 | 4718 | 85 |
| 12.4 | 7.124 | 1890 | 34 |
| 14.8 | 5.986 | 2001 | 36 |
| 15.8 | 5.598 | 1165 | 21 |
| 17.0 | 5.201 | 1906 | 34 |
| 18.0 | 4.917 | 2370 | 43 |
| 19.1 | 4.641 | 4525 | 81 |
| 20.8 | 4.271 | 4688 | 84 |
| 22.6 | 3.927 | 1518 | 27 |
| 23.9 | 3.718 | 1924 | 35 |
| 26.2 | 3.394 | 3365 | 61 |

Example-21

Example-21a; (−)-4-((2S,4S)-4-methoxy-1-((5-methoxy-7-methyl-1H-indol-4-yl)methyl)piperidin-2-yl)benzoic acid

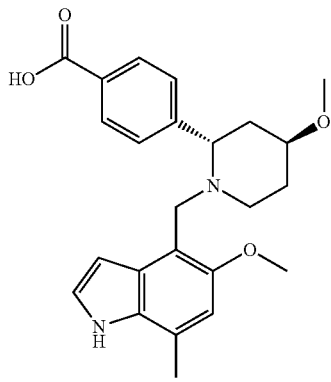 [SMILES: COc1cc(C)c2[nH]ccc2c1CN1CC[C@H](OC)C[C@H]1c1ccc(C(=O)O)cc1]

A mixture of tert-butyl 5-methoxy-4-(2S,4S)-(4-methoxy-2-(4-(methoxycarbonyl)phenyl)piperidin-1-yl)methyl)-7-methyl-1H-indole-1-carboxylate, Intermediate 5-2b peak-2 ($t_r$=5.5 min), (30 mg, 0.057 mmol) and LiOH in H$_2$O (500 μL, 0.500 mmol) in THF (0.5 mL)/MeOH (0.5 mL) was stirred at 70° C. for 4 h, and then cooled to room temperature. The mixture was then acidified with AcOH. The mixture was then partially concentrated. The resulting residue was purified by RP-HPLC (HC-B) to afford the title compound. The absolute stereochemistry was determined by comparison with enantiopure synthesis in Example-21c.
$^1$H NMR (400 MHz, D$_2$O) δ 7.99 (d, J=8.10 Hz, 2H), 7.63 (br. d, J=8.10 Hz, 2H), 7.34 (d, J=3.03 Hz, 1H), 6.80 (s, 1H), 6.30 (d, J=3.03 Hz, 1H), 3.79-4.02 (m, 2H), 3.73-3.79 (m, 1H), 3.69 (s, 3H), 3.29-3.49 (m, 4H), 2.89 (br. d, J=10.90 Hz, 1H), 2.63-2.83 (m, 1H), 2.45 (s, 3H), 2.07-2.20 (m, 1H), 1.88-2.06 (m, 2H), 1.61-1.87 (m, 1H); HRMS calcd. for C$_{24}$H$_{29}$N$_2$O$_4$ (M+H)$^+$ 409.2127, found 409.2119.

Example-21b; (+)-4-((2R,4R)-4-methoxy-1-((5-methoxy-7-methyl-1H-indol-4-yl)methyl)piperidin-2-yl)benzoic acid

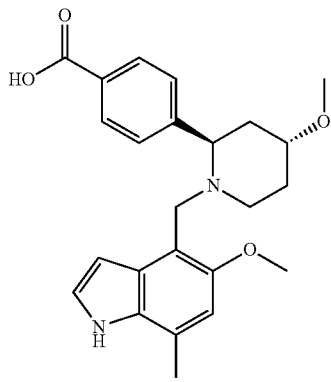

The title compound was synthesized from tert-butyl 5-methoxy-4-(2R,4R)-(4-methoxy-2-(4-(methoxycarbonyl)phenyl)piperidin-1-yl)methyl)-7-methyl-1H-indole-1-carboxylate, Intermediate 5-2b peak-1 ($t_r$=2.8 min), analogously to the preparation of Example-21a. Analytical data; same as Example-21a.

Example-21c; (−)-4-((2S,4S)-4-methoxy-1-((5-methoxy-7-methyl-1H-indol-4-yl)methyl)piperidin-2-yl)benzoic acid

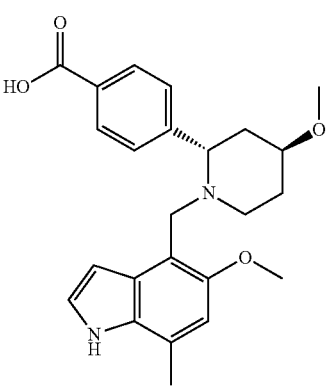 [SMILES: COc1cc(C)c2[nH]ccc2c1CN1CC[C@H](OC)C[C@H]1c1ccc(C(=O)O)cc1]

To a solution of tert-butyl 4-formyl-5-methoxy-7-methyl-1H-indole-1-carboxylate, Intermediate 1-3, (1.5 g, 5.18 mmol) and methyl ((2S,4S)-4-(4-methoxypiperidin-2-yl))benzoate, Intermediate 2-12b, (1 g, 4.01 mmol) in DCE (20 mL) was added NaBH(OAc)$_3$ (3 g, 14.15 mmol). The mixture was then stirred at room temperature for 3 days. The reaction was then quenched with NaBH$_4$ (200 mg), followed by MeOH (5 mL). The mixture was then stirred at room temperature for 0.5 h. The reaction mixture was diluted with EtOAc. The mixture was then washed successively with 5% aq. NaHCO$_3$, H$_2$O, and brine, dried over Na$_2$SO$_4$, filtered, and concentrated. The resulting residue was mixed with LiOH in H$_2$O (15 mL, 15 mmol) and THF (10 mL)/MeOH (20 mL) and was stirred at 70° C. for 22 h, and then cooled to room temperature. The reaction mixture was with H$_2$O, and then acidified with half satd. aq. KHSO$_4$ and citric acid. The mixture was then saturated with sodium chloride. The mixture was then extracted with CH$_2$Cl$_2$/TFE (c.a. 9/1). The organic layer was then dried over Na$_2$SO$_4$, filtered, and then concentrated. The resulting residue was purified by RP-HPLC (HC-B) to afford the title compound. Analytical data; same as Example-21a.

Following examples were prepared from the corresponding peak of the enantiomer by the method described above.

| Example | Chemical name structure Starting material for enantiomer-a Starting material for enantiomer-b | NMR and HRMS |
|---|---|---|
| 22-1 | (+) and (−)-5-(rel-(2S,4S)-4-ethoxy-1-((5-methoxy-7-methyl-1H-indol-4-yl)methyl)piperidin-2-yl)picolinic acid 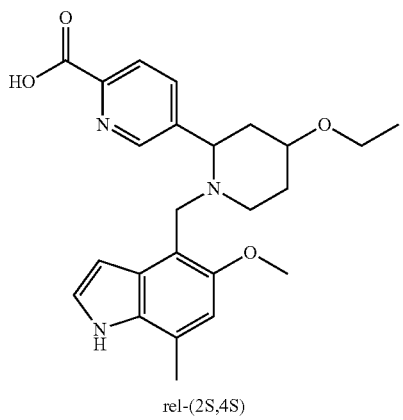 [SMILES: CCOC1CCN(Cc2c(OC)cc(C)c3[nH]ccc23)C(c2ccc(C(=O)O)nc2)C1] rel-(2S,4S) | $^1$H NMR (400 MHz, D$_2$O) δ 8.61 (d, J = 0.90 Hz, 1H), 8.01 (dd, J = 1.80, 8.10 Hz, 1H), 7.94 (d, J = 8.10 Hz, 1H), 7.34 (d, J = 3.18 Hz, 1H), 6.77 (s, 1H), 6.35 (d, J = 3.06 Hz, 1H), 3.77-3.85 (m, 2H), 3.65-3.76 (m, 4H), 3.61 (q, J = 7.10 Hz, 2H), 3.34 (d, J = 12.80 Hz, 1H), 2.84 (br. d, J = 11.90 Hz, 1H), 2.63-2.72 (m, 1H), 2.42 (s, 3H), 1.99-2.08 (m, 1H), 1.82-1.93 (m, 2H), 1.68-1.79 (m, 1H), 1.26 (t, J = 7.10 Hz, 3H); HRMS calcd. for C$_{24}$H$_{30}$N$_3$O$_4$ (M + H)$^+$ 424.2236, found 424.2226. |
| 22-1a | (−)-5-(rel-(2S,4S)-4-ethoxy-1-((5-methoxy-7-methyl-1H-indol-4-yl)methyl)piperidin-2-yl)picolinic acid was prepared from Intermediate 5-3-1b enantiomer-1 (peak-1, t$_r$ = 4.9 min). | |
| 22-1b | (+)-5-(rel-(2S,4S)-4-ethoxy-1-((5-methoxy-7-methyl-1H-indol-4-yl)methyl)piperidin-2-yl)picolinic acid was prepared from Intermediate 5-3-1b enantiomer-2 (peak-2, t$_r$ = 6.0 min). | |
| 22-2 | (+) and (−)-4-(1-((5-methoxy-7-methyl-1H-indol-4-yl)methyl)-4,4-dimethylpiperidin-2-yl)benzoic acid 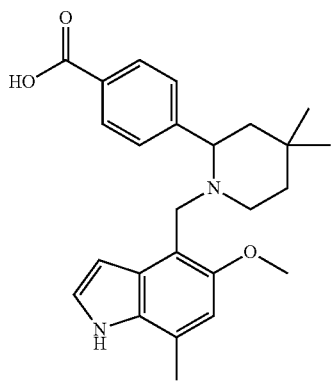 | $^1$H NMR (400 MHz, CD$_3$COCD$_3$) δ 9.94 (br. s., 1H), 8.07 (d, J = 8.56 Hz, 2H), 7.73 (br. d, J = 7.50 Hz, 2H), 7.23-7.23 (m, 1H), 6.70 (s, 1H), 6.67 (dd, J = 2.02, 3.12 Hz, 1H), 3.78 (s, 3H), 3.74 (d, J = 11.98 Hz, 1H), 3.46 (dd, J = 3.12, 11.43 Hz, 1H), 3.36 (d, J = 11.98 Hz, 1H), 2.67-2.74 (m, 1H), 2.45 (s, 3H), 2.23-2.33 (m, 1H), 1.50-1.58 (m, 1H), 1.36-1.48 (m, 2H), 1.20-1.30 (m, 1H), 1.07 (s, 3H), 0.91 (s, 3H); HRMS calcd. for C$_{25}$H$_{31}$N$_2$O$_3$ 407.2335, found 407.2344. |
| 22-2a | (+)-4-(1-((5-methoxy-7-methyl-1H-indol-4-yl)methyl)-4,4-dimethylpiperidin-2-yl)benzoic acid was prepared from Intermediate 5-3-2b enantiomer-1 (peak-1, t$_r$ = 2.4 min). | |
| 22-2b | (−)-4-(1-((5-methoxy-7-methyl-1H-indol-4-yl)methyl)-4,4-dimethylpiperidin-2-yl)benzoic acid was prepared from Intermediate 5-3-2b enantiomer-2 (peak-2, t$_r$ = 4.4 min). | |

Example-23

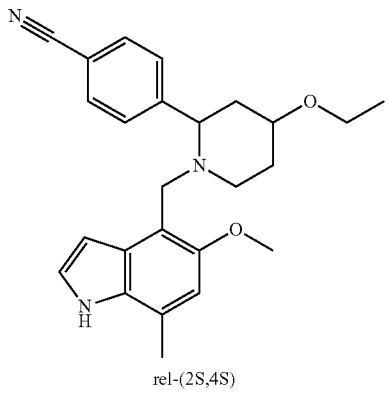 [SMILES: CCOC1CCN(Cc2c(OC)cc(C)c3[nH]ccc23)C(c2ccc(C#N)cc2)C1]

rel-(2S,4S)

Example-23a; (+)-4-(rel-(2S,4S)-4-ethoxy-1-((5-methoxy-7-methyl-1H-indol-4-yl)methyl)piperidin-2-yl)benzonitrile To a solution of tert-butyl 4-(rel-(2S,4S)-(2-(4-cyanophenyl)-4-ethoxypiperidin-1-yl)methyl)-5-methoxy-7-methyl-1H-indole-1-carboxylate (enantiomer-1), Intermediate 5-3-3b peak-1 ($t_r$=1.7 min), (25 mg, 0.050 mmol) in $CH_2Cl_2$ (1 mL) at 0° C. was added TFA (0.5 mL). The mixture was then stirred at 0° C. for ca. 3 h, and then quenched with 5% aq. $NaHCO_3$ at the same temperature. The mixture was then extracted with $CH_2Cl_2$. The organic phase was then washed successively with $H_2O$ and brine, dried over $Na_2SO_4$, filtered, and concentrated. The resulting residue was purified by RP-HPLC (HC-B) to afford the title compound. $^1$H NMR (600 MHz, $CD_3CN$) δ 9.06 (br. s., 1H), 7.72 (s, 4H), 7.20 (t, J=2.57 Hz, 1H), 6.70 (s, 1H), 6.52 (dd, J=2.40, 2.60 Hz, 1H), 3.73 (s, 3H), 3.60 (d, J=12.01 Hz, 1H), 3.56-3.58 (m, 1H), 3.53 (dd, J=2.80, 11.60 Hz, 1H), 3.46 (dq, J=1.56, 6.97 Hz, 2H), 3.25 (d, J=12.10 Hz, 1H), 2.52 (td, J=3.56, 11.76 Hz, 1H), 2.43 (s, 3H), 2.34-2.40 (m, 1H), 1.83-1.89 (m, 1H), 1.72 (td, J=2.84, 13.94 Hz, 1H), 1.63-1.70 (m, 1H), 1.46-1.55 (m, 1H), 1.18 (t, J=6.97 Hz, 3H). HRMS calcd. for $C_{25}H_{30}N_3O_2$ (M+H)$^+$ 404.2338, found 404.2333.

Example-23b

(−)-4-(rel-(2S,4S)-4-ethoxy-1-((5-methoxy-7-methyl-1H-indol-4-yl)methyl)piperidin-2-yl)benzonitrile The title compound was synthesized from tert-butyl 4-(rel-(2S,4S)-(2-(4-cyanophenyl)-4-ethoxypiperidin-1-yl)methyl)-5-methoxy-7-methyl-1H-indole-1-carboxylate (enantiomer-2), Intermediate 5-3-3b peak-2 ($t_r$=3.4 min), analogously to the preparation of Example-23a. Analytical data; same as Example-23a.

Example-24

(+)-4-(rel-(2S,4S)-4-ethoxy-1-((5-methoxy-7-methyl-1H-indol-4-yl)methyl)piperidin-2-yl)benzamide

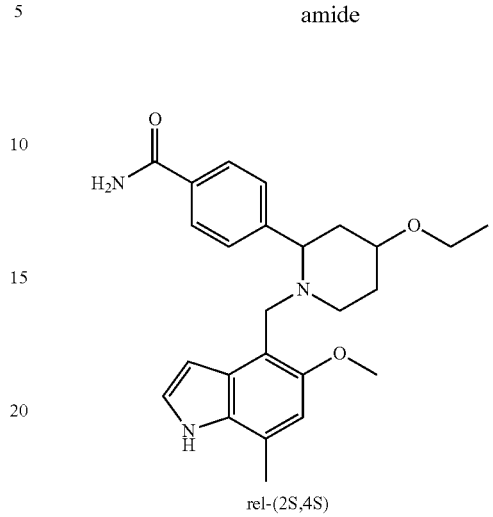

rel-(2S,4S)

The title compound was synthesized tert-butyl 4-(rel-(2S,4S)-(2-(4-cyanophenyl)-4-ethoxypiperidin-1-yl)methyl)-5-methoxy-7-methyl-1H-indole-1-carboxylate (enantiomer-1), Intermediate 5-3-3b peak-1 ($t_r$=1.7 min), analogously to the preparation of Example-8. $^1$H NMR (400 MHz, $CD_3COCD_3$) δ 9.83 (br. s., 1H), 7.85 (d, J=8.44 Hz, 2H), 7.57 (br. d, J=7.80 Hz, 2H), 7.28 (br. s., 1H), 7.13 (dd, J=2.60, 2.70 Hz, 1H), 6.58 (s, 1H), 6.53-6.56 (m, 1H), 6.39 (br. s., 1H), 3.66 (s, 3H), 3.59 (d, J=11.98 Hz, 1H), 3.50 (br. s., 1H), 3.42-3.48 (m, 1H), 3.38 (q, J=6.97 Hz, 2H), 3.22 (d, J=12.00 Hz, 1H), 2.45-2.53 (m, 1H), 2.33 (s, 3H), 2.24-2.32 (m, 1H), 1.78-1.87 (m, 1H), 1.55-1.73 (m, 2H), 1.36-1.53 (m, 1H), 1.09 (t, J=6.97 Hz, 3H); HRMS calcd. for $C_{25}H_{32}N_3O_2$ (M+H)$^+$ 422.2444, found 422.2435.

Example-25

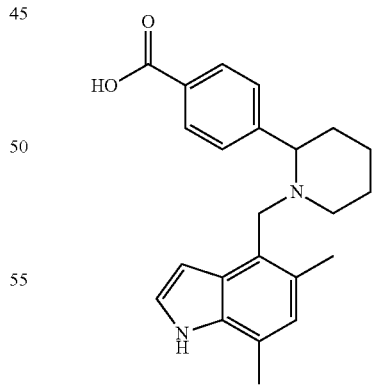

Example-25a; (+)-4-(1-((5,7-dimethyl-1H-indol-4-yl)methyl)piperidin-2-yl)benzoic acid A mixture of methyl 4-(1-((5,7-dimethyl-1H-indol-4-yl)methyl)piperidin-2-yl)benzoate (enantiomer-1), Intermediate 6-1b peak-1 ($t_r$=2.6 min), (150 mg, 0.398 mmol) and KOH (50 mg, 0.891 mmol) in THF (1 mL) was stirred at room temperature for 1.5 h. The mixture was then concentrated. The resulting residue was purified by RP-HPLC (HC-B) to afford the title compound. $^1$H NMR (400 MHz, D$_2$O) δ 7.95 (d, J=8.59 Hz, 2H), 7.58 (br. d, J=7.80 Hz, 2H), 7.20 (d, J=3.00 Hz, 1H), 6.71 (s, 1H), 6.08 (br. s., 1H), 4.32-4.39 (m, 1H), 4.13 (d, J=13.60 Hz, 1H), 4.06 (d, J=13.60 Hz, 1H), 3.27 (br. d, J=12.40 Hz, 1H), 3.07-3.17 (m, 1H), 2.25 (s, 3H), 1.92-2.03 (m, 5H), 1.74-1.82 (m, 1H), 1.65-1.74 (m, 1H), 1.44-1.61 (m, 2H); HRMS calcd. for C$_{23}$H$_{27}$N$_2$O$_2$ (M+H)$^+$ 363.2073, found 363.2064.

Example-25b; (−)-4-(1-((5,7-dimethyl-1H-indol-4-yl)methyl)piperidin-2-yl)benzoic acid The title compound was synthesized from corresponding enantiomer, methyl 4-(1-((5,7-dimethyl-1H-indol-4-yl)methyl)piperidin-2-yl)benzoate (enantiomer-2), Intermediate 6-1 peak-2 (t$_r$=4.1 min), analogously to the preparation of Example-25a. Analytical data; same as Example-25a.

Example-26

Example-26a; 4-((2S,4S)-(4-ethoxy-1-((5-methoxy-7-methyl-1H-indol-4-yl)methyl)piperidin-2-yl))benzoic acid ((+) as TFA Salt)

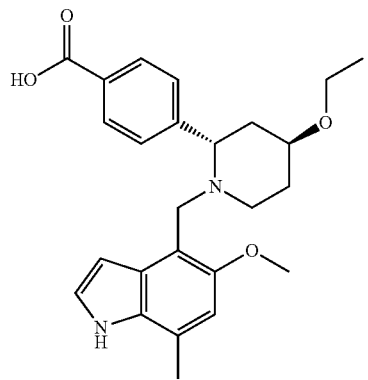 [SMILES: CCO[C@H]1CCN(Cc2c(OC)cc(C)c3[nH]ccc23)[C@H](c2ccc(C(=O)O)cc2)C1]

A mixture of methyl 4-((2S,4S)-4-ethoxy-1-((5-methoxy-7-methyl-1H-indol-4-yl)methyl)piperidin-2-yl)benzoate, Intermediate 6-2b peak-1 (tr=1.9 min), (84 mg, 0.192 mmol) and LiOH in H$_2$O (1 mL, 1 mmol) in THF (1 mL)/MeOH (2 mL) was stirred at room temperature for 16 h, and then concentrated. The resulting residue was purified by RP-HPLC (HC-A) to afford the title compound. Absolute stereochemistry was determined by comparison with enantiopure synthesis in Example-26c. $^1$H NMR (TFA salt, 400 MHz, D$_2$O) δ 8.12 (d, J=8.19 Hz, 2H), 7.66 (br. d, J=8.20 Hz, 2H), 7.35 (d, J=3.06 Hz, 1H), 6.67 (s, 1H), 6.25 (d, J=3.06 Hz, 1H), 4.65 (dd, J=4.28, 11.49 Hz, 1H), 4.04 (d, J=13.00 Hz, 1H), 3.87-3.98 (m, 2H), 3.53-3.69 (m, 5H), 3.38-3.50 (m, 1H), 3.20-3.35 (m, 1H), 2.40 (s, 3H), 2.17-2.33 (m, 2H), 2.08 (br. d, J=15.70 Hz, 1H), 1.82-1.99 (m, 1H), 1.28 (t, J=7.03 Hz, 3H); HRMS calcd. for C$_{26}$H$_{31}$N$_2$O$_3$ (M+H)$^+$ 423.2284, found 423.2263.

Example-26b; 4-((2R,4R)-(4-ethoxy-1-((5-methoxy-7-methyl-1H-indol-4-yl)methyl)piperidin-2-yl))benzoic acid ((−) as TFA Salt)

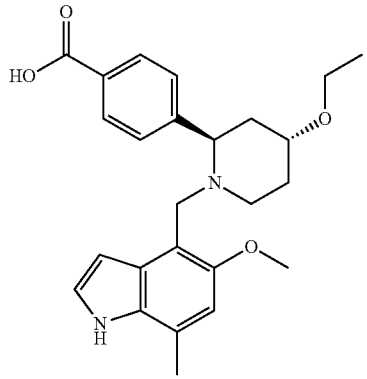 [SMILES: CCO[C@@H]1CCN(Cc2c(OC)cc(C)c3[nH]ccc23)[C@@H](c2ccc(C(=O)O)cc2)C1]

4-((2R,4R)-(4-ethoxy-1-((5-methoxy-7-methyl-1H-indol-4-yl)methyl)piperidin-2-yl))benzoic acid ((−) as TFA salt) was synthesized from methyl 4-((2R,4R)-4-ethoxy-1-((5-methoxy-7-methyl-1H-indol-4-yl)methyl)piperidin-2-yl)benzoate (enantiomer-2), Intermediate 6-2b peak-2 (t$_r$=3.4 min), analogously to the preparation of Example-26a. Analytical data; same as Example-26a.

Example-26c; 4-((2S,4S)-(4-ethoxy-1-((5-methoxy-7-methyl-1H-indol-4-yl)methyl)piperidin-2-yl))benzoic acid ((+) as TFA Salt)

To a solution of tert-butyl 4-formyl-5-methoxy-7-methyl-1H-indole-1-carboxylate, Intermediate 1-3, (1.5 g, 5.18 mmol) and methyl 4-((2S,4S)-4-ethoxypiperidin-2-yl)benzoate, Intermediate 2-13a, (1.185 g, 4.5 mmol) in DCE (20 mL) was added NaBH(OAc)$_3$ (3 g, 14.15 mmol). The mixture was then stirred at room temperature for 21.5 h. To the mixture was then added additional amount of tert-butyl 4-formyl-5-methoxy-7-methyl-1H-indole-1-carboxylate (500 mg, 4.50 mmol). The mixture was then stirred at room temperature for another 20 h. The reaction mixture was then diluted with EtOAc, and then washed successively with 5% aq. NaHCO$_3$, H$_2$O, and brine, dried over Na$_2$SO$_4$, filtered, and concentrated. The resulting residue was mixed with LiOH in H$_2$O (15 mL, 15 mmol) and THF (10 mL)/MeOH (20 mL) and was stirred at 70° C. for 8 h, and then cooled to room temperature. The reaction mixture was then diluted with H₂O, and then acidified with half satd. aq. KHSO₄ and citric acid. The mixture was then saturated with sodium chloride. The mixture was then extracted with CH₂Cl₂/TFE (c.a. 9/1). The organic layer was then dried over Na₂SO₄, filtered, and then concentrated. The resulting residue was purified by RP-HPLC (HC-B) to afford the title compound. Analytical data; same as Example-26a.

Example-26d; 4-((2S,4S)-(4-ethoxy-1-((5-methoxy-7-methyl-1H-indol-4-yl)methyl)piperidin-2-yl))benzoic acid hydrochloride

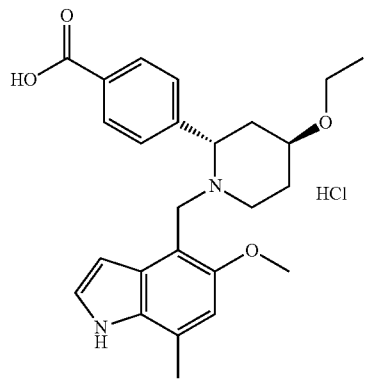 [SMILES: CCO[C@H]1CCN(Cc2c(OC)cc(C)c3[nH]ccc23)[C@H](c2ccc(C(=O)O)cc2)C1 ; Cl]

To a solution of 4-((2S,4S)-(4-ethoxy-1-((5-methoxy-7-methyl-1H-indol-4-yl)methyl)piperidin-2-yl))benzoic acid (620 mg, 1.467 mmol) in H₂O/CH₃CN (10/3 mL) was added 5M aq. HCl (500 µL, 2.500 mmol). The mixture was then lyophilized. The resulting amorphous compound was then suspended in iPrOH (300 mL). The mixture was heated to 70° C. The mixture turned to a solution after 1.5 h. The solution was then cooled to room temperature with stirring for approx. 5 h. The resulting solid was collected by filtration. The solid was dried up under high vacuum at 50° C. to afford the title compound as a crystalline solid. ¹H NMR (HCl salt, 400 MHz, CD₃OD) δ 10.73 (br. s., 1H), 8.23 (d, J=8.44 Hz, 2H), 7.74 (d, J=8.44 Hz, 2H), 7.31-7.36 (m, 1H), 6.77 (s, 1H), 6.37 (dd, J=1.77, 3.12 Hz, 1H), 4.33 (d, J=12.72 Hz, 1H), 4.25 (d, J=12.72 Hz, 1H), 3.79-3.85 (m, 1H), 3.76 (s, 3H), 3.51-3.67 (m, 4H), 3.37-3.44 (m, 1H), 2.51 (s, 3H), 2.21-2.29 (m, 2H), 1.90-2.15 (m, 2H), 1.31 (t, J=6.97 Hz, 3H). X-ray powder diffraction:

| Angle 2-Theta ° | d value Angstrom | Intensity Count | Intensity % % |
|---|---|---|---|
| 10.0 | 8.842 | 2532 | 41 |
| 11.6 | 7.631 | 4461 | 72 |
| 15.3 | 5.783 | 6231 | 100 |
| 16.5 | 5.360 | 4451 | 71 |
| 17.3 | 5.131 | 4119 | 66 |
| 20.1 | 4.418 | 4812 | 77 |
| 21.0 | 4.220 | 5911 | 95 |
| 22.8 | 3.900 | 3170 | 51 |
| 23.3 | 3.815 | 4537 | 73 |
| 25.3 | 3.520 | 3255 | 52 |
| 26.2 | 3.393 | 2968 | 48 |
| 31.0 | 2.887 | 1556 | 25 |

The following Examples were synthesized from appropriate starting materials by applying similar methods described in the examples above:

| | Chemical name |
|---|---|
| Example | structure<br>Starting material for enantimer-a<br>Starting material for enantimer-b | NMR and HRMS |

27-1 (+) and (−)-4-(rel-(2S,4S)-1-((5,7-dimethyl-1H-indol-4-yl)methyl)-4-methoxypiperidin-2-yl)benzoic acid

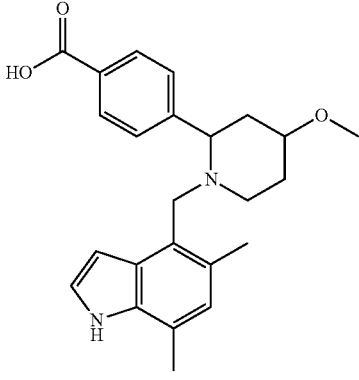

rel-(2S,4S)

¹H NMR (400 MHz, D₂O) δ 7.81 (d, J = 8.08 Hz, 2H), 7.47 (d, J = 8.10 Hz, 2H), 7.11 (d, J = 3.03 Hz, 1H), 6.60 (s, 1H), 6.06 (br. s., 1H), 3.92 (br. s., 1H), 3.70 (d, J = 12.63 Hz, 1H), 3.59 (br. s., 1H), 3.28-3.53 (m, 1H), 3.22 (s, 3H), 2.74 (br. s., 2H), 2.19 (s, 3H), 1.94-2.10 (m, 2H), 1.88 (s, 3H), 1.70-1.84 (m, 1H), 1.40-1.69 (m, 1H); HRMS calcd. for C₂₄H₂₉N₂O₃ (M + H)⁺ 393.2178, found 393.2179.

27-1a (+)-4-(rel-(2S,4S)-1-((5,7-dimethyl-1H-indol-4-yl)methyl)-4-methoxypiperidin-2-yl)benzoic acid was prepared from Example-14a enantiomer-1 (peak-1, t$_r$ = 2.4 min)

27-1b (−)-4-(rel-(2S,4S)-1-((5,7-dimethyl-1H-indol-4-yl)methyl)-4-methoxypiperidin-2-yl)benzoic acid was prepared from Example-14b enantiomer-2 (peak-2, t$_r$ = 3.4 min)

27-2 4-(rel-(2S,4S)-1-((5,7-dimethyl-1H-indol-4-yl)methyl)-4-ethoxypiperidin-2-yl)benzoic acid ((+)-as TFA salt and (−)-as TFA salt)

| Chemical name | |
|---|---|
| structure | NMR and HRMS |
| Starting material for enantimer-a | |
| Example Starting material for enantimer-b | |

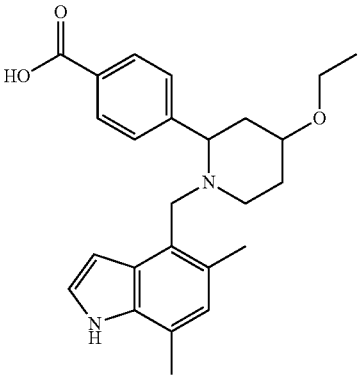

rel-(2S,4S)

¹H NMR (TFA salt, 600 MHz, D$_2$O) δ 8.04 (d, J = 7.79 Hz, 2H), 7.73 (br. d, J = 7.40 Hz, 2H), 7.38 (d, J = 2.84 Hz, 1H), 6.89 (s, 1H), 6.29 (br. s., 1H), 4.64 (br. s., 1H), 4.28 (br. s, 1H), 4.13 (br. s, 1H), 3.97 (br. s, 1H), 3.65 (q, J = 6.94 Hz, 2H), 3.40 (br. s., 1H), 3.22 (br. s., 1H), 2.45 (s, 3H), 2.34 (br. s., 2H), 2.15 (br. s., 3H), 2.03-2.11 (m, 1H), 1.90 (br. s., 1H), 1.29 (t, J = 7.02 Hz, 3H); HRMS calcd. for C$_{25}$H$_{31}$N$_2$O$_3$ (M + H)$^+$ 407.2335, found 407.2332.

27-2a  4-(rel-(2S,4S)-1-((5,7-dimethyl-1H-indol-4-yl)methyl)-4-ethoxypiperidin-2-yl)benzoic acid (+) as TFA salt) was prepared from Intermediate 6-2-2b enantiomer-1 (peak-1, t$_r$ = 1.7 min).

27-2b  4-(rel-(2S,4S)-1-((5,7-dimethyl-1H-indol-4-yl)methyl)-4-ethoxypiperidin-2-yl)benzoic acid ((−) as TFA salt) was prepared from Intermediate 6-2-2b enantiomer-2 (peak-2, t$_r$ = 4.4 min).

27-3  (+) and (−)-4-(rel-(2S,4S)-1-((5-cyclopropyl-7-methyl-1H-indol-4-yl)methyl)-4-methoxypiperidin-2-yl)benzoic acid

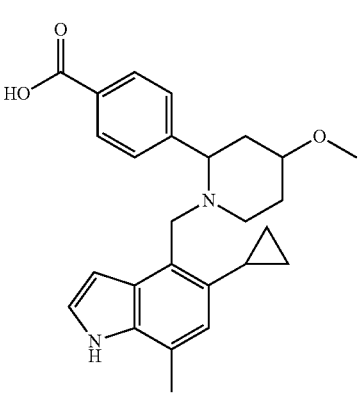

rel-(2S,4S)

¹H NMR (400 MHz, D$_2$O) δ 7.81 (br. d, J = 8.30 Hz, 2H), 7.51 (br. d, J = 7.80 Hz, 2H), 7.20 (d, J = 3.28 Hz, 1H), 6.52 (s, 1H), 6.16 (br. s., 1H), 4.15-4.46 (m, 2H), 3.97 (br. s., 1H), 3.66 (br. s., 1H), 3.24 (s, 3H), 2.96-3.20 (m, 2H), 2.23 (s, 3H), 2.14 (br. s., 2H), 1.90 (br. d, J = 15.40 Hz, 1H), 1.70 (br. s., 1H), 1.45 (br. s., 1H), 0.66 (br. s., 1H), 0.55 (br. s., 1H), 0.14 (br. s., 1H),-0.11 (br. s., 1H). HRMS calcd. for C$_{26}$H$_{31}$N$_2$O$_3$ (M + H)$^+$ 419.2335, found 419.2335.

27-3a  (−)-4-(rel-(2S,4S)-1-((5-cyclopropyl-7-methyl-1H-indol-4-yl)methyl)-4-methoxypiperidin-2-yl)benzoic acid was prepared from Intermediate 6-2-3b enantiomer-1 (peak-1, t$_r$ = 2.0 min)

27-3b  (+)-4-(rel-(2S,4S)-1-((5-cyclopropyl-7-methyl-1H-indol-4-yl)methyl)-4-methoxypiperidin-2-yl)benzoic acid was prepared from Intermediate 6-2-3b enantiomer-2 (peak-2, t$_r$ = 4.3 min)

27-4  (+) and (−)-4-(rel-(2S,4S)-1-((5-cyclopropyl-7-methyl-1H-indol-4-yl)methyl)-4-ethoxypiperidin-2-yl)benzoic acid

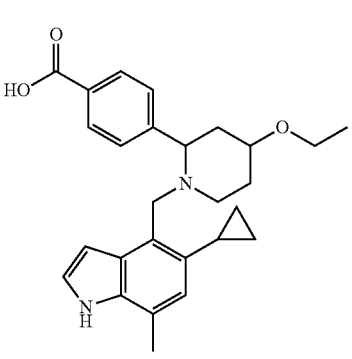

rel-(2S,4S)

¹H NMR (600 MHz, D$_2$O) δ 8.03 (d, J = 8.25 Hz, 2H), 7.71 (br. d, J = 7.80 Hz, 2H), 7.41 (d, J = 2.93 Hz, 1H), 6.71 (s, 1H), 6.32 (br. s., 1H), 4.63-4.73 (m, 1H), 4.52 (d, J = 12.30 Hz, 1H), 4.30 (d, J = 12.30 Hz, 1H), 3.98 (br. s., 1H), 3.65 (q, J = 7.00 Hz, 2H), 3.42-3.56 (m, 1H), 3.34 (br. d, J = 11.00 Hz, 1H), 2.43 (s, 3H), 2.26-2.40 (m, 2H), 2.10 (d, J = 15.31 Hz, 1H), 1.92 (br. s., 1H), 1.61 (br. s., 1H), 1.29 (t, J = 7.00 Hz, 3H), 0.87 (br. s., 1H), 0.76 (br. s., 1H), 0.34 (br. s., 1H), 0.08 (br. s., 1H). HRMS calcd. for C$_{27}$H$_{33}$N$_2$O$_3$ (M + H)$^+$ 433.2491, found 433.2482.

| Chemical name |
|---|
| structure NMR and HRMS |
| Starting material for enantimer-a |
| Example Starting material for enantimer-b |

27-4a (+)-4-(rel-(2S,4S)-1-((5-cyclopropyl-7-methyl-1H-indol-4-yl)methyl)-4-ethoxypiperidin-2-yl)benzoic acid was prepared from Intermediate 6-2-4b enantiomer-1 and isolated as a TFA salt (peak-1, $t_r$ = 1.3 min)

27-4b (−)-4-(rel-(2S,4S)-1-((5-cyclopropyl-7-methyl-1H-indol-4-yl)methyl)-4-ethoxypiperidin-2-yl)benzoic acid was prepared from Intermediate 6-2-4b enantiomer-2 and isolated as a TFA salt (peak-2, $t_r$ = 2.9 min)

Example-28

(±)-4-(5-Methoxy-1-((5-methoxy-7-methyl-1H-indol-4-yl)methyl)piperidin-2-yl)benzoic acid (Diastereomer-1)

Example-29

(±)-4-(5-Methoxy-1-((5-methoxy-7-methyl-1H-indol-4-yl)methyl)piperidin-2-yl)benzamide (Diastereomer-1)

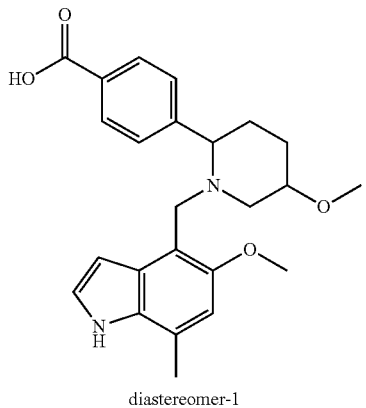 [SMILES: COc1cc(C)c2[nH]ccc2c1CN1CC(OC)CCC1c1ccc(C(=O)O)cc1]

diastereomer-1

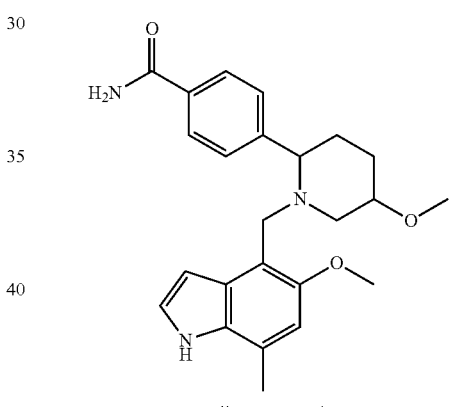

diastereomer-1

A mixture of Ba(OH)$_2$ (200 mg, 0.716 mmol) and (±)-tert-butyl 4-((2-(4-cyanophenyl)-5-methoxypiperidin-1-yl)methyl)-5-methoxy-7-methyl-1H-indole-1-carboxylate (diastereomer-1), Intermediate 4-4-19, (60 mg, 0.154 mmol) in iPrOH/H$_2$O (0.5/2 mL) was stirred at 100° C. for 36 h. The mixture was cooled to room temperature. The aqueous layer was acidified with AcOH. The mixture was filtered through a plug of celite, which was rinsed with H$_2$O/MeOH (ca. 4/1). The aqueous filtrate was purified by RP-HPLC (HC-B) to afford the title compound. $^1$H NMR (TFA salt, 400 MHz, D$_2$O) δ 8.07 (d, J=8.31 Hz, 2H), 7.63 (d, J=8.31 Hz, 2H), 7.36 (d, J=3.06 Hz, 1H), 6.69 (s, 1H), 6.22 (d, J=3.06 Hz, 1H), 4.40 (dd, J=2.81, 12.23 Hz, 1H), 4.12 (d, J=12.80 Hz, 1H), 3.98 (d, J=12.96 Hz, 1H), 3.59-3.71 (m, 4H), 3.52-3.58 (m, 1H), 3.26 (s, 3H), 2.99 (dd, J=11.50, 11.60 Hz, 1H), 2.41 (s, 3H), 2.34 (br. d, J=13.60 Hz, 1H), 2.19-2.28 (m, 1H), 2.03-2.17 (m, 1H), 1.54-1.68 (m, 1H); HRMS calcd. for C$_{24}$H$_{29}$N$_2$O$_4$ (M+H)$^+$ 409.2127, found 409.2117.

The title compound was isolated in the synthesis of Example-28 as a minor product. $^1$H NMR (400 MHz, CD$_3$OD) δ 10.77 (br. s., 1H), 8.09 (d, J=8.44 Hz, 2H), 7.69 (d, J=8.44 Hz, 2H), 7.33-7.38 (m, 1H), 6.79 (s, 1H), 6.31-6.34 (m, 1H), 4.50 (dd, J=2.87, 12.29 Hz, 1H), 4.38 (d, J=12.59 Hz, 1H), 4.24 (d, J=12.59 Hz, 1H), 3.76 (s, 3H), 3.53-3.64 (m, 2H), 3.28 (s, 3H), 3.03-3.12 (m, 1H), 2.52 (s, 3H), 2.31-2.40 (m, 1H), 2.17-2.25 (m, 1H), 1.99-2.13 (m, 1H), 1.56-1.70 (m, 1H); HRMS calcd. for C$_{24}$H$_{30}$N$_3$O$_3$(M+H)$^+$ 408.2280, found 408.2287.

The following Examples were synthesized from appropriate starting materials by applying similar methods described in the examples above:

| Example | chemical name<br>Starting material<br>NMR and HRMS |
|---|---|

30-1 (±)-4-(5-methoxy-1-((5-methoxy-7-methyl-1H-indol-4-yl)methyl)piperidin-2-yl)benzoic acid (diastereomer-2)

Intermediate 4-4-20
$^1$H NMR (400 MHz, D$_2$O) δ 7.90-7.99 (m, 2H), 7.60 (br. d, J = 7.90 Hz, 2H), 7.33 (t, J = 2.93 Hz, 1H), 6.71 (br. d, J = 7.30 Hz, 1H), 6.18-6.24 (m, 1H), 4.46-4.54 (m, J = 12.30 Hz, 1H), 4.14-4.24 (m, 1H), 4.02-4.12 (m, 1H), 3.79 (m, 4H), 3.48-3.56 (m, 1H), 3.33-3.42 (m, 1H), 3.21 (br. d, J = 1.20 Hz, 3H), 2.29-2.43 (m, 4H), 2.15-2.23 (m, 1H), 1.99-2.07 (m, 1H), 1.83-1.94 (m, 1H); HRMS calcd. for C$_{24}$H$_{29}$N$_2$O$_4$ (M + H)$^+$ 409.2127, found 409.2119.

30-2 (±)-4-(5-hydroxy-1-((5-methoxy-7-methyl-1H-indol-4-yl)methyl)piperidin-2-yl)benzoic acid (diastereomer-1)

Intermediate 4-5
$^1$H NMR (400 MHz, D$_2$O) δ 7.99 (br. d, J = 8.15 Hz, 2H), 7.63 (br. d, J = 8.15 Hz, 2H), 7.37 (d, J = 3.11 Hz, 1H), 6.82 (s, 1H), 6.29 (d, J = 3.11 Hz, 1H), 3.93-4.04 (m, 1H), 3.81-3.92 (m, 2H), 3.72 (s, 3H), 3.58-3.79 (m, 1H), 3.22-3.31 (m, 1H), 2.47 (s, 3H), 2.44-2.66 (m, 1H), 2.15 (br. d, J = 11.50 Hz, 1H), 2.01-2.09 (m, 1H), 1.92 (br. s., 1H), 1.50-1.64 (m, 1H); HRMS calcd. for C$_{23}$H$_{27}$N$_2$O$_4$ (M + H)$^+$ 395.1953, found 395.1971.

30-3 (±)-4-(5-hydroxy-1-((5-methoxy-7-methyl-1H-indol-4-yl)methyl)piperidin-2-yl)benzoic acid (diastereomer-2)

Intermediate 4-6
$^1$H NMR (400 MHz, D$_2$O) δ 7.98 (br. d, J = 8.30 Hz, 2H), 7.61 (br. d, J = 7.90 Hz, 2H), 7.34 (d, J = 3.06 Hz, 1H), 6.81 (s, 1H), 6.28 (d, J = 3.06 Hz, 1H), 3.73-3.82 (m, 2H), 3.71 (s, 3H), 3.49 (br. d, J = 10.30 Hz, 1H), 3.37 (br. d, J = 12.30 Hz, 1H), 3.09-3.18 (m, 1H), 2.46 (s, 3H), 2.25 (app. br. t, J = 10.90 Hz, 1H), 2.05-2.14 (m, 1H), 1.90-1.98 (m, 1H), 1.70-1.85 (m, 1H), 1.41-1.54 (m, 1H); HRMS calcd. for C$_{23}$H$_{27}$N$_2$O$_4$ (M + H)$^+$ 395.1953, found 395.1965.

Example-31

(±)-1-((5,7-Dimethyl-1H-indol-4-yl)methyl)-N-methyl-2-phenylpiperidin-4-amine-(Diastereomer-1)

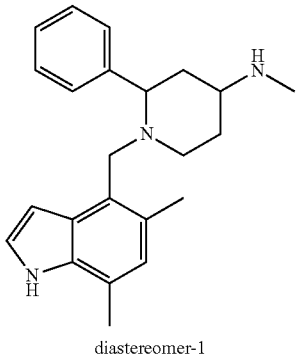 [SMILES: CNC1CCN(Cc2c(C)cc(C)c3[nH]ccc23)C(c2ccccc2)C1]

diastereomer-1

To a solution of (±)-benzyl (1-((5,7-dimethyl-1-tosyl-1H-indol-4-yl)methyl)-2-phenylpiperidin-4-yl)carbamate (diastereomer-1), Intermediate 3-2-2, (100 mg, 0.161 mmol) in THF (5 mL) was added LiAlH$_4$ (60 mg, 1.581 mmol). The mixture was stirred at 50° C. for 15 h. The reaction mixture was cooled to 0° C. The reaction was then quenched with H$_2$O (60 uL), 15% aq. NaOH (60 uL), and H$_2$O (120 uL). The mixture was then diluted with THF. The mixture was then filtered through a plug of Celite®, which was rinsed with THF. The filtrate was then concentrated. The resulting residue was purified by RP-HPLC (HC-A) to afford the title compound. $^1$H NMR (400 MHz, CD$_3$OD) δ 7.53 (d, J=7.30 Hz, 2H), 7.36 (dd, J=7.30, 7.80 Hz, 2H), 7.25-7.30 (m, 1H), 7.14 (d, J=3.30 Hz, 1H), 6.68 (s, 1H), 6.54 (d, J=3.28 Hz, 1H), 3.75 (d, J=12.13 Hz, 1H), 3.50 (dd, J=3.16, 11.49 Hz, 1H), 3.29 (br. d, J=12.10 Hz, 1H), 2.79-2.83 (m, 1H), 2.58-2.65 (m, 1H), 2.42-2.47 (m, 1H), 2.39 (br. s, 6H), 2.25 (s, 3H), 1.96-2.06 (m, 1H), 1.83-1.90 (m, 1H), 1.68-1.77 (m, 2H); HRMS calcd. for C$_{23}$H$_{30}$N$_3$ (M+H)$^+$ 348.2440, found 348.2426.

The following examples were synthesized from the appropriate starting material by applying similar methods described in the examples above:

| Example | chemical name / chemical structure | Starting material / NMR and HRMS |
|---|---|---|
| 32-1 | (±)-1-((5,7-dimethyl-1H-indol-4-yl)methyl)-N-methyl-2-phenylpiperidin-4-amine (diastereomer-2)<br><br>diastereomer-2 | Intermediate 3-2-3<br>$^1$H NMR (400 MHz, CD$_3$OD) δ 7.53 (br. d, J = 7.10 Hz, 2H), 7.37 (dd, J = 7.30, 8.10 Hz, 2H), 7.26-7.32 (m, 1H), 7.14 (d, J = 3.15 Hz, 1H), 6.67 (s, 1H), 6.51 (d, J = 3.15 Hz, 1H), 3.71 (d, J = 12.13 Hz, 1H), 3.11-3.20 (m, 2H), 2.85 (td, J = 3.35, 12.00 Hz, 1H), 2.50-2.60 (m, 1H), 2.40 (s, 3H), 2.34 (s, 3H), 2.24 (s, 3H), 2.03-2.11 (m, 1H), 1.96-2.03 (m, 1H), 1.77-1.85 (m, 1H), 1.53-1.63 (m, 1H), 1.23-1.35 (m, 1H); HRMS calcd. for C$_{23}$H$_{30}$N$_3$ (M + H)$^+$ 348.2440, found 348.2430. |
| 32-2 | (±)-(4-(1-((5,7-dimethy-1H-indol-4-yl)methyl)piperidin-2-yl)phenyl)methanamine | Intermediate 3-2-11<br>$^1$H NMR (TFA salt, 400 MHz, D$_2$O) δ 7.64 (br. d, J = 7.94 Hz, 2H), 7.55 (br. d, J = 7.94 Hz, 2H), 7.29 (d, J = 3.03 Hz, 1H), 6.81 (s, 1H), 6.17 (br. s., 1H), 4.36-4.42 (m, 1H), 4.24 (d, J = 13.40 Hz, 1H), 4.12-4.18 (m, 3H), 3.34 (br. d, J = 12.10 Hz, 1H), 3.14-3.24 (m, 1H), 2.34 (s, 3H), 1.98-2.11 (m, 5H), 1.72-1.89 (m, 2H), 1.50-1.68 (m, 2H); HRMS calcd. for C$_{23}$H$_{30}$N$_3$ (M + H)$^+$ 348.2434, found 348.2434. |

| chemical name | |
|---|---|
| Example chemical structure | Starting material<br>NMR and HRMS |

32-3    (4-((2S,4S)-4-methoxy-1-((5-methoxy-7-methyl-1H-indol-4-yl)methyl)piperidin-2-yl)phenyl)methanol

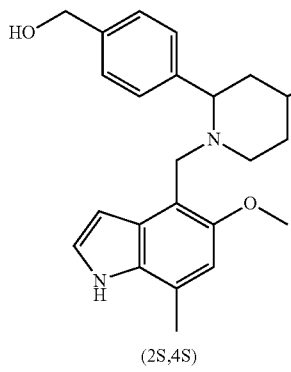

(2S,4S)

Example-21b
¹H NMR (400 MHz, CD₃OD) δ 9.05 (br. s., 1H), 7.79 (br. d, J = 8.60 Hz, 2H), 7.63 (br. d, J = 7.90 Hz, 2H), 7.19 (app. t, J = 2.81 Hz, 1H), 7.02 (br. s., 1H), 6.70 (s, 1H), 6.52 (dd, J = 2.08, 3.18 Hz, 1H), 3.73 (s, 3H), 3.62 (d, J = 11.92 Hz, 1H), 3.43-3.54 (m, 6H), 3.31 (s, 3H), 3.28 (s, 3H), 3.23 (d, J = 11.92 Hz, 1H), 2.47-2.54 (m, 1H), 2.42 (s, 3H), 2.28-2.37 (m, 1H), 1.86-1.89 (m, 1H), 1.67-1.80 (m, 2H), 1.45-1.55 (m, 1H); HRMS calcd. for C₂₇H₃₆N₃O₄ (M + H)⁺ 466.2706, found 466.2696.

Example-33

(±)-4-((2-(3-(2H-tetrazol-5-yl)phenyl)piperidin-1-yl)methyl)-5,7-dimethyl-1H-indole

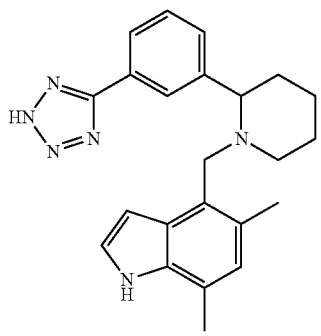 [SMILES: Cc1cc(C)c2[nH]ccc2c1CN1CCCCC1c1cccc(-c2nn[nH]n2)c1]

A mixture of (±)-tert-butyl 4-((2-(3-cyanophenyl)piperidin-1-yl)methyl)-5,7-dimethyl-1H-indole-1-carboxylate, Intermediate 4-7, (130 mg, 0.293 mmol), NaN₃ (58 mg, 0.88 mmol) and CdCl₂ (11 mg, 0.06 mmol) in DMF (1.5 mL) was stirred at 100° C. for 6 h, and then cooled to room temperature. The mixture was diluted with EtOAc. The organic phase was then washed successively with H₂O (twice), and brine, dried over Na₂SO₄, filtered, and concentrated. The resulting residue was purified by RP-HPLC (HC-A) to afford the title compound. ¹H NMR (HCl salt, 400 MHz, CD₃OD) δ 8.16-8.31 (m, 2H), 7.54-7.74 (m, 2H), 7.25 (d, J=2.78 Hz, 1H), 6.80 (s, 1H), 6.34 (br. s., 1H), 4.53 (br. d, J=10.10 Hz, 1H), 4.38 (d, J=13.40 Hz, 1H), 4.30 (d, J=13.40 Hz, 1H), 3.54 (br. d, J=11.90 Hz, 1H), 3.35-3.43 (m, 1H), 2.43 (s, 3H), 2.22-2.31 (m, 1H), 2.13-2.21 (m, J=13.40 Hz, 1H), 2.09 (br. s., 3H), 1.96-2.04 (m, 1H), 1.72-1.96 (m, 3H); HRMS calcd. for C₂₃H₂₇N₆ (M+H)⁺ 385.2141, found 385.2142.

Example-34

(±)-3-(1-((5,7-Dimethyl-1H-indol-4-yl)methyl)piperidin-2-yl)benzamide

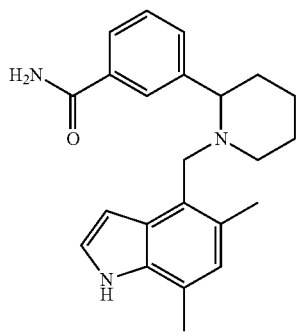 [SMILES: Cc1cc(C)c2[nH]ccc2c1CN1CCCCC1c1cccc(C(N)=O)c1]

A mixture of (±)-methyl 3-(1-((5,7-dimethyl-1H-indol-4-yl)methyl)piperidin-2-yl)benzoate, Intermediate 4-8, (80 mg, 0.212 mmol), CaCl₂ (100 mg, 0.901 mmol), and NH₄OH (33%, 10 m) in MeOH (10 mL) was stirred at 80° C. for ca. 16 h. The reaction mixture was then cooled to room temperature. The mixture was diluted with EtOAc. The organic phase was then washed successively with H₂O (twice), and brine, dried over Na₂SO₄, filtered, and concentrated. The resulting residue was purified by silica gel flash column chromatography (HC-A) to afford the title compound. ¹H NMR (400 MHz, CD₃OD) δ 8.03 (s, 1H), 7.80 (d, J=7.80 Hz, 1H), 7.74 (br. d, J=7.60 Hz, 1H), 7.47 (dd, J=7.60, 7.80 Hz, 1H), 7.14 (d, J=3.28 Hz, 1H), 6.66 (s, 1H), 6.49 (d, J=3.20 Hz, 1H), 3.68 (d, J=12.13 Hz, 1H), 3.14-3.25 (m, J=11.40 Hz, 2H), 2.87 (d, J=11.62 Hz, 1H), 2.39 (s, 3H), 2.16-2.28 (m, 3H), 1.93-2.15 (m, 1H), 1.65-1.89 (m, 3H), 1.34-1.63 (m, 3H); HRMS calcd. for C₂₃H₂₈N₃O (M+H)⁺ 362.2232, found 362.2223.

Example-35

(±)-(3-(1-((5,7-Dimethyl-1H-indol-4-yl)methyl)piperidin-2-yl)phenyl)methanol

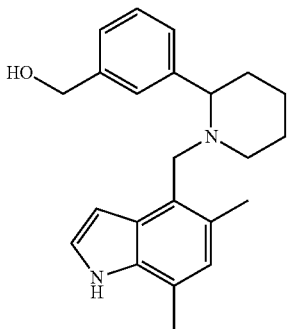 [SMILES: Cc1cc(C)c2[nH]ccc2c1CN1CCCCC1c1cccc(CO)c1]

A mixture of (±)-methyl 3-(1-((5,7-dimethyl-1H-indol-4-yl)methyl)piperidin-2-yl)benzoate, Intermediate 4-8, (230 mg, 0.611 mmol) and NaBH$_4$ (200 mg, 5.29 mmol) in THF/MeOH (10 mL/5 mL) was stirred under the reflux condition for 3 h. The mixture was partially concentrated. The resulting residue was then diluted with EtOAc. The mixture was then washed successively with H$_2$O and brine, dried over Na$_2$SO$_4$, filtered, and concentrated. The resulting residue was purified by silica gel flash column chromatography (HC-A) to afford the title compound. 1H NMR (400 MHz, DMSO-d$_6$) δ 10.82 (br. s., 1H), 7.46 (br. s., 1H), 7.37 (br. d, J=7.60 Hz, 1H), 7.32 (dd, J=7.30, 7.60 Hz, 1H), 7.22 (br. d, J=7.60 Hz, 1H), 7.20 (br. dd, J=2.80, 3.00 Hz, 1H), 6.63 (s, 1H), 6.50 (dd, J=2.02, 2.80 Hz, 1H), 5.18 (t, J=5.81 Hz, 1H), 4.52 (d, J=5.81 Hz, 2H), 3.59 (d, J=12.13 Hz, 1H), 3.00-3.12 (m, 2H), 2.57-2.66 (m, 1H), 2.36 (s, 3H), 2.22 (s, 3H), 1.84-1.94 (m, 1H), 1.54-1.75 (m, 3H), 1.46 (br. d, J=8.30 Hz, 1H), 1.26-1.41 (m, 2H); HRMS calcd. for C$_{23}$H$_{29}$N$_2$O (M+H)$^+$ 349.2280, found 349.2276.

Example-36

(±)-(4-(rel-(2S,4S)-(2-(4-(1H-tetrazol-5-yl)phenyl)-4-ethoxypiperidin-1-yl)methyl)-5-methoxy-7-methyl-1H-indole

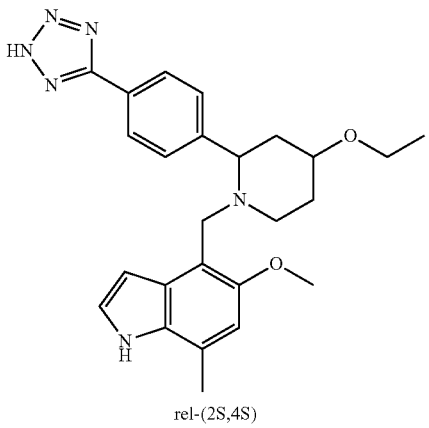 [SMILES: CCOC1CCN(Cc2c(OC)cc(C)c3[nH]ccc23)C(c2ccc(-c3nn[nH]n3)cc2)C1]

rel-(2S,4S)

To a solution of (±)-tert-butyl 4-(rel-(2S,4S)-(2-(4-cyanophenyl)-4-ethoxypiperidin-1-yl)methyl)-5-methoxy-7-methyl-1H-indole-1-carboxylate, Intermediate 5-3-3a, (50 mg, 0.099 mmol) in DMF (1 mL) was added NaN$_3$ (30 mg, 0.461 mmol), followed by phosphomolybdic acid hydrate (CAS: 51429-74-4, 30 mg, 0.099 mmol). The mixture was then stirred at 110° C. for 3 days, and then cooled to room temperature. The reaction mixture was diluted with EtOAc. The mixture was then filtered through a plug of silica gel, which was rinsed with EtOAc/MeOH (ca. 4/1). The filtrate was then concentrated. The resulting residue was purified by RP-HPLC (HC-B) to afford the title compound. 1H NMR (400 MHz, D$_2$O) δ 8.11 (br. d, J=7.80 Hz, 2H), 7.68 (br. d, J=8.10 Hz, 2H), 7.36 (br. s., 1H), 6.75 (br. s., 1H), 6.30 (br. s., 1H), 4.51 (br. s., 1H), 4.15-4.26 (m, 1H), 3.91-4.01 (m, 2H), 3.60-3.71 (m, 5H), 3.14-3.41 (m, 2H), 2.40 (s, 3H), 2.19-2.35 (m, 2H), 1.86-2.12 (m, 2H), 1.29 (t, J=6.82 Hz, 3H); HRMS calcd. for C$_{25}$H$_{31}$N$_6$O$_2$ (M+H)$^+$ 447.2508, found 447.2489.

Example-37

(+)-4-((2S,4S)-4-ethoxy-1-((5-methoxy-7-methyl-1H-indol-4-yl)methyl)piperidin-2-yl)-N-(methylsulfonyl)benzamide

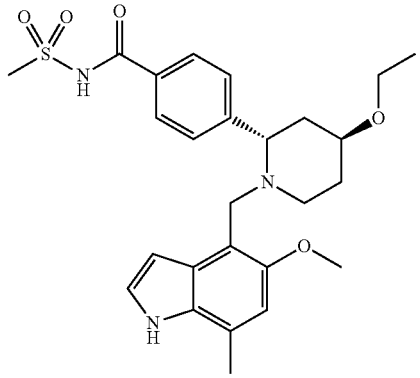 [SMILES: CCO[C@H]1CCN(Cc2c(OC)cc(C)c3[nH]ccc23)[C@H](c2ccc(C(=O)NS(C)(=O)=O)cc2)C1]

To a solution of 4-((2S,4S)-(4-ethoxy-1-((5-methoxy-7-methyl-1H-indol-4-yl)methyl)piperidin-2-yl)benzoic acid, Example-26a, (98 mg, 0.232 mmol) in DMF (1 mL) were added methanesulfonamide (33.1 mg, 0.348 mmol) and HATU (97 mg, 0.255 mmol), followed by Et$_3$N (0.097 mL, 0.696 mmol). The mixture was then stirred at room temperature for 20 h. To the mixture was added an additional amount of methanesulfonamide (20 mg, 0.21 mmol), and then the mixture was stirred for 48 h. The reaction was quenched with MeOH/H$_2$O (ca. 1/1), which was purified by RP-HPLC (HC-B) to afford the title compound. 1H NMR (400 MHz, CD$_3$OD) δ 8.21 (d, J=8.1 Hz, 2H), 7.62 (d, J=8.2 Hz, 2H), 7.32 (d, J=2.8 Hz, 1H), 6.77 (s, 1H), 6.33 (d, J=3.2 Hz, 1H), 4.77-4.70 (m, 1H), 4.37-4.29 (m, 1H), 4.27-4.16 (m, 1H), 3.81 (br. s., 1H), 3.77 (s, 3H), 3.70-3.65 (m, 1H), 3.64-3.54 (m, 3H), 3.16-3.10 (m, 5H), 2.51 (s, 3H), 2.29-2.20 (m, 2H), 2.11-1.92 (m, 2H), 1.31 (t, J=7.0 Hz, 3H); HRMS calcd. for C$_{26}$H$_{34}$N$_3$O$_5$S (M+H)$^+$ 500.2219, found 500.2207.

Example-38

4-((2S,4S)-4-methoxy-1-((5-methoxy-7-methyl-1H-indol-4-yl)methyl)piperidin-2-yl)-N-methylbenzamide

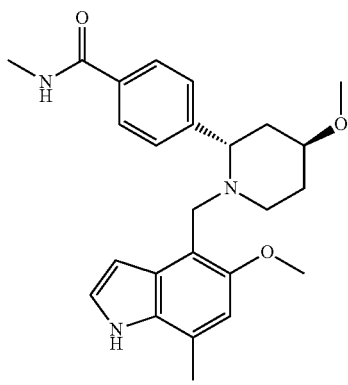

To a solution of 4-(4-methoxy-1-(2S,4S-(5-methoxy-7-methyl-1H-indol-4-yl)methyl)piperidin-2-yl)benzoic acid, Example-21b, (30 mg, 0.073 mmol) and methylamine (in THF, 100 µL, 0.2 mmol) in DMF (0.5 mL) was added a solution of EDC-HCl (20 mg, 0.104 mmol) and HOAt (10 mg, 0.073 mmol) in DMF (0.5 mL). The mixture was stirred at room temperature for 13 h. To the mixture was then added additional amount of EDC-HCl (20 mg, 0.104 mmol). The mixture was stirred at room temperature for 2 h. The reaction was quenched with H$_2$O. The mixture was purified by RP-HPLC (HC-B) to afford the title compound. $^1$H NMR (400 MHz, CD$_3$CN) δ 9.05 (br. s., 1H), 7.78 (d, J=8.60 Hz, 2H), 7.63 (br. d, J=8.10 Hz, 2H), 7.18-7.21 (m, 1H), 6.93 (br. s., 1H), 6.70 (s, 1H), 6.52 (dd, J=2.10, 3.10 Hz, 1H), 3.73 (s, 3H), 3.62 (d, J=11.98 Hz, 1H), 3.44-3.51 (m, 2H), 3.28 (s, 3H), 3.23 (d, J=11.98 Hz, 1H), 2.85 (d, J=4.77 Hz, 3H), 2.47-2.54 (m, 1H), 2.42 (s, 3H), 2.28-2.37 (m, 1H), 1.68-1.79 (m, 2H), 1.44-1.55 (m, 1H) HRMS calcd. for C$_{25}$H$_{32}$N$_3$O$_3$ (M+H)$^+$ 422.2444, found 422.2430.

The following examples were synthesized from appropriate starting materials by applying similar methods described in the examples above:

| Example | Chemical structure | Chemical name / starting material / NMR; HRMS |
|---|---|---|
| 39-1 | (structure shown) | 4-((2S,4S)-4-methoxy-1-((5-methoxy-7-methyl-1H-indol-4-yl)methyl)piperidin-2-yl)-N,N-dimethylbenzamide<br>Example-21b and dimethylamine<br>$^1$H NMR (400 MHz, CD$_3$CN) δ 9.05 (br. s., 1H), 7.60 (br. d, J = 7.90 Hz, 2H), 7.39 (br. d, J = 8.40 Hz, 2H), 7.19 (dd, J = 2.80, 2.90 Hz, 1H), 6.70 (s, 1H), 6.53 (dd, J = 2.08, 3.06 Hz, 1H), 3.73 (s, 3H), 3.66 (d, J = 12.23 Hz, 1H), 3.42-3.50 (m, 2H), 3.29 (s, 3H), 3.25 (d, J = 11.40 Hz, 1H), 2.89-3.04 (m, 6H), 2.48-2.55 (m, 1H), 2.42 (s, 3H), 2.29-2.38 (m, 1H), 1.69-1.80 (m, 3H), 1.46-1.56 (m, 1H); HRMS calcd. for C$_{26}$H$_{34}$N$_3$O$_3$ (M + H)$^+$ 436.2600, found 436.2589. |
| 39-2 | (structure shown) | (4-((2S,4S)-4-methoxy-1-((5-methoxy-7-methyl-1H-indol-4-yl)methyl)piperidin-2-yl)phenyl)(morpholino)methanone<br>Example-21b and morpholine<br>$^1$H NMR (400 MHz, CD$_3$CN) δ 9.07 (br. s., 1H), 7.61 (br. d, J = 7.80 Hz, 2H), 7.39 (d, J = 8.31 Hz, 2H), 7.18 (dd, J = 2.81, 2.93 Hz, 1H), 6.69 (s, 1H), 6.50-6.58 (m, 1H), 3.73 (s, 3H), 3.31-3.70 (m, 11H), 3.28 (s, 3H), 3.25 (d, J = 11.70 Hz, 1H), 2.48-2.57 (m, 1H), 2.42 (s, 3H), 2.28-2.39 (m, 1H), 1.86-1.91 (m, 1H), 1.69-1.80 (m, 2H), 1.45-1.56 (m, 1H); HRMS calcd. for C$_{28}$H$_{36}$N$_3$O$_4$ (M + H)$^+$ 478.2706, found 478.2696. |

| Example | Chemical structure | Chemical name<br>starting material<br>NMR; HRMS |
|---|---|---|
| 39-3 | N-(2-hydroxyethyl)-4-((2S,4S)-4-methoxy-1-((5-methoxy-7-methyl-1H-indol-4-yl)methyl)piperidin-2-yl)benzamide<br>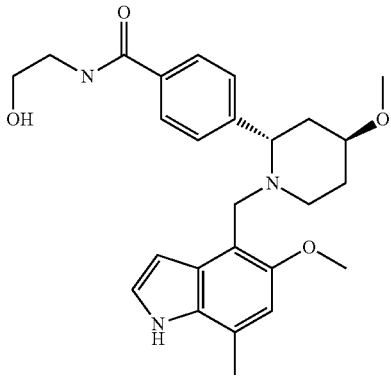 [SMILES: COc1cc(C)c2[nH]ccc2c1CN1CC[C@H](OC)C[C@H]1c1ccc(C(=O)NCCO)cc1] | Example-21b and 2-ethanolamine<br>$^1$H NMR (400 MHz, CD$_3$CN) δ 9.06 (br. s., 1H), 7.82 (br. d, J = 8.60 Hz, 2H), 7.64 (br. d, J = 8.10 Hz, 2H), 7.20 (app. t, J = 2.81 Hz, 1H), 7.10-7.17 (m, 1H), 6.70 (s, 1H), 6.53 (dd, J = 2.10, 3.20 Hz, 1H), 3.74 (s, 3H), 3.59-3.66 (m, 3H), 3.41-3.52 (m, 4H), 3.28 (s, 3H), 3.24 (d, J = 12.00 Hz, 1H), 3.10-3.17 (m, 1H), 2.47-2.54 (m, 1H), 2.42 (s, 3H), 2.28-2.38 (m, 1H), 1.87-1.90 (m, 1H), 1.66-1.80 (m, 2H), 1.44-1.56 (m, 1H); HRMS calcd. for C$_{26}$H$_{34}$N$_3$O$_4$ (M + H)$^+$ 452.2549, found 452.2532. |
| 39-4 | 4-((2S,4S)-4-methoxy-1-((5-methoxy-7-methyl-1H-indol-4-yl)methyl)piperidin-2-yl)-N-(2-methoxyethyl)benzamide<br>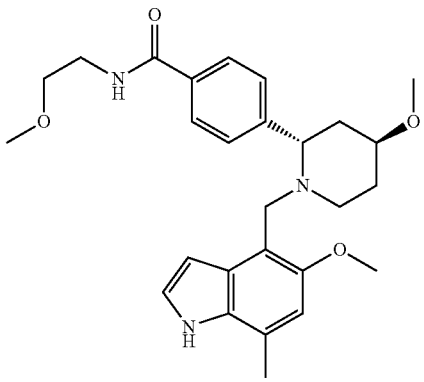 | Example-21b and 2-methoxyethylamine<br>$^1$H NMR (400 MHz, CD$_3$CN) δ 9.05 (br. s., 1H), 7.79 (br. d, J = 8.60 Hz, 2H), 7.63 (br. d, J = 7.90 Hz, 2H), 7.19 (app. t, J = 2.81 Hz, 1H), 7.02 (br. s., 1H), 6.70 (s, 1H), 6.52 (dd, J = 2.08, 3.18 Hz, 1H), 3.73 (s, 3H), 3.62 (d, J = 11.92 Hz, 1H), 3.43-3.54 (m, 6H), 3.31 (s, 3H), 3.28 (s, 3H), 3.23 (d, J = 11.92 Hz, 1H), 2.47-2.54 (m, 1H), 2.42 (s, 3H), 2.28-2.37 (m, 1H), 1.86-1.89 (m, 1H), 1.67-1.80 (m, 2H), 1.45-1.55 (m, 1H); HRMS calcd. for C$_{27}$H$_{36}$N$_3$O$_4$ (M + H)$^+$ 466.2706, found 466.2696. |

Example-40

(±)-N-((4-(1-((5-cyclopropyl-7-methyl-1H-indol-4-yl)methyl)piperidin-2-yl)phenyl)sulfonyl)acetamide

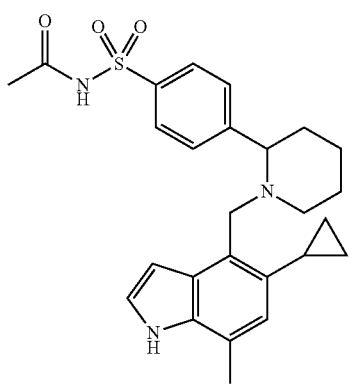 [SMILES: CC(=O)NS(=O)(=O)c1ccc(C2CCCCN2Cc2c(C3CC3)cc(C)c3[nH]ccc23)cc1]

The title compound was synthesized from (±)-tert-butyl 4-((2-(4-(N-acetylsulfamoyl)phenyl)piperidin-1-yl)methyl)-5-cyclopropyl-7-methyl-1H-indole-1-carboxylate, Intermediate 3-2-26, analogously to the preparation of Example-22.

$^1$H NMR (400 MHz, CD$_3$COCD$_3$) δ 10.55 (br. s., 1H), 9.98 (br. s., 1H), 8.01 (d, J=8.5 Hz, 2H), 7.79 (d, J=8.5 Hz, 2H), 7.24 (app. t, J=2.8 Hz, 1H), 6.69 (dd, J=2.0, 3.1 Hz, 1H), 6.55 (s, 1H), 3.84 (d, J=12.1 Hz, 1H), 3.43 (d, J=12.1 Hz, 1H), 3.29 (dd, J=3.0, 10.6 Hz, 1H), 2.88-2.82 (m, 1H), 2.40 (s, 3H), 2.27-2.22 (m, 1H), 2.00 (s, 3H), 1.81-1.74 (m, 2H), 1.74-1.67 (m, 1H), 1.57-1.52 (m, 1H), 1.51-1.39 (m, 2H), 0.89-0.79 (m, 1H), 0.76-0.69 (m, 1H), 0.62-0.54 (m, 1H), 0.20-0.12 (m, 1H). HRMS calcd. for C$_{26}$H$_{32}$N$_3$O$_3$S (M+H)$^+$ 466.2159, found 466.2140.

Example-41

Ethyl 4-((2S,4R)-1-((5-methoxy-7-methyl-1H-indol-4-yl)methyl)-4-methylpiperidin-2-yl)benzoate

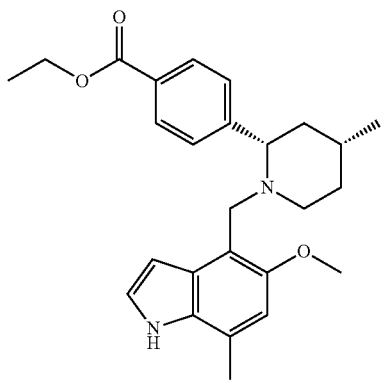 [SMILES: CCOC(=O)c1ccc([C@@H]2C[C@H](C)CCN2Cc2c(OC)cc(C)c3[nH]ccc23)cc1]

To a solution of EtOH (200 mL) was added AcCl (2.0 mL), and then the mixture was stirred at room temperature for 5 min. To the solution was added (+)-4-((2S,4R)-1-((5-methoxy-7-methyl-1H-indol-4-yl)methyl)-4-methylpiperidin-2-yl)benzoic acid, Example-20a, (300 mg, 0.764 mmol), and then the mixture was stirred for 12 h under the reflux condition. The reaction mixture was then cooled to room temperature. The mixture was then rendered basic by satd. aq. NaHCO3, and then concentrated to remove EtOH. The mixture was then extracted with EtOAc. The organic phase was then washed with brine, dried over Na$_2$SO$_4$, filtered, and concentrated. The resulting residue was purified by silica gel flash column chromatography (heptanes/EtOAc=100:0 to 40:60) to afford the title compound. $^1$H NMR (400 MHz, CD$_3$OD) δ 8.04 (d, J=8.46 Hz, 2H) 7.65 (d, J=7.71 Hz, 2H) 7.19 (d, J=3.03 Hz, 1H) 6.67 (s, 1H) 6.40 (d, J=3.16 Hz, 1H) 4.38 (q, J=7.07 Hz, 2H) 3.75-3.81 (m, 1H) 3.74 (s, 3H) 3.20-3.27 (m, 2H) 3.21 (d, J=12.00 Hz, 1H) 3.02 (d, J=12.38 Hz, 1H) 2.45 (s, 3H) 2.18 (d, J=8.84 Hz, 1H) 1.70 (d, J=12.63 Hz, 1H) 1.49-1.63 (m, 2H) 1.40 (t, J=7.14 Hz, 3H) 1.26-1.36 (m, 1H) 0.90 (d, J=6.32 Hz, 3H). HRMS calcd. for C$_{26}$H$_{33}$N$_2$O$_3$ (M+H) 421.2491, found 421.2475.

Example-42

Ethyl 4-((2S,4S)-4-ethoxy-1-((5-methoxy-7-methyl-1H-indol-4-yl)methyl)piperidin-2-yl)benzoate

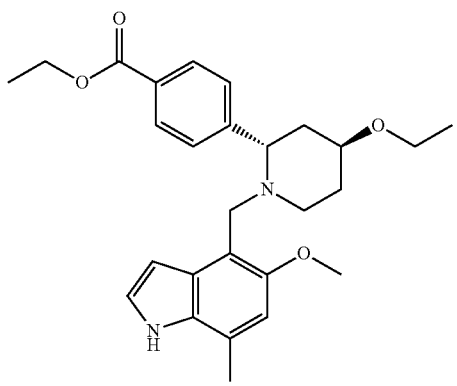 [SMILES: CCOC(=O)c1ccc([C@@H]2C[C@@H](OCC)CCN2Cc2c(OC)cc(C)c3[nH]ccc23)cc1]

The title compound was synthesized analogoulsy as described in Example 41 starting from 4-((2S,4S)-(4-ethoxy-1-((5-methoxy-7-methyl-1H-indol-4-yl)methyl)piperidin-2-yl))benzoic acid, Example-26c. $^1$H NMR (400 MHz, CD$_3$OD) δ ppm 8.05 (d, J=8.46 Hz, 2H), 7.67 (d, J=8.08 Hz, 2H), 7.19 (d, J=3.12 Hz, 1H), 6.67 (s, 1H), 6.40 (d, J=3.12 Hz, 1H), 4.38 (q, J=7.12 Hz, 2H), 3.71-3.80 (m, 4H), 3.59-3.69 (m, 2H), 3.46-3.58 (m, 2H), 3.20-3.28 (m, 1H), 2.70-2.81 (m, 1H), 2.47-2.60 (m, 1H), 2.45 (s, 3H), 1.88-1.98 (m, 1H), 1.64-1.88 (m, 3H), 1.40 (t, J=7.12 Hz, 3H), 1.26 (t, J=7.01 Hz, 3H). HRMS calcd. for C$_{27}$H$_{35}$N$_2$O$_4$ (M+H)$^+$ 451.2597, found 451.2603.

Biological Example 1: Human Complement Factor B ELISA Assay

CVF-Bb complex prepared from purified cobra venom factor (1 μM), recombinant human complement factor B (expressed in drosophila cells and purified using standard methods) and human complement factor D (expressed in *E. Coli*, refolded and purified using standard methods). CVF-Bb complex at 3 nM concentration was incubated with test compound at various concentrations for 1 hour at room temperature in PBS pH 7.4 containing 10 mM MgCl$_2$ and 0.05% (w/v) CHAPS. Human complement C3 substrate purified from plasma was added to a final concentration of 1 μM. After 1 hour incubation at room temperature, the enzyme reaction was stopped by addition of a cocktail of concentrated pan-protease inhibitors. The product of the reaction, C3a, was quantified by means of an enzyme-linked-immunosorbent assay. IC$_{50}$ values were calculated from percentage of inhibition of CVF-Bb activity as a function of test compound concentration.

Biological Example 2: Human Complement Factor B TR-FRET Assay

Biological Example 2.1. (+) or (−)-tert-Butyl 3-(3-hydroxyphenyl)piperazine-1-carboxylate

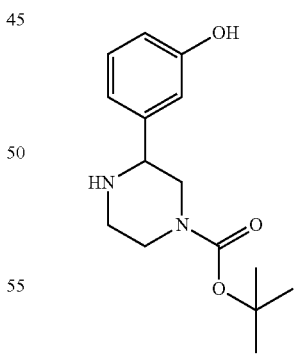

Resolution of the enantiomers of (±)-tert-butyl 3-(3-hydroxyphenyl)piperazine-1-carboxylate (CAS: 889956-76-7) was achieved by chiral HPLC using a CHIRALPAK AD column with heptane/EtOAc/MeOH 90/5/5+0.1 diethylamine to give (+) or (−)-tert-butyl 3-(3-hydroxyphenyl)piperazine-1-carboxylate (t$_r$=9.7 min) and (−) or (+)-tert-butyl 3-(3-hydroxyphenyl)piperazine-1-carboxylate (t$_r$=15.7 min).

Biological Example 2.2. (+) or (−)-tert-Butyl 3-(3-(2-(((benzyloxy)carbonyl)amino)ethoxy)phenyl)piperazine-1-carboxylate

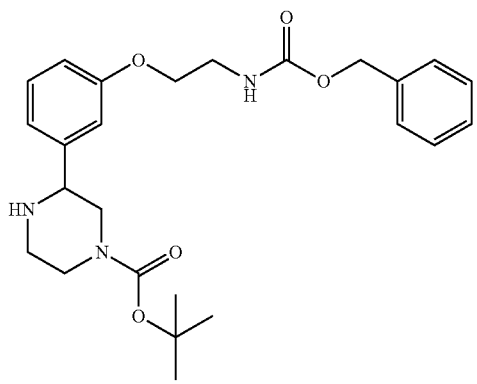 [SMILES: CC(C)(C)OC(=O)N1CCNC(c2cccc(OCCNC(=O)OCc3ccccc3)c2)C1]

(+) or (−)-tert-butyl 3-(3-hydroxyphenyl)piperazine-1-carboxylate (t$_r$=9.7 min) (Biological Example 2.1) (300 mg, 1.078 mmol) and benzyl 2-hydroxyethylcarbamate (210 mg, 1.078 mmol) were dissolved in THF (10 ml). Tributylphosphine (0.404 ml, 1.617 mmol) was added, and after cooling to 0° C., DEAD 40% in toluene (0.640 ml, 1.617 mmol) was added dropwise. The reaction was stirred for 2 h at 0° C., then for ca. 16 h at rt. The reaction mixture was diluted with aqueous NaHCO$_3$. The layers were separated and the aqueous layer was extracted with AcOEt. The organic phase dried over MgSO$_4$ and concentrated in vacuum. The resulting residue was purified by preparative HPLC (Macherey-Nagel Nucleosil 100-10 C18, CH$_3$CN/H$_2$O (0.1% TFA)) to give the title compound. MS (ESI+) m/z 455.2 (M+H).

Biological Example 2.3. (+) or (−)-tert-Butyl 4-(4-amino-6,7-dimethoxyquinazolin-2-yl)-3-(3-(2-(((benzyloxy)carbonyl)amino)ethoxy)phenyl)piperazine-1-carboxylate

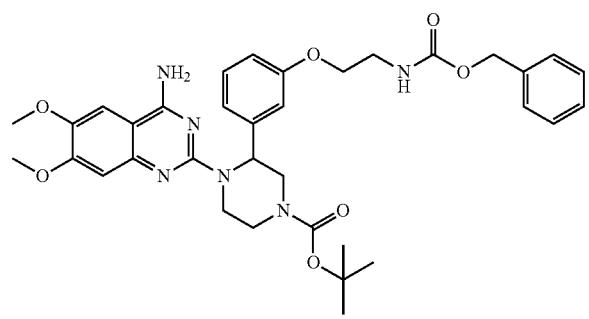 [SMILES: COc1cc2nc(N3CCN(C(=O)OC(C)(C)C)CC3c3cccc(OCCNC(=O)OCc4ccccc4)c3)nc(N)c2cc1OC]

A solution of 2-chloro-6,7-dimethoxyquinazolin-4-amine (CAS: 23680-84-4) (105 mg, 0.439 mmol) and (+) or (−)-tert-butyl 3-(3-(2-(((benzyloxy)carbonyl)amino)ethoxy) phenyl)piperazine-1-carboxylate (100 mg, 0.220 mmol) in isoamyl alcohol (5 ml) was stirred for 16 hr at 135° C. After evaporation, the resulting residue was purified by preparative HPLC (Macherey-Nagel Nucleosil® 100-10 C18, CH$_3$CN/H$_2$O (0.1% TFA)) to give the title compound. MS (ESI+) m/z 659.2 (M+H).

Biological Example 2.4. (+) or (−)-tert-Butyl ((1R)-3-(4-(4-amino-6,7-dimethoxyquinazolin-2-yl)-3-(3-(2-(((benzyloxy)carbonyl)amino)ethoxy)phenyl)piperazin-1-yl)-3-oxo-1-phenylpropyl)carbamate

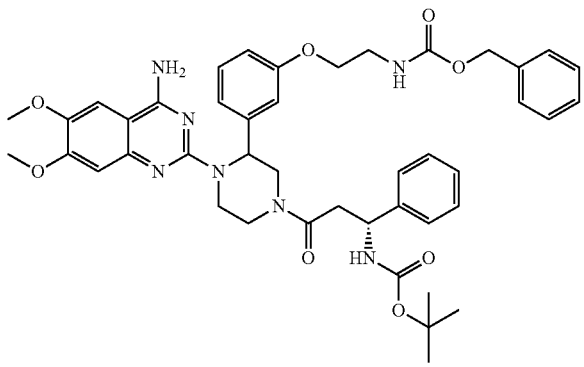 [SMILES: COc1cc2nc(N3CCN(C(=O)C[C@@H](NC(=O)OC(C)(C)C)c4ccccc4)CC3c3cccc(OCCNC(=O)OCc4ccccc4)c3)nc(N)c2cc1OC]

(+) or (−)-tert-Butyl 4-(4-amino-6,7-dimethoxyquinazolin-2-yl)-3-(3-(2-(((benzyloxy)carbonyl)amino)ethoxy)phenyl)piperazine-1-carboxylate (60 mg, 0.078 mmol) was dissolved in 4N HCl in dioxane (5 ml) and stirred for 1 hr at rt. The reaction mixture was evaporated. The resulting residue was dissolved in DMF (3 ml), and (R)-3-((tert-butoxycarbonyl)amino)-3-phenylpropanoic acid (21.0 mg, 0.079 mmol), DIPEA (0.041 ml, 0.238 mmol) and HATU (60.2 mg, 0.158 mmol) were added. The solution was stirred for 16 hr at rt. The reaction mixture was filtrated and evaporated in vacuum. The resulting residue was purified by preparative HPLC (Waters SunFire™ Prep C18 OBD, CH$_3$CN/H$_2$O (0.1% TFA)) to give the title compound. MS (ESI+) m/z 806.2 (M+H).

Biological Example 2.5. (+) or (−)-2-((1E,3E,5E)-5-(1-(6-((2-(3-(1-(4-amino-6,7-dimethoxyquinazolin-2-yl)-4-((R)-3-((tert-butoxycarbonyl)amino)-3-phenylpropanoyl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium

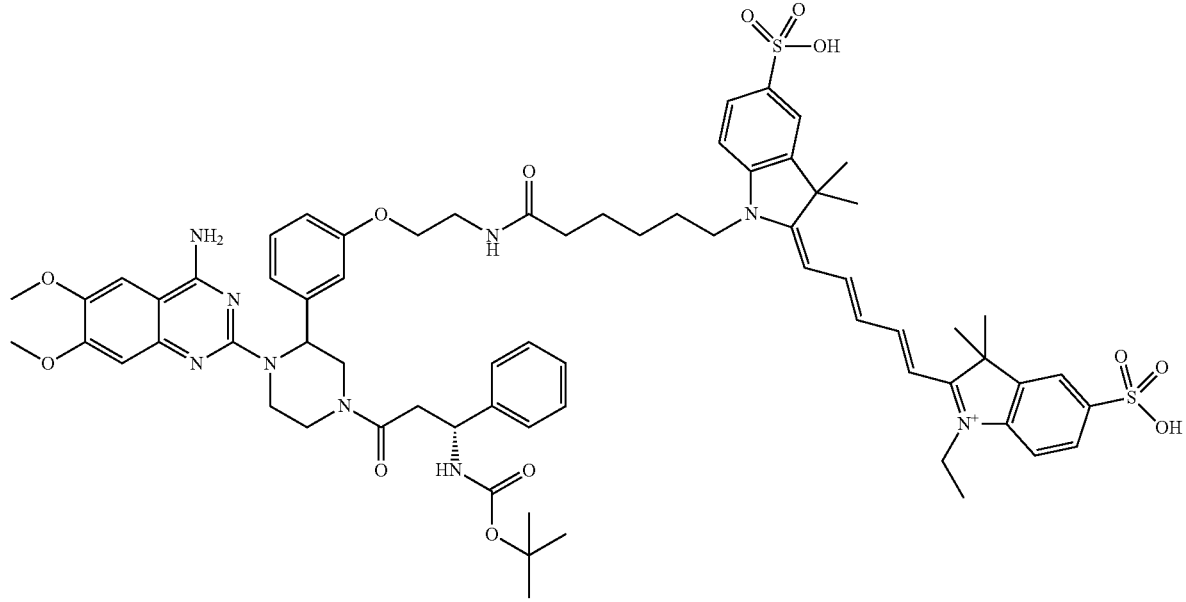 [SMILES: CC[N+]1=C(/C=C/C=C/C=C2/N(CCCCCC(=O)NCCOc3cccc(C4CN(C(=O)C[C@@H](NC(=O)OC(C)(C)C)c5ccccc5)CCN4c4nc(N)c5cc(OC)c(OC)cc5n4)c3)c3ccc(S(=O)(=O)O)cc3C2(C)C)C(C)(C)c2cc(S(=O)(=O)O)ccc21]

(+) or (−)-tert-Butyl ((1R)-3-(4-(4-amino-6,7-dimethoxyquinazolin-2-yl)-3-(3-(2-(((benzyloxy)carbonyl)amino)ethoxy)phenyl)piperazin-1-yl)-3-oxo-1-phenylpropyl)carbamate (17 mg, 0.021 mmol) was dissolved in EtOH (5 ml), and added Pd/C (2.24 mg, 2.109 µmol). The reaction was stirred under $H_2$ for 16 hr at room temperature. The reaction mixture was filtered and evaporated. The resulting residue was dissolved in DMF (2 ml), and 2-((1E,3E,5E)-5-(1-(6-((2,5-dioxopyrrolidin-1-yl)oxy)-6-oxohexyl)-3,3-dimethyl-5-sulfoindolin-2-ylidene)penta-1,3-dien-1-yl)-1-ethyl-3,3-dimethyl-3H-indol-1-ium-5-sulfonate (Cy-5, CAS: 146368-14-1) (13.32 mg, 0.020 mmol), DIPEA (0.018 ml, 0.101 mmol) and HATU (15.40 mg, 0.040 mmol) were added. The solution stirred for 16 hr at rt. The reaction mixture evaporated in vacuum and purified by preparative HPLC (Macherey-Nagel Nucleosil® 100-10 C18, $CH_3CN/H_2O$ (0.1% TFA)) to give the title compound. MS (ESI+) m/z 656.1 (M/2).

Biological Example 2.6. (+) or (−)-2-((1E,3E,5E)-5-(1-(6-((2-(3-(4-((R)-3-amino-3-phenylpropanoyl)-1-(4-amino-6,7-dimethoxyquinazolin-2-yl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium

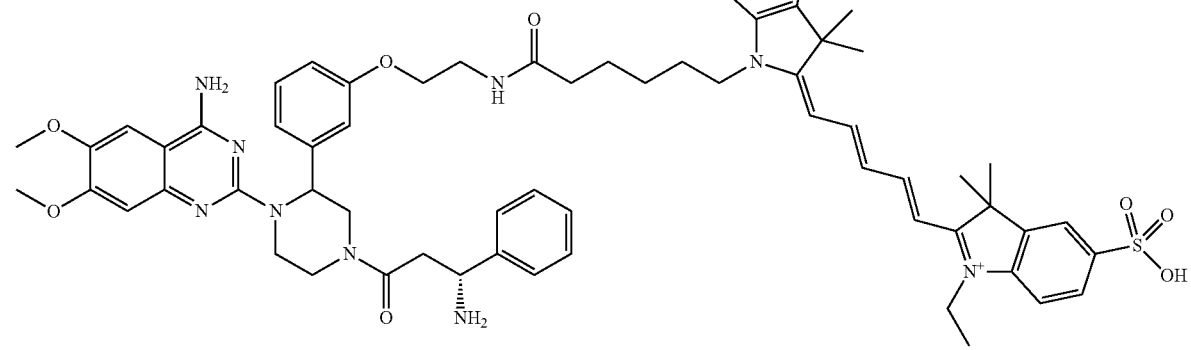

(+) or (−)-2-((1E,3E,5E)-5-(1-(6-((2-(3-(1-(4-amino-6,7-dimethoxyquinazolin-2-yl)-4-((R)-3-((tert-butoxycarbonyl)amino)-3-phenylpropanoyl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium (4 mg, 3.05 μmol) was dissolved in 4N HCl in dioxane (3 ml) and stirred for 1 hr at rt. The mixture was purified by preparative HPLC (Waters Sunfire™ C18 OBD, $CH_3CN/H_2O$ (0.1% TFA)) to give the title compound. Fractions were combined and evaporated to dryness. The residue was dissolved in a minimum amount of $CH_3CN$ and 1M aqueous HCl solution (3 ml, 3.00 mmol) was added. Mixture was then evaporated to give the title compound as HCl salt. $^1$H NMR (HCl salt, 400 MHz, $CD_3OD$) δ 8.30 (m, 2H), 7.90 (s, 1H), 7.89 (d, J=5.4 Hz, 1H), 7.86 (d, J=5.6 Hz, 1H), 7.72 (dd, J=8.1, 37 Hz, 1H), 7.55 (d, J=7.2 Hz, 1H), 7.37-7.47 (m, 5H), 7.07-7.28 (m, 4H), 6.86-6.95 (m, 3H), 6.68 (t, J=12.5 Hz, 1H), 6.38 (dd, J=4.5, 18.4 Hz, 1H), 6.31 (d, J=13.9 Hz, 1H), 5.95 (br. s, 1H), 4.76-4.84 (m, 1H), 4.68-4.71 (m, 1H), 4.46-4.57 (m, 1H), 4.18-4.31 (m, 3H), 4.05-4.11 (m, 3H), 3.80-4.00 (m, 8H), 3.41-3.60 (m, 3H), 3.06-3.09 (m, 2H), 2.84 (dd, J=3.8, 22.5 Hz, 1H), 2.12-2.22 (m, 2H), 1.75-1.86 (m, 2H), 1.73 (s, 6H), 1.70 (s, 6H), 1.59-1.69 (m, 2H), 1.39 (t, J=7.3 Hz, 3H), 1.29-1.37 (m, 2H). UPLC-MS (ESI+) m/z 606.1 (M/2); Instrument: Waters UPLC Acquity; column: Acquity HSS T3 1.8 μm 2.1×50 mm at 50° C., eluent A: water+0.05% HCOOH+3.75 mM ammonium acetate, B: $CH_3CN$+0.04% HCOOH, Gradient: 5 to 98% B in 1.4 min, flow: 1.0 ml/min; Retention time: 0.64 min.

Biological Example 2.7

Recombinant human factor B (expressed in drosophila cells and purified using standard methods) labeled with biotin (10 nM), europium-labeled streptavidin (5 nM) and (+) or (−)-2-((1E,3E,5E)-5-(1-(6-((2-(3-(4-((R)-3-amino-3-phenylpropanoyl)-1-(4-amino-6,7-dimethoxyquinazolin-2-yl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium (Biological Example 2.6, 240 nM activity against factor B when tested using the assay of Biological Example 1) (75 nM) were incubated with test compound at various concentrations up to 2 hours at room temperature in 20 mM Tris/HCl, pH 7.4, 0.005% (v/v) Tween20.

The time-gated decrease in fluorescence intensity related to the competition between labeled and unlabeled factor B ligands was recorded at both 620 nm and 665 nm, 70 μs after excitation at 337 nm using a microplate spectrofluorimeter. $IC_{50}$ values were calculated from percentage of inhibition of complement factor B-(+) or (−)-2-((1E,3E,5E)-5-(1-(6-((2-(3-(4-((R)-3-amino-3-phenylpropanoyl)-1-(4-amino-6,7-dimethoxyquinazolin-2-yl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium (Biological Example 2.6, 240 nM activity against factor B when tested using the assay of Biological Example 1) displacement as a function of test compound concentration.

Compounds of invention are active on factor B inhibition. Data on Table 1 collected using the assay of Biological Example 2.

TABLE 1

| Example number | $IC_{50}$ (μM) |
|---|---|
| Example-1 | >100 |
| Example-2b (+) | >100 |
| Example-2b (−) | 7.9 |
| Example-3 | 6 |
| Example-4b (+) | 67 |
| Example-4b (−) | 0.72 |
| Example-5-1 | 7.2 |
| Example-5-2 | 7.9 |
| Example-5-3 | 2.6 |
| Example-5-4 | 0.18 |
| Example-5-5 | 3.5 |
| Example-5-6 | 0.66 |
| Example-5-7 | 8.3 |
| Example-5-8 | 24 |
| Example-5-9 | 7.1 |
| Example-5-10 | 1.5 |
| Example-5-11 | 1.3 |
| Example-5-12 | 0.037 |
| Example-6 | 14 |
| Example-7 | 9.4 |
| Example-8 | 0.71 |
| Example-9-1 | 2 |
| Example-9-2 | 0.64 |
| Example-10 | 11 |
| Example-11 | 0.23 |
| Example-12 | 2.3 |
| Example-13 | 0.14 |
| Example-14a | 1.7 |
| Example-15 | 8.7 |
| Example-16 | 0.03 |
| Example-17-1 | 0.019 |
| Example-17-2 | 0.12 |
| Example-17-3 | 0.038 |
| Example-17-4 | 0.087 |
| Example-17-5 | 0.03 |
| Example-17-6 | 6.6 |
| Example-17-7 | 4.5 |
| Example-17-8 | 0.07 |
| Example-17-9 | 5 |
| Example-17-10 | 0.1 |
| Example-17-11 | 0.015 |
| Example-17-12 | 0.45 |
| Example-17-13 | 0.063 |
| Example-17-14 | 1.8 |
| Example-17-15 | 0.023 |
| Example-17-16 | 1.9 |
| Example-17-17 | 2.1 |
| Example-17-18 | 0.027 |
| Example-17-19 | 29 |
| Example-17-20 | 2.8 |
| Example-17-21 | 0.84 |
| Example-17-22 | 0.1 |
| Example-17-23 | 1.7 |
| Example-17-29 | 0.011 |
| Example-17-30 | 0.013 |
| Example-17-24 | 0.035 |
| Example-17-25 | 0.045 |
| Example-17-26 | 4.6 |
| Example-17-27 | >100 |
| Example-17-28 | 0.16 |
| Example-18 | 2.8 |
| Example-19 | >100 |
| Example-20a | 0.009 |
| Example-20b | 0.29 |
| Example-21a | 0.019 |
| Example-21b | 0.65 |
| Example-22-1a | 0.019 |
| Example-22-1b | 1.8 |
| Example-22-2a | 2.2 |
| Example-22-2b | 0.013 |
| Example-23a | >100 |
| Example-23b | 1.8 |
| Example-24 | 8.7 |
| Example-25a | 15 |
| Example-25b | 0.047 |
| Example-26a | 0.01 |
| Example-26b | 1.1 |
| Example-27-1a | 3.7 |

TABLE 1-continued

| Example number | IC$_{50}$ (μM) |
| --- | --- |
| Example-27-1b | 0.022 |
| Example-27-2a | 0.015 |
| Example-27-2b | 16 |
| Example-27-3a | 0.014 |
| Example-27-3b | 0.74 |
| Example-27-4a | 0.009 |
| Example-27-4b | 1.7 |
| Example-28 | 1.5 |
| Example-29 | 33 |
| Example-30-1 | 3.4 |
| Example-30-2 | 8.2 |
| Example-30-3 | 1.3 |
| Example-30-1 | 3.4 |
| Example-30-2 | 8.2 |
| Example-30-3 | 1.3 |
| Example-31 | 6.8 |
| Example-32-1 | 36 |
| Example-32-2 | 36 |
| Example-32-3 | 0.34 |
| Example-33 | 1.2 |
| Example-34 | 2.9 |
| Example-35 | 2.7 |
| Example-36 | 0.02 |
| Example-37 | 0.022 |
| Example-38 | 0.13 |
| Example-39-1 | 1.7 |
| Example-39-2 | 1.8 |
| Example-39-3 | 0.28 |
| Example-39-4 | 0.3 |
| Example-40 | 0.055 |
| Example-41 | 0.165 |
| Example-42 | 0.24 |

What is claimed is:

1. A method of treating a subject suffering from a disorder or disease mediated by activation of the complement alternative pathway, wherein the disease or disorder is selected from the group consisting of age-related macular degeneration, diabetic retinopathy, rheumatoid arthritis, systemic lupus erythematosus (SLE), SLE nephritis, asthma, and glomerulonephritis, wherein the method comprises administering to the subject a therapeutically effective amount of the compound, of salt or tautomer thereof, of Formula (I):

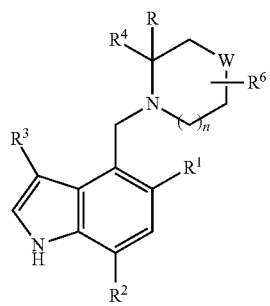

(I)

Wherein
n is 0, 1 or 2;
R is hydrogen, $C_1$-$C_4$alkyl, or hydroxy$C_1$-$C_4$alkyl;
$R^1$ is halogen, hydroxy, $C_1$-$C_6$alkyl, $C_2$-$C_6$alkenyl, $C_3$-$C_6$cycloalkyl, $C_1$-$C_6$alkoxy, halo$C_1$-$C_6$alkyl, hydroxy$C_1$-$C_6$alkyl, amino$C_1$-$C_6$alkyl, $C_1$-$C_6$alkoxy$C_1$-$C_6$alkyl, $C_1$-$C_6$alkoxy$C_1$-$C_6$alkoxy, $C_3$-$C_6$cycloalkyl$C_1$-$C_6$alkoxy, halo$C_1$-$C_6$alkoxy, —S(O)$_p$$C_1$-$C_6$alkyl, —CH$_2$NHC(O)$C_1$-$C_4$alkyl or —OCH$_2$C(O)$R^7$, p is 0, 1, or 2;
$R^2$ is $C_1$-$C_6$alkyl, $C_1$-$C_6$alkoxy, hydroxy$C_1$-$C_6$alkyl or halogen;
$R^3$ is hydrogen, halogen, cyano, $C_1$-$C_4$alkyl, halo$C_1$-$C_4$alkyl, —CH$_2$C(O)$R^7$, phenyl or 5 or 6 member heteroaryl having 1, 2 or 3 ring heteroatoms independently selected from N, O or S, wherein the phenyl or heteroaryl is optionally substituted with 0, 1, or 2 $C_1$-$C_4$alkyl groups, and wherein alkyl and haloalkyl optionally substituted with 0 or 1 hydroxy;
$R^4$ is phenyl, naphthyl or heteroaryl, where the heteroaryl is a five or six member heteroaryl having 1, 2 or 3 ring heteroatoms independently selected from N, O or S, and where the phenyl or heteroaryl is optionally substituted by $R^5$ and further substituted by 0 or 1 substituents selected from halogen, $C_1$-$C_4$alkyl, $C_1$-$C_4$alkoxy, hydroxy $C_1$-$C_4$alkyl, hydroxy, and cyanomethyl;
$R^5$ is —C(O)$R^8$, —CH$_2$C(O)$R^8$, $R^9$, —C(O)NHSO$_2$$C_1$-$C_4$alkyl, —SO$_2$NHC(O)$C_1$-$C_4$alkyl, —SO$_2$N(H)$_m$($C_1$-$C_4$alkyl)$_{2-m}$, —SO$_2$$C_1$-$C_4$alkyl, cyano, halogen, hydroxy$C_1$-$C_4$alkyl and 5 member heteroaryl having 1-4 ring nitrogen atoms and 0 or 1 ring sulfur or oxygen atoms;
m is 0, 1, or 2;
W is O or C($R^6$)$_2$;
$R^6$ is independently selected at each occurrence from the group consisting of hydrogen, hydroxy, amino, mono- and di-$C_1$-$C_4$alkylamino, $C_1$-$C_4$alkyl, hydroxy$C_1$-$C_4$alkyl, cyano$C_1$-$C_4$alkyl or $C_1$-$C_4$alkoxy; or
C($R^6$)$_2$, taken in combination, form a spirocyclic carbocycle having 3 to 6 ring atoms;
$R^7$ is hydroxy, $C_1$-$C_4$alkoxy, amino or mono- and di-$C_1$-$C_4$alkylamino;
$R^8$ is hydroxy, $C_1$-$C_4$alkoxy, amino or a 5 to 7 member saturated heterocycle having 1, 2, or 3 ring heteroatoms independently selected from N, O or S; or
$R^8$ is mono- and di-$C_1$-$C_4$alkylamino which is unsubstituted or substituted with halogen, hydroxy or $C_1$-$C_4$alkyl; and
$R^9$ is a 5 membered heteroaryl having 1 to 4 ring nitrogen atoms and 0 or 1 ring oxygen or sulfur atoms, which heterocycle is optionally substituted by 0 to 2 $C_1$-$C_4$alkyl groups.

2. A method of claim 1, or salt or tautomer thereof, wherein n is 1.

3. The method of claim 1, or a salt or tautomer thereof, wherein W is CHR$^6$ or C(CH$_3$)R$^6$.

4. The method of claim 1, or a salt or tautomer thereof, wherein $R^1$ is $C_1$-$C_4$alkyl, $C_1$-$C_4$alkoxy, or cyclopropyl.

5. The method of claim 1, or a salt or tautomer thereof, wherein $R^2$ is methyl.

6. The method of claim 1, or a salt or tautomer thereof, wherein $R^3$ is hydrogen, halogen or $C_1$-$C_4$alkyl.

7. The method of claim 1, or a salt or tautomer thereof, wherein $R^3$ is hydrogen.

8. The method of claim 1, or salt or tautomer thereof, according to Formula (IIa) or (IIb):

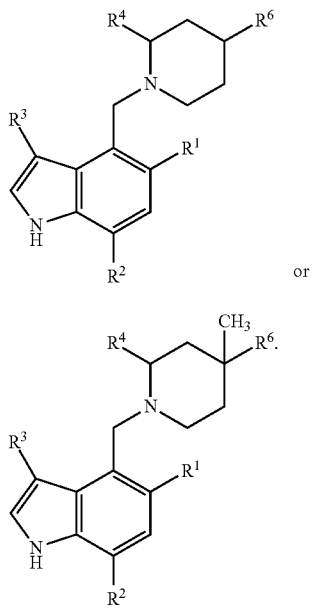

(IIa)

or (IIb)

9. The method of claim 1, or salt or tautomer thereof, according to Formula (IIIa) or (IIIb):

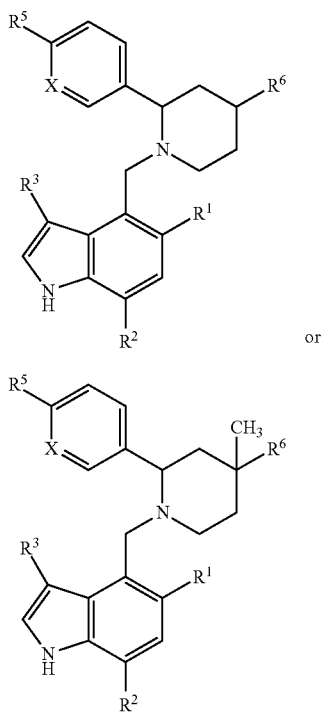

(IIIa)

or (IIIb)

Wherein X is N or CH.

10. The method of claim 1, or a salt or tautomer thereof, wherein $R^4$ is pyridin-3-yl which is substituted para to the piperidine ring with $R^5$.

11. The method of claim 1, or a salt or tautomer thereof, wherein $R^4$ is phenyl substituted para to the piperidine ring with $R^5$ and optionally substituted with fluoro, methoxy, hydroxymethyl or hydroxy.

12. The method of claim 11, or a salt or tautomer thereof, wherein $R^4$ is phenyl substituted para to the piperidine ring with $R^5$.

13. The method of claim 1, or salt or tautomer thereof, according to Formula (IVa) or (IVb):

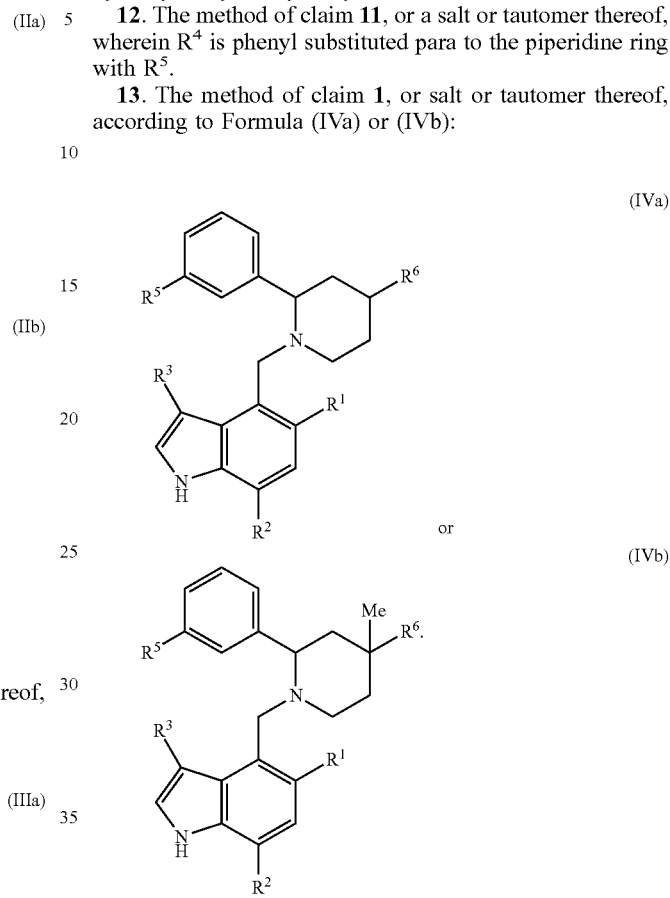

(IVa)

or (IVb)

14. The method of claim 1, or a salt or tautomer thereof, wherein $R^5$ is $CO_2H$, $CO_2NH_2$, $SO_2NH_2$ or tetrazolyl.

15. The method of claim 1, which compound is selected from the group consisting of
- 1-((5,7-dimethyl-1H-indol-4-yl)methyl)-2-phenylpiperidin-4-ol;
- 4-((4-methoxy-2-phenylpiperidin-1-yl)methyl)-5,7-dimethyl-1H-indole;
- 5,7-dimethyl-4-((2-phenylpiperidin-1-yl)methyl)-1H-indole;
- 1-((5,7-dimethyl-1H-indol-4-yl)methyl)-2-phenyl-piperidin-4-yl)methanol;
- 4-(1-((5,7-dimethyl-1H-indol-4-yl)methyl)piperidin-2-yl)benzenesulfonamide;
- 3-(1-((5,7-dimethyl-1H-indol-4-yl)methyl)piperidin-2-yl)benzenesulfonamide;
- 4-(1-((5,7-dimethyl-1H-indol-4-yl)methyl)piperidin-2-yl)-N-methylbenzenesulfonamide;
- 3-(1-((5,7-dimethyl-1H-indol-4-yl)methyl)piperidin-2-yl)-N-methylbenzenesulfonamide;
- 4-((2-(4-fluorophenyl)-4-methoxypiperidin-1-yl)methyl)-5,7-dimethyl-1H-indole;
- (1-((5,7-dimethyl-1H-indol-4-yl)methyl)-2-phenylpiperidin-2-yl)methanol;
- (4-(1-((5,7-dimethyl-1H-indol-4-yl)methyl)piperidin-2-yl)phenyl)methanol;
- 5,7-dimethyl-4-((2-(4-(methylsulfonyl)phenyl)piperidin-1-yl)methyl)-1H-indole;

4-((2-(4-(2H-tetrazol-5-yl)phenyl)piperidin-1-yl)methyl)-5,7-dimethyl-1H-indole;
1-((5,7-dimethyl-1H-indol-4-yl)methyl)-2-phenylpiperidin-4-amine;
4-(1-((5,7-dimethyl-1H-indol-4-yl)methyl)piperidin-2-yl)benzamide;
4-(1-((5-chloro-7-methyl-1H-indol-4-yl)methyl)piperidin-2-yl)benzamide;
4-(1-((5,7-dimethyl-1H-indol-4-yl)methyl)-4-methoxypiperidin-2-yl)benzamide;
4-(4-methoxy-1-((5-methoxy-7-methyl-1H-indol-4-yl)methyl)-4-methylpiperidin-2-yl)benzamide;
4-(1-((5,7-dimethyl-1H-indol-4-yl)methyl)-4-hydroxypiperidin-2-yl)benzoic acid;
4-(1-((5-chloro-7-methyl-1H-indol-4-yl)methyl)piperidin-2-yl)benzoic acid;
methyl 4-(1-((5,7-dimethyl-1H-indol-4-yl)methyl)-4-methoxypiperidin-2-yl)benzoate;
4-(1-((5-cyclopropyl-7-methyl-1H-indol-4-yl)methyl)piperidin-2-yl)-2-fluorobenzoic acid;
4-(1-((5-cyclopropyl-7-methyl-1H-indol-4-yl)methyl)pyrrolidin-2-yl)benzoic acid;
5-(1-((5-cyclopropyl-7-methyl-1H-indol-4-yl)methyl)piperidin-2-yl)picolinic acid;
4-(1-((5-cyclopropyl-7-methyl-1H-indol-4-yl)methyl)piperidin-2-yl)-3-methoxybenzoic acid;
4-(1-((5-methoxy-7-methyl-1H-indol-4-yl)methyl)piperidin-2-yl)benzoic acid;
5-methoxy-7-methyl-4-((2-(pyridin-4-yl)piperidin-1-yl)methyl)-1H-indole;
5-methoxy-7-methyl-4-((2-(pyridin-3-yl)piperidin-1-yl)methyl)-1H-indole;
3-fluoro-4-(1-((5-methoxy-7-methyl-1H-indol-4-yl)methyl)piperidin-2-yl)benzoic acid;
4-(4-((5-methoxy-7-methyl-1H-indol-4-yl)methyl)morpholin-3-yl)benzoic acid;
6-(1-((5-methoxy-7-methyl-1H-indol-4-yl)methyl)piperidin-2-yl)nicotinic acid;
4-(1-((5-methoxy-7-methyl-1H-indol-4-yl)methyl)-4-propoxypiperidin-2-yl)benzoic acid;
4-(4-hydroxy-1-((5-methoxy-7-methyl-1H-indol-4-yl)methyl)piperidin-2-yl)benzoic acid;
4-(1-((5-methoxy-7-methyl-1H-indol-4-yl)methyl)piperidin-2-yl)-3-methylbenzoic acid;
4-(1-((5-methoxy-7-methyl-1H-indol-4-yl)methyl)-5-methylpiperidin-2-yl)benzoic acid;
4-(1-((5-methoxy-7-methyl-1H-indol-4-yl)methyl)-4-ethylpiperidin-2-yl)benzoic acid;
2-(4-(1-((5-methoxy-7-methyl-1H-indol-4-yl)methyl)piperidin-2-yl)phenyl)acetic acid;
2-(3-(1-((5-methoxy-7-methyl-1H-indol-4-yl)methyl)piperidin-2-yl)phenyl)acetic acid;
5-(1-((5-cyclopropyl-7-methyl-1H-indol-4-yl)methyl)-4-methoxypiperidin-2-yl)picolinic acid;
2-(1-((5-methoxy-7-methyl-1H-indol-4-yl)methyl)piperidin-2-yl)thiazole-4-carboxylic acid;
2-(1-((5-methoxy-7-methyl-1H-indol-4-yl)methyl)piperidin-2-yl)-4-methylthiazole-5-carboxylic acid;
3-(1-((5,7-dimethyl-1H-indol-4-yl)methyl)piperidin-2-yl)benzoic acid;
4-(1-((5-methoxy-7-methyl-1H-indol-4-yl)methyl)azepan-2-yl)benzoic acid;
4-((2-(4-(1H-pyrazol-4-yl)phenyl)piperidin-1-yl)methyl)-5-methoxy-7-methyl-1H-indole;
4-((2-(4-(1H-pyrazol-3-yl)phenyl)piperidin-1-yl)methyl)-5-methoxy-7-methyl-1H-indole;
4-(1-((5-methoxy-7-methyl-1H-indol-4-yl)methyl)piperidin-2-yl)-1-naphthoic acid;
1-(2,2,2-trifluoro-1-(5-methoxy-7-methyl-1H-indol-4-yl)ethyl)piperidin-2-yl)benzoic acid;
2-methoxy-4-(1-((5-methoxy-7-methyl-1H-indol-4-yl)methyl)piperidin-2-yl)benzoic acid;
2-(1-((5,7-dimethyl-1H-indol-4-yl)methyl)-2-phenylpiperidin-4-yl)acetonitrile;
4-(1-((5-methoxy-7-methyl-1H-indol-4-yl)methyl)-4-methylpiperidin-2-yl)benzoic acid;
4-(4-methoxy-1-((5-methoxy-7-methyl-1H-indol-4-yl)methyl)piperidin-2-yl)benzoic acid;
5-(4-ethoxy-1-((5-methoxy-7-methyl-1H-indol-4-yl)methyl)piperidin-2-yl)picolinic acid;
4-(1-((5-methoxy-7-methyl-1H-indol-4-yl)methyl)-4,4-dimethylpiperidin-2-yl)benzoic acid;
4-(4-ethoxy-1-((5-methoxy-7-methyl-1H-indol-4-yl)methyl)piperidin-2-yl)benzonitrile;
4-(1-((5,7-dimethyl-1H-indol-4-yl)methyl)piperidin-2-yl)benzoic acid;
4-((4-ethoxy-1-((5-methoxy-7-methyl-1H-indol-4-yl)methyl)piperidin-2-yl)benzoic acid;
4-(1-((5,7-dimethyl-1H-indol-4-yl)methyl)-4-methoxypiperidin-2-yl)benzoic acid;
4-(1-((5,7-dimethyl-1H-indol-4-yl)methyl)-4-ethoxypiperidin-2-yl)benzoic acid;
4-(1-((5,7-dimethyl-1H-indol-4-yl)methyl)-4-ethoxypiperidin-2-yl)benzoic acid;
4-(1-((5-cyclopropyl-7-methyl-1H-indol-4-yl)methyl)-4-methoxypiperidin-2-yl)benzoic acid;
4-(1-((5-cyclopropyl-7-methyl-1H-indol-4-yl)methyl)-4-ethoxypiperidin-2-yl)benzoic acid;
4-(1-((5-cyclopropyl-7-methyl-1H-indol-4-yl)methyl)-4-ethoxypiperidin-2-yl)benzoic acid;
4-(5-methoxy-1-((5-methoxy-7-methyl-1H-indol-4-yl)methyl)piperidin-2-yl)benzoic acid;
4-(5-methoxy-1-((5-methoxy-7-methyl-1H-indol-4-yl)methyl)piperidin-2-yl)benzamide;
4-(5-methoxy-1-((5-methoxy-7-methyl-1H-indol-4-yl)methyl)piperidin-2-yl)benzoic acid;
4-(5-hydroxy-1-((5-methoxy-7-methyl-1H-indol-4-yl)methyl)piperidin-2-yl)benzoic acid;
1-((5,7-dimethyl-1H-indol-4-yl)methyl)-N-methyl-2-phenylpiperidin-4-amine;
(4-(1-((5,7-dimethyl-1H-indol-4-yl)methyl)piperidin-2-yl)phenyl)methanamine;
(4-(4-methoxy-1-((5-methoxy-7-methyl-1H-indol-4-yl)methyl)piperidin-2-yl)phenyl)methanol;
4-((2-(3-(2H-tetrazol-5-yl)phenyl)piperidin-1-yl)methyl)-5,7-dimethyl-1H-indole;
3-(1-((5,7-dimethyl-1H-indol-4-yl)methyl)piperidin-2-yl)benzamide;
(3-(1-((5,7-dimethyl-1H-indol-4-yl)methyl)piperidin-2-yl)phenyl)methanol;
(4-((2-(4-(1H-tetrazol-5-yl)phenyl)-4-ethoxypiperidin-1-yl)methyl)-5-methoxy-7-methyl-1H-indole;
4-(4-ethoxy-1-((5-methoxy-7-methyl-1H-indol-4-yl)methyl)piperidin-2-yl)-N-(methylsulfonyl)benzamide;
4-(4-methoxy-1-((5-methoxy-7-methyl-1H-indol-4-yl)methyl)piperidin-2-yl)-N-methylbenzamide;
4-(4-methoxy-1-((5-methoxy-7-methyl-1H-indol-4-yl)methyl)piperidin-2-yl)-N,N-dimethylbenzamide;
(4-(4-methoxy-1-((5-methoxy-7-methyl-1H-indol-4-yl)methyl)piperidin-2-yl)phenyl)(morpholino)methanone;

N-(2-hydroxyethyl)-4-(4-methoxy-1-((5-methoxy-7-methyl-1H-indol-4-yl)methyl)piperidin-2-yl)benzamide;
4-(4-methoxy-1-((5-methoxy-7-methyl-1H-indol-4-yl)methyl)piperidin-2-yl)-N-(2-methoxyethyl)benzamide;
N-((4-(1-((5-cyclopropyl-7-methyl-1H-indol-4-yl)methyl)piperidin-2-yl)phenyl)sulfonyl)acetamide;
4-(6-((5-methoxy-7-methyl-1H-indol-4-yl)methyl)-6-azaspiro[2.5]octan-5-yl)benzoic acid;
4-ethyl-1-((5-methoxy-7-methyl-1H-indol-4-yl)methyl)piperidin-2-yl)benzoic acid; and
ethyl 4-((2S,4R)-1-((5-methoxy-7-methyl-1H-indol-4-yl)methyl)-4-methylpiperidin-2-yl)benzoate;
ethyl 4-((2S,4S)-4-ethoxy-1-((5-methoxy-7-methyl-1H-indol-4-yl)methyl)piperidin-2-yl)benzoate and salts, stereoisomers and tautomers thereof.

16. The method of claim 1, which compound is 4-((2S,4S)-4-ethoxy-1-((5-methoxy-7-methyl-1H-indol-4-yl)methyl)piperidin-2-yl)benzoic acid or a pharmaceutically acceptable salt thereof.

17. The method of claim 1, in which the disease or disorder is glomerulonephritis.

18. The method of claim 1, wherein the disorder or disease is age-related macular degeneration.

* * * * *

UNITED STATES PATENT AND TRADEMARK OFFICE
CERTIFICATE OF CORRECTION

| | | |
|---|---|---|
| PATENT NO. | : 10,093,663 B2 | Page 1 of 1 |
| APPLICATION NO. | : 15/626981 | |
| DATED | : October 9, 2018 | |
| INVENTOR(S) | : Christopher Michael Adams et al. | |

It is certified that error appears in the above-identified patent and that said Letters Patent is hereby corrected as shown below:

In the Specification

At Column 9, Lines 45-46, delete "1-((5, 7-dimethyl-1 H-indol-4-yl)methyl)-2-phenyl-piperidin-4-yl)methanol;" and insert --(1-((5, 7-dimethyl-1 H-indol-4-yl)methyl)-2-phenyl-piperidin-4-yl)methanol;--.

At Column 11, Lines 18-19, delete "4-((4-ethoxy-1-((5-methoxy-7-methyl-1H-indol-4-yl)methyl)piperidin-2-yl)benzoic acid;" and insert --4-(4-ethoxy-1-((5-methoxy-7-methyl-1H-indol-4-yl)methyl)piperidin-2-yl)benzoic acid;--.

At Column 12, Lines 3-4, delete "4-ethyl-1-((5-methoxy-7-methyl-1H-indol-4-yl)methyl)piperidin-2-yl)benzoic acid;" and insert --4-(ethyl-1-((5-methoxy-7-methyl-1H-indol-4-yl)methyl)piperidin-2-yl)benzoic acid;--.

In the Claims

At Column 252, Lines 50-51, delete "1-((5, 7-dimethyl-1 H-indol-4-yl)methyl)-2-phenyl-piperidin-4-yl)methanol;" and insert --(1-((5, 7-dimethyl-1 H-indol-4-yl)methyl)-2-phenyl-piperidin-4-yl)methanol;--.

At Column 254, Lines 22-23, delete "4-((4-ethoxy-1-((5-methoxy-7-methyl-1H-indol-4-yl)methyl)piperidin-2-yl)benzoic acid;" and insert --4-(4-ethoxy-1-((5-methoxy-7-methyl-1H-indol-4-yl)methyl)piperidin-2-yl)benzoic acid;--.

At Column 255, Lines 10-11, delete "4-ethyl-1-((5-methoxy-7-methyl-1H-indol-4-yl)methyl)piperidin-2-yl)benzoic acid;" and insert --4-(ethyl-1-((5-methoxy-7-methyl-1H-indol-4-yl)methyl)piperidin-2-yl)benzoic acid;--.

Signed and Sealed this
Eleventh Day of February, 2025

Coke Morgan Stewart
*Acting Director of the United States Patent and Trademark Office*